(12) United States Patent
Crellin et al.

(10) Patent No.: US 12,103,958 B2
(45) Date of Patent: Oct. 1, 2024

(54) LYMPHOCYTE FUNCTION-ASSOCIATED ANTIGEN 3 (LFA3) VARIANT POLYPEPTIDES AND METHODS OF USE THEREOF TO TREAT CD2-MEDIATED IMMUNE DISEASES, DISORDERS OR CONDITIONS

(71) Applicants: PFIZER INC., New York, NY (US); THE REGENTS OF THE UNIVERSITY OF CALIFORNIA, Oakland, CA (US)

(72) Inventors: Natasha Kay Crellin, New York, NY (US); Lauren Kate Ely, New York, NY (US); Jason Robles Reyes, New York, NY (US); Chia Chi Ho, New York, NY (US); Jeffrey A. Bluestone, Oakland, CA (US); Eleonora Trotta, Oakland, CA (US); Qizhi Tang, Oakland, CA (US)

(73) Assignees: Pfizer Inc., New York, NY (US); The Regents of the University of California, Oakland, CA (US)

( * ) Notice: Subject to any disclaimer, the term of this patent is extended or adjusted under 35 U.S.C. 154(b) by 936 days.

(21) Appl. No.: 17/035,327

(22) Filed: Sep. 28, 2020

(65) Prior Publication Data

US 2021/0032308 A1   Feb. 4, 2021

Related U.S. Application Data

(63) Continuation of application No. PCT/US2019/023883, filed on Mar. 25, 2019.

(60) Provisional application No. 62/783,986, filed on Dec. 21, 2018, provisional application No. 62/650,022, filed on Mar. 29, 2018.

(51) Int. Cl.
| | |
|---|---|
| *C07K 14/705* | (2006.01) |
| *A61K 39/00* | (2006.01) |
| *C12N 15/63* | (2006.01) |
| *G01N 33/50* | (2006.01) |
| *G01N 33/68* | (2006.01) |

(52) U.S. Cl.
CPC ............ *C07K 14/70528* (2013.01); *A61K 39/001129* (2018.08); *C12N 15/63* (2013.01); *G01N 33/505* (2013.01); *G01N 33/68* (2013.01); *C07K 2319/30* (2013.01); *G01N 2333/70507* (2013.01)

(58) Field of Classification Search
CPC .......... C07K 14/70528; C07K 2319/30; A61K 39/001129; C12N 15/63; G01N 33/505; G01N 2333/70507
See application file for complete search history.

(56) References Cited

U.S. PATENT DOCUMENTS

| | | | |
|---|---|---|---|
| 5,547,853 A | 8/1996 | Wallner et al. | |
| 5,556,943 A | 9/1996 | Yamashita et al. | |
| 2002/0009446 A1 | 1/2002 | Magilavy | |
| 2002/0009449 A1 | 1/2002 | Wallner et al. | |

FOREIGN PATENT DOCUMENTS

| | | |
|---|---|---|
| CN | 1315866 A | 10/2001 |
| CN | 1527723 A | 9/2004 |
| CN | 101089180 A | 12/2007 |
| JP | 2007531707 A | 11/2007 |
| KR | 20140021799 A | 2/2014 |
| WO | 93/06852 | 4/1993 |
| WO | 9306852 A2 | 4/1993 |
| WO | 2005037867 A1 | 4/2005 |
| WO | 2005115436 A1 | 12/2005 |
| WO | 2014025198 A2 | 2/2014 |

OTHER PUBLICATIONS

Application No. MX/A/2020/010183, Office Action, Mailed On Sep. 17, 2021, 5 pages.
Application No. PCT/US2019/023883, International Preliminary Report on Patentability, Mailed On Oct. 8, 2020, 11 pages.
Application No. SA520420207, Office Action, Mailed On Oct. 9, 2021, 2 pages.
PCT/US2019/023883, "International Preliminary Report on Patentability", Oct. 8, 2020, 11 pages.
2020/0013557, "Office Action", Feb. 28, 2023.
PCT/US2019/023883, "International Search Report and Written Opinion", Jun. 7, 2019, 14 pages.
International Search Report in PCT/US2019/023883, mailed Jun. 7, 2019, 3 pages.
Chinese Application No. 201980036181.4, Office Action mailed on Jun. 25, 2024, 14 pages (8 pages of Original Document and 6 pages of English Translation).
Korean Application No. 10-2020-7030735, Office Action mailed on Jul. 22, 2024, 18 pages (10 pages of Original Document and 8 pages of English Translation).
Osborn et al., Amino Acid Residues Required for Binding of Lymphocyte Function—Associated Antigen 3 (CD58) to its Counter-Receptor CD2, Journal of Experimental Medicine, vol. 181, No. 1, Jan. 1, 1995, pp. 429-434.
Zhu et al., Recombinant Expression and Activity Analysis of the CD2 Binding Domain of the Extracellular Segment of Rhesus Monkey LFA3 in Pichia Yeast, Journal of Biomedical Engineering, vol. 32, No. 1, Feb. 25, 2015, pp. 120-125.

*Primary Examiner* — Robert S Landsman
(74) *Attorney, Agent, or Firm* — Kilpatrick Townsend & Stockton LLP

(57) ABSTRACT

The invention provides LFA3 polypeptide molecules, e.g., variant LFA3 fusion polypeptide molecules. The invention includes uses, and associated methods of using the LFA3 polypeptide molecules.

16 Claims, 50 Drawing Sheets

Specification includes a Sequence Listing.

FIG. 1

AS library (affinity + stability)

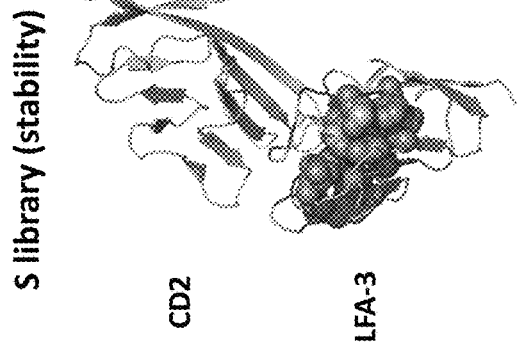

S library (stability)

CD2

LFA-3

| Contact Library | | Total theoretical diversity = 2.4x10^10 | | | |
|---|---|---|---|---|---|
| Residue | Position | Mutagenesis | Codon | Diversity | |
| Glu | 25 | D,E,N,K,Q,H | VAK | 3x1x2 | 6 |
| Leu | 27 | F,I,L,V | NTT | 4x1x1 | 4 |
| Lys | 29 | K,R,M,T | ANG | 1X4X1 | 4 |
| Lys | 32 | K,R,M,T | ANG | 1X4X1 | 4 |
| Asp | 33 | D,E,N,K,Q,H | VAM | 3x1x2 | 6 |
| Lys | 34 | K,R,M,T | ANG | 1X4X1 | 4 |
| Glu | 37 | D,E,N,K,Q,H | VAK | 3x1x2 | 6 |
| Glu | 39 | D,E,N,K,Q,H | VAM | 3x1x2 | 6 |
| Glu | 42 | D,E,N,K,Q,H | VAK | 3x1x2 | 6 |
| Arg | 44 | K,R,M,T | ANG | 1X4X1 | 4 |
| Phe | 46 | F,Y,L,H,I,N,V,D | NWT | 4x2x1 | 8 |
| Ser | 47 | S,T,A,G | RST | 2x2x1 | 4 |
| Pro | 80 | P,L,H,R | CNT | 1x4x1 | 4 |
| Ile | 82 | F,I,L,V | NTT | 4x1x1 | 4 |
| Asp | 84 | D,E,N,K,Q,H | VAM | 3x1x2 | 6 |

| Core library | | Total theoretical diversity = 4.3 x 10^9 | | | |
|---|---|---|---|---|---|
| Residue | Position | Mutagenesis | Codon | Diversity | |
| Phe | 15 | F,I,L,V | NTT | 4x1x1 | 4 |
| Val | 17 | F,I,L,V | NTT | 4x1x1 | 4 |
| Leu | 23 | F,I,L,V | NTT | 4x1x1 | 4 |
| Val | 26 | F,I,L,V | NTT | 4x1x1 | 4 |
| Trp | 28 | W,F,L,C | TKS | 1x2x2 | 4 |
| Val | 35 | F,I,L,V | NTT | 4x1x1 | 4 |
| Ala | 36 | A,V,S,L | KYA | 2x2x1 | 4 |
| Leu | 38 | F,I,L,V | NTT | 4x1x1 | 4 |
| Phe | 43 | F,I,L,V | NTT | 4x1x1 | 4 |
| Ala | 45 | A,V,S,L | KYA | 2x2x1 | 4 |
| Leu | 55 | F,I,L,V | NTT | 4x1x1 | 4 |
| Gly | 60 | S,T,A,G | RST | 2x2x1 | 4 |
| Leu | 62 | F,I,L,V | NTT | 4x1x1 | 4 |
| Met | 77 | M,L,I,F | WTS | 2x1x2 | 4 |
| Met | 86 | M,L,I,F | WTS | 2x1x2 | 4 |
| Phe | 88 | F,I,L,V | NTT | 4x1x1 | 4 |

FIG. 2A
Hotspot residues
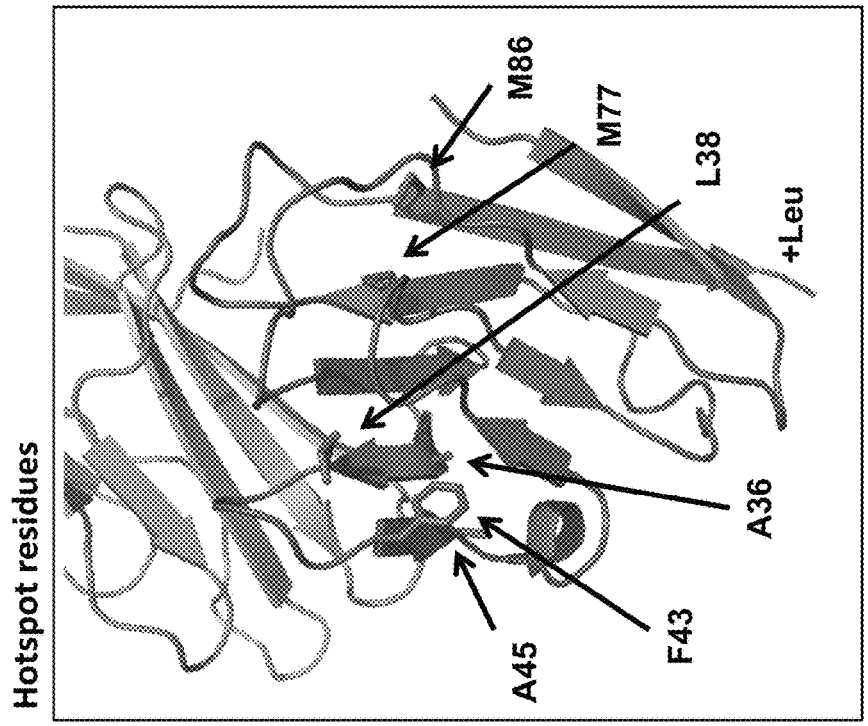
FIG. 2B
LFA3 residues targeted in libraries
FSQQIYGVVYGNVTFHVPSNVPLKEVLWKKQKDKV
AELENSEFRAFSSFKNRVYLDTVSGSLTIYNLTSS
DEDEYEMESPNITDTMKFFLYV (SEQ ID NO: 3)
FIG. 2C
Frequency of amino acid variation in hotspot positions
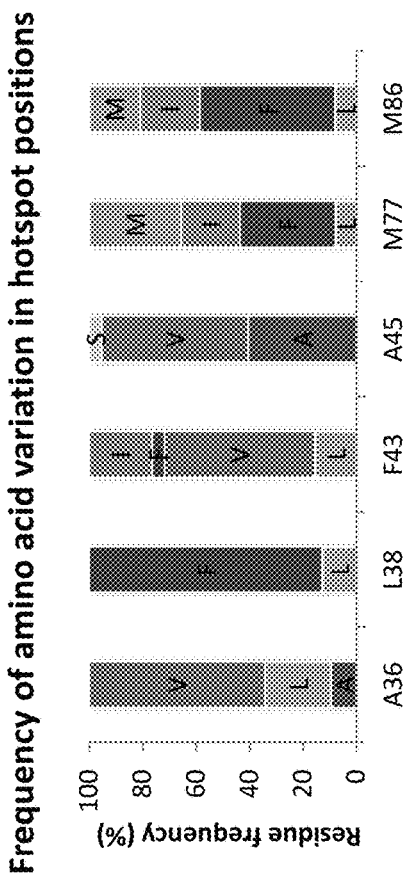
FIG. 2D
Recombinant variants
| | 36 | 38 | 43 | 45 | 77 | 86 |
|---|---|---|---|---|---|---|
| M1 | V | F | V | A | M | F |
| M2 | V | F | V | A | F | F |
| M3 | V | F | V | V | M | F |
| M4 | V | F | V | V | F | F |
| M5 | V | F | I | V | F | F |
| M6 | L | F | L | V | F | F |
CD2 binding affinity by SPR

| Construct | Affinity (μM) |
|---|---|
| WT LFA3-Fc | 1.41 |
| M1d1-Pfe | 0.73 |
| M4d1-Pfe | 0.75 |
| ML1d1-Pfe | 0.082 |
| ML3d1-Pfe | 0.052 |
| CM1d1-Pfe | 0.13 |
| CM2d1-Pfe | 0.10 |
| CM3d1-Pfe | 0.088 |
| CM5d1-Pfe | 0.063 |
| CM6d1-Pfe | 0.061 |

*n=1-3 exp*

FIG. 7A
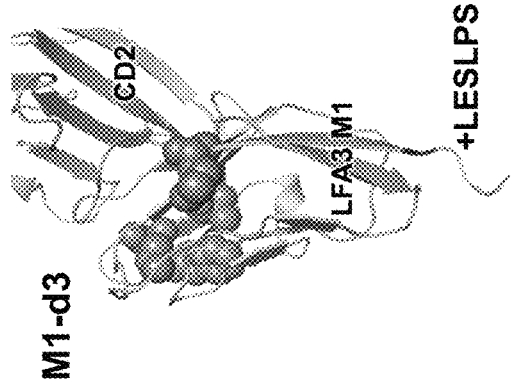
FIG. 7B
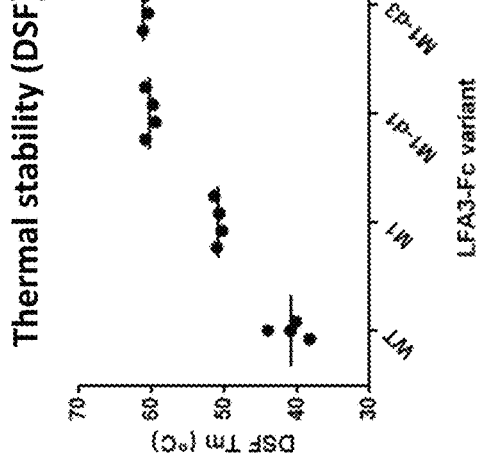
FIG. 7C
Affinity by SPR
| construct | human (µM) | cyno (µM) |
|---|---|---|
| LFA3-WT | 1.47 | 1.50 |
| M1-d1 | 1.08 | 1.06 |
| M1-d3 | 1.04 | 1.08 |
Average of triplicate measurements
FIG. 7D
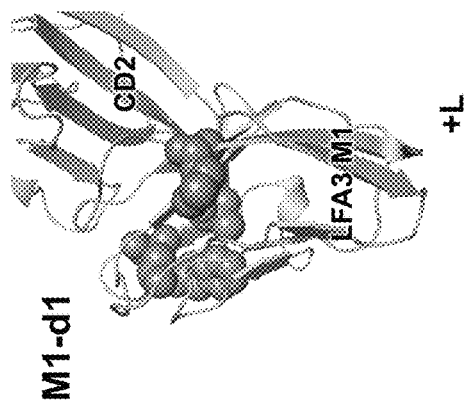

FIG. 8A
Sequence
| | 36 | 38 | 43 | 45 | 77 | 86 |
|---|---|---|---|---|---|---|
| WT | A | L | F | A | M | M |
| M1 | V | F | V | | | F |
| M4 | V | F | V | V | F | F |
| M7 | V | F | V | | | |
FIG. 8B
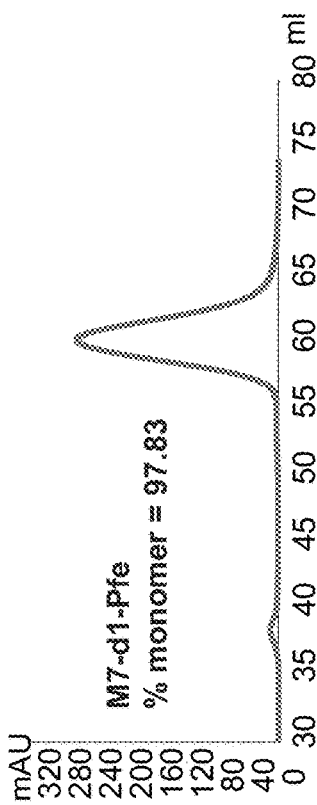
SEC chromatogram
M7-d1-Pfe
% monomer = 97.83
FIG. 8C
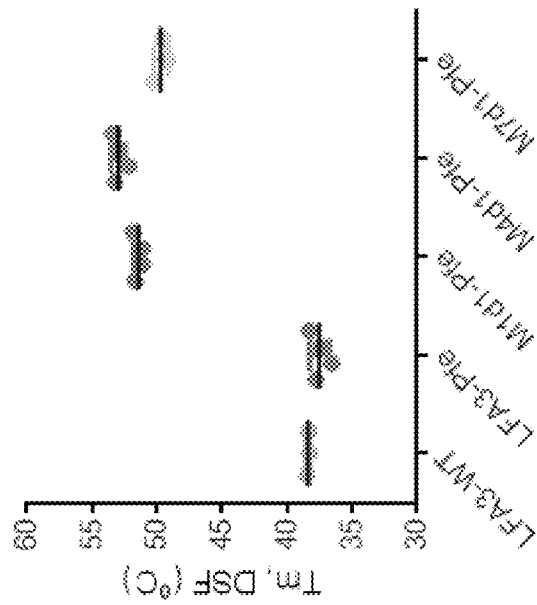
Thermal stability by DSF
FIG. 8D
Affinity by SPR
| Construct | Affinity (μM) |
|---|---|
| WT | 1.41 |
| M1-d1 Pfe | 0.73 |
| M4-d1 Pfe | 0.75 |
| M7-d1-Pfe | 0.92 |
n=4-7

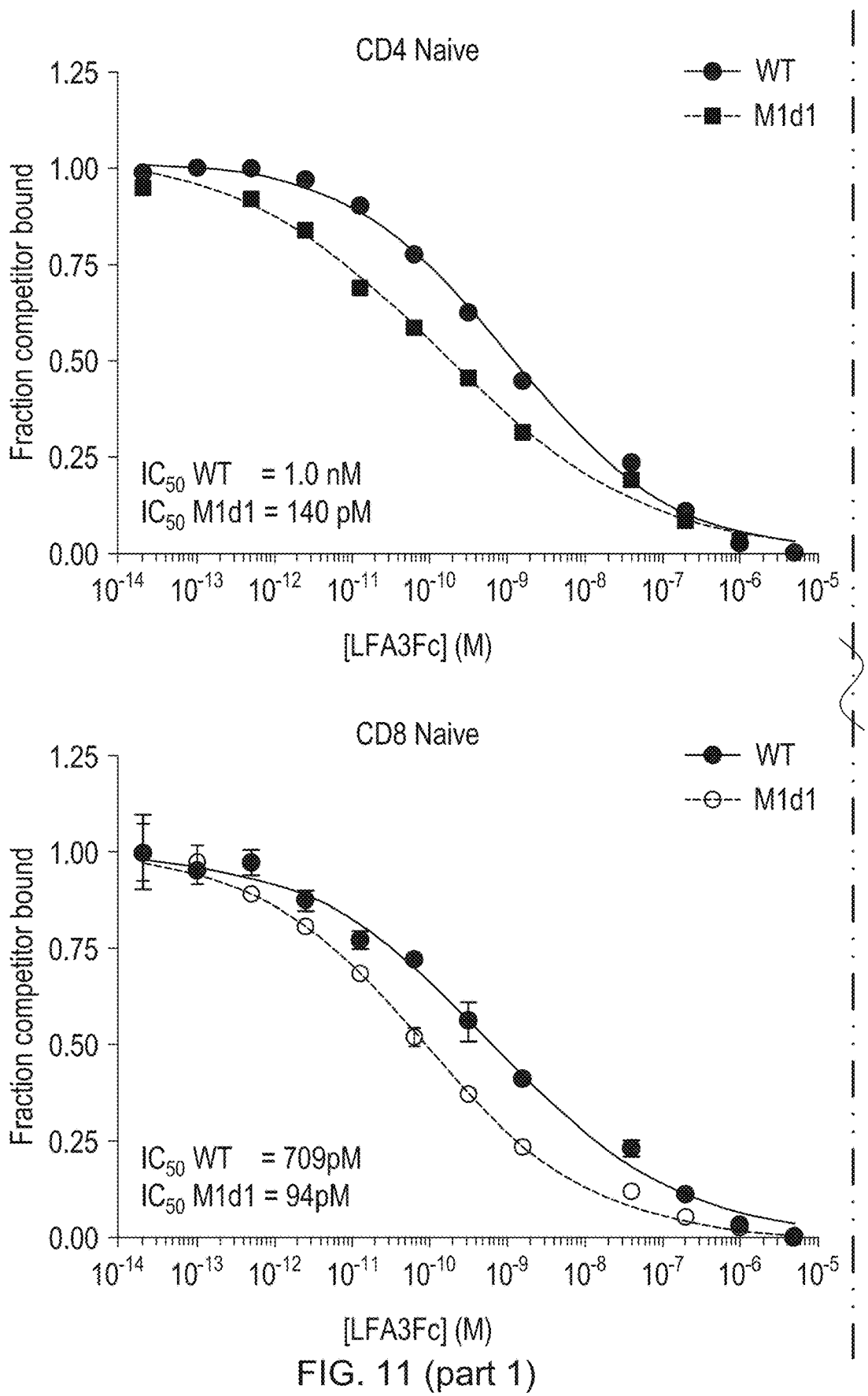
FIG. 11 (part 1)

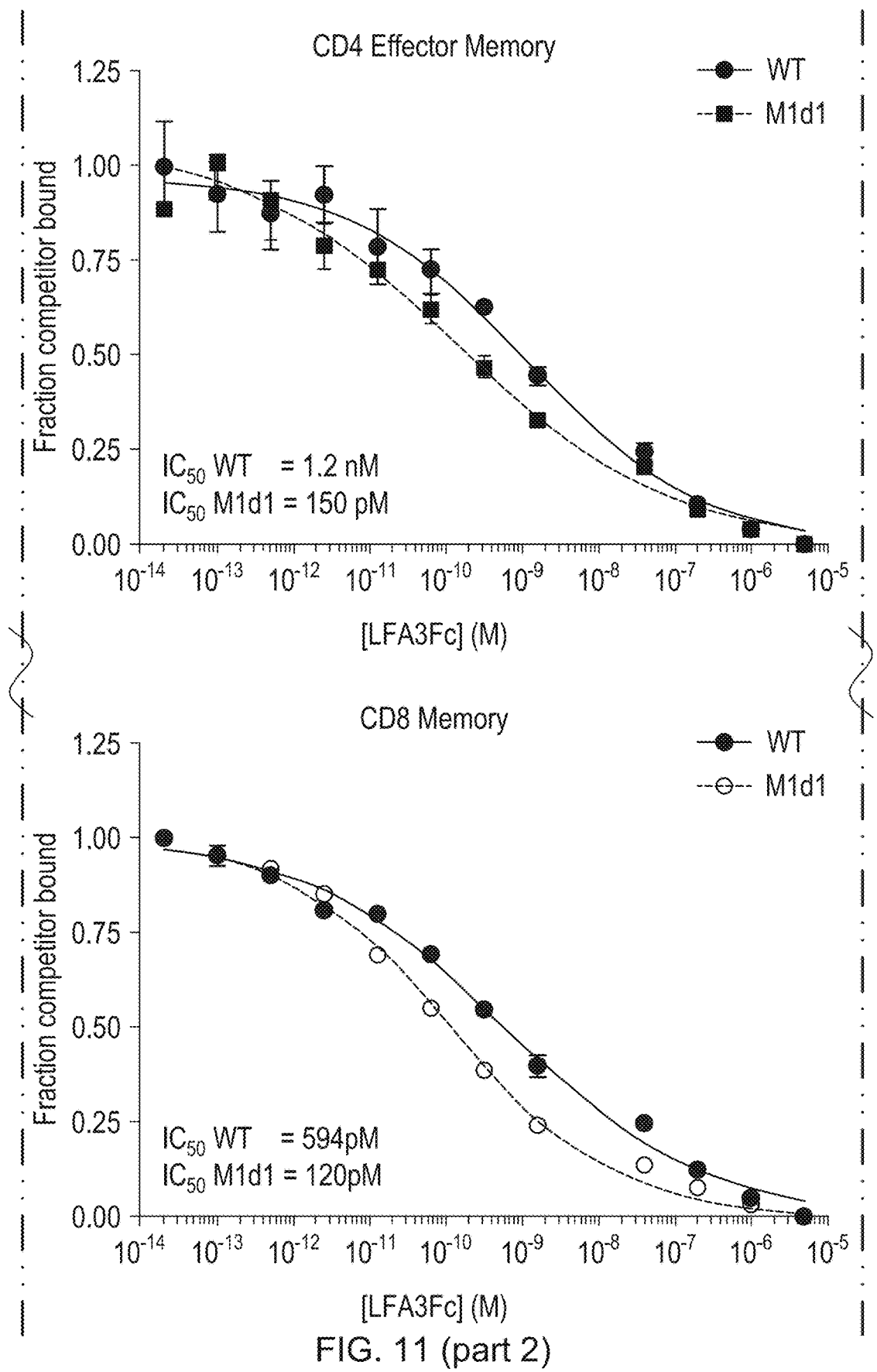
FIG. 11 (part 2)

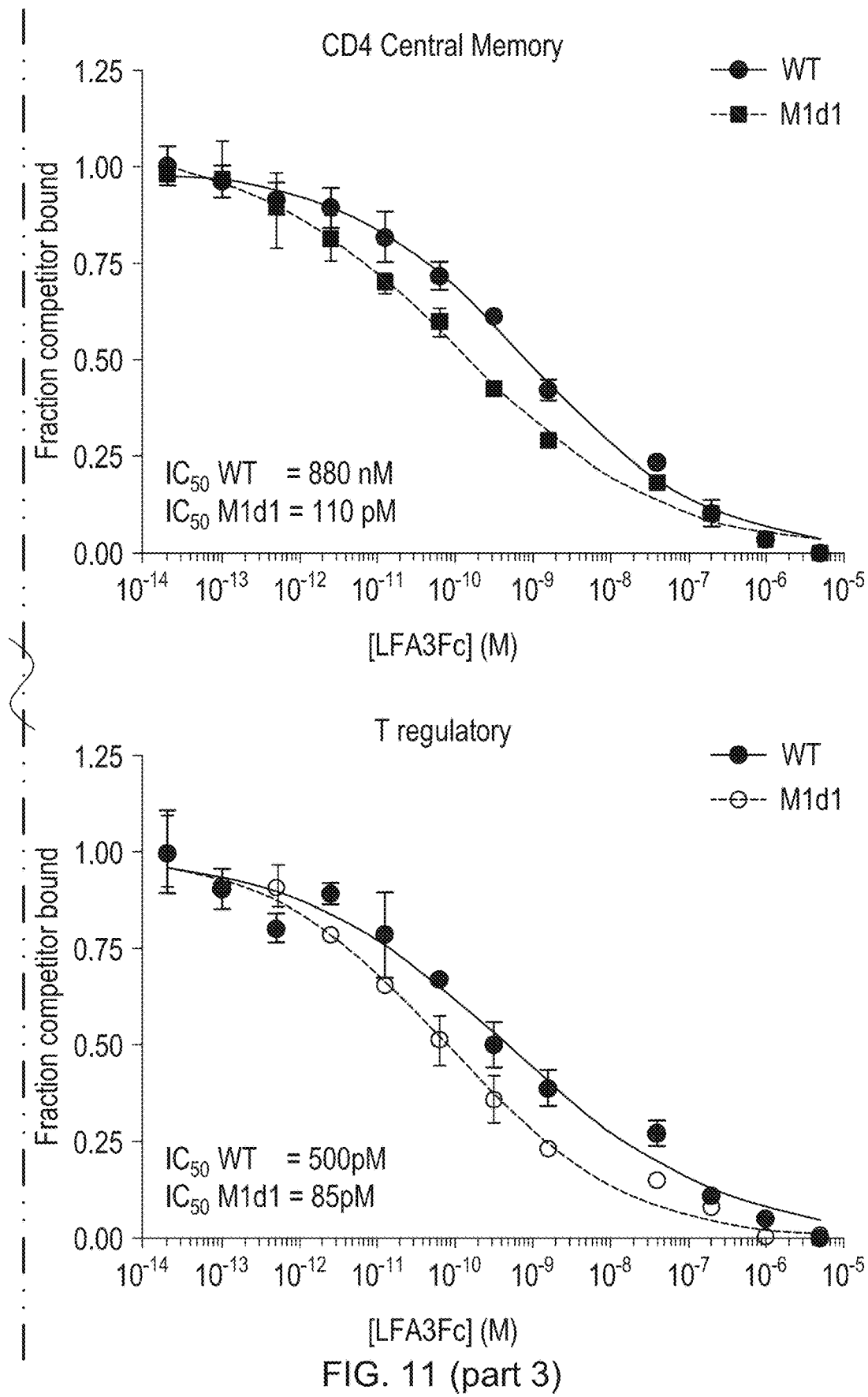
FIG. 11 (part 3)

FIG. 19
Goal: Establish in vivo PK/PD repeat dose response relationship for $T_{mem}$ depletion and ratio of $Tregs/T_{EM}$. Include WT LFA3-Fc to enable comparison to clinical Alefacept dataset.
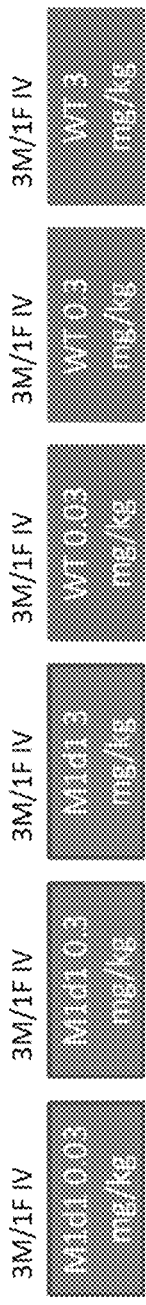
- PK analysis
- Extensive immune-phenotype analysis, including T cell subsets, markers of activation and proliferation, and exploratory biomarkers
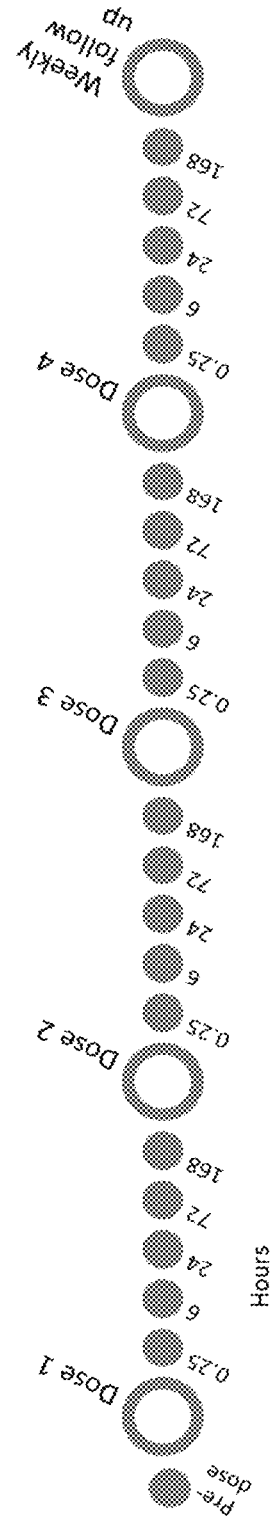

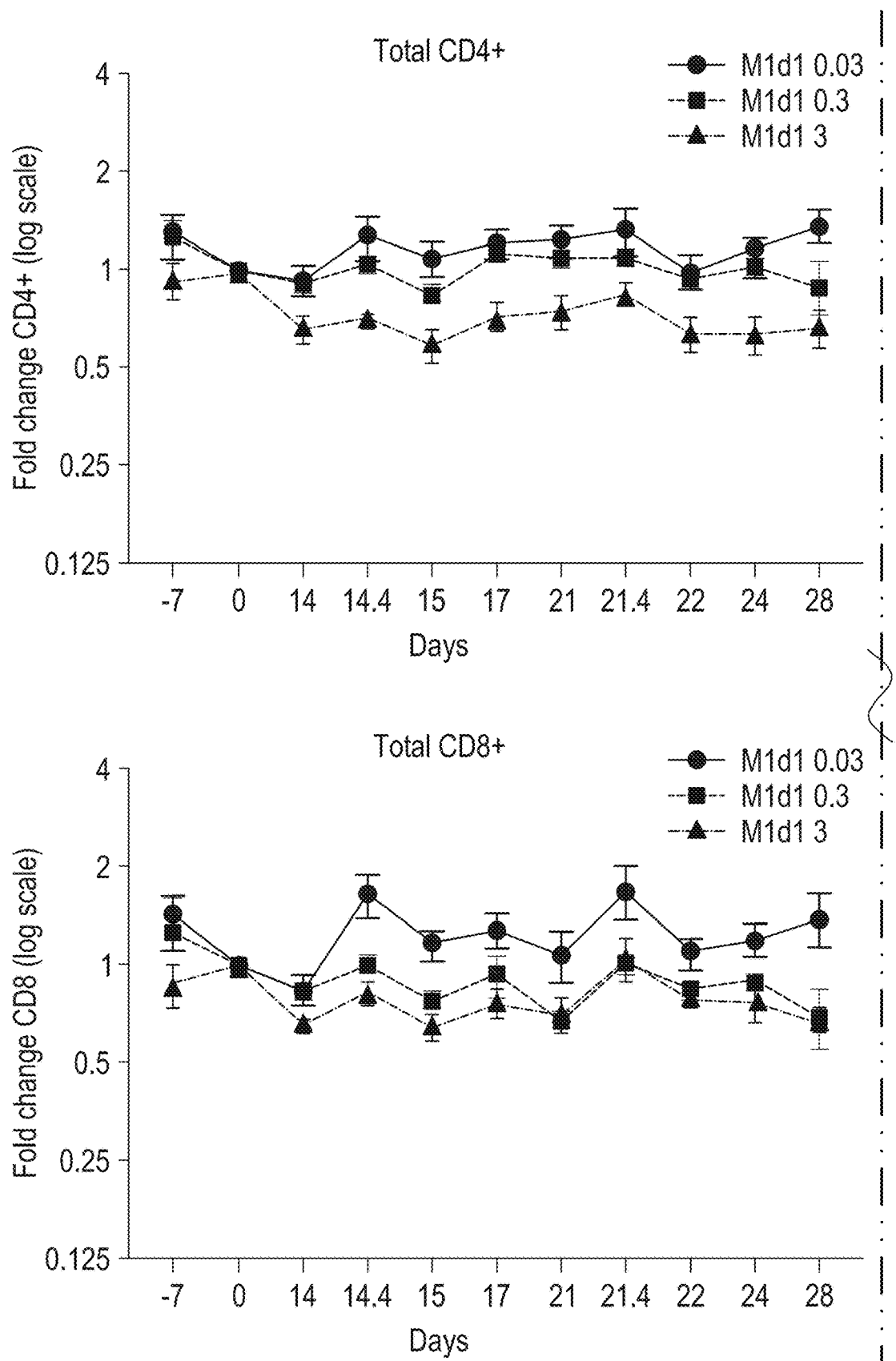
FIG. 21 (part 1)

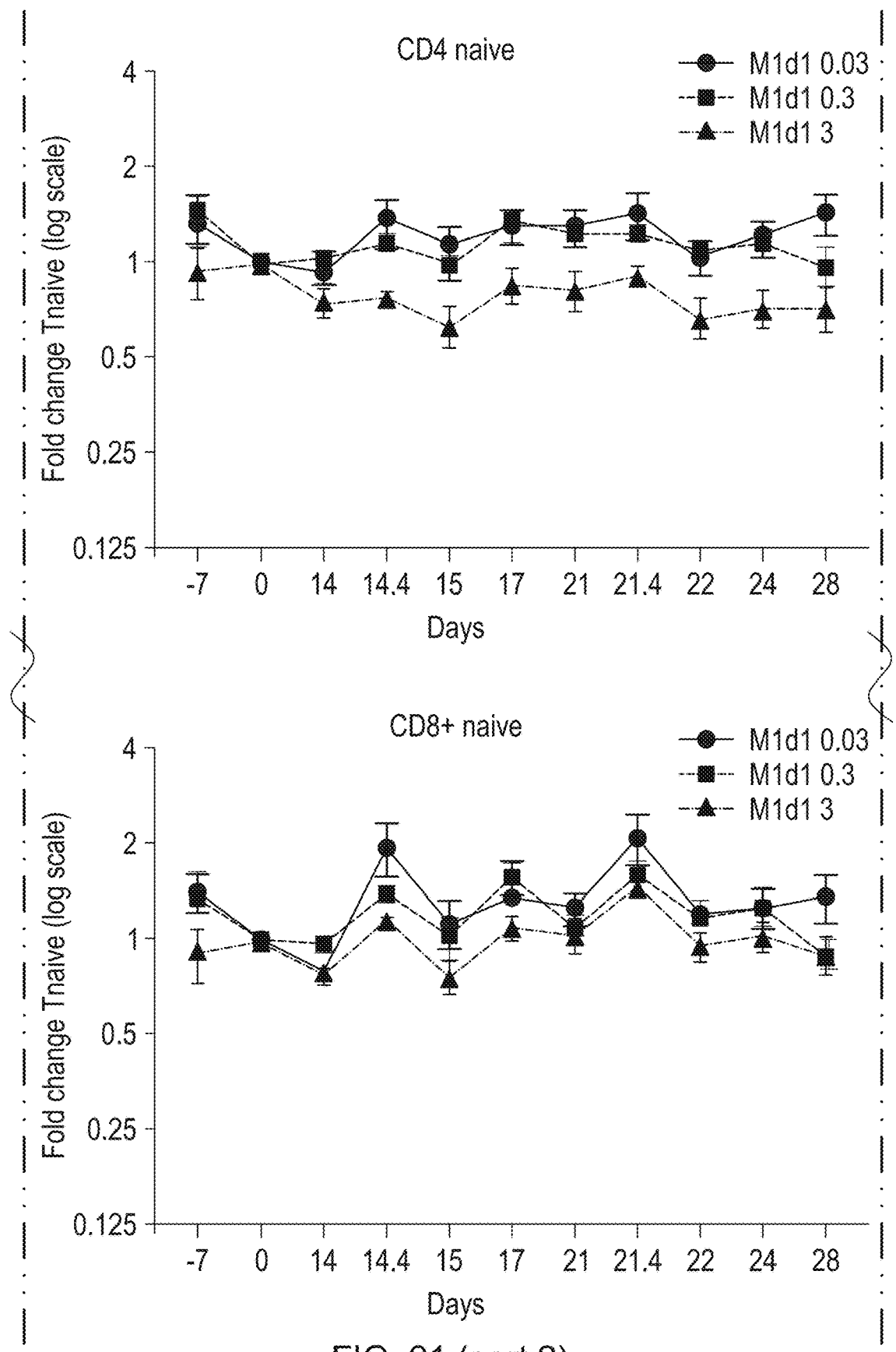
FIG. 21 (part 2)

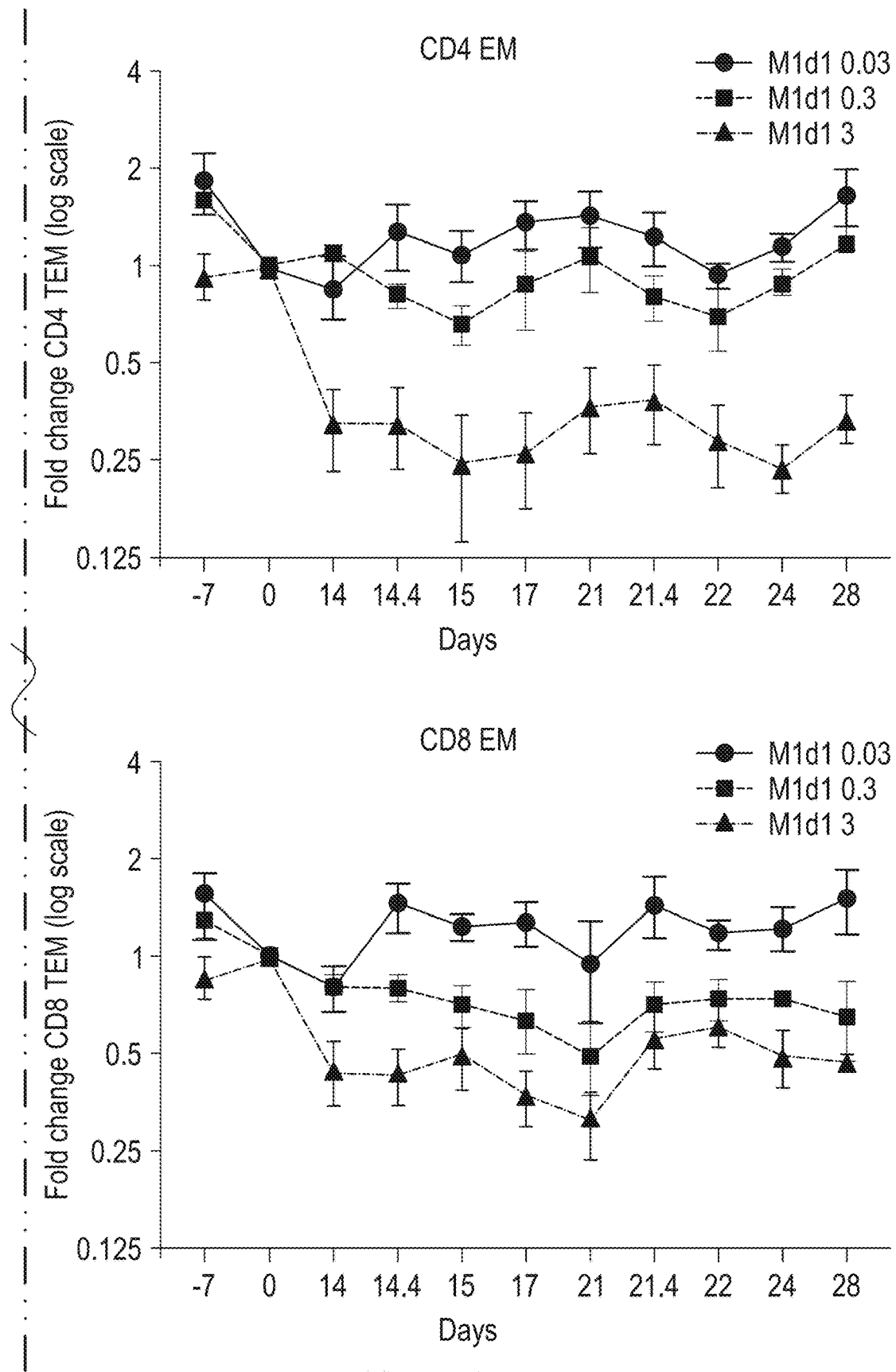
FIG. 21 (part 3)

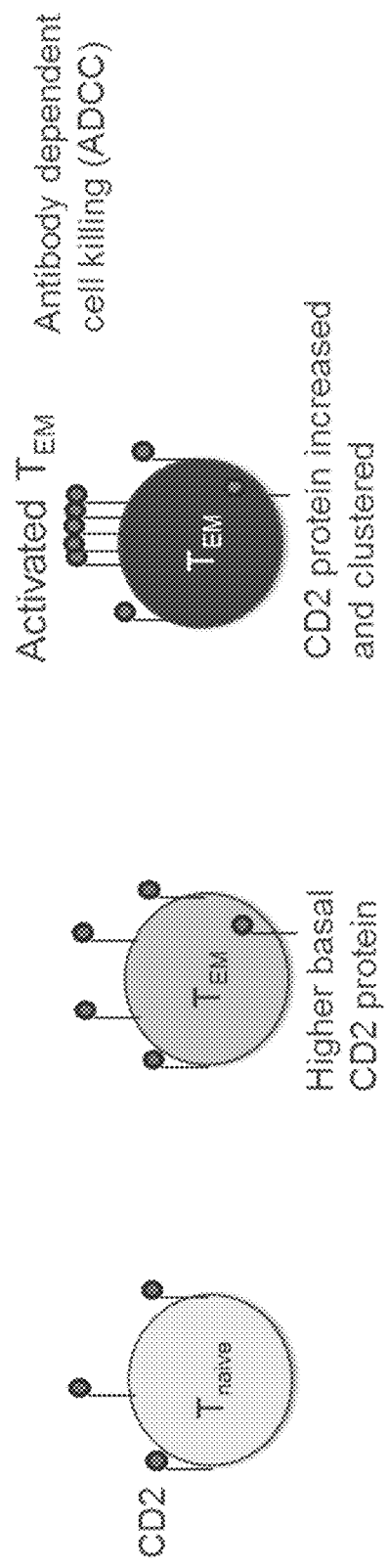
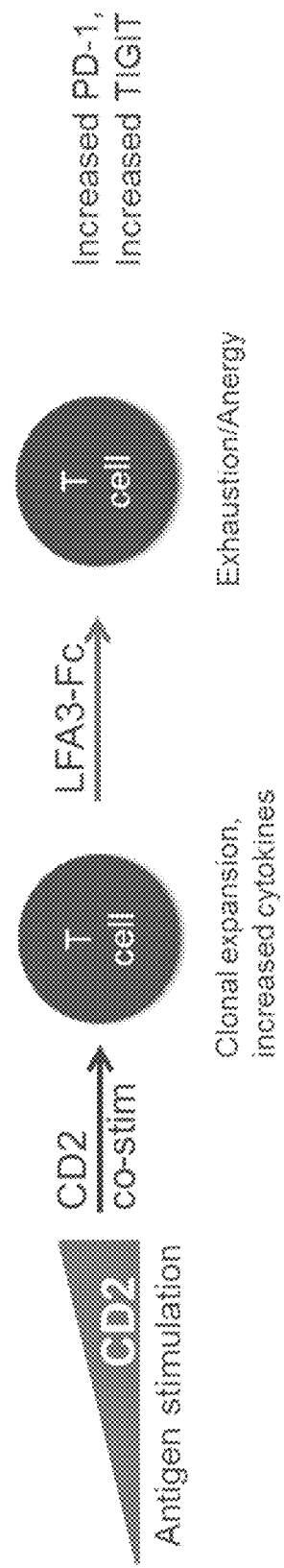
FIG. 24

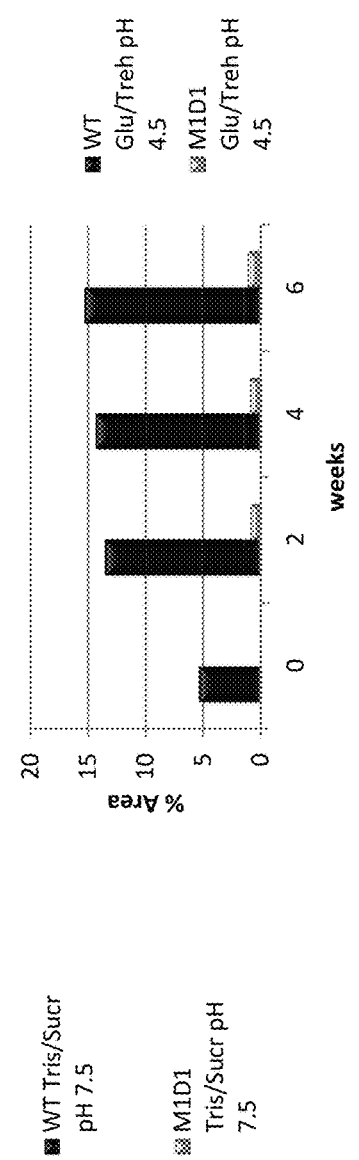
FIG. 32A
FIG. 32C
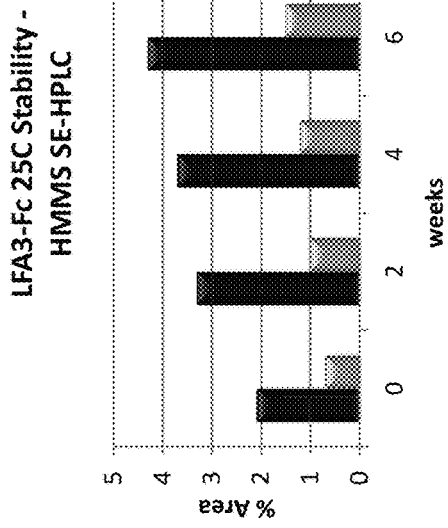
FIG. 32B
FIG. 32D
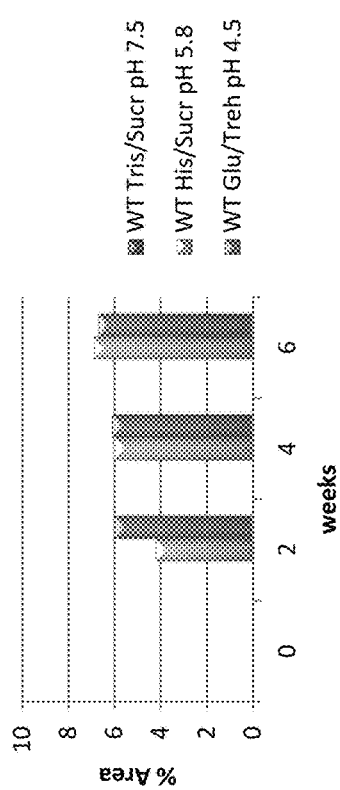
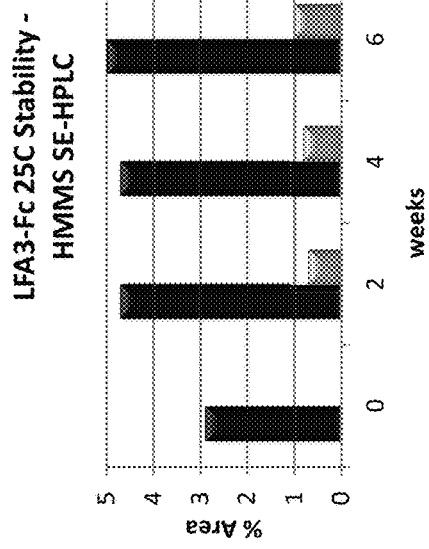

```
SEQUENCE LISTING

<160> NUMBER OF SEQ ID NOS: 130

<210> SEQ ID NO 1
<211> LENGTH: 250
<212> TYPE: PRT
<213> ORGANISM: Artificial Sequence
<220> FEATURE:
<223> OTHER INFORMATION: SYNTHETIC CONSTRUCT

<400> SEQUENCE: 1

Met Val Ala Gly Ser Asp Ala Gly Arg Ala Leu Gly Val Leu Ser Val
1               5                   10                  15

Val Cys Leu Leu His Cys Phe Gly Phe Ile Ser Cys Phe Ser Gln Gln
                20                  25                  30

Ile Tyr Gly Val Val Tyr Gly Asn Val Thr Phe His Val Pro Ser Asn
            35                  40                  45

Val Pro Leu Lys Glu Val Leu Trp Lys Lys Gln Lys Asp Lys Val Ala
        50                  55                  60

Glu Leu Glu Asn Ser Glu Phe Arg Ala Phe Ser Ser Phe Lys Asn Arg
65                  70                  75                  80

Val Tyr Leu Asp Thr Val Ser Gly Ser Leu Thr Ile Tyr Asn Leu Thr
                85                  90                  95

Ser Ser Asp Glu Asp Glu Tyr Glu Met Glu Ser Pro Asn Ile Thr Asp
            100                 105                 110

Thr Met Lys Phe Phe Leu Tyr Val Leu Glu Ser Leu Pro Ser Pro Thr
        115                 120                 125

Leu Thr Cys Ala Leu Thr Asn Gly Ser Ile Glu Val Gln Cys Met Ile
    130                 135                 140

Pro Glu His Tyr Asn Ser His Arg Gly Leu Ile Met Tyr Ser Trp Asp
145                 150                 155                 160

Cys Pro Met Glu Gln Cys Lys Arg Asn Ser Thr Ser Ile Tyr Phe Lys
                165                 170                 175

Met Glu Asn Asp Leu Pro Gln Lys Ile Gln Cys Thr Leu Ser Asn Pro
            180                 185                 190

Leu Phe Asn Thr Thr Ser Ser Ile Ile Leu Thr Thr Cys Ile Pro Ser
        195                 200                 205

Ser Gly His Ser Arg His Arg Tyr Ala Leu Ile Pro Ile Pro Leu Ala
    210                 215                 220

Val Ile Thr Thr Cys Ile Val Leu Tyr Met Asn Gly Ile Leu Lys Cys
225                 230                 235                 240

Asp Arg Lys Pro Asp Arg Thr Asn Ser Asn
                245                 250

<210> SEQ ID NO 2
```

```
<211> LENGTH: 222
<212> TYPE: PRT
<213> ORGANISM: Artificial Sequence
<220> FEATURE:
<223> OTHER INFORMATION: SYNTHETIC CONSTRUCT

<400> SEQUENCE: 2

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Ala Glu Leu Glu Asn Ser Glu Phe Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Pro
65                  70                  75                  80

Asn Ile Thr Asp Thr Met Lys Phe Phe Leu Tyr Val Leu Glu Ser Leu
                85                  90                  95

Pro Ser Pro Thr Leu Thr Cys Ala Leu Thr Asn Gly Ser Ile Glu Val
            100                 105                 110

Gln Cys Met Ile Pro Glu His Tyr Asn Ser His Arg Gly Leu Ile Met
        115                 120                 125

Tyr Ser Trp Asp Cys Pro Met Glu Gln Cys Lys Arg Asn Ser Thr Ser
    130                 135                 140

Ile Tyr Phe Lys Met Glu Asn Asp Leu Pro Gln Lys Ile Gln Cys Thr
145                 150                 155                 160

Leu Ser Asn Pro Leu Phe Asn Thr Thr Ser Ser Ile Ile Leu Thr Thr
                165                 170                 175

Cys Ile Pro Ser Ser Gly His Ser Arg His Arg Tyr Ala Leu Ile Pro
            180                 185                 190

Ile Pro Leu Ala Val Ile Thr Thr Cys Ile Val Leu Tyr Met Asn Gly
        195                 200                 205

Ile Leu Lys Cys Asp Arg Lys Pro Asp Arg Thr Asn Ser Asn
    210                 215                 220

<210> SEQ ID NO 3
<211> LENGTH: 92
<212> TYPE: PRT
<213> ORGANISM: Artificial Sequence
<220> FEATURE:
<223> OTHER INFORMATION: SYNTHETIC CONSTRUCT

<400> SEQUENCE: 3

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Ala Glu Leu Glu Asn Ser Glu Phe Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Pro
65                  70                  75                  80

Asn Ile Thr Asp Thr Met Lys Phe Phe Leu Tyr Val
                85                  90
```

-continued

```
<210> SEQ ID NO 4
<211> LENGTH: 319
<212> TYPE: PRT
<213> ORGANISM: Artificial Sequence
<220> FEATURE:
<223> OTHER INFORMATION: SYNTHETIC CONSTRUCT

<400> SEQUENCE: 4
```

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Ala Glu Leu Glu Asn Ser Glu Phe Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Pro
65                  70                  75                  80

Asn Ile Thr Asp Thr Met Lys Phe Phe Leu Tyr Val Asp Lys Thr His
                85                  90                  95

Thr Cys Pro Pro Cys Pro Ala Pro Glu Leu Leu Gly Gly Pro Ser Val
            100                 105                 110

Phe Leu Phe Pro Pro Lys Pro Lys Asp Thr Leu Met Ile Ser Arg Thr
        115                 120                 125

Pro Glu Val Thr Cys Val Val Val Asp Val Ser His Glu Asp Pro Glu
    130                 135                 140

Val Lys Phe Asn Trp Tyr Val Asp Gly Val Glu Val His Asn Ala Lys
145                 150                 155                 160

Thr Lys Pro Arg Glu Glu Gln Tyr Asn Ser Thr Tyr Arg Val Val Ser
                165                 170                 175

Val Leu Thr Val Leu His Gln Asp Trp Leu Asn Gly Lys Glu Tyr Lys
            180                 185                 190

Cys Lys Val Ser Asn Lys Ala Leu Pro Ala Pro Ile Glu Lys Thr Ile
        195                 200                 205

Ser Lys Ala Lys Gly Gln Pro Arg Glu Pro Gln Val Tyr Thr Leu Pro
    210                 215                 220

Pro Ser Arg Asp Glu Leu Thr Lys Asn Gln Val Ser Leu Thr Cys Leu
225                 230                 235                 240

Val Lys Gly Phe Tyr Pro Ser Asp Ile Ala Val Glu Trp Glu Ser Asn
                245                 250                 255

Gly Gln Pro Glu Asn Asn Tyr Lys Thr Thr Pro Pro Val Leu Asp Ser
            260                 265                 270

Asp Gly Ser Phe Phe Leu Tyr Ser Lys Leu Thr Val Asp Lys Ser Arg
        275                 280                 285

Trp Gln Gln Gly Asn Val Phe Ser Cys Ser Val Met His Glu Ala Leu
    290                 295                 300

His Asn His Tyr Thr Gln Lys Ser Leu Ser Leu Ser Pro Gly Lys
305                 310                 315

```
<210> SEQ ID NO 5
<211> LENGTH: 69
<212> TYPE: DNA
<213> ORGANISM: Artificial Sequence
<220> FEATURE:
<223> OTHER INFORMATION: SYNTHETIC CONSTRUCT
<220> FEATURE:
<221> NAME/KEY: misc_feature
<222> LOCATION: (20)..(20)
```

```
<223> OTHER INFORMATION: V is A, C or G
<220> FEATURE:
<221> NAME/KEY: misc_feature
<222> LOCATION: (22)..(22)
<223> OTHER INFORMATION: K is G or T
<220> FEATURE:
<221> NAME/KEY: misc_feature
<222> LOCATION: (26)..(26)
<223> OTHER INFORMATION: N is A, C, G or T
<220> FEATURE:
<221> NAME/KEY: misc_feature
<222> LOCATION: (33)..(33)
<223> OTHER INFORMATION: N is A, C, G or T
<220> FEATURE:
<221> NAME/KEY: misc_feature
<222> LOCATION: (42)..(42)
<223> OTHER INFORMATION: N is A, C, G or T
<220> FEATURE:
<221> NAME/KEY: misc_feature
<222> LOCATION: (44)..(44)
<223> OTHER INFORMATION: V is A, C or G
<220> FEATURE:
<221> NAME/KEY: misc_feature
<222> LOCATION: (46)..(46)
<223> OTHER INFORMATION: M is A or C
<220> FEATURE:
<221> NAME/KEY: misc_feature
<222> LOCATION: (48)..(48)
<223> OTHER INFORMATION: N is A, C, G or T

<400> SEQUENCE: 5
gagtaacgtt cctttgaagv akgtcntttg gangaaacaa angvamangg tggcagaatt      60
agagaatag                                                              69

<210> SEQ ID NO 6
<211> LENGTH: 76
<212> TYPE: DNA
<213> ORGANISM: Artificial Sequence
<220> FEATURE:
<223> OTHER INFORMATION: SYNTHETIC CONSTRUCT
<220> FEATURE:
<221> NAME/KEY: misc_feature
<222> LOCATION: (26)..(26)
<223> OTHER INFORMATION: V is A, C or G
<220> FEATURE:
<221> NAME/KEY: misc_feature
<222> LOCATION: (28)..(28)
<223> OTHER INFORMATION: K is G or T
<220> FEATURE:
<221> NAME/KEY: misc_feature
<222> LOCATION: (34)..(34)
<223> OTHER INFORMATION: M is A or C
<220> FEATURE:
<221> NAME/KEY: misc_feature
<222> LOCATION: (41)..(41)
<223> OTHER INFORMATION: V is A, C or G
<220> FEATURE:
<221> NAME/KEY: misc_feature
<222> LOCATION: (43)..(43)
<223> OTHER INFORMATION: K is G or T
<220> FEATURE:
<221> NAME/KEY: misc_feature
<222> LOCATION: (48)..(48)
<223> OTHER INFORMATION: N is A, C, G, or T
<220> FEATURE:
<221> NAME/KEY: misc_feature
<222> LOCATION: (53)..(53)
<223> OTHER INFORMATION: N is A, C, G, or T
<220> FEATURE:
<221> NAME/KEY: misc_feature
<222> LOCATION: (54)..(54)
<223> OTHER INFORMATION: W is A or T
<220> FEATURE:
<221> NAME/KEY: misc_feature
<222> LOCATION: (56)..(56)
<223> OTHER INFORMATION: R is A or G
```

```
<220> FEATURE:
<221> NAME/KEY: misc_feature
<222> LOCATION: (57)..(57)
<223> OTHER INFORMATION: S is G or C

<400> SEQUENCE: 6
gaaaaaacaa aaagataaag tggcavaktt avamaatagt vaktttangg ctnwtrsttc      60
atttaagaat agggtc                                                     76

<210> SEQ ID NO 7
<211> LENGTH: 52
<212> TYPE: DNA
<213> ORGANISM: Artificial Sequence
<220> FEATURE:
<223> OTHER INFORMATION: SYNTHETIC CONSTRUCT
<220> FEATURE:
<221> NAME/KEY: misc_feature
<222> LOCATION: (18)..(18)
<223> OTHER INFORMATION: N is A, C, G or T
<220> FEATURE:
<221> NAME/KEY: misc_feature
<222> LOCATION: (23)..(23)
<223> OTHER INFORMATION: N is A, C, G or T
<220> FEATURE:
<221> NAME/KEY: misc_feature
<222> LOCATION: (29)..(29)
<223> OTHER INFORMATION: V is A, C or G
<220> FEATURE:
<221> NAME/KEY: misc_feature
<222> LOCATION: (31)..(31)
<223> OTHER INFORMATION: M is A or C

<400> SEQUENCE: 7
gtacgaaatg gagtcccnta atnttacava macaatgaag ttttttttgt ac             52

<210> SEQ ID NO 8
<211> LENGTH: 81
<212> TYPE: DNA
<213> ORGANISM: Artificial Sequence
<220> FEATURE:
<223> OTHER INFORMATION: SYNTHETIC CONSTRUCT
<220> FEATURE:
<221> NAME/KEY: misc_feature
<222> LOCATION: (19)..(19)
<223> OTHER INFORMATION: N is A, C, G or T
<220> FEATURE:
<221> NAME/KEY: misc_feature
<222> LOCATION: (25)..(25)
<223> OTHER INFORMATION: N is A, C, G or T
<220> FEATURE:
<221> NAME/KEY: misc_feature
<222> LOCATION: (43)..(43)
<223> OTHER INFORMATION: N is A, C, G or T
<220> FEATURE:
<221> NAME/KEY: misc_feature
<222> LOCATION: (52)..(52)
<223> OTHER INFORMATION: N is A, C, G or T
<220> FEATURE:
<221> NAME/KEY: misc_feature
<222> LOCATION: (59)..(59)
<223> OTHER INFORMATION: K is G or T
<220> FEATURE:
<221> NAME/KEY: misc_feature
<222> LOCATION: (60)..(60)
<223> OTHER INFORMATION: S is G or C

<400> SEQUENCE: 8
gtttacggta atgtgactnt tcacnttccg agtaacgttc ctnttaagga antttttatks    60 aaaaaacaaa aagataaagt g                                               81

<210> SEQ ID NO 9
```

-continued

```
<211> LENGTH: 78
<212> TYPE: DNA
<213> ORGANISM: Artificial Sequence
<220> FEATURE:
<223> OTHER INFORMATION: SYNTHETIC CONSTRUCT
<220> FEATURE:
<221> NAME/KEY: misc_feature
<222> LOCATION: (26)..(26)
<223> OTHER INFORMATION: N is A, C, G, or T
<220> FEATURE:
<221> NAME/KEY: misc_feature
<222> LOCATION: (29)..(29)
<223> OTHER INFORMATION: K is G or T
<220> FEATURE:
<221> NAME/KEY: misc_feature
<222> LOCATION: (30)..(30)
<223> OTHER INFORMATION: Y is C or T
<220> FEATURE:
<221> NAME/KEY: misc_feature
<222> LOCATION: (35)..(35)
<223> OTHER INFORMATION: N is A, C, G, or T
<220> FEATURE:
<221> NAME/KEY: misc_feature
<222> LOCATION: (50)..(50)
<223> OTHER INFORMATION: N is A, C, G, or T
<220> FEATURE:
<221> NAME/KEY: misc_feature
<222> LOCATION: (56)..(56)
<223> OTHER INFORMATION: K is G or T
<220> FEATURE:
<221> NAME/KEY: misc_feature
<222> LOCATION: (57)..(57)
<223> OTHER INFORMATION: Y is C or T

<400> SEQUENCE: 9
cttatggaaa aaacaaaaag ataaanttky agaanttgag aatagtgagn ttaggkyatt    60
tagttcattt aagaatag                                                 78

<210> SEQ ID NO 10
<211> LENGTH: 67
<212> TYPE: DNA
<213> ORGANISM: Artificial Sequence
<220> FEATURE:
<223> OTHER INFORMATION: SYNTHETIC CONSTRUCT
<220> FEATURE:
<221> NAME/KEY: misc_feature
<222> LOCATION: (21)..(21)
<223> OTHER INFORMATION: N is A, C, G or T
<220> FEATURE:
<221> NAME/KEY: misc_feature
<222> LOCATION: (36)..(36)
<223> OTHER INFORMATION: R is A or G
<220> FEATURE:
<221> NAME/KEY: misc_feature
<222> LOCATION: (37)..(37)
<223> OTHER INFORMATION: S is G or C
<220> FEATURE:
<221> NAME/KEY: misc_feature
<222> LOCATION: (42)..(42)
<223> OTHER INFORMATION: N is A, C, G or T

<400> SEQUENCE: 10
catttaagaa tagggtctat nttgatactg tatccrsttc tnttaccatt tataatttaa    60
caagtag                                                             67

<210> SEQ ID NO 11
<211> LENGTH: 71
<212> TYPE: DNA
<213> ORGANISM: Artificial Sequence
<220> FEATURE:
<223> OTHER INFORMATION: SYNTHETIC CONSTRUCT
<220> FEATURE:
<221> NAME/KEY: misc_feature
```

<222> LOCATION: (19)..(19)
<223> OTHER INFORMATION: W is A or T
<220> FEATURE:
<221> NAME/KEY: misc_feature
<222> LOCATION: (21)..(21)
<223> OTHER INFORMATION: S is G or C
<220> FEATURE:
<221> NAME/KEY: misc_feature
<222> LOCATION: (46)..(46)
<223> OTHER INFORMATION: W is A or T
<220> FEATURE:
<221> NAME/KEY: misc_feature
<222> LOCATION: (48)..(48)
<223> OTHER INFORMATION: S is G or C
<220> FEATURE:
<221> NAME/KEY: misc_feature
<222> LOCATION: (52)..(52)
<223> OTHER INFORMATION: N is A, C, G or T

<400> SEQUENCE: 11
gatgaagacg agtacgaawt sgagtcccct aatattacag acacawtsaa gnttttttg    60 tacgttttgg g                                                        71

<210> SEQ ID NO 12
<211> LENGTH: 66
<212> TYPE: DNA
<213> ORGANISM: Artificial Sequence
<220> FEATURE:
<223> OTHER INFORMATION: SYNTHETIC CONSTRUCT
<220> FEATURE:
<221> NAME/KEY: misc_feature
<222> LOCATION: (22)..(23)
<223> OTHER INFORMATION: N is A, C, G, or T
<220> FEATURE:
<221> NAME/KEY: misc_feature
<222> LOCATION: (24)..(24)
<223> OTHER INFORMATION: K is G or T
<220> FEATURE:
<221> NAME/KEY: misc_feature
<222> LOCATION: (25)..(26)
<223> OTHER INFORMATION: N is A, C, G, or T
<220> FEATURE:
<221> NAME/KEY: misc_feature
<222> LOCATION: (27)..(27)
<223> OTHER INFORMATION: K is G or T
<220> FEATURE:
<221> NAME/KEY: misc_feature
<222> LOCATION: (28)..(29)
<223> OTHER INFORMATION: N is A, C, G, or T
<220> FEATURE:
<221> NAME/KEY: misc_feature
<222> LOCATION: (30)..(30)
<223> OTHER INFORMATION: K is G or T
<220> FEATURE:
<221> NAME/KEY: misc_feature
<222> LOCATION: (31)..(32)
<223> OTHER INFORMATION: N is A, C, G, or T
<220> FEATURE:
<221> NAME/KEY: misc_feature
<222> LOCATION: (33)..(33)
<223> OTHER INFORMATION: K is G or T
<220> FEATURE:
<221> NAME/KEY: misc_feature
<222> LOCATION: (34)..(35)
<223> OTHER INFORMATION: N is A, C, G, or T
<220> FEATURE:
<221> NAME/KEY: misc_feature
<222> LOCATION: (36)..(36)
<223> OTHER INFORMATION: K is G or T
<220> FEATURE:
<221> NAME/KEY: misc_feature
<222> LOCATION: (37)..(38)
<223> OTHER INFORMATION: N is A, C, G, or T
<220> FEATURE:
<221> NAME/KEY: misc_feature
<222> LOCATION: (39)..(39)

```
<223> OTHER INFORMATION: K is G or T
<220> FEATURE:
<221> NAME/KEY: misc_feature
<222> LOCATION: (40)..(41)
<223> OTHER INFORMATION: N is A, C, G, or T
<220> FEATURE:
<221> NAME/KEY: misc_feature
<222> LOCATION: (42)..(42)
<223> OTHER INFORMATION: K is G or T

<400> SEQUENCE: 12
gaagacgagt acgaaatgga gnnknnknnk nnknnknnkn nkatgaagtt tttttgtac     60 gttttg                                                              66

<210> SEQ ID NO 13
<211> LENGTH: 65
<212> TYPE: DNA
<213> ORGANISM: Artificial Sequence
<220> FEATURE:
<223> OTHER INFORMATION: SYNTHETIC CONSTRUCT
<220> FEATURE:
<221> NAME/KEY: misc_feature
<222> LOCATION: (22)..(23)
<223> OTHER INFORMATION: N is A, C, G, or T
<220> FEATURE:
<221> NAME/KEY: misc_feature
<222> LOCATION: (24)..(24)
<223> OTHER INFORMATION: K is G or T
<220> FEATURE:
<221> NAME/KEY: misc_feature
<222> LOCATION: (25)..(26)
<223> OTHER INFORMATION: N is A, C, G, or T
<220> FEATURE:
<221> NAME/KEY: misc_feature
<222> LOCATION: (27)..(27)
<223> OTHER INFORMATION: K is G or T
<220> FEATURE:
<221> NAME/KEY: misc_feature
<222> LOCATION: (28)..(29)
<223> OTHER INFORMATION: N is A, C, G, or T
<220> FEATURE:
<221> NAME/KEY: misc_feature
<222> LOCATION: (30)..(30)
<223> OTHER INFORMATION: K is G or T
<220> FEATURE:
<221> NAME/KEY: misc_feature
<222> LOCATION: (31)..(32)
<223> OTHER INFORMATION: N is A, C, G, or T
<220> FEATURE:
<221> NAME/KEY: misc_feature
<222> LOCATION: (33)..(33)
<223> OTHER INFORMATION: K is G or T
<220> FEATURE:
<221> NAME/KEY: misc_feature
<222> LOCATION: (34)..(35)
<223> OTHER INFORMATION: N is A, C, G, or T
<220> FEATURE:
<221> NAME/KEY: misc_feature
<222> LOCATION: (36)..(36)
<223> OTHER INFORMATION: K is G or T
<220> FEATURE:
<221> NAME/KEY: misc_feature
<222> LOCATION: (37)..(38)
<223> OTHER INFORMATION: N is A, C, G, or T
<220> FEATURE:
<221> NAME/KEY: misc_feature
<222> LOCATION: (39)..(39)
<223> OTHER INFORMATION: K is G or T
<220> FEATURE:
<221> NAME/KEY: misc_feature
<222> LOCATION: (40)..(41)
<223> OTHER INFORMATION: N is A, C, G, or T
<220> FEATURE:
<221> NAME/KEY: misc_feature
<222> LOCATION: (42)..(42)
<223> OTHER INFORMATION: K is G or T
```

-continued

<400> SEQUENCE: 13
gaagacgagt acgaaatgga gnnknnknnk nnknnknnkn nkttcaagtt tttttgtac    60 gttgg    65

<210> SEQ ID NO 14
<211> LENGTH: 64
<212> TYPE: DNA
<213> ORGANISM: Artificial Sequence
<220> FEATURE:
<223> OTHER INFORMATION: SYNTHETIC CONSTRUCT
<220> FEATURE:
<221> NAME/KEY: misc_feature
<222> LOCATION: (22)..(23)
<223> OTHER INFORMATION: N is A, C, G or T
<220> FEATURE:
<221> NAME/KEY: misc_feature
<222> LOCATION: (24)..(24)
<223> OTHER INFORMATION: K is G or T
<220> FEATURE:
<221> NAME/KEY: misc_feature
<222> LOCATION: (25)..(26)
<223> OTHER INFORMATION: N is A, C, G or T
<220> FEATURE:
<221> NAME/KEY: misc_feature
<222> LOCATION: (27)..(27)
<223> OTHER INFORMATION: K is G or T
<220> FEATURE:
<221> NAME/KEY: misc_feature
<222> LOCATION: (28)..(29)
<223> OTHER INFORMATION: N is A, C, G or T
<220> FEATURE:
<221> NAME/KEY: misc_feature
<222> LOCATION: (30)..(30)
<223> OTHER INFORMATION: K is G or T
<220> FEATURE:
<221> NAME/KEY: misc_feature
<222> LOCATION: (31)..(32)
<223> OTHER INFORMATION: N is A, C, G or T
<220> FEATURE:
<221> NAME/KEY: misc_feature
<222> LOCATION: (33)..(33)
<223> OTHER INFORMATION: K is G or T
<220> FEATURE:
<221> NAME/KEY: misc_feature
<222> LOCATION: (34)..(35)
<223> OTHER INFORMATION: N is A, C, G or T
<220> FEATURE:
<221> NAME/KEY: misc_feature
<222> LOCATION: (36)..(36)
<223> OTHER INFORMATION: K is G or T
<220> FEATURE:
<221> NAME/KEY: misc_feature
<222> LOCATION: (37)..(38)
<223> OTHER INFORMATION: N is A, C, G or T
<220> FEATURE:
<221> NAME/KEY: misc_feature
<222> LOCATION: (39)..(39)
<223> OTHER INFORMATION: K is G or T
<220> FEATURE:
<221> NAME/KEY: misc_feature
<222> LOCATION: (40)..(41)
<223> OTHER INFORMATION: N is A, C, G or T
<220> FEATURE:
<221> NAME/KEY: misc_feature
<222> LOCATION: (42)..(42)
<223> OTHER INFORMATION: K is G or T

<400> SEQUENCE: 14
gaagacgagt acgaattcga gnnknnknnk nnknnknnkn nkttcaagtt tttttgtac    60 gttg    64

<210> SEQ ID NO 15

<211> LENGTH: 19
<212> TYPE: PRT
<213> ORGANISM: Artificial Sequence
<220> FEATURE:
<223> OTHER INFORMATION: SYNTHETIC CONSTRUCT

<400> SEQUENCE: 15

Met Gly Trp Ser Cys Ile Ile Leu Phe Leu Val Ala Thr Ala Thr Gly
1               5                   10                  15

Val His Ser

<210> SEQ ID NO 16
<211> LENGTH: 226
<212> TYPE: PRT
<213> ORGANISM: Artificial Sequence
<220> FEATURE:
<223> OTHER INFORMATION: SYNTHETIC CONSTRUCT

<400> SEQUENCE: 16

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 17
<211> LENGTH: 92
<212> TYPE: PRT
<213> ORGANISM: Artificial Sequence
<220> FEATURE:
<223> OTHER INFORMATION: SYNTHETIC CONSTRUCT

<400> SEQUENCE: 17

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Pro
65                  70                  75                  80

Asn Ile Thr Asp Thr Phe Lys Phe Phe Leu Tyr Val
                85                  90

<210> SEQ ID NO 18
<211> LENGTH: 92
<212> TYPE: PRT
<213> ORGANISM: Artificial Sequence
<220> FEATURE:
<223> OTHER INFORMATION: SYNTHETIC CONSTRUCT

<400> SEQUENCE: 18

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Phe Glu Ser Pro
65                  70                  75                  80

Asn Ile Thr Asp Thr Phe Lys Phe Phe Leu Tyr Val
                85                  90

<210> SEQ ID NO 19
<211> LENGTH: 92
<212> TYPE: PRT
<213> ORGANISM: Artificial Sequence
<220> FEATURE:
<223> OTHER INFORMATION: SYNTHETIC CONSTRUCT

<400> SEQUENCE: 19

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Val Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Pro
65                  70                  75                  80

Asn Ile Thr Asp Thr Phe Lys Phe Phe Leu Tyr Val
                85                  90

<210> SEQ ID NO 20

<211> LENGTH: 92
<212> TYPE: PRT
<213> ORGANISM: Artificial Sequence
<220> FEATURE:
<223> OTHER INFORMATION: SYNTHETIC CONSTRUCT

<400> SEQUENCE: 20

Phe Ser Gln Gln Ile Tyr Gly Val Val Tyr Gly Asn Val Thr Phe His
1               5                   10                  15
Val Pro Ser Asn Val Pro Leu Lys Glu Val Leu Trp Lys Lys Gln Lys
            20                  25                  30
Asp Lys Val Val Glu Phe Glu Asn Ser Glu Val Arg Val Phe Ser Ser
        35                  40                  45
Phe Lys Asn Arg Val Tyr Leu Asp Thr Val Ser Gly Ser Leu Thr Ile
    50                  55                  60
Tyr Asn Leu Thr Ser Ser Asp Glu Asp Glu Tyr Glu Phe Glu Ser Pro
65                  70                  75                  80
Asn Ile Thr Asp Thr Phe Lys Phe Phe Leu Tyr Val
                85                  90

<210> SEQ ID NO 21
<211> LENGTH: 92
<212> TYPE: PRT
<213> ORGANISM: Artificial Sequence
<220> FEATURE:
<223> OTHER INFORMATION: SYNTHETIC CONSTRUCT

<400> SEQUENCE: 21

Phe Ser Gln Gln Ile Tyr Gly Val Val Tyr Gly Asn Val Thr Phe His
1               5                   10                  15
Val Pro Ser Asn Val Pro Leu Lys Glu Val Leu Trp Lys Lys Gln Lys
            20                  25                  30
Asp Lys Val Val Glu Phe Glu Asn Ser Glu Ile Arg Val Phe Ser Ser
        35                  40                  45
Phe Lys Asn Arg Val Tyr Leu Asp Thr Val Ser Gly Ser Leu Thr Ile
    50                  55                  60
Tyr Asn Leu Thr Ser Ser Asp Glu Asp Glu Tyr Glu Phe Glu Ser Pro
65                  70                  75                  80
Asn Ile Thr Asp Thr Phe Lys Phe Phe Leu Tyr Val
                85                  90

<210> SEQ ID NO 22
<211> LENGTH: 92
<212> TYPE: PRT
<213> ORGANISM: Artificial Sequence
<220> FEATURE:
<223> OTHER INFORMATION: SYNTHETIC CONSTRUCT

<400> SEQUENCE: 22

Phe Ser Gln Gln Ile Tyr Gly Val Val Tyr Gly Asn Val Thr Phe His
1               5                   10                  15
Val Pro Ser Asn Val Pro Leu Lys Glu Val Leu Trp Lys Lys Gln Lys
            20                  25                  30
Asp Lys Val Leu Glu Phe Glu Asn Ser Glu Leu Arg Val Phe Ser Ser
        35                  40                  45
Phe Lys Asn Arg Val Tyr Leu Asp Thr Val Ser Gly Ser Leu Thr Ile
    50                  55                  60
Tyr Asn Leu Thr Ser Ser Asp Glu Asp Glu Tyr Glu Phe Glu Ser Pro
65                  70                  75                  80

-continued

```
Asn Ile Thr Asp Thr Phe Lys Phe Phe Leu Tyr Val
                85                  90

<210> SEQ ID NO 23
<211> LENGTH: 92
<212> TYPE: PRT
<213> ORGANISM: Artificial Sequence
<220> FEATURE:
<223> OTHER INFORMATION: SYNTHETIC CONSTRUCT

<400> SEQUENCE: 23

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Pro
65                  70                  75                  80

Asn Ile Thr Asp Thr Met Lys Phe Phe Leu Tyr Val
                85                  90

<210> SEQ ID NO 24
<211> LENGTH: 93
<212> TYPE: PRT
<213> ORGANISM: Artificial Sequence
<220> FEATURE:
<223> OTHER INFORMATION: SYNTHETIC CONSTRUCT

<400> SEQUENCE: 24

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Ala Glu Leu Glu Asn Ser Glu Phe Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Pro
65                  70                  75                  80

Asn Ile Thr Asp Thr Met Lys Phe Phe Leu Tyr Val Leu
                85                  90

<210> SEQ ID NO 25
<211> LENGTH: 98
<212> TYPE: PRT
<213> ORGANISM: Artificial Sequence
<220> FEATURE:
<223> OTHER INFORMATION: SYNTHETIC CONSTRUCT

<400> SEQUENCE: 25

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Ala Glu Leu Glu Asn Ser Glu Phe Arg Ala Phe Ser Ser
        35                  40                  45
```

Phe Lys Asn Arg Val Tyr Leu Asp Thr Val Ser Gly Ser Leu Thr Ile
 50                  55                  60

Tyr Asn Leu Thr Ser Ser Asp Glu Asp Glu Tyr Glu Met Glu Ser Pro
 65                  70                  75                  80

Asn Ile Thr Asp Thr Met Lys Phe Phe Leu Tyr Val Leu Glu Ser Leu
                 85                  90                  95

Pro Ser

<210> SEQ ID NO 26
<211> LENGTH: 93
<212> TYPE: PRT
<213> ORGANISM: Artificial Sequence
<220> FEATURE:
<223> OTHER INFORMATION: SYNTHETIC CONSTRUCT

<400> SEQUENCE: 26

Phe Ser Gln Gln Ile Tyr Gly Val Val Tyr Gly Asn Val Thr Phe His
 1               5                  10                  15

Val Pro Ser Asn Val Pro Leu Lys Glu Val Leu Trp Lys Lys Gln Lys
                 20                  25                  30

Asp Lys Val Val Glu Phe Glu Asn Ser Glu Val Arg Ala Phe Ser Ser
             35                  40                  45

Phe Lys Asn Arg Val Tyr Leu Asp Thr Val Ser Gly Ser Leu Thr Ile
 50                  55                  60

Tyr Asn Leu Thr Ser Ser Asp Glu Asp Glu Tyr Glu Met Glu Ser Pro
 65                  70                  75                  80

Asn Ile Thr Asp Thr Phe Lys Phe Phe Leu Tyr Val Leu
                 85                  90

<210> SEQ ID NO 27
<211> LENGTH: 98
<212> TYPE: PRT
<213> ORGANISM: Artificial Sequence
<220> FEATURE:
<223> OTHER INFORMATION: SYNTHETIC CONSTRUCT

<400> SEQUENCE: 27

Phe Ser Gln Gln Ile Tyr Gly Val Val Tyr Gly Asn Val Thr Phe His
 1               5                  10                  15

Val Pro Ser Asn Val Pro Leu Lys Glu Val Leu Trp Lys Lys Gln Lys
                 20                  25                  30

Asp Lys Val Val Glu Phe Glu Asn Ser Glu Val Arg Ala Phe Ser Ser
             35                  40                  45

Phe Lys Asn Arg Val Tyr Leu Asp Thr Val Ser Gly Ser Leu Thr Ile
 50                  55                  60

Tyr Asn Leu Thr Ser Ser Asp Glu Asp Glu Tyr Glu Met Glu Ser Pro
 65                  70                  75                  80

Asn Ile Thr Asp Thr Phe Lys Phe Phe Leu Tyr Val Leu Glu Ser Leu
                 85                  90                  95

Pro Ser

<210> SEQ ID NO 28
<211> LENGTH: 93
<212> TYPE: PRT
<213> ORGANISM: Artificial Sequence
<220> FEATURE:
<223> OTHER INFORMATION: SYNTHETIC CONSTRUCT

<400> SEQUENCE: 28

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Val Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Phe Glu Ser Pro
65                  70                  75                  80

Asn Ile Thr Asp Thr Phe Lys Phe Phe Leu Tyr Val Leu
                85                  90

<210> SEQ ID NO 29
<211> LENGTH: 93
<212> TYPE: PRT
<213> ORGANISM: Artificial Sequence
<220> FEATURE:
<223> OTHER INFORMATION: SYNTHETIC CONSTRUCT

<400> SEQUENCE: 29

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Pro
65                  70                  75                  80

Asn Ile Thr Asp Thr Met Lys Phe Phe Leu Tyr Val Leu
                85                  90

<210> SEQ ID NO 30
<211> LENGTH: 93
<212> TYPE: PRT
<213> ORGANISM: Artificial Sequence
<220> FEATURE:
<223> OTHER INFORMATION: SYNTHETIC CONSTRUCT

<400> SEQUENCE: 30

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Arg
65                  70                  75                  80

Asn Gly Gly Pro Asp Phe Lys Phe Phe Leu Tyr Val Leu
                85                  90

<210> SEQ ID NO 31

```
<211> LENGTH: 93
<212> TYPE: PRT
<213> ORGANISM: Artificial Sequence
<220> FEATURE:
<223> OTHER INFORMATION: SYNTHETIC CONSTRUCT

<400> SEQUENCE: 31

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Arg
65                  70                  75                  80

Asn Pro Tyr Arg Arg Phe Lys Phe Phe Leu Tyr Val Leu
                85                  90

<210> SEQ ID NO 32
<211> LENGTH: 93
<212> TYPE: PRT
<213> ORGANISM: Artificial Sequence
<220> FEATURE:
<223> OTHER INFORMATION: SYNTHETIC CONSTRUCT

<400> SEQUENCE: 32

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Arg
65                  70                  75                  80

Asn Pro Tyr Arg Asp Phe Lys Phe Phe Leu Tyr Val Leu
                85                  90

<210> SEQ ID NO 33
<211> LENGTH: 93
<212> TYPE: PRT
<213> ORGANISM: Artificial Sequence
<220> FEATURE:
<223> OTHER INFORMATION: SYNTHETIC CONSTRUCT

<400> SEQUENCE: 33

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Trp
65                  70                  75                  80
```

-continued

Asn Gly Gly Pro Asp Phe Lys Phe Phe Leu Tyr Val Leu
                85                  90

<210> SEQ ID NO 34
<211> LENGTH: 93
<212> TYPE: PRT
<213> ORGANISM: Artificial Sequence
<220> FEATURE:
<223> OTHER INFORMATION: SYNTHETIC CONSTRUCT

<400> SEQUENCE: 34

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Trp
65                  70                  75                  80

Asn Pro Tyr Arg Arg Phe Lys Phe Phe Leu Tyr Val Leu
                85                  90

<210> SEQ ID NO 35
<211> LENGTH: 93
<212> TYPE: PRT
<213> ORGANISM: Artificial Sequence
<220> FEATURE:
<223> OTHER INFORMATION: SYNTHETIC CONSTRUCT

<400> SEQUENCE: 35

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Trp
65                  70                  75                  80

Asn Pro Tyr Arg Asp Phe Lys Phe Phe Leu Tyr Val Leu
                85                  90

<210> SEQ ID NO 36
<211> LENGTH: 93
<212> TYPE: PRT
<213> ORGANISM: Artificial Sequence
<220> FEATURE:
<223> OTHER INFORMATION: SYNTHETIC CONSTRUCT

<400> SEQUENCE: 36

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Ala Phe Ser Ser
        35                  40                  45

Phe Lys Asn Arg Val Tyr Leu Asp Thr Val Ser Gly Ser Leu Thr Ile
            50                  55                  60

Tyr Asn Leu Thr Ser Ser Asp Glu Asp Glu Tyr Glu Met Glu Gly Arg
 65                  70                  75                  80

Tyr Pro Tyr Glu Ser Phe Lys Phe Phe Leu Tyr Val Leu
                85                  90

<210> SEQ ID NO 37
<211> LENGTH: 93
<212> TYPE: PRT
<213> ORGANISM: Artificial Sequence
<220> FEATURE:
<223> OTHER INFORMATION: SYNTHETIC CONSTRUCT

<400> SEQUENCE: 37

Phe Ser Gln Gln Ile Tyr Gly Val Val Tyr Gly Asn Val Thr Phe His
 1               5                   10                  15

Val Pro Ser Asn Val Pro Leu Lys Glu Val Leu Trp Lys Lys Gln Lys
                20                  25                  30

Asp Lys Val Val Glu Phe Glu Asn Ser Glu Val Arg Val Phe Ser Ser
            35                  40                  45

Phe Lys Asn Arg Val Tyr Leu Asp Thr Val Ser Gly Ser Leu Thr Ile
            50                  55                  60

Tyr Asn Leu Thr Ser Ser Asp Glu Asp Glu Tyr Glu Phe Glu Ser Trp
 65                  70                  75                  80

Glu Pro Gly Arg Glu Phe Lys Phe Phe Leu Tyr Val Leu
                85                  90

<210> SEQ ID NO 38
<211> LENGTH: 93
<212> TYPE: PRT
<213> ORGANISM: Artificial Sequence
<220> FEATURE:
<223> OTHER INFORMATION: SYNTHETIC CONSTRUCT

<400> SEQUENCE: 38

Phe Ser Gln Gln Ile Tyr Gly Val Val Tyr Gly Asn Val Thr Phe His
 1               5                   10                  15

Val Pro Ser Asn Val Pro Leu Lys Glu Val Leu Trp Lys Lys Gln Lys
                20                  25                  30

Asp Lys Val Val Glu Phe Glu Asn Ser Glu Val Arg Ala Phe Ser Ser
            35                  40                  45

Phe Lys Asn Arg Val Tyr Leu Asp Thr Val Ser Gly Ser Leu Thr Ile
            50                  55                  60

Tyr Asn Leu Thr Ser Ser Asp Glu Asp Glu Tyr Glu Met Glu Ala Arg
 65                  70                  75                  80

Tyr Pro Tyr Arg Gln Phe Lys Phe Phe Leu Tyr Val Leu
                85                  90

<210> SEQ ID NO 39
<211> LENGTH: 93
<212> TYPE: PRT
<213> ORGANISM: Artificial Sequence
<220> FEATURE:
<223> OTHER INFORMATION: SYNTHETIC CONSTRUCT

<400> SEQUENCE: 39

Phe Ser Gln Gln Ile Tyr Gly Val Val Tyr Gly Asn Val Thr Phe His
 1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Ala Phe Ser Ser
            35                  40                  45

Phe Lys Asn Arg Val Tyr Leu Asp Thr Val Ser Gly Ser Leu Thr Ile
        50                  55                  60

Tyr Asn Leu Thr Ser Ser Asp Glu Asp Glu Tyr Glu Met Glu Met Arg
65                  70                  75                  80

Asn Gly Gly Pro Asp Phe Lys Phe Phe Leu Tyr Val Leu
                85                  90

<210> SEQ ID NO 40
<211> LENGTH: 93
<212> TYPE: PRT
<213> ORGANISM: Artificial Sequence
<220> FEATURE:
<223> OTHER INFORMATION: SYNTHETIC CONSTRUCT

<400> SEQUENCE: 40

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ala Arg
65                  70                  75                  80

Asp Gly Gly Pro Asp Phe Lys Phe Phe Leu Tyr Val Leu
                85                  90

<210> SEQ ID NO 41
<211> LENGTH: 93
<212> TYPE: PRT
<213> ORGANISM: Artificial Sequence
<220> FEATURE:
<223> OTHER INFORMATION: SYNTHETIC CONSTRUCT

<400> SEQUENCE: 41

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Trp
65                  70                  75                  80

Ser Pro Tyr Lys Ala Phe Lys Phe Phe Leu Tyr Val Leu
                85                  90

<210> SEQ ID NO 42
<211> LENGTH: 57
<212> TYPE: DNA
<213> ORGANISM: Artificial Sequence
<220> FEATURE:
<223> OTHER INFORMATION: SYNTHETIC CONSTRUCT

<400> SEQUENCE: 42

```
atgggctggt cctgtatcat cctctttctg gtggccacag ctaccggagt gcatagc       57
```

<210> SEQ ID NO 43
<211> LENGTH: 678
<212> TYPE: DNA
<213> ORGANISM: Artificial Sequence
<220> FEATURE:
<223> OTHER INFORMATION: SYNTHETIC CONSTRUCT

<400> SEQUENCE: 43

```
gacaaaactc acacatgccc accgtgccca gcacctgaac tcctgggggg accgtcagtc     60
ttcctcttcc cccaaaacc caaggacacc ctcatgatct cccggacccc tgaggtcaca    120
tgcgtggtgg tggacgtgag ccacgaagac cctgaggtca agttcaactg gtacgtggac    180
ggcgtggagg tgcataatgc caagacaaag ccgcgggagg agcagtacaa cagcacgtac    240
cgtgtggtca gcgtcctcac cgtcctgcac caggactggc tgaatggcaa ggagtacaag    300
tgcaaggtct ccaacaaagc cctcccagcc cccatcgaga aaaccatctc caaagccaaa    360
gggcagcccc gagaaccaca ggtgtacacc ctgcccccat cccgggaaga tgaccaag      420
aaccaggtca gcctgacctg cctggtcaaa ggcttctatc ccagcgacat cgccgtggag    480
tgggagagca atgggcagcc ggagaacaac tacaagacca cgcctcccgt gttggactcc    540
gacggctcct tcttcctcta cagcaagctc accgtggaca gagcaggtg gcagcagggg     600
aacgtcttct catgctccgt gatgcatgag gctctgcaca accactacac gcagaagagc    660
ctctccctgt ctccgggt                                                 678
```

<210> SEQ ID NO 44
<211> LENGTH: 276
<212> TYPE: DNA
<213> ORGANISM: Artificial Sequence
<220> FEATURE:
<223> OTHER INFORMATION: SYNTHETIC CONSTRUCT

<400> SEQUENCE: 44

```
ttttcacagc agatttacgg tgttgtttac ggtaatgtga cttttcacgt tccgagtaac     60
gttcctttga aggaagtctt atggaaaaaa caaaaagata agttgtaga atttgagaat    120
agtgaggtta gggcatttag ttcatttaag aatagggtct atttggatac tgtatccggt    180
tctttgacca tttataattt aacaagtagt gatgaagacg agtacgaaat ggagtcccct    240
aatattacag acacattcaa gttttttttg tacgtt                              276
```

<210> SEQ ID NO 45
<211> LENGTH: 276
<212> TYPE: DNA
<213> ORGANISM: Artificial Sequence
<220> FEATURE:
<223> OTHER INFORMATION: SYNTHETIC CONSTRUCT

<400> SEQUENCE: 45

```
ttttcacagc agatttacgg tgttgtttac ggtaatgtga cttttcacgt tccgagtaac     60
gttcctttga aggaagtctt atggaaaaaa caaaaagata agttgtaga atttgagaat    120
agtgaggtta gggcatttag ttcatttaag aatagggtct atttggatac tgtatccggt    180
tctttgacca tttataattt aacaagtagt gatgaagacg agtacgaatt cgagtcccct    240
aatattacag acacattcaa gttttttttg tacgtt                              276
```

```
<210> SEQ ID NO 46
<211> LENGTH: 276
<212> TYPE: DNA
<213> ORGANISM: Artificial Sequence
<220> FEATURE:
<223> OTHER INFORMATION: SYNTHETIC CONSTRUCT

<400> SEQUENCE: 46
ttttcacagc agatttacgg tgttgtttac ggtaatgtga cttttcacgt tccgagtaac      60
gttcctttga aggaagtctt atggaaaaaa caaaaagata aagttgtaga atttgagaat     120
agtgaggtta gggtatttag ttcatttaag aatagggtct atttggatac tgtatccggt     180
tctttgacca tttataattt aacaagtagt gatgaagacg agtacgaaat ggagtcccct     240
aatattacag acacattcaa gttttttttg tacgtt                               276

<210> SEQ ID NO 47
<211> LENGTH: 276
<212> TYPE: DNA
<213> ORGANISM: Artificial Sequence
<220> FEATURE:
<223> OTHER INFORMATION: SYNTHETIC CONSTRUCT

<400> SEQUENCE: 47
ttttcacagc agatttacgg tgttgtttac ggtaatgtga cttttcacgt tccgagtaac      60
gttcctttga aggaagtctt atggaaaaaa caaaaagata aagttgtaga atttgagaat     120
agtgaggtta gggtatttag ttcatttaag aatagggtct atttggatac tgtatccggt     180
tctttgacca tttataattt aacaagtagt gatgaagacg agtacgaatt cgagtcccct     240
aatattacag acacattcaa gttttttttg tacgtt                               276

<210> SEQ ID NO 48
<211> LENGTH: 276
<212> TYPE: DNA
<213> ORGANISM: Artificial Sequence
<220> FEATURE:
<223> OTHER INFORMATION: SYNTHETIC CONSTRUCT

<400> SEQUENCE: 48
ttttcacagc agatttacgg tgttgtttac ggtaatgtga cttttcacgt tccgagtaac      60
gttcctttga aggaagtctt atggaaaaaa caaaaagata aagttgtaga atttgagaat     120
agtgagatta gggtatttag ttcatttaag aatagggtct atttggatac tgtatccggt     180
tctttgacca tttataattt aacaagtagt gatgaagacg agtacgaatt cgagtcccct     240
aatattacag acacattcaa gttttttttg tacgtt                               276

<210> SEQ ID NO 49
<211> LENGTH: 276
<212> TYPE: DNA
<213> ORGANISM: Artificial Sequence
<220> FEATURE:
<223> OTHER INFORMATION: SYNTHETIC CONSTRUCT

<400> SEQUENCE: 49
ttttcacagc agatttacgg tgttgtttac ggtaatgtga cttttcacgt tccgagtaac      60
gttcctttga aggaagtctt atggaaaaaa caaaaagata aagttttaga atttgagaat     120
agtgagctta gggtatttag ttcatttaag aatagggtct atttggatac tgtatccggt     180
tctttgacca tttataattt aacaagtagt gatgaagacg agtacgaatt cgagtcccct     240
aatattacag acacattcaa gttttttttg tacgtt                               276
```

```
<210> SEQ ID NO 50
<211> LENGTH: 276
<212> TYPE: DNA
<213> ORGANISM: Artificial Sequence
<220> FEATURE:
<223> OTHER INFORMATION: SYNTHETIC CONSTRUCT

<400> SEQUENCE: 50
ttttcacagc agatttacgg tgttgtttac ggtaatgtga cttttcacgt tccgagtaac    60
gttcctttga aggaagtctt atggaaaaaa caaaagata aagttgtaga atttgagaat    120
agtgaggtta gggcatttag ttcatttaag aatagggtct atttggatac tgtatccggt   180
tctttgacca tttataattt aacaagtagt gatgaagacg agtacgaaat ggagtcccct   240
aatattacag acacaatgaa gttttttttg tacgtt                             276

<210> SEQ ID NO 51
<211> LENGTH: 279
<212> TYPE: DNA
<213> ORGANISM: Artificial Sequence
<220> FEATURE:
<223> OTHER INFORMATION: SYNTHETIC CONSTRUCT

<400> SEQUENCE: 51
ttttcccaac aaatatatgg tgttgtgtat gggaatgtaa ctttccatgt accaagcaat    60
gtgcctttaa aagaggtcct atggaaaaaa caaaaggata aagttgcaga actgaaaat    120
tctgaattca gagctttctc atcttttaaa aatagggttt atttagacac tgtgtcaggt   180
agcctcacta tctacaactt aacatcatca gatgaagatg agtatgaaat ggaatcgcca   240
aatattactg ataccatgaa gttctttctt tatgtcctc                          279

<210> SEQ ID NO 52
<211> LENGTH: 294
<212> TYPE: DNA
<213> ORGANISM: Artificial Sequence
<220> FEATURE:
<223> OTHER INFORMATION: SYNTHETIC CONSTRUCT

<400> SEQUENCE: 52
ttttcccaac aaatatatgg tgttgtgtat gggaatgtaa ctttccatgt accaagcaat    60
gtgcctttaa aagaggtcct atggaaaaaa caaaaggata aagttgcaga actgaaaat    120
tctgaattca gagctttctc atcttttaaa aatagggttt atttagacac tgtgtcaggt   180
agcctcacta tctacaactt aacatcatca gatgaagatg agtatgaaat ggaatcgcca   240
aatattactg ataccatgaa gttctttctt tatgtccttg agagtctgcc cagc         294

<210> SEQ ID NO 53
<211> LENGTH: 279
<212> TYPE: DNA
<213> ORGANISM: Artificial Sequence
<220> FEATURE:
<223> OTHER INFORMATION: SYNTHETIC CONSTRUCT

<400> SEQUENCE: 53
ttttcacagc agatttacgg tgttgtttac ggtaatgtga cttttcacgt tccgagtaac    60
gttcctttga aggaagtctt atggaaaaaa caaaagata aagttgtaga atttgagaat    120
agtgaggtta gggcatttag ttcatttaag aatagggtct atttggatac tgtatccggt   180
tctttgacca tttataattt aacaagtagt gatgaagacg agtacgaaat ggagtcccct   240
aatattacag acacattcaa gttttttttg tacgttctc                          279
```

<210> SEQ ID NO 54
<211> LENGTH: 294
<212> TYPE: DNA
<213> ORGANISM: Artificial Sequence
<220> FEATURE:
<223> OTHER INFORMATION: SYNTHETIC CONSTRUCT

<400> SEQUENCE: 54

```
ttttcacagc agatttacgg tgttgtttac ggtaatgtga cttttcacgt tccgagtaac      60
gttcctttga aggaagtctt atggaaaaaa caaaaagata aagttgtaga atttgagaat     120
agtgaggtta gggcatttag ttcatttaag aatagggtct atttggatac tgtatccggt     180
tctttgacca tttataattt aacaagtagt gatgaagacg agtacgaaat ggagtcccct     240
aatattacag acacattcaa gttttttttg tacgttcttg agagtctgcc cagc           294
```

<210> SEQ ID NO 55
<211> LENGTH: 279
<212> TYPE: DNA
<213> ORGANISM: Artificial Sequence
<220> FEATURE:
<223> OTHER INFORMATION: SYNTHETIC CONSTRUCT

<400> SEQUENCE: 55

```
ttttcacagc agatttacgg tgttgtttac ggtaatgtga cttttcacgt tccgagtaac      60
gttcctttga aggaagtctt atggaaaaaa caaaaagata aagttgtaga atttgagaat     120
agtgaggtta gggtatttag ttcatttaag aatagggtct atttggatac tgtatccggt     180
tctttgacca tttataattt aacaagtagt gatgaagacg agtacgaatt cgagtcccct     240
aatattacag acacattcaa gttttttttg tacgttctc                            279
```

<210> SEQ ID NO 56
<211> LENGTH: 279
<212> TYPE: DNA
<213> ORGANISM: Artificial Sequence
<220> FEATURE:
<223> OTHER INFORMATION: SYNTHETIC CONSTRUCT

<400> SEQUENCE: 56

```
ttttcacagc agatttacgg tgttgtttac ggtaatgtga cttttcacgt tccgagtaac      60
gttcctttga aggaagtctt atggaaaaaa caaaaagata aagttgtaga atttgagaat     120
agtgaggtta gggcatttag ttcatttaag aatagggtct atttggatac tgtatccggt     180
tctttgacca tttataattt aacaagtagt gatgaagacg agtacgaaat ggagtcccct     240
aatattacag acacaatgaa gttttttttg tacgttctc                            279
```

<210> SEQ ID NO 57
<211> LENGTH: 279
<212> TYPE: DNA
<213> ORGANISM: Artificial Sequence
<220> FEATURE:
<223> OTHER INFORMATION: SYNTHETIC CONSTRUCT

<400> SEQUENCE: 57

```
ttttcacagc agatttacgg tgttgtttac ggtaatgtga cttttcacgt tccgagtaac      60
gttcctttga aggaagtctt atggaaaaaa caaaaagata aagttgtaga atttgagaat     120
agtgaggtta gggcatttag ttcatttaag aatagggtct atttggatac tgtatccggt     180
```

```
tctttgacca tttataattt aacaagtagt gatgaagacg agtacgaaat ggagtccagg    240
aatggtggac ctgatttcaa gttttttttg tacgttttg                          279
```

<210> SEQ ID NO 58
<211> LENGTH: 279
<212> TYPE: DNA
<213> ORGANISM: Artificial Sequence
<220> FEATURE:
<223> OTHER INFORMATION: SYNTHETIC CONSTRUCT

<400> SEQUENCE: 58

```
ttttcacagc agatttacgg tgttgtttac ggtaatgtga cttttcacgt tccgagtaac     60
gttcctttga aggaagtctt atggaaaaaa caaaagata aagttgtaga atttgagaat    120
agtgaggtta gggcatttag ttcatttaag aatagggtct atttggatac tgtatccggt   180
tctttgacca tttataattt aacaagtagt gatgaagacg agtacgaaat ggagtccagg   240
aatccttata gaaggttcaa gttttttttg tacgttttg                          279
```

<210> SEQ ID NO 59
<211> LENGTH: 279
<212> TYPE: DNA
<213> ORGANISM: Artificial Sequence
<220> FEATURE:
<223> OTHER INFORMATION: SYNTHETIC CONSTRUCT

<400> SEQUENCE: 59

```
ttttcacagc agatttacgg tgttgtttac ggtaatgtga cttttcacgt tccgagtaac     60
gttcctttga aggaagtctt atggaaaaaa caaaagata aagttgtaga atttgagaat    120
agtgaggtta gggcatttag ttcatttaag aatagggtct atttggatac tgtatccggt   180
tctttgacca tttataattt aacaagtagt gatgaagacg agtacgaaat ggagtccagg   240
aatccttata gagacttcaa gttttttttg tacgttttg                          279
```

<210> SEQ ID NO 60
<211> LENGTH: 279
<212> TYPE: DNA
<213> ORGANISM: Artificial Sequence
<220> FEATURE:
<223> OTHER INFORMATION: SYNTHETIC CONSTRUCT

<400> SEQUENCE: 60

```
ttttcacagc agatttacgg tgttgtttac ggtaatgtga cttttcacgt tccgagtaac     60
gttcctttga aggaagtctt atggaaaaaa caaaagata aagttgtaga atttgagaat    120
agtgaggtta gggcatttag ttcatttaag aatagggtct atttggatac tgtatccggt   180
tctttgacca tttataattt aacaagtagt gatgaagacg agtacgaaat ggagtcctgg   240
aatggtggac ctgatttcaa gttttttttg tacgttttg                          279
```

<210> SEQ ID NO 61
<211> LENGTH: 279
<212> TYPE: DNA
<213> ORGANISM: Artificial Sequence
<220> FEATURE:
<223> OTHER INFORMATION: SYNTHETIC CONSTRUCT

<400> SEQUENCE: 61

```
ttttcacagc agatttacgg tgttgtttac ggtaatgtga cttttcacgt tccgagtaac     60
gttcctttga aggaagtctt atggaaaaaa caaaagata aagttgtaga atttgagaat    120
```

```
agtgaggtta gggcatttag ttcatttaag aatagggtct atttggatac tgtatccggt    180
tctttgacca tttataattt aacaagtagt gatgaagacg agtacgaaat ggagtcctgg    240
aatccttata gaaggttcaa gttttttttg tacgttttg                           279

<210> SEQ ID NO 62
<211> LENGTH: 279
<212> TYPE: DNA
<213> ORGANISM: Artificial Sequence
<220> FEATURE:
<223> OTHER INFORMATION: SYNTHETIC CONSTRUCT

<400> SEQUENCE: 62
ttttcacagc agatttacgg tgttgtttac ggtaatgtga cttttcacgt tccgagtaac     60
gttcctttga aggaagtctt atggaaaaaa caaaaagata agttgtaga atttgagaat    120 agtgaggtta gggcatttag ttcatttaag aatagggtct atttggatac tgtatccggt    180
tctttgacca tttataattt aacaagtagt gatgaagacg agtacgaaat ggagtcctgg    240
aatccttata gagacttcaa gttttttttg tacgttttg                           279

<210> SEQ ID NO 63
<211> LENGTH: 279
<212> TYPE: DNA
<213> ORGANISM: Artificial Sequence
<220> FEATURE:
<223> OTHER INFORMATION: SYNTHETIC CONSTRUCT

<400> SEQUENCE: 63
ttttcacagc agatttacgg tgttgtttac ggtaatgtga cttttcacgt tccgagtaac     60
gttcctttga aggaagtctt atggaaaaaa caaaaagata agttgtaga atttgagaat    120 agtgaggtta gggcatttag ttcatttaag aatagggtct atttggatac tgtatccggt    180
tctttgacca tttataattt aacaagtagt gatgaagacg agtacgaaat ggagggtcgg    240
tatccgtatg agtcgttcaa gttttttttg tacgttttg                           279

<210> SEQ ID NO 64
<211> LENGTH: 279
<212> TYPE: DNA
<213> ORGANISM: Artificial Sequence
<220> FEATURE:
<223> OTHER INFORMATION: SYNTHETIC CONSTRUCT

<400> SEQUENCE: 64
ttttcacagc agatttacgg tgttgtttac ggtaatgtga cttttcacgt tccgagtaac     60
gttcctttga aggaagtctt atggaaaaaa caaaaagata agttgtaga atttgagaat    120 agtgaggtta gggtatttag ttcatttaag aatagggtct atttggatac tgtatccggt    180
tctttgacca tttataattt aacaagtagt gatgaagacg agtacgaatt cgagagttgg    240
gagcctggga gggagttcaa gttttttttg tacgttttg                           279

<210> SEQ ID NO 65
<211> LENGTH: 279
<212> TYPE: DNA
<213> ORGANISM: Artificial Sequence
<220> FEATURE:
<223> OTHER INFORMATION: SYNTHETIC CONSTRUCT

<400> SEQUENCE: 65
ttttcacagc agatttacgg tgttgtttac ggtaatgtga cttttcacgt tccgagtaac     60
gttcctttga aggaagtctt atggaaaaaa caaaaagata agttgtaga atttgagaat    120
```
agtgaggtta gggcatttag ttcatttaag aatagggtct atttggatac tgtatccggt    180
tctttgacca tttataattt aacaagtagt gatgaagacg agtacgaaat ggaggctcgg    240
tatccttatc ggcagttcaa gttttttttg tacgttttg                            279

<210> SEQ ID NO 66
<211> LENGTH: 279
<212> TYPE: DNA
<213> ORGANISM: Artificial Sequence
<220> FEATURE:
<223> OTHER INFORMATION: SYNTHETIC CONSTRUCT

<400> SEQUENCE: 66
ttttcacagc agatttacgg tgttgtttac ggtaatgtga cttttcacgt tccgagtaac     60
gttcctttga aggaagtctt atggaaaaaa caaaagata aagttgtaga atttgagaat    120
agtgaggtta gggcatttag ttcatttaag aatagggtct atttggatac tgtatccggt    180
tctttgacca tttataattt aacaagtagt gatgaagacg agtacgaaat ggagatgcgg    240
aatggtggtc ctgatttcaa gttttttttg tacgttttg                            279

<210> SEQ ID NO 67
<211> LENGTH: 279
<212> TYPE: DNA
<213> ORGANISM: Artificial Sequence
<220> FEATURE:
<223> OTHER INFORMATION: SYNTHETIC CONSTRUCT

<400> SEQUENCE: 67
ttttcacagc agatttacgg tgttgtttac ggtaatgtga cttttcacgt tccgagtaac     60
gttcctttga aggaagtctt atggaaaaaa caaaagata aagttgtaga atttgagaat    120
agtgaggtta gggcatttag ttcatttaag aatagggtct atttggatac tgtatccggt    180
tctttgacca tttataattt aacaagtagt gatgaagacg agtacgaaat ggaggcgcgg    240 gatggggtc ctgatttcaa gttttttttg tacgttttg                             279

<210> SEQ ID NO 68
<211> LENGTH: 279
<212> TYPE: DNA
<213> ORGANISM: Artificial Sequence
<220> FEATURE:
<223> OTHER INFORMATION: SYNTHETIC CONSTRUCT

<400> SEQUENCE: 68
ttttcacagc agatttacgg tgttgtttac ggtaatgtga cttttcacgt tccgagtaac     60
gttcctttga aggaagtctt atggaaaaaa caaaagata aagttgtaga atttgagaat    120
agtgaggtta gggcatttag ttcatttaag aatagggtct atttggatac tgtatccggt    180
tctttgacca tttataattt aacaagtagt gatgaagacg agtacgaaat ggagtcgtgg    240
tctccttata aggcgttcaa gttttttttg tacgttttg                            279

<210> SEQ ID NO 69
<211> LENGTH: 319
<212> TYPE: PRT
<213> ORGANISM: Artificial Sequence
<220> FEATURE:
<223> OTHER INFORMATION: SYNTHETIC CONSTRUCT

<400> SEQUENCE: 69

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
        20                  25                  30

Asp Lys Val Val Glu Phe Glu Asn Ser Glu Val Arg Ala Phe Ser Ser
            35                  40                  45

Phe Lys Asn Arg Val Tyr Leu Asp Thr Val Ser Gly Ser Leu Thr Ile
 50                  55                  60

Tyr Asn Leu Thr Ser Ser Asp Glu Asp Glu Tyr Glu Met Glu Ser Pro
 65                  70                  75                  80

Asn Ile Thr Asp Thr Phe Lys Phe Phe Leu Tyr Val Leu Asp Lys Thr
                    85                  90                  95

His Thr Cys Pro Pro Cys Pro Ala Pro Glu Leu Leu Gly Gly Pro Ser
            100                 105                 110

Val Phe Leu Phe Pro Pro Lys Pro Lys Asp Thr Leu Met Ile Ser Arg
        115                 120                 125

Thr Pro Glu Val Thr Cys Val Val Asp Val Ser His Glu Asp Pro
130                 135                 140

Glu Val Lys Phe Asn Trp Tyr Val Asp Gly Val Glu Val His Asn Ala
145                 150                 155                 160

Lys Thr Lys Pro Arg Glu Glu Gln Tyr Asn Ser Thr Tyr Arg Val Val
                165                 170                 175

Ser Val Leu Thr Val Leu His Gln Asp Trp Leu Asn Gly Lys Glu Tyr
            180                 185                 190

Lys Cys Lys Val Ser Asn Lys Ala Leu Pro Ala Pro Ile Glu Lys Thr
        195                 200                 205

Ile Ser Lys Ala Lys Gly Gln Pro Arg Glu Pro Gln Val Tyr Thr Leu
210                 215                 220

Pro Pro Ser Arg Glu Glu Met Thr Lys Asn Gln Val Ser Leu Thr Cys
225                 230                 235                 240

Leu Val Lys Gly Phe Tyr Pro Ser Asp Ile Ala Val Glu Trp Glu Ser
                245                 250                 255

Asn Gly Gln Pro Glu Asn Asn Tyr Lys Thr Thr Pro Pro Val Leu Asp
            260                 265                 270

Ser Asp Gly Ser Phe Phe Leu Tyr Ser Lys Leu Thr Val Asp Lys Ser
        275                 280                 285

Arg Trp Gln Gln Gly Asn Val Phe Ser Cys Ser Val Met His Glu Ala
290                 295                 300

Leu His Asn His Tyr Thr Gln Lys Ser Leu Ser Leu Ser Pro Gly
305                 310                 315

```
<210> SEQ ID NO 70
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
```

```
<222> LOCATION: (32)..(34)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (46)..(47)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 70

Phe Ser Gln Gln Ile Tyr Gly Val Val Tyr Gly Asn Val Thr Phe His
1               5                   10                  15

Val Pro Ser Asn Val Pro Leu Lys Xaa Val Xaa Trp Xaa Lys Gln Xaa
            20                  25                  30

Xaa Xaa Val Ala Xaa Leu Xaa Asn Ser Xaa Phe Xaa Ala Xaa Xaa Ser
        35                  40                  45

Phe Lys Asn Arg Val Tyr Leu Asp Thr Val Ser Gly Ser Leu Thr Ile
50                  55                  60

Tyr Asn Leu Thr Ser Ser Asp Glu Asp Glu Tyr Glu Met Glu Ser Xaa
65                  70                  75                  80

Asn Xaa Thr Xaa Thr Met Lys Phe Phe Leu Tyr Val Xaa
                85                  90

<210> SEQ ID NO 71
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (25)..(25)
<223> OTHER INFORMATION: Xaa is D, E, N, K, Q, or H
<220> FEATURE:
<221> NAME/KEY: MISC_FEATURE
<222> LOCATION: (27)..(27)
<223> OTHER INFORMATION: Xaa is F, I, L, V, Nle, M, or A
<220> FEATURE:
<221> NAME/KEY: MISC_FEATURE
<222> LOCATION: (29)..(29)
<223> OTHER INFORMATION: Xaa is K, R, M, T, Q, or N
<220> FEATURE:
```

<220> FEATURE:
<221> NAME/KEY: MISC_FEATURE
<222> LOCATION: (32)..(32)
<223> OTHER INFORMATION: Xaa is K, R, M, T, Q, or N
<220> FEATURE:
<221> NAME/KEY: MISC_FEATURE
<222> LOCATION: (33)..(33)
<223> OTHER INFORMATION: Xaa is D, E, N, K, Q, or H
<220> FEATURE:
<221> NAME/KEY: MISC_FEATURE
<222> LOCATION: (34)..(34)
<223> OTHER INFORMATION: Xaa is K, R, M, T, Q, or N
<220> FEATURE:
<221> NAME/KEY: MISC_FEATURE
<222> LOCATION: (37)..(37)
<223> OTHER INFORMATION: Xaa is D, E, N, K, Q, or H
<220> FEATURE:
<221> NAME/KEY: MISC_FEATURE
<222> LOCATION: (39)..(39)
<223> OTHER INFORMATION: Xaa is D, E, N, K, Q, or H
<220> FEATURE:
<221> NAME/KEY: MISC_FEATURE
<222> LOCATION: (42)..(42)
<223> OTHER INFORMATION: Xaa is D, E, N, K, Q, or H
<220> FEATURE:
<221> NAME/KEY: MISC_FEATURE
<222> LOCATION: (44)..(44)
<223> OTHER INFORMATION: Xaa is K, R, M, T, Q, or N
<220> FEATURE:
<221> NAME/KEY: MISC_FEATURE
<222> LOCATION: (46)..(46)
<223> OTHER INFORMATION: Xaa is F, Y, L, H, I, N, V, D, A, or Y
<220> FEATURE:
<221> NAME/KEY: MISC_FEATURE
<222> LOCATION: (47)..(47)
<223> OTHER INFORMATION: Xaa is S, T, A, or G
<220> FEATURE:
<221> NAME/KEY: MISC_FEATURE
<222> LOCATION: (80)..(80)
<223> OTHER INFORMATION: Xaa is P, L, H, R, or A
<220> FEATURE:
<221> NAME/KEY: MISC_FEATURE
<222> LOCATION: (82)..(82)
<223> OTHER INFORMATION: Xaa is F, I, L, V, M, A, or Nle
<220> FEATURE:
<221> NAME/KEY: MISC_FEATURE
<222> LOCATION: (84)..(84)
<223> OTHER INFORMATION: Xaa is D, E, N, K, Q, or H
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 71

Phe Ser Gln Gln Ile Tyr Gly Val Val Tyr Gly Asn Val Thr Phe His
1               5                   10                  15

Val Pro Ser Asn Val Pro Leu Lys Xaa Val Xaa Trp Xaa Lys Gln Xaa
            20                  25                  30

Xaa Xaa Val Ala Xaa Leu Xaa Asn Ser Xaa Phe Xaa Ala Xaa Xaa Ser
        35                  40                  45

Phe Lys Asn Arg Val Tyr Leu Asp Thr Val Ser Gly Ser Leu Thr Ile
50                  55                  60

Tyr Asn Leu Thr Ser Ser Asp Glu Asp Glu Tyr Glu Met Glu Ser Xaa
65                  70                  75                  80

Asn Xaa Thr Xaa Thr Met Lys Phe Phe Leu Tyr Val Xaa
            85                  90

<210> SEQ ID NO 72
<211> LENGTH: 93
<212> TYPE: PRT
<213> ORGANISM: Artificial Sequence
<220> FEATURE:
<223> OTHER INFORMATION: SYNTHETIC CONSTRUCT

```
<220> FEATURE:
<221> NAME/KEY: MISC_FEATURE
<222> LOCATION: (25)..(25)
<223> OTHER INFORMATION: Xaa is D, E, N, K, Q, or H
<220> FEATURE:
<221> NAME/KEY: MISC_FEATURE
<222> LOCATION: (27)..(27)
<223> OTHER INFORMATION: Xaa is F, I, L, or V
<220> FEATURE:
<221> NAME/KEY: MISC_FEATURE
<222> LOCATION: (29)..(29)
<223> OTHER INFORMATION: Xaa is K, R, M, or T
<220> FEATURE:
<221> NAME/KEY: MISC_FEATURE
<222> LOCATION: (32)..(32)
<223> OTHER INFORMATION: Xaa is K, R, M, or T
<220> FEATURE:
<221> NAME/KEY: MISC_FEATURE
<222> LOCATION: (33)..(33)
<223> OTHER INFORMATION: Xaa is D, E, N, K, Q, or H
<220> FEATURE:
<221> NAME/KEY: MISC_FEATURE
<222> LOCATION: (34)..(34)
<223> OTHER INFORMATION: Xaa is K, R, M, or T
<220> FEATURE:
<221> NAME/KEY: MISC_FEATURE
<222> LOCATION: (37)..(37)
<223> OTHER INFORMATION: Xaa is D, E, N, K, Q, or H
<220> FEATURE:
<221> NAME/KEY: MISC_FEATURE
<222> LOCATION: (39)..(39)
<223> OTHER INFORMATION: Xaa is D, E, N, K, Q, or H
<220> FEATURE:
<221> NAME/KEY: MISC_FEATURE
<222> LOCATION: (42)..(42)
<223> OTHER INFORMATION: Xaa is D, E, N, K, Q, or H
<220> FEATURE:
<221> NAME/KEY: MISC_FEATURE
<222> LOCATION: (44)..(44)
<223> OTHER INFORMATION: Xaa is K, R, M, or T
<220> FEATURE:
<221> NAME/KEY: MISC_FEATURE
<222> LOCATION: (46)..(46)
<223> OTHER INFORMATION: Xaa is F, Y, L, H, I, N, V, or D
<220> FEATURE:
<221> NAME/KEY: MISC_FEATURE
<222> LOCATION: (47)..(47)
<223> OTHER INFORMATION: Xaa is S, T, A, or G
<220> FEATURE:
<221> NAME/KEY: MISC_FEATURE
<222> LOCATION: (80)..(80)
<223> OTHER INFORMATION: Xaa is P, L, H, or R
<220> FEATURE:
<221> NAME/KEY: MISC_FEATURE
<222> LOCATION: (82)..(82)
<223> OTHER INFORMATION: Xaa is F, I, L, or V
<220> FEATURE:
<221> NAME/KEY: MISC_FEATURE
<222> LOCATION: (84)..(84)
<223> OTHER INFORMATION: Xaa is D, E, N, K, Q, or H
<220> FEATURE:
<221> NAME/KEY: MISC_FEATURE
<222> LOCATION: (93)..(93)
<223> OTHER INFORMATION: X is absent, L, or LESLPS

<400> SEQUENCE: 72

Phe Ser Gln Gln Ile Tyr Gly Val Val Tyr Gly Asn Val Thr Phe His
1               5                   10                  15

Val Pro Ser Asn Val Pro Leu Lys Xaa Val Xaa Trp Xaa Lys Gln Xaa
            20                  25                  30

Xaa Xaa Val Ala Xaa Leu Xaa Asn Ser Xaa Phe Xaa Ala Xaa Xaa Ser
        35                  40                  45

Phe Lys Asn Arg Val Tyr Leu Asp Thr Val Ser Gly Ser Leu Thr Ile
    50                  55                  60
```

Tyr Asn Leu Thr Ser Ser Asp Glu Asp Glu Tyr Glu Met Glu Ser Xaa
65                  70                  75                  80

Asn Xaa Thr Xaa Thr Met Lys Phe Phe Leu Tyr Val Xaa
                85                  90

<210> SEQ ID NO 73
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 73

Phe Ser Gln Gln Ile Tyr Gly Val Val Tyr Gly Asn Val Thr Xaa His
1               5                   10                  15

Xaa Pro Ser Asn Val Pro Xaa Lys Glu Xaa Leu Xaa Lys Lys Gln Lys
            20                  25                  30

Asp Lys Xaa Xaa Glu Xaa Glu Asn Ser Glu Xaa Arg Xaa Phe Ser Ser
        35                  40                  45

Phe Lys Asn Arg Val Tyr Xaa Asp Thr Val Ser Xaa Ser Xaa Thr Ile
50                  55                  60

Tyr Asn Leu Thr Ser Ser Asp Glu Asp Glu Tyr Glu Xaa Glu Ser Pro
65                  70                  75                  80

Asn Ile Thr Asp Thr Xaa Lys Xaa Phe Leu Tyr Val Xaa
                85                  90

<210> SEQ ID NO 74
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (15)..(15)
<223> OTHER INFORMATION: Xaa is F, I, L, V, A, or Y
<220> FEATURE:
<221> NAME/KEY: MISC_FEATURE
<222> LOCATION: (17)..(17)
<223> OTHER INFORMATION: Xaa is F, I, L, V, M, A, or Nle
<220> FEATURE:
<221> NAME/KEY: MISC_FEATURE
<222> LOCATION: (23)..(23)
<223> OTHER INFORMATION: X is F, I, L, V, Nle, M, or A
<220> FEATURE:
<221> NAME/KEY: MISC_FEATURE
<222> LOCATION: (26)..(26)
<223> OTHER INFORMATION: Xaa is F, I, L, V, M, A, or Nle
<220> FEATURE:
<221> NAME/KEY: MISC_FEATURE
<222> LOCATION: (28)..(28)
<223> OTHER INFORMATION: Xaa is W, F, L, C, or Y
<220> FEATURE:
<221> NAME/KEY: MISC_FEATURE
<222> LOCATION: (35)..(35)
<223> OTHER INFORMATION: Xaa is F, I, L, V, M, A, or Nle
<220> FEATURE:
<221> NAME/KEY: MISC_FEATURE
<222> LOCATION: (36)..(36)
<223> OTHER INFORMATION: Xaa is A, V, S, L, or I
<220> FEATURE:
<221> NAME/KEY: MISC_FEATURE
<222> LOCATION: (38)..(38)
<223> OTHER INFORMATION: Xaa is F, I, L, V, Nle, M, or A
<220> FEATURE:
<221> NAME/KEY: MISC_FEATURE
<222> LOCATION: (43)..(43)
<223> OTHER INFORMATION: Xaa is F, I, L, V, A, or Y
<220> FEATURE:
<221> NAME/KEY: MISC_FEATURE
<222> LOCATION: (45)..(45)
<223> OTHER INFORMATION: Xaa is A, V, S, L, or I
<220> FEATURE:
<221> NAME/KEY: MISC_FEATURE
<222> LOCATION: (55)..(55)
<223> OTHER INFORMATION: Xaa is F, I, L, V, Nle, M, or A
<220> FEATURE:
<221> NAME/KEY: MISC_FEATURE
<222> LOCATION: (60)..(60)
<223> OTHER INFORMATION: Xaa is S, T, A, or G
<220> FEATURE:
<221> NAME/KEY: MISC_FEATURE
<222> LOCATION: (62)..(62)

-continued

```
<223> OTHER INFORMATION: Xaa is F, I, L, V, Nle, M, or A
<220> FEATURE:
<221> NAME/KEY: MISC_FEATURE
<222> LOCATION: (77)..(77)
<223> OTHER INFORMATION: Xaa is M, L, I, or F
<220> FEATURE:
<221> NAME/KEY: MISC_FEATURE
<222> LOCATION: (86)..(86)
<223> OTHER INFORMATION: Xaa is M, L, I, or F
<220> FEATURE:
<221> NAME/KEY: MISC_FEATURE
<222> LOCATION: (88)..(88)
<223> OTHER INFORMATION: Xaa is F, I, L, V, A, or Y
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 74

Phe Ser Gln Gln Ile Tyr Gly Val Val Tyr Gly Asn Val Thr Xaa His
1               5                   10                  15

Xaa Pro Ser Asn Val Pro Xaa Lys Glu Xaa Leu Xaa Lys Lys Gln Lys
            20                  25                  30

Asp Lys Xaa Xaa Glu Xaa Glu Asn Ser Glu Xaa Arg Xaa Phe Ser Ser
        35                  40                  45

Phe Lys Asn Arg Val Tyr Xaa Asp Thr Val Ser Xaa Ser Xaa Thr Ile
50                  55                  60

Tyr Asn Leu Thr Ser Ser Asp Glu Asp Glu Tyr Glu Xaa Glu Ser Pro
65                  70                  75                  80

Asn Ile Thr Asp Thr Xaa Lys Xaa Phe Leu Tyr Val Xaa
            85                  90

<210> SEQ ID NO 75
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (15)..(15)
<223> OTHER INFORMATION: Xaa is F, I, L, or V
<220> FEATURE:
<221> NAME/KEY: MISC_FEATURE
<222> LOCATION: (17)..(17)
<223> OTHER INFORMATION: X is F, I, L, or V
<220> FEATURE:
<221> NAME/KEY: MISC_FEATURE
<222> LOCATION: (23)..(23)
<223> OTHER INFORMATION: Xaa is F, I, L, or V
<220> FEATURE:
<221> NAME/KEY: MISC_FEATURE
<222> LOCATION: (26)..(26)
<223> OTHER INFORMATION: Xaa is F, I, L, or V
<220> FEATURE:
<221> NAME/KEY: MISC_FEATURE
<222> LOCATION: (28)..(28)
<223> OTHER INFORMATION: Xaa is W, F, L, or C
<220> FEATURE:
<221> NAME/KEY: MISC_FEATURE
<222> LOCATION: (35)..(35)
<223> OTHER INFORMATION: Xaa is F, I, L, or V
<220> FEATURE:
<221> NAME/KEY: MISC_FEATURE
<222> LOCATION: (36)..(36)
<223> OTHER INFORMATION: Xaa is A, V, S, or L
<220> FEATURE:
<221> NAME/KEY: MISC_FEATURE
<222> LOCATION: (38)..(38)
<223> OTHER INFORMATION: Xaa is F, I, L, or V
<220> FEATURE:
<221> NAME/KEY: MISC_FEATURE
```

```
<222> LOCATION: (43)..(43)
<223> OTHER INFORMATION: Xaa is F, I, L, or V
<220> FEATURE:
<221> NAME/KEY: MISC_FEATURE
<222> LOCATION: (45)..(45)
<223> OTHER INFORMATION: Xaa is A, V, S, or L
<220> FEATURE:
<221> NAME/KEY: MISC_FEATURE
<222> LOCATION: (55)..(55)
<223> OTHER INFORMATION: Xaa is F, I, L, or V
<220> FEATURE:
<221> NAME/KEY: MISC_FEATURE
<222> LOCATION: (60)..(60)
<223> OTHER INFORMATION: Xaa is S, T, A, or G
<220> FEATURE:
<221> NAME/KEY: MISC_FEATURE
<222> LOCATION: (62)..(62)
<223> OTHER INFORMATION: Xaa is F, I, L, or V
<220> FEATURE:
<221> NAME/KEY: MISC_FEATURE
<222> LOCATION: (77)..(77)
<223> OTHER INFORMATION: Xaa is M, L, I, or F
<220> FEATURE:
<221> NAME/KEY: MISC_FEATURE
<222> LOCATION: (86)..(86)
<223> OTHER INFORMATION: Xaa is M, L, I, or F
<220> FEATURE:
<221> NAME/KEY: MISC_FEATURE
<222> LOCATION: (88)..(88)
<223> OTHER INFORMATION: Xaa is F, I, L, or V
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 75

Phe Ser Gln Gln Ile Tyr Gly Val Val Tyr Gly Asn Val Thr Xaa His
1               5                   10                  15

Xaa Pro Ser Asn Val Pro Xaa Lys Glu Xaa Leu Xaa Lys Lys Gln Lys
            20                  25                  30

Asp Lys Xaa Xaa Glu Xaa Glu Asn Ser Glu Xaa Arg Xaa Phe Ser Ser
        35                  40                  45

Phe Lys Asn Arg Val Tyr Xaa Asp Thr Val Ser Xaa Ser Xaa Thr Ile
    50                  55                  60

Tyr Asn Leu Thr Ser Ser Asp Glu Asp Glu Tyr Glu Xaa Glu Ser Pro
65                  70                  75                  80

Asn Ile Thr Asp Thr Xaa Lys Xaa Phe Leu Tyr Val Xaa
                85                  90

<210> SEQ ID NO 76
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
```

```
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 76

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Xaa Glu Xaa Glu Asn Ser Glu Xaa Arg Xaa Phe Ser Ser
        35                  40                  45

Phe Lys Asn Arg Val Tyr Leu Asp Thr Val Ser Gly Ser Leu Thr Ile
50                  55                  60

Tyr Asn Leu Thr Ser Ser Asp Glu Asp Glu Tyr Glu Xaa Glu Ser Pro
65                  70                  75                  80

Asn Ile Thr Asp Thr Xaa Lys Phe Phe Leu Tyr Val Xaa
                85                  90

<210> SEQ ID NO 77
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (36)..(36)
<223> OTHER INFORMATION: Xaa is A, V, S, L, or I
<220> FEATURE:
<221> NAME/KEY: MISC_FEATURE
<222> LOCATION: (38)..(38)
<223> OTHER INFORMATION: Xaa is F, I, L, V, Nle, M, or A
<220> FEATURE:
<221> NAME/KEY: MISC_FEATURE
<222> LOCATION: (43)..(43)
<223> OTHER INFORMATION: Xaa is F, I, L, V, A, or Y
<220> FEATURE:
<221> NAME/KEY: MISC_FEATURE
<222> LOCATION: (45)..(45)
<223> OTHER INFORMATION: Xaa is A, V, S, L, or I
<220> FEATURE:
<221> NAME/KEY: MISC_FEATURE
<222> LOCATION: (77)..(77)
<223> OTHER INFORMATION: Xaa is M, L, I, or F
<220> FEATURE:
<221> NAME/KEY: MISC_FEATURE
<222> LOCATION: (86)..(86)
<223> OTHER INFORMATION: Xaa is M, L, I, or F
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 77

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Xaa Glu Xaa Glu Asn Ser Glu Xaa Arg Xaa Phe Ser Ser
        35                  40                  45
```

```
Phe Lys Asn Arg Val Tyr Leu Asp Thr Val Ser Gly Ser Leu Thr Ile
        50                  55                  60

Tyr Asn Leu Thr Ser Ser Asp Glu Asp Glu Tyr Glu Xaa Glu Ser Pro
 65                  70                  75                  80

Asn Ile Thr Asp Thr Xaa Lys Phe Phe Leu Tyr Val Xaa
                 85                  90
```

<210> SEQ ID NO 78
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (36)..(36)
<223> OTHER INFORMATION: Xaa is A, V, S, or L
<220> FEATURE:
<221> NAME/KEY: MISC_FEATURE
<222> LOCATION: (38)..(38)
<223> OTHER INFORMATION: Xaa is F, I, L, or V
<220> FEATURE:
<221> NAME/KEY: MISC_FEATURE
<222> LOCATION: (43)..(43)
<223> OTHER INFORMATION: Xaa is F, I, L, or V
<220> FEATURE:
<221> NAME/KEY: MISC_FEATURE
<222> LOCATION: (45)..(45)
<223> OTHER INFORMATION: Xaa is A, V, S, or L
<220> FEATURE:
<221> NAME/KEY: MISC_FEATURE
<222> LOCATION: (77)..(77)
<223> OTHER INFORMATION: Xaa is M, L, I, or F
<220> FEATURE:
<221> NAME/KEY: MISC_FEATURE
<222> LOCATION: (86)..(86)
<223> OTHER INFORMATION: Xaa is M, L, I, or F
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 78

```
Phe Ser Gln Gln Ile Tyr Gly Val Val Tyr Gly Asn Val Thr Phe His
 1               5                  10                  15

Val Pro Ser Asn Val Pro Leu Lys Glu Val Leu Trp Lys Lys Gln Lys
                 20                  25                  30

Asp Lys Val Xaa Glu Xaa Glu Asn Ser Glu Xaa Arg Xaa Phe Ser Ser
             35                  40                  45

Phe Lys Asn Arg Val Tyr Leu Asp Thr Val Ser Gly Ser Leu Thr Ile
        50                  55                  60

Tyr Asn Leu Thr Ser Ser Asp Glu Asp Glu Tyr Glu Xaa Glu Ser Pro
 65                  70                  75                  80

Asn Ile Thr Asp Thr Xaa Lys Phe Phe Leu Tyr Val Xaa
                 85                  90
```

<210> SEQ ID NO 79
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (36)..(36)
<223> OTHER INFORMATION: Xaa is V, L, or A
<220> FEATURE:
<221> NAME/KEY: MISC_FEATURE
<222> LOCATION: (38)..(38)

<223> OTHER INFORMATION: Xaa is F or L
<220> FEATURE:
<221> NAME/KEY: MISC_FEATURE
<222> LOCATION: (43)..(43)
<223> OTHER INFORMATION: Xaa is V, I, L, or F
<220> FEATURE:
<221> NAME/KEY: MISC_FEATURE
<222> LOCATION: (45)..(45)
<223> OTHER INFORMATION: Xaa is A, V, or S
<220> FEATURE:
<221> NAME/KEY: MISC_FEATURE
<222> LOCATION: (77)..(77)
<223> OTHER INFORMATION: Xaa is M, F, I, or L
<220> FEATURE:
<221> NAME/KEY: MISC_FEATURE
<222> LOCATION: (86)..(86)
<223> OTHER INFORMATION: Xaa is F, M, I, or L
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 79

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Xaa Glu Xaa Glu Asn Ser Glu Xaa Arg Xaa Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Xaa Glu Ser Pro
65                  70                  75                  80

Asn Ile Thr Asp Thr Xaa Lys Phe Phe Leu Tyr Val Xaa
                85                  90

<210> SEQ ID NO 80
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (36)..(36)
<223> OTHER INFORMATION: Xaa is V or L
<220> FEATURE:
<221> NAME/KEY: MISC_FEATURE
<222> LOCATION: (43)..(43)
<223> OTHER INFORMATION: Xaa is V, I, or L
<220> FEATURE:
<221> NAME/KEY: MISC_FEATURE
<222> LOCATION: (45)..(45)
<223> OTHER INFORMATION: Xaa is A or V
<220> FEATURE:
<221> NAME/KEY: MISC_FEATURE
<222> LOCATION: (77)..(77)
<223> OTHER INFORMATION: Xaa is M or F
<220> FEATURE:
<221> NAME/KEY: MISC_FEATURE
<222> LOCATION: (86)..(86)
<223> OTHER INFORMATION: Xaa is F or M
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 80

Phe Ser Gln Gln Ile Tyr Gly Val Val Tyr Gly Asn Val Thr Phe His
1               5                   10                  15

```
Val Pro Ser Asn Val Pro Leu Lys Glu Val Leu Trp Lys Lys Gln Lys
            20                  25                  30

Asp Lys Val Xaa Glu Phe Glu Asn Ser Glu Xaa Arg Xaa Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Xaa Glu Ser Pro
65                  70                  75                  80

Asn Ile Thr Asp Thr Xaa Lys Phe Phe Leu Tyr Val Xaa
                85                  90
```

<210> SEQ ID NO 81
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (36)..(36)
<223> OTHER INFORMATION: Xaa is V or L
<220> FEATURE:
<221> NAME/KEY: MISC_FEATURE
<222> LOCATION: (43)..(43)
<223> OTHER INFORMATION: Xaa is V, I, or L
<220> FEATURE:
<221> NAME/KEY: MISC_FEATURE
<222> LOCATION: (45)..(45)
<223> OTHER INFORMATION: Xaa is A or V
<220> FEATURE:
<221> NAME/KEY: MISC_FEATURE
<222> LOCATION: (77)..(77)
<223> OTHER INFORMATION: Xaa is M or F
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 81

```
Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Xaa Glu Phe Glu Asn Ser Glu Xaa Arg Xaa Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Xaa Glu Ser Pro
65                  70                  75                  80

Asn Ile Thr Asp Thr Phe Lys Phe Phe Leu Tyr Val Xaa
                85                  90
```

<210> SEQ ID NO 82
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (43)..(43)
<223> OTHER INFORMATION: Xaa is V or I
<220> FEATURE:
<221> NAME/KEY: MISC_FEATURE
<222> LOCATION: (45)..(45)
<223> OTHER INFORMATION: Xaa is A or V
<220> FEATURE:

```
<221> NAME/KEY: MISC_FEATURE
<222> LOCATION: (77)..(77)
<223> OTHER INFORMATION: Xaa is M or F
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 82

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Xaa Arg Xaa Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Xaa Glu Ser Pro
65                  70                  75                  80

Asn Ile Thr Asp Thr Phe Lys Phe Phe Leu Tyr Val Xaa
                85                  90

<210> SEQ ID NO 83
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 83

Ser Pro Asn Ile Thr Asp Thr
1               5

<210> SEQ ID NO 84
<211> LENGTH: 7
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (1)..(1)
<223> OTHER INFORMATION: Xaa is S, G, A, M, or T
<220> FEATURE:
<221> NAME/KEY: MISC_FEATURE
<222> LOCATION: (2)..(2)
<223> OTHER INFORMATION: Xaa is R, W, P, or A
<220> FEATURE:
<221> NAME/KEY: MISC_FEATURE
<222> LOCATION: (3)..(3)
<223> OTHER INFORMATION: Xaa is N, Y, S, E, D, Q, H, K, or R
<220> FEATURE:
<221> NAME/KEY: MISC_FEATURE
<222> LOCATION: (4)..(4)
<223> OTHER INFORMATION: Xaa is P, G, I, L, V, M, A, F, or Nle
<220> FEATURE:
<221> NAME/KEY: MISC_FEATURE
<222> LOCATION: (5)..(5)
<223> OTHER INFORMATION: Xaa is Y, G, T, or S
<220> FEATURE:
<221> NAME/KEY: MISC_FEATURE
<222> LOCATION: (6)..(6)
<223> OTHER INFORMATION: Xaa is R, E, K, P, D, or N
<220> FEATURE:
<221> NAME/KEY: MISC_FEATURE
<222> LOCATION: (7)..(7)
<223> OTHER INFORMATION: Xaa is R, D, S, Q, A, E, T, or S
```

<400> SEQUENCE: 84

Xaa Xaa Xaa Xaa Xaa Xaa Xaa
1               5

<210> SEQ ID NO 85
<211> LENGTH: 7
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (1)..(1)
<223> OTHER INFORMATION: Xaa is S, G, A, or M
<220> FEATURE:
<221> NAME/KEY: MISC_FEATURE
<222> LOCATION: (2)..(2)
<223> OTHER INFORMATION: Xaa is R, W, or P
<220> FEATURE:
<221> NAME/KEY: MISC_FEATURE
<222> LOCATION: (3)..(3)
<223> OTHER INFORMATION: Xaa is N, Y, S, E, or D
<220> FEATURE:
<221> NAME/KEY: MISC_FEATURE
<222> LOCATION: (4)..(4)
<223> OTHER INFORMATION: Xaa is P, G, or I
<220> FEATURE:
<221> NAME/KEY: MISC_FEATURE
<222> LOCATION: (5)..(5)
<223> OTHER INFORMATION: Xaa is Y, G, or T
<220> FEATURE:
<221> NAME/KEY: MISC_FEATURE
<222> LOCATION: (6)..(6)
<223> OTHER INFORMATION: Xaa is R, E, K, P, or D
<220> FEATURE:
<221> NAME/KEY: MISC_FEATURE
<222> LOCATION: (7)..(7)
<223> OTHER INFORMATION: Xaa is R, D, S, Q, A, E, or T

<400> SEQUENCE: 85

Xaa Xaa Xaa Xaa Xaa Xaa Xaa
1               5

<210> SEQ ID NO 86
<211> LENGTH: 7
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (1)..(1)
<223> OTHER INFORMATION: Xaa is S, G, A, or M
<220> FEATURE:
<221> NAME/KEY: MISC_FEATURE
<222> LOCATION: (2)..(2)
<223> OTHER INFORMATION: Xaa is R or W
<220> FEATURE:
<221> NAME/KEY: MISC_FEATURE
<222> LOCATION: (3)..(3)
<223> OTHER INFORMATION: Xaa is N, Y, S, E, or D
<220> FEATURE:
<221> NAME/KEY: MISC_FEATURE
<222> LOCATION: (4)..(4)
<223> OTHER INFORMATION: Xaa is P or G
<220> FEATURE:
<221> NAME/KEY: MISC_FEATURE
<222> LOCATION: (5)..(5)
<223> OTHER INFORMATION: Xaa is Y or G
<220> FEATURE:
<221> NAME/KEY: MISC_FEATURE
<222> LOCATION: (6)..(6)
<223> OTHER INFORMATION: Xaa is R, E, K, or P
<220> FEATURE:

```
<221> NAME/KEY: MISC_FEATURE
<222> LOCATION: (7)..(7)
<223> OTHER INFORMATION: Xaa is R, D, S, Q, A, or E

<400> SEQUENCE: 86

Xaa Xaa Xaa Xaa Xaa Xaa Xaa
1               5

<210> SEQ ID NO 87
<211> LENGTH: 7
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (2)..(2)
<223> OTHER INFORMATION: Xaa is R, W, P, or A
<220> FEATURE:
<221> NAME/KEY: MISC_FEATURE
<222> LOCATION: (4)..(4)
<223> OTHER INFORMATION: Xaa is P, G, I, L, V, M, A, F, or Nle
<220> FEATURE:
<221> NAME/KEY: MISC_FEATURE
<222> LOCATION: (5)..(5)
<223> OTHER INFORMATION: Xaa is Y, G, T, or S
<220> FEATURE:
<221> NAME/KEY: MISC_FEATURE
<222> LOCATION: (6)..(6)
<223> OTHER INFORMATION: Xaa is R, P, D, or N
<220> FEATURE:
<221> NAME/KEY: MISC_FEATURE
<222> LOCATION: (7)..(7)
<223> OTHER INFORMATION: Xaa is R, D, T, or S

<400> SEQUENCE: 87

Ser Xaa Asn Xaa Xaa Xaa Xaa
1               5

<210> SEQ ID NO 88
<211> LENGTH: 7
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (2)..(2)
<223> OTHER INFORMATION: Xaa is R, W, or P
<220> FEATURE:
<221> NAME/KEY: MISC_FEATURE
<222> LOCATION: (4)..(4)
<223> OTHER INFORMATION: Xaa is P, G, or I
<220> FEATURE:
<221> NAME/KEY: MISC_FEATURE
<222> LOCATION: (5)..(5)
<223> OTHER INFORMATION: Xaa is Y, G, or T
<220> FEATURE:
<221> NAME/KEY: MISC_FEATURE
<222> LOCATION: (6)..(6)
<223> OTHER INFORMATION: Xaa is R, P, or D
<220> FEATURE:
<221> NAME/KEY: MISC_FEATURE
<222> LOCATION: (7)..(7)
<223> OTHER INFORMATION: Xaa is R, D, or T

<400> SEQUENCE: 88

Ser Xaa Asn Xaa Xaa Xaa Xaa
1               5

<210> SEQ ID NO 89
<211> LENGTH: 7
<212> TYPE: PRT
```

-continued

```
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (2)..(2)
<223> OTHER INFORMATION: Xaa is R or W
<220> FEATURE:
<221> NAME/KEY: MISC_FEATURE
<222> LOCATION: (4)..(4)
<223> OTHER INFORMATION: Xaa is P or G
<220> FEATURE:
<221> NAME/KEY: MISC_FEATURE
<222> LOCATION: (5)..(5)
<223> OTHER INFORMATION: Xaa is Y or G
<220> FEATURE:
<221> NAME/KEY: MISC_FEATURE
<222> LOCATION: (6)..(6)
<223> OTHER INFORMATION: Xaa is R or P
<220> FEATURE:
<221> NAME/KEY: MISC_FEATURE
<222> LOCATION: (7)..(7)
<223> OTHER INFORMATION: Xaa is R or D

<400> SEQUENCE: 89

Ser Xaa Asn Xaa Xaa Xaa Xaa
1               5

<210> SEQ ID NO 90
<211> LENGTH: 7
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (1)..(1)
<223> OTHER INFORMATION: Xaa is S, G, A, M, or T
<220> FEATURE:
<221> NAME/KEY: MISC_FEATURE
<222> LOCATION: (2)..(2)
<223> OTHER INFORMATION: Xaa is R, W, P, or A
<220> FEATURE:
<221> NAME/KEY: MISC_FEATURE
<222> LOCATION: (3)..(3)
<223> OTHER INFORMATION: Xaa is N, Y, S, E, D, Q, H, K, or R
<220> FEATURE:
<221> NAME/KEY: MISC_FEATURE
<222> LOCATION: (4)..(4)
<223> OTHER INFORMATION: Xaa is P, G, I, L, V, M, A, F, or Nle
<220> FEATURE:
<221> NAME/KEY: MISC_FEATURE
<222> LOCATION: (5)..(5)
<223> OTHER INFORMATION: Xaa is Y, G, T, or S
<220> FEATURE:
<221> NAME/KEY: MISC_FEATURE
<222> LOCATION: (6)..(6)
<223> OTHER INFORMATION: Xaa is R, E, K, P, D, or N
<220> FEATURE:
<221> NAME/KEY: MISC_FEATURE
<222> LOCATION: (7)..(7)
<223> OTHER INFORMATION: Xaa is D, S, Q, A, E, T, or S

<400> SEQUENCE: 90

Xaa Xaa Xaa Xaa Xaa Xaa Xaa
1               5

<210> SEQ ID NO 91
<211> LENGTH: 7
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
```

```
<222> LOCATION: (1)..(1)
<223> OTHER INFORMATION: Xaa is S, G, A, or M
<220> FEATURE:
<221> NAME/KEY: MISC_FEATURE
<222> LOCATION: (2)..(2)
<223> OTHER INFORMATION: X is R, W, or P
<220> FEATURE:
<221> NAME/KEY: MISC_FEATURE
<222> LOCATION: (3)..(3)
<223> OTHER INFORMATION: Xaa is N, Y, S, E, or D
<220> FEATURE:
<221> NAME/KEY: MISC_FEATURE
<222> LOCATION: (4)..(4)
<223> OTHER INFORMATION: Xaa is P, G, or I
<220> FEATURE:
<221> NAME/KEY: MISC_FEATURE
<222> LOCATION: (5)..(5)
<223> OTHER INFORMATION: Xaa is Y, G, or T
<220> FEATURE:
<221> NAME/KEY: MISC_FEATURE
<222> LOCATION: (6)..(6)
<223> OTHER INFORMATION: Xaa is R, E, K, P, or D
<220> FEATURE:
<221> NAME/KEY: MISC_FEATURE
<222> LOCATION: (7)..(7)
<223> OTHER INFORMATION: Xaa is D, S, Q, A, E, or T

<400> SEQUENCE: 91

Xaa Xaa Xaa Xaa Xaa Xaa Xaa
1               5

<210> SEQ ID NO 92
<211> LENGTH: 7
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (1)..(1)
<223> OTHER INFORMATION: Xaa is S, G, A, or M
<220> FEATURE:
<221> NAME/KEY: MISC_FEATURE
<222> LOCATION: (2)..(2)
<223> OTHER INFORMATION: Xaa is R or W
<220> FEATURE:
<221> NAME/KEY: MISC_FEATURE
<222> LOCATION: (3)..(3)
<223> OTHER INFORMATION: Xaa is N, Y, S, E, or D
<220> FEATURE:
<221> NAME/KEY: MISC_FEATURE
<222> LOCATION: (4)..(4)
<223> OTHER INFORMATION: Xaa is P or G
<220> FEATURE:
<221> NAME/KEY: MISC_FEATURE
<222> LOCATION: (5)..(5)
<223> OTHER INFORMATION: Xaa is Y or G
<220> FEATURE:
<221> NAME/KEY: MISC_FEATURE
<222> LOCATION: (6)..(6)
<223> OTHER INFORMATION: Xaa is R, E, K, or P
<220> FEATURE:
<221> NAME/KEY: MISC_FEATURE
<222> LOCATION: (7)..(7)
<223> OTHER INFORMATION: Xaa is D, S, Q, A, or E

<400> SEQUENCE: 92

Xaa Xaa Xaa Xaa Xaa Xaa Xaa
1               5

<210> SEQ ID NO 93
<211> LENGTH: 93
<212> TYPE: PRT
<213> ORGANISM: Artificial Sequence
<220> FEATURE:
```

```
<223> OTHER INFORMATION: SYNTHETIC CONSTRUCT
<220> FEATURE:
<221> NAME/KEY: MISC_FEATURE
<222> LOCATION: (36)..(36)
<223> OTHER INFORMATION: Xaa is V, L, or A
<220> FEATURE:
<221> NAME/KEY: MISC_FEATURE
<222> LOCATION: (38)..(38)
<223> OTHER INFORMATION: Xaa is F or L
<220> FEATURE:
<221> NAME/KEY: MISC_FEATURE
<222> LOCATION: (43)..(43)
<223> OTHER INFORMATION: Xaa is V, I, L, or F
<220> FEATURE:
<221> NAME/KEY: MISC_FEATURE
<222> LOCATION: (45)..(45)
<223> OTHER INFORMATION: Xaa is A, V, or S
<220> FEATURE:
<221> NAME/KEY: MISC_FEATURE
<222> LOCATION: (77)..(77)
<223> OTHER INFORMATION: Xaa is M, F, I, or L
<220> FEATURE:
<221> NAME/KEY: MISC_FEATURE
<222> LOCATION: (79)..(79)
<223> OTHER INFORMATION: Xaa is S, G, A, or M
<220> FEATURE:
<221> NAME/KEY: MISC_FEATURE
<222> LOCATION: (80)..(80)
<223> OTHER INFORMATION: Xaa is R or W
<220> FEATURE:
<221> NAME/KEY: MISC_FEATURE
<222> LOCATION: (81)..(81)
<223> OTHER INFORMATION: Xaa is N, Y, S, E, or D
<220> FEATURE:
<221> NAME/KEY: MISC_FEATURE
<222> LOCATION: (82)..(82)
<223> OTHER INFORMATION: Xaa is P or G
<220> FEATURE:
<221> NAME/KEY: MISC_FEATURE
<222> LOCATION: (83)..(83)
<223> OTHER INFORMATION: Xaa is Y or G
<220> FEATURE:
<221> NAME/KEY: MISC_FEATURE
<222> LOCATION: (84)..(84)
<223> OTHER INFORMATION: Xaa is R, E, K, or P
<220> FEATURE:
<221> NAME/KEY: MISC_FEATURE
<222> LOCATION: (85)..(85)
<223> OTHER INFORMATION: Xaa is R, D, S, Q, A, or E
<220> FEATURE:
<221> NAME/KEY: MISC_FEATURE
<222> LOCATION: (86)..(86)
<223> OTHER INFORMATION: Xaa is F, M, I, or L
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 93

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Xaa Glu Xaa Glu Asn Ser Glu Xaa Arg Xaa Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Xaa Glu Xaa Xaa
65                  70                  75                  80

Xaa Xaa Xaa Xaa Xaa Xaa Lys Phe Phe Leu Tyr Val Xaa
                85                  90
```

-continued

```
<210> SEQ ID NO 94
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (36)..(36)
<223> OTHER INFORMATION: Xaa is V or A
<220> FEATURE:
<221> NAME/KEY: MISC_FEATURE
<222> LOCATION: (38)..(38)
<223> OTHER INFORMATION: Xaa is F or L
<220> FEATURE:
<221> NAME/KEY: MISC_FEATURE
<222> LOCATION: (43)..(43)
<223> OTHER INFORMATION: Xaa is V, I, or F
<220> FEATURE:
<221> NAME/KEY: MISC_FEATURE
<222> LOCATION: (45)..(45)
<223> OTHER INFORMATION: Xaa is A or V
<220> FEATURE:
<221> NAME/KEY: MISC_FEATURE
<222> LOCATION: (77)..(77)
<223> OTHER INFORMATION: Xaa is M or F
<220> FEATURE:
<221> NAME/KEY: MISC_FEATURE
<222> LOCATION: (79)..(79)
<223> OTHER INFORMATION: Xaa is S, G, A, or M
<220> FEATURE:
<221> NAME/KEY: MISC_FEATURE
<222> LOCATION: (80)..(80)
<223> OTHER INFORMATION: Xaa is R or W
<220> FEATURE:
<221> NAME/KEY: MISC_FEATURE
<222> LOCATION: (81)..(81)
<223> OTHER INFORMATION: Xaa is N, Y, S, E, or D
<220> FEATURE:
<221> NAME/KEY: MISC_FEATURE
<222> LOCATION: (82)..(82)
<223> OTHER INFORMATION: Xaa is P or G
<220> FEATURE:
<221> NAME/KEY: MISC_FEATURE
<222> LOCATION: (83)..(83)
<223> OTHER INFORMATION: Xaa is Y or G
<220> FEATURE:
<221> NAME/KEY: MISC_FEATURE
<222> LOCATION: (84)..(84)
<223> OTHER INFORMATION: Xaa is R, E, K, or P
<220> FEATURE:
<221> NAME/KEY: MISC_FEATURE
<222> LOCATION: (85)..(85)
<223> OTHER INFORMATION: Xaa is R, D, S, Q, A, or E
<220> FEATURE:
<221> NAME/KEY: MISC_FEATURE
<222> LOCATION: (86)..(86)
<223> OTHER INFORMATION: Xaa is F or M
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 94

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
                20                  25                  30

Asp Lys Val Xaa Glu Xaa Glu Asn Ser Glu Xaa Arg Xaa Phe Ser Ser
            35                  40                  45

Phe Lys Asn Arg Val Tyr Leu Asp Thr Val Ser Gly Ser Leu Thr Ile
        50                  55                  60

Tyr Asn Leu Thr Ser Ser Asp Glu Asp Glu Tyr Glu Xaa Glu Xaa Xaa
65                  70                  75                  80
```

Xaa Xaa Xaa Xaa Xaa Xaa Lys Phe Phe Leu Tyr Val Xaa
                    85                  90

<210> SEQ ID NO 95
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (79)..(85)
<223> OTHER INFORMATION: Xaa can be any naturally occurring amino acid
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 95

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Xaa Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Xaa Glu Xaa Xaa
65                  70                  75                  80

Xaa Xaa Xaa Xaa Xaa Phe Lys Phe Phe Leu Tyr Val Xaa
                85                  90

<210> SEQ ID NO 96
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (45)..(45)
<223> OTHER INFORMATION: Xaa is A, V, L, or I
<220> FEATURE:
<221> NAME/KEY: MISC_FEATURE
<222> LOCATION: (77)..(77)
<223> OTHER INFORMATION: Xaa is M, F, L, or I
<220> FEATURE:
<221> NAME/KEY: MISC_FEATURE
<222> LOCATION: (79)..(79)
<223> OTHER INFORMATION: Xaa is S, G, A, M, or T
<220> FEATURE:
<221> NAME/KEY: MISC_FEATURE
<222> LOCATION: (80)..(80)
<223> OTHER INFORMATION: Xaa is R, W, P, or A
<220> FEATURE:
<221> NAME/KEY: MISC_FEATURE
<222> LOCATION: (81)..(81)
<223> OTHER INFORMATION: Xaa is N, Y, S, E, D, Q, H, K, or R
<220> FEATURE:
<221> NAME/KEY: MISC_FEATURE
<222> LOCATION: (82)..(82)
<223> OTHER INFORMATION: Xaa is P, G, I, L, V, M, A, F, or Nle -continued

```
<220> FEATURE:
<221> NAME/KEY: MISC_FEATURE
<222> LOCATION: (83)..(83)
<223> OTHER INFORMATION: Xaa is Y, G, T, or S
<220> FEATURE:
<221> NAME/KEY: MISC_FEATURE
<222> LOCATION: (84)..(84)
<223> OTHER INFORMATION: Xaa is R, E, K, P, D, or N
<220> FEATURE:
<221> NAME/KEY: MISC_FEATURE
<222> LOCATION: (85)..(85)
<223> OTHER INFORMATION: Xaa is R, D, S, Q, A, E, T, or S
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 96

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
                20                  25                  30

Asp Lys Val Val Glu Phe Glu Asn Ser Glu Val Arg Xaa Phe Ser Ser
            35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Xaa Glu Xaa Xaa
65                  70                  75                  80

Xaa Xaa Xaa Xaa Xaa Phe Lys Phe Phe Leu Tyr Val Xaa
                85                  90

<210> SEQ ID NO 97
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (45)..(45)
<223> OTHER INFORMATION: Xaa is A or V
<220> FEATURE:
<221> NAME/KEY: MISC_FEATURE
<222> LOCATION: (77)..(77)
<223> OTHER INFORMATION: Xaa is M or F
<220> FEATURE:
<221> NAME/KEY: MISC_FEATURE
<222> LOCATION: (79)..(79)
<223> OTHER INFORMATION: Xaa is S, G, A, or M
<220> FEATURE:
<221> NAME/KEY: MISC_FEATURE
<222> LOCATION: (80)..(80)
<223> OTHER INFORMATION: Xaa is R, W, or P
<220> FEATURE:
<221> NAME/KEY: MISC_FEATURE
<222> LOCATION: (81)..(81)
<223> OTHER INFORMATION: Xaa is N, Y, S, E, or D
<220> FEATURE:
<221> NAME/KEY: MISC_FEATURE
<222> LOCATION: (82)..(82)
<223> OTHER INFORMATION: Xaa is P, G, or I
<220> FEATURE:
<221> NAME/KEY: MISC_FEATURE
<222> LOCATION: (83)..(83)
<223> OTHER INFORMATION: Xaa is Y, G, or T
<220> FEATURE:
<221> NAME/KEY: MISC_FEATURE
<222> LOCATION: (84)..(84)
<223> OTHER INFORMATION: Xaa is R, E, K, P, or D
<220> FEATURE:
<221> NAME/KEY: MISC_FEATURE
<222> LOCATION: (85)..(85)
```

<223> OTHER INFORMATION: Xaa is R, D, S, Q, A, E, or T
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 97

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Xaa Phe Ser Ser
                35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Xaa Glu Xaa Xaa
65                  70                  75                  80

Xaa Xaa Xaa Xaa Xaa Phe Lys Phe Phe Leu Tyr Val Xaa
                85                  90

<210> SEQ ID NO 98
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (45)..(45)
<223> OTHER INFORMATION: Xaa is A or V
<220> FEATURE:
<221> NAME/KEY: MISC_FEATURE
<222> LOCATION: (77)..(77)
<223> OTHER INFORMATION: Xaa is M or F
<220> FEATURE:
<221> NAME/KEY: MISC_FEATURE
<222> LOCATION: (79)..(79)
<223> OTHER INFORMATION: Xaa is S, G, A, or M
<220> FEATURE:
<221> NAME/KEY: MISC_FEATURE
<222> LOCATION: (80)..(80)
<223> OTHER INFORMATION: Xaa is R or W
<220> FEATURE:
<221> NAME/KEY: MISC_FEATURE
<222> LOCATION: (81)..(81)
<223> OTHER INFORMATION: Xaa is N, Y, S, E, or D
<220> FEATURE:
<221> NAME/KEY: MISC_FEATURE
<222> LOCATION: (82)..(82)
<223> OTHER INFORMATION: Xaa is P or G
<220> FEATURE:
<221> NAME/KEY: MISC_FEATURE
<222> LOCATION: (83)..(83)
<223> OTHER INFORMATION: Xaa is Y or G
<220> FEATURE:
<221> NAME/KEY: MISC_FEATURE
<222> LOCATION: (84)..(84)
<223> OTHER INFORMATION: Xaa is R, E, K, or P
<220> FEATURE:
<221> NAME/KEY: MISC_FEATURE
<222> LOCATION: (85)..(85)
<223> OTHER INFORMATION: Xaa is R, D, S, Q, A, or E
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 98

Phe Ser Gln Gln Ile Tyr Gly Val Val Tyr Gly Asn Val Thr Phe His
1               5                   10                  15

```
Val Pro Ser Asn Val Pro Leu Lys Glu Val Leu Trp Lys Lys Gln Lys
            20                  25                  30

Asp Lys Val Val Glu Phe Glu Asn Ser Glu Val Arg Xaa Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Xaa Glu Xaa Xaa
65                  70                  75                  80

Xaa Xaa Xaa Xaa Xaa Phe Lys Phe Phe Leu Tyr Val Xaa
                85                  90
```

<210> SEQ ID NO 99
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(85)
<223> OTHER INFORMATION: Xaa can be any naturally occurring amino acid
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 99

```
Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Xaa
65                  70                  75                  80

Asn Xaa Xaa Xaa Xaa Phe Lys Phe Phe Leu Tyr Val Xaa
                85                  90
```

<210> SEQ ID NO 100
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (80)..(80)
<223> OTHER INFORMATION: Xaa is R, W, P, or A
<220> FEATURE:
<221> NAME/KEY: MISC_FEATURE
<222> LOCATION: (82)..(82)
<223> OTHER INFORMATION: Xaa is P, G, I, L, V, M, A, F, or Nle
<220> FEATURE:
<221> NAME/KEY: MISC_FEATURE
<222> LOCATION: (83)..(83)
<223> OTHER INFORMATION: Xaa is Y, G, T, or S
<220> FEATURE:
<221> NAME/KEY: MISC_FEATURE
<222> LOCATION: (84)..(84)
<223> OTHER INFORMATION: Xaa is R, P, D, or N
<220> FEATURE:

```
<221> NAME/KEY: MISC_FEATURE
<222> LOCATION: (85)..(85)
<223> OTHER INFORMATION: Xaa is R, D, T, or S
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 100
```

| | | | | | | | | | | | | | | | |
|---|---|---|---|---|---|---|---|---|---|---|---|---|---|---|---|
| Phe | Ser | Gln | Gln | Ile | Tyr | Gly | Val | Val | Tyr | Gly | Asn | Val | Thr | Phe | His |
| 1 | | | | 5 | | | | | 10 | | | | | 15 | |
| Val | Pro | Ser | Asn | Val | Pro | Leu | Lys | Glu | Val | Leu | Trp | Lys | Lys | Gln | Lys |
| | | | 20 | | | | | 25 | | | | | 30 | | |
| Asp | Lys | Val | Val | Glu | Phe | Glu | Asn | Ser | Glu | Val | Arg | Ala | Phe | Ser | Ser |
| | | 35 | | | | | 40 | | | | | 45 | | | |
| Phe | Lys | Asn | Arg | Val | Tyr | Leu | Asp | Thr | Val | Ser | Gly | Ser | Leu | Thr | Ile |
| 50 | | | | | 55 | | | | | 60 | | | | | |
| Tyr | Asn | Leu | Thr | Ser | Ser | Asp | Glu | Asp | Glu | Tyr | Glu | Met | Glu | Ser | Xaa |
| 65 | | | | | 70 | | | | | 75 | | | | | 80 |
| Asn | Xaa | Xaa | Xaa | Xaa | Phe | Lys | Phe | Phe | Leu | Tyr | Val | Xaa | | | |
| | | | | 85 | | | | | 90 | | | | | | |

```
<210> SEQ ID NO 101
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (80)..(80)
<223> OTHER INFORMATION: Xaa is R, W, or P
<220> FEATURE:
<221> NAME/KEY: MISC_FEATURE
<222> LOCATION: (82)..(82)
<223> OTHER INFORMATION: Xaa is P, G, or I
<220> FEATURE:
<221> NAME/KEY: MISC_FEATURE
<222> LOCATION: (83)..(83)
<223> OTHER INFORMATION: Xaa is Y, G, or T
<220> FEATURE:
<221> NAME/KEY: MISC_FEATURE
<222> LOCATION: (84)..(84)
<223> OTHER INFORMATION: Xaa is R, P, or D
<220> FEATURE:
<221> NAME/KEY: MISC_FEATURE
<222> LOCATION: (85)..(85)
<223> OTHER INFORMATION: Xaa is R, D, or T
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 101
```

| | | | | | | | | | | | | | | | |
|---|---|---|---|---|---|---|---|---|---|---|---|---|---|---|---|
| Phe | Ser | Gln | Gln | Ile | Tyr | Gly | Val | Val | Tyr | Gly | Asn | Val | Thr | Phe | His |
| 1 | | | | 5 | | | | | 10 | | | | | 15 | |
| Val | Pro | Ser | Asn | Val | Pro | Leu | Lys | Glu | Val | Leu | Trp | Lys | Lys | Gln | Lys |
| | | | 20 | | | | | 25 | | | | | 30 | | |
| Asp | Lys | Val | Val | Glu | Phe | Glu | Asn | Ser | Glu | Val | Arg | Ala | Phe | Ser | Ser |
| | | 35 | | | | | 40 | | | | | 45 | | | |
| Phe | Lys | Asn | Arg | Val | Tyr | Leu | Asp | Thr | Val | Ser | Gly | Ser | Leu | Thr | Ile |
| 50 | | | | | 55 | | | | | 60 | | | | | |
| Tyr | Asn | Leu | Thr | Ser | Ser | Asp | Glu | Asp | Glu | Tyr | Glu | Met | Glu | Ser | Xaa |
| 65 | | | | | 70 | | | | | 75 | | | | | 80 |
| Asn | Xaa | Xaa | Xaa | Xaa | Phe | Lys | Phe | Phe | Leu | Tyr | Val | Xaa | | | |
| | | | | 85 | | | | | 90 | | | | | | |

```
<210> SEQ ID NO 102
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (80)..(80)
<223> OTHER INFORMATION: Xaa is R or W
<220> FEATURE:
<221> NAME/KEY: MISC_FEATURE
<222> LOCATION: (82)..(82)
<223> OTHER INFORMATION: Xaa is P or G
<220> FEATURE:
<221> NAME/KEY: MISC_FEATURE
<222> LOCATION: (83)..(83)
<223> OTHER INFORMATION: Xaa is Y or G
<220> FEATURE:
<221> NAME/KEY: MISC_FEATURE
<222> LOCATION: (84)..(84)
<223> OTHER INFORMATION: Xaa is R or P
<220> FEATURE:
<221> NAME/KEY: MISC_FEATURE
<222> LOCATION: (85)..(85)
<223> OTHER INFORMATION: Xaa is R or D
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 102

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
                20                  25                  30

Asp Lys Val Val Glu Phe Glu Asn Ser Glu Val Arg Ala Phe Ser Ser
            35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Xaa
65                  70                  75                  80

Asn Xaa Xaa Xaa Xaa Phe Lys Phe Phe Leu Tyr Val Xaa
                85                  90

<210> SEQ ID NO 103
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (45)..(45)
<223> OTHER INFORMATION: Xaa is A, V, L, or I
<220> FEATURE:
<221> NAME/KEY: MISC_FEATURE
<222> LOCATION: (77)..(77)
<223> OTHER INFORMATION: Xaa is M, F, L, or I
<220> FEATURE:
<221> NAME/KEY: MISC_FEATURE
<222> LOCATION: (79)..(79)
<223> OTHER INFORMATION: Xaa is S, G, A, M, or T
<220> FEATURE:
<221> NAME/KEY: MISC_FEATURE
<222> LOCATION: (80)..(80)
<223> OTHER INFORMATION: Xaa is R, W, P, or A
<220> FEATURE:
<221> NAME/KEY: MISC_FEATURE
<222> LOCATION: (81)..(81)
```

```
<223> OTHER INFORMATION: Xaa is  N, Y, S, E, D, Q, H, K, or R
<220> FEATURE:
<221> NAME/KEY: MISC_FEATURE
<222> LOCATION: (82)..(82)
<223> OTHER INFORMATION: Xaa is  P, G, I, L, V, M, A, F, or Nle
<220> FEATURE:
<221> NAME/KEY: MISC_FEATURE
<222> LOCATION: (83)..(83)
<223> OTHER INFORMATION: Xaa is  Y, G, T, or S
<220> FEATURE:
<221> NAME/KEY: MISC_FEATURE
<222> LOCATION: (84)..(84)
<223> OTHER INFORMATION: Xaa is R, E, K, P, D, or N
<220> FEATURE:
<221> NAME/KEY: MISC_FEATURE
<222> LOCATION: (85)..(85)
<223> OTHER INFORMATION: Xaa is D, S, Q, A, E, T, or S
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 103

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Xaa Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Xaa Glu Xaa Xaa
65                  70                  75                  80

Xaa Xaa Xaa Xaa Xaa Phe Lys Phe Phe Leu Tyr Val Xaa
                85                  90

<210> SEQ ID NO 104
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (45)..(45)
<223> OTHER INFORMATION: Xaa is A or V
<220> FEATURE:
<221> NAME/KEY: MISC_FEATURE
<222> LOCATION: (77)..(77)
<223> OTHER INFORMATION: Xaa is M or F
<220> FEATURE:
<221> NAME/KEY: MISC_FEATURE
<222> LOCATION: (79)..(79)
<223> OTHER INFORMATION: Xaa is S, G, A, or M
<220> FEATURE:
<221> NAME/KEY: MISC_FEATURE
<222> LOCATION: (80)..(80)
<223> OTHER INFORMATION: Xaa is R, W, or P
<220> FEATURE:
<221> NAME/KEY: MISC_FEATURE
<222> LOCATION: (81)..(81)
<223> OTHER INFORMATION: Xaa is N, Y, S, E, or D
<220> FEATURE:
<221> NAME/KEY: MISC_FEATURE
<222> LOCATION: (82)..(82)
<223> OTHER INFORMATION: Xaa is P, G, or I
<220> FEATURE:
<221> NAME/KEY: MISC_FEATURE
<222> LOCATION: (83)..(83)
<223> OTHER INFORMATION: Xaa is Y, G, or T
<220> FEATURE:
<221> NAME/KEY: MISC_FEATURE
```

<222> LOCATION: (84)..(84)
<223> OTHER INFORMATION: Xaa is R, E, K, P, or D
<220> FEATURE:
<221> NAME/KEY: MISC_FEATURE
<222> LOCATION: (85)..(85)
<223> OTHER INFORMATION: Xaa is D, S, Q, A, E, or T
<220> FEATURE:
<221> NAME/KEY: MISC_FEATURE
<222> LOCATION: (93)..(93)
<223> OTHER INFORMATION: Xaa is absent, L, or LESLPS

<400> SEQUENCE: 104

```
Phe Ser Gln Gln Ile Tyr Gly Val Val Tyr Gly Asn Val Thr Phe His
 1               5                  10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Xaa Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Xaa Glu Xaa Xaa
65                  70                  75                  80

Xaa Xaa Xaa Xaa Xaa Phe Lys Phe Phe Leu Tyr Val Xaa
                85                  90
```

<210> SEQ ID NO 105
<211> LENGTH: 93
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (45)..(45)
<223> OTHER INFORMATION: Xaa is A or V
<220> FEATURE:
<221> NAME/KEY: MISC_FEATURE
<222> LOCATION: (77)..(77)
<223> OTHER INFORMATION: Xaa is M or F
<220> FEATURE:
<221> NAME/KEY: MISC_FEATURE
<222> LOCATION: (79)..(79)
<223> OTHER INFORMATION: Xaa is S, G, A, or M
<220> FEATURE:
<221> NAME/KEY: MISC_FEATURE
<222> LOCATION: (80)..(80)
<223> OTHER INFORMATION: Xaa is R or W
<220> FEATURE:
<221> NAME/KEY: MISC_FEATURE
<222> LOCATION: (81)..(81)
<223> OTHER INFORMATION: Xaa is N, Y, S, E, or D
<220> FEATURE:
<221> NAME/KEY: MISC_FEATURE
<222> LOCATION: (82)..(82)
<223> OTHER INFORMATION: Xaa is P or G
<220> FEATURE:
<221> NAME/KEY: MISC_FEATURE
<222> LOCATION: (83)..(83)
<223> OTHER INFORMATION: Xaa is Y or G
<220> FEATURE:
<221> NAME/KEY: MISC_FEATURE
<222> LOCATION: (84)..(84)
<223> OTHER INFORMATION: Xaa is R, E, K, or P
<220> FEATURE:
<221> NAME/KEY: MISC_FEATURE
<222> LOCATION: (85)..(85)
<223> OTHER INFORMATION: Xaa is D, S, Q, A, or E
<220> FEATURE:
<221> NAME/KEY: MISC_FEATURE
<222> LOCATION: (93)..(93)
<223> OTHER INFORMATION: Xaa is absent, L, or LESLPS

```
<400> SEQUENCE: 105

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Val Glu Phe Glu Asn Ser Glu Val Arg Xaa Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Xaa Glu Xaa Xaa
65                  70                  75                  80

Xaa Xaa Xaa Xaa Xaa Phe Lys Phe Phe Leu Tyr Val Xaa
                85                  90

<210> SEQ ID NO 106
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 106

Ser Arg Asn Gly Gly Pro Asp
1               5

<210> SEQ ID NO 107
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 107

Ser Arg Asn Pro Tyr Arg Arg
1               5

<210> SEQ ID NO 108
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 108

Ser Arg Asn Pro Tyr Arg Asp
1               5

<210> SEQ ID NO 109
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 109

Ser Trp Asn Gly Gly Pro Asp
1               5

<210> SEQ ID NO 110
<211> LENGTH: 7
<212> TYPE: PRT
<213> ORGANISM: Artificial Sequence
<220> FEATURE:
<223> OTHER INFORMATION: SYNTHETIC CONSTRUCT
```

```
<400> SEQUENCE: 110

Ser Trp Asn Pro Tyr Arg Arg
1               5

<210> SEQ ID NO 111
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 111

Ser Trp Asn Pro Tyr Arg Asp
1               5

<210> SEQ ID NO 112
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 112

Gly Arg Tyr Pro Tyr Glu Ser
1               5

<210> SEQ ID NO 113
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 113

Ser Trp Glu Pro Gly Arg Glu
1               5

<210> SEQ ID NO 114
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 114

Ala Arg Tyr Pro Tyr Arg Gln
1               5

<210> SEQ ID NO 115
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 115

Met Arg Asn Gly Gly Pro Asp
1               5

<210> SEQ ID NO 116
<211> LENGTH: 7
<212> TYPE: PRT
<213> ORGANISM: Artificial Sequence
<220> FEATURE:
<223> OTHER INFORMATION: SYNTHETIC CONSTRUCT
```

```
<400> SEQUENCE: 116

Ala Arg Asp Gly Gly Pro Asp
1               5

<210> SEQ ID NO 117
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 117

Ser Trp Ser Pro Tyr Lys Ala
1               5

<210> SEQ ID NO 118
<211> LENGTH: 6
<212> TYPE: PRT
<213> ORGANISM: Artificial Sequence
<220> FEATURE:
<223> OTHER INFORMATION: SYNTHETIC CONSTRUCT

<400> SEQUENCE: 118

Leu Glu Ser Leu Pro Ser
1               5

<210> SEQ ID NO 119
<211> LENGTH: 20
<212> TYPE: PRT
<213> ORGANISM: Artificial Sequence
<220> FEATURE:
<223> OTHER INFORMATION: SYNTHETIC CONSTRUCT

<400> SEQUENCE: 119

Leu Glu Ser Leu Pro Ser Pro Thr Leu Thr Cys Ala Leu Thr Asn Gly
1               5                   10                  15

Ser Ile Glu Val
            20

<210> SEQ ID NO 120
<211> LENGTH: 318
<212> TYPE: PRT
<213> ORGANISM: Artificial Sequence
<220> FEATURE:
<223> OTHER INFORMATION: SYNTHETIC CONSTRUCT

<400> SEQUENCE: 120

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
                20                  25                  30

Asp Lys Val Ala Glu Leu Glu Asn Ser Glu Phe Arg Ala Phe Ser Ser
            35                  40                  45

Phe Lys Asn Arg Val Tyr Leu Asp Thr Val Ser Gly Ser Leu Thr Ile
        50                  55                  60

Tyr Asn Leu Thr Ser Ser Asp Glu Asp Glu Tyr Glu Met Glu Ser Pro
65                  70                  75                  80

Asn Ile Thr Asp Thr Met Lys Phe Phe Leu Tyr Val Asp Lys Thr His
                85                  90                  95

Thr Cys Pro Pro Cys Pro Ala Pro Glu Leu Leu Gly Gly Pro Ser Val
                100                 105                 110
```

-continued

Phe Leu Phe Pro Pro Lys Pro Lys Asp Thr Leu Met Ile Ser Arg Thr
            115                 120                 125

Pro Glu Val Thr Cys Val Val Val Asp Val Ser His Glu Asp Pro Glu
130                 135                 140

Val Lys Phe Asn Trp Tyr Val Asp Gly Val Glu Val His Asn Ala Lys
145                 150                 155                 160

Thr Lys Pro Arg Glu Glu Gln Tyr Asn Ser Thr Tyr Arg Val Val Ser
            165                 170                 175

Val Leu Thr Val Leu His Gln Asp Trp Leu Asn Gly Lys Glu Tyr Lys
            180                 185                 190

Cys Lys Val Ser Asn Lys Ala Leu Pro Ala Pro Ile Glu Lys Thr Ile
            195                 200                 205

Ser Lys Ala Lys Gly Gln Pro Arg Glu Pro Gln Val Tyr Thr Leu Pro
            210                 215                 220

Pro Ser Arg Glu Glu Met Thr Lys Asn Gln Val Ser Leu Thr Cys Leu
225                 230                 235                 240

Val Lys Gly Phe Tyr Pro Ser Asp Ile Ala Val Glu Trp Glu Ser Asn
            245                 250                 255

Gly Gln Pro Glu Asn Asn Tyr Lys Thr Thr Pro Pro Val Leu Asp Ser
            260                 265                 270

Asp Gly Ser Phe Phe Leu Tyr Ser Lys Leu Thr Val Asp Lys Ser Arg
            275                 280                 285

Trp Gln Gln Gly Asn Val Phe Ser Cys Ser Val Met His Glu Ala Leu
            290                 295                 300

His Asn His Tyr Thr Gln Lys Ser Leu Ser Leu Ser Pro Gly
305                 310                 315

<210> SEQ ID NO 121
<211> LENGTH: 327
<212> TYPE: PRT
<213> ORGANISM: Artificial Sequence
<220> FEATURE:
<223> OTHER INFORMATION: SYNTHETIC CONSTRUCT

<400> SEQUENCE: 121

Lys Glu Ile Thr Asn Ala Leu Glu Thr Trp Gly Ala Leu Gly Gln Asp
1               5                   10                  15

Ile Asn Leu Asp Ile Pro Ser Phe Gln Met Ser Asp Asp Ile Asp Asp
            20                  25                  30

Ile Lys Trp Glu Lys Thr Ser Asp Lys Lys Lys Ile Ala Gln Phe Arg
            35                  40                  45

Lys Glu Lys Glu Thr Phe Lys Glu Lys Asp Thr Tyr Lys Leu Phe Lys
50                  55                  60

Asn Gly Thr Leu Lys Ile Lys His Leu Lys Thr Asp Asp Gln Asp Ile
65                  70                  75                  80

Tyr Lys Val Ser Ile Tyr Asp Thr Lys Gly Lys Asn Val Leu Glu Lys
            85                  90                  95

Ile Phe Asp Leu Lys Ile Gln Glu Arg Val Ser Lys Pro Lys Ile Ser
            100                 105                 110

Trp Thr Cys Ile Asn Thr Thr Leu Thr Cys Glu Val Met Asn Gly Thr
            115                 120                 125

Asp Pro Glu Leu Asn Leu Tyr Gln Asp Gly Lys His Leu Lys Leu Ser
            130                 135                 140

Gln Arg Val Ile Thr His Lys Trp Thr Thr Ser Leu Ser Ala Lys Phe
145                 150                 155                 160

Lys Cys Thr Ala Gly Asn Lys Val Ser Lys Glu Ser Ser Val Glu Pro
                165                 170                 175

Val Ser Cys Pro Glu Lys Gly Leu Asp Ile Tyr Leu Ile Ile Gly Ile
            180                 185                 190

Cys Gly Gly Gly Ser Leu Leu Met Val Phe Val Ala Leu Leu Val Phe
        195                 200                 205

Tyr Ile Thr Lys Arg Lys Lys Gln Arg Ser Arg Arg Asn Asp Glu Glu
    210                 215                 220

Leu Glu Thr Arg Ala His Arg Val Ala Thr Glu Glu Arg Gly Arg Lys
225                 230                 235                 240

Pro His Gln Ile Pro Ala Ser Thr Pro Gln Asn Pro Ala Thr Ser Gln
                245                 250                 255

His Pro Pro Pro Pro Gly His Arg Ser Gln Ala Pro Ser His Arg
            260                 265                 270

Pro Pro Pro Pro Gly His Arg Val Gln His Gln Pro Gln Lys Arg Pro
            275                 280                 285

Pro Ala Pro Ser Gly Thr Gln Val His Gln Gln Lys Gly Pro Pro Leu
        290                 295                 300

Pro Arg Pro Arg Val Gln Pro Lys Pro Pro His Gly Ala Ala Glu Asn
305                 310                 315                 320

Ser Leu Ser Pro Ser Ser Asn
                325

<210> SEQ ID NO 122
<211> LENGTH: 1014
<212> TYPE: DNA
<213> ORGANISM: Artificial Sequence
<220> FEATURE:
<223> OTHER INFORMATION: SYNTHETIC CONSTRUCT

<400> SEQUENCE: 122

| | | |
|---|---|---|
| atgggctggt cctgtatcat cctctttctg gtggccacag ctaccggagt gcatagcttt | 60 |
| tcacagcaga tttacggtgt tgtttacggt aatgtgactt tcacgttcc gagtaacgtt | 120 |
| cctttgaagg aagtcttatg gaaaaaacaa aaagataaag ttgtagaatt tgagaatagt | 180 |
| gaggttaggg catttagttc atttaagaat agggtctatt tggatactgt atccggttct | 240 |
| ttgaccattt ataatttaac aagtagtgat gaagacgagt acgaaatgga gtcccctaat | 300 |
| attacagaca cattcaagtt ttttttgtac gttctcgaca aaactcacac atgcccaccg | 360 |
| tgcccagcac ctgaactcct ggggggaccg tcagtcttcc tcttcccccc aaaacccaag | 420 |
| gacaccctca tgatctcccg gacccctgag gtcacatgcg tggtggtgga cgtgagccac | 480 |
| gaagaccctg aggtcaagtt caactggtac gtggacggcg tggaggtgca taatgccaag | 540 |
| acaaagccgc gggaggagca gtacaacagc acgtaccgtg tggtcagcgt cctcaccgtc | 600 |
| ctgcaccagg actggctgaa tggcaaggag tacaagtgca aggtctccaa caaagccctc | 660 |
| ccagccccca tcgagaaaac catctccaaa gccaagggc agccccgaga accacaggtg | 720 |
| tacaccctgc ccccatcccg ggaagagatg accaagaacc aggtcagcct gacctgcctg | 780 |
| gtcaaaggct tctatcccag cgacatcgcc gtggagtggg agagcaatgg gcagccggag | 840 |
| aacaactaca agaccacgcc tcccgtgttg gactccgacg gctccttctt cctctacagc | 900 |
| aagctcaccg tggacaagag caggtggcag caggggaacg tcttctcatg ctccgtgatg | 960 |
| catgaggctc tgcacaacca ctacacgcag aagagcctct ccctgtctcc gggt | 1014 |

<210> SEQ ID NO 123
<211> LENGTH: 957
<212> TYPE: DNA
<213> ORGANISM: Artificial Sequence
<220> FEATURE:
<223> OTHER INFORMATION: SYNTHETIC CONSTRUCT

<400> SEQUENCE: 123

```
ttttcacagc agatttacgg tgttgtttac ggtaatgtga cttttcacgt tccgagtaac      60
gttcctttga aggaagtctt atggaaaaaa caaaaagata agttgtaga atttgagaat     120
agtgaggtta gggcatttag ttcatttaag aatagggtct atttggatac tgtatccggt     180
tctttgacca tttataattt aacaagtagt gatgaagacg agtacgaaat ggagtcccct     240
aatattacag acacattcaa gttttttttg tacgttctcg acaaaactca cacatgccca     300
ccgtgcccag cacctgaact cctgggggga ccgtcagtct tcctcttccc cccaaaaccc     360
aaggacaccc tcatgatctc ccggacccct gaggtcacat gcgtggtggt ggacgtgagc     420
cacgaagacc ctgaggtcaa gttcaactgg tacgtggacg gcgtggaggt gcataatgcc     480
aagacaaagc cgcgggagga gcagtacaac agcacgtacc gtgtggtcag cgtcctcacc     540
gtcctgcacc aggactggct gaatggcaag gagtacaagt gcaaggtctc caacaaagcc     600
ctcccagccc ccatcgagaa aaccatctcc aaagccaaag gcagccccg agaaccacag     660
gtgtacaccc tgcccccatc ccgggaagag atgaccaaga accaggtcag cctgacctgc     720
ctggtcaaag gcttctatcc cagcgacatc gccgtggagt gggagagcaa tgggcagccg     780
gagaacaact acaagaccac gcctcccgtg ttggactccg acggctcctt cttcctctac     840
agcaagctca ccgtggacaa gagcaggtgg cagcagggga acgtcttctc atgctccgtg     900
atgcatgagg ctctgcacaa ccactacacg cagaagagcc tctccctgtc tccgggt        957
```

<210> SEQ ID NO 124
<211> LENGTH: 1041
<212> TYPE: DNA
<213> ORGANISM: Artificial Sequence
<220> FEATURE:
<223> OTHER INFORMATION: SYNTHETIC CONSTRUCT

<400> SEQUENCE: 124

```
atggttgctg ggagcgacgc ggggcgggcc ctggggtcc tcagcgtggt ctgcctgctg      60
cactgctttg gtttcatcag ctgttttttcc caacaaatat atggtgttgt gtatgggaat     120
gtaactttcc atgtaccaag caatgtgcct ttaaagagg tcctatggaa aaacaaaag     180
gataaagttg cagaactgga aaattctgaa ttcagagctt tctcatcttt taaaaatagg     240
gtttatttag acactgtgtc aggtagcctc actatctaca acttaacatc atcagatgaa     300
gatgagtatg aaatggaatc gccaaatatt actgatacca tgaagttctt tctttatgtc     360
gacaaaactc acacatgccc accgtgccca gcacctgaac tcctgggggg accgtcagtc     420
ttcctcttcc cccaaaaccc aaggacaccc tcatgatct cccggacccc tgaggtcaca     480
tgcgtggtgg tggacgtgag ccacgaagac cctgaggtca gttcaactg gtacgtggac     540
ggcgtggagg tgcataatgc caagacaaag ccgcgggagg agcagtacaa cagcacgtac     600
cgtgtggtca gcgtcctcac cgtcctgcac caggactggc tgaatggcaa ggagtacaag     660
tgcaaggtct ccaacaaagc cctcccagcc ccatcgaga aaccatctc caaagccaaa     720
gggcagcccc gagaaccaca ggtgtacacc ctgcccccat cccggatga gctgaccaag     780
aaccaggtca gcctgacctg cctggtcaaa ggcttctatc ccagcgacat cgccgtggag     840
```

```
tgggagagca atgggcagcc ggagaacaac tacaagacca cgcctcccgt gttggactcc    900
gacggctcct tcttcctcta cagcaagctc accgtggaca agagcaggtg gcagcagggg    960
aacgtcttct catgctccgt gatgcatgag gctctgcaca accactacac gcagaagagc   1020 ctctcccctgt ctccgggtaa a                                            1041
```

<210> SEQ ID NO 125
<211> LENGTH: 957
<212> TYPE: DNA
<213> ORGANISM: Artificial Sequence
<220> FEATURE:
<223> OTHER INFORMATION: SYNTHETIC CONSTRUCT

<400> SEQUENCE: 125

```
ttttcccaac aaatatatgg tgttgtgtat gggaatgtaa ctttccatgt accaagcaat     60
gtgcctttaa aagaggtcct atggaaaaaa caaaaggata aagttgcaga actggaaaat    120
tctgaattca gagctttctc atcttttaaa aatagggttt atttagacac tgtgtcaggt    180
agcctcacta tctacaactt aacatcatca gatgaagatg agtatgaaat ggaatcgcca    240
aatattactg ataccatgaa gttctttctt tatgtcgaca aaactcacac atgcccaccg    300
tgcccagcac ctgaactcct gggggaccg tcagtcttcc tcttcccccc aaaacccaag    360
gacaccctca tgatctcccg gacccctgag gtcacatgcg tggtggtgga cgtgagccac    420
gaagaccctg aggtcaagtt caactggtac gtggacggcg tggaggtgca taatgccaag    480
acaaagccgc gggaggagca gtacaacagc acgtaccgtg tggtcagcgt cctcaccgtc    540
ctgcaccagg actggctgaa tggcaaggag tacaagtgca aggtctccaa caaagccctc    600
ccagccccca tcgagaaaac catctccaaa gccaagggc agccccgaga accacaggtg    660
tacaccctgc cccatcccg ggatgagctg accaagaacc aggtcagcct gacctgcctg    720
gtcaaaggct tctatcccag cgacatcgcc gtggagtggg agagcaatgg gcagccggag    780
aacaactaca agaccacgcc tcccgtgttg gactccgacg gctccttctt cctctacagc    840
aagctcaccg tggacaagag caggtggcag caggggaacg tcttctcatg ctccgtgatg    900
catgaggctc tgcacaacca ctacacgcag aagagcctct ccctgtctcc gggtaaa      957
```

<210> SEQ ID NO 126
<211> LENGTH: 276
<212> TYPE: DNA
<213> ORGANISM: Artificial Sequence
<220> FEATURE:
<223> OTHER INFORMATION: SYNTHETIC CONSTRUCT

<400> SEQUENCE: 126

```
ttttcccaac aaatatatgg tgttgtgtat gggaatgtaa ctttccatgt accaagcaat     60
gtgcctttaa aagaggtcct atggaaaaaa caaaaggata aagttgcaga actggaaaat    120
tctgaattca gagctttctc atcttttaaa aatagggttt atttagacac tgtgtcaggt    180
agcctcacta tctacaactt aacatcatca gatgaagatg agtatgaaat ggaatcgcca    240
aatattactg ataccatgaa gttctttctt tatgtc                              276
```

<210> SEQ ID NO 127
<211> LENGTH: 681
<212> TYPE: DNA
<213> ORGANISM: Artificial Sequence
<220> FEATURE:
<223> OTHER INFORMATION: SYNTHETIC CONSTRUCT

<400> SEQUENCE: 127

```
gacaaaactc acacatgccc accgtgccca gcacctgaac tcctgggggg accgtcagtc      60
ttcctcttcc ccccaaaacc caaggacacc ctcatgatct cccggacccc tgaggtcaca    120
tgcgtggtgg tggacgtgag ccacgaagac cctgaggtca agttcaactg gtacgtggac    180
ggcgtggagg tgcataatgc caagacaaag ccgcgggagg agcagtacaa cagcacgtac    240
cgtgtggtca gcgtcctcac cgtcctgcac caggactggc tgaatggcaa ggagtacaag    300
tgcaaggtct ccaacaaagc cctcccagcc cccatcgaga aaaccatctc caaagccaaa    360
gggcagcccc gagaaccaca ggtgtacacc ctgcccccat cccgggatga gctgaccaag    420
aaccaggtca gcctgacctg cctggtcaaa ggcttctatc ccagcgacat cgccgtggag    480
tgggagagca atgggcagcc ggagaacaac tacaagacca cgcctcccgt gttggactcc    540
gacggctcct tcttcctcta cagcaagctc accgtggaca agagcaggtg gcagcagggg    600
aacgtcttct catgctccgt gatgcatgag gctctgcaca accactacac gcagaagagc    660
ctctccctgt ctccgggtaa a                                              681
```

<210> SEQ ID NO 128
<211> LENGTH: 227
<212> TYPE: PRT
<213> ORGANISM: Artificial Sequence
<220> FEATURE:
<223> OTHER INFORMATION: SYNTHETIC CONSTRUCT

<400> SEQUENCE: 128

```
Asp Lys Thr His Thr Cys Pro Pro Cys Pro Ala Pro Glu Leu Leu Gly
  1               5                  10                  15
Gly Pro Ser Val Phe Leu Phe Pro Pro Lys Pro Lys Asp Thr Leu Met
                 20                  25                  30
Ile Ser Arg Thr Pro Glu Val Thr Cys Val Val Val Asp Val Ser His
             35                  40                  45
Glu Asp Pro Glu Val Lys Phe Asn Trp Tyr Val Asp Gly Val Glu Val
         50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
```

Pro Gly Lys
225

<210> SEQ ID NO 129
<211> LENGTH: 28
<212> TYPE: PRT
<213> ORGANISM: Artificial Sequence
<220> FEATURE:
<223> OTHER INFORMATION: SYNTHETIC CONSTRUCT

<400> SEQUENCE: 129

Met Val Ala Gly Ser Asp Ala Gly Arg Ala Leu Gly Val Leu Ser Val
1               5                   10                  15

Val Cys Leu Leu His Cys Phe Gly Phe Ile Ser Cys
            20                  25

<210> SEQ ID NO 130
<211> LENGTH: 84
<212> TYPE: DNA
<213> ORGANISM: Artificial Sequence
<220> FEATURE:
<223> OTHER INFORMATION: SYNTHETIC CONSTRUCT

<400> SEQUENCE: 130
atggttgctg ggagcgacgc ggggcgggcc ctgggggtcc tcagcgtggt ctgcctgctg    60
cactgctttg gtttcatcag ctgt    84

LYMPHOCYTE FUNCTION-ASSOCIATED ANTIGEN 3 (LFA3) VARIANT POLYPEPTIDES AND METHODS OF USE THEREOF TO TREAT CD2-MEDIATED IMMUNE DISEASES, DISORDERS OR CONDITIONS

RELATED APPLICATIONS

The present application is a continuation of International Application No. PCT/US2019/023883, filed Mar. 25, 2019, now expired, which claims priority to U.S. Provisional Patent Application No. 62/650,022 filed Mar. 29, 2018, and to U.S. Provisional Patent Application No. 62/783,986 filed Dec. 21, 2018, the contents of each of which are incorporated herein by reference in their entirety.

REFERENCE TO SEQUENCE LISTING

This application is being filed electronically and includes an electronically submitted sequence listing in .txt format. The .txt file contains a sequence listing entitled "Sequence_Listing_1142687_1210270_ST25.txt" created on Sep. 17, 2020 and having a size of 127,762 bytes. The sequence listing contained in this .txt file is part of the specification and is herein incorporated by reference in its entirety.

PARTIES TO A JOINT RESEARCH STATEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are THE REGENTS OF THE UNIVERSITY OF CALIFORNIA on behalf of its SAN FRANCISCO CAMPUS and PFIZER INC.

FIELD

The present invention relates to polypeptide molecules that comprise a lymphocyte function-associated antigen 3 (LFA3) domain, and compositions, methods and uses thereof.

BACKGROUND

Lymphocyte function-associated antigen 3 (LFA3), also known as CD58, is a ligand of CD2 and is expressed on many cell types, including antigen presenting cells (APCs) (Miller et al., J. Exp. Med. 1993 178(1):211-22; Krueger et al., Expert Opin. Biol. Ther. 2002 2(4):431-41; Haider et al., J. Immunol. 2007 393:411-20; Punch et al., Transplantation 1999 67(5):741-8; Leitner et al., J. Immunol. 2015 195(2): 477-87). CD2 is expressed on all T cells, but expression is greater on memory T cells as compared to naïve or regulatory T cells (Chamian et al., Proc. Natl. Acad. Sci. 2005 102(6):2075-80; Rigby et al., J. Clin. Invest. 2015 125(8): 3285-96). In humans, CD2 is also expressed on NK cells and some dendritic cell populations. Interaction of CD2 on T cells or NK cells and LFA3 on accessory cells can deliver a costimulatory signal for both naïve lymphocytes and previously activated or memory lymphocytes. This costimulatory signal potentially involves increasing the avidity of cell-cell interaction and/or delivering a direct costimulatory signal through CD2 (Kaizuka et al. J. Cell Biol. 2009 185(3):521-34; Skanland et al., Biochem. J. 2014 460(3):399-410). As such, targeting CD2, e.g., using soluble LFA3 molecules, may have therapeutic benefit for treating autoimmune diseases, such as Type 1 Diabetes (T1D) and/or psoriatic arthritis. Accordingly, in view of the prominent role of CD2 and LFA3 in mediating immune responses, the need exists for developing strategies for modulating the activity of CD2 as well as depleting CD2-expressing immune effector cells.

SUMMARY OF THE INVENTION

The present disclosure provides, in part, the discovery that certain LFA3-Fc fusion polypeptides modulate the activity of CD2, as well as deplete CD2-expressing cells. Modulation of CD2-expressing cells may have beneficial effects in the treatment of autoimmune disease, such as diabetes and or psoriatic arthritis. This application discloses LFA3 polypeptide molecules, e.g., variant LFA3 polypeptide molecules, e.g., variant LFA3 fusion polypeptide molecules, e.g., variant LFA3-Fc fusion polypeptide molecules. In certain aspects, the LFA3 polypeptide molecules bind to CD2, modulate CD2-LFA3 interaction, and selectively deplete CD2-expressing memory T cells.

Without wishing to be bound by theory, the LFA3 polypeptide molecules disclosed herein, e.g., the variant LFA3-Fc fusion polypeptide molecules, e.g., M1d1 (also referred to herein as M1-d1, LFA3-Fc M1d1 and LFA3-Fc M1-d1), modulate the function of and selective depletion of CD2+ $T_{EM}$ cells to rebalance the regulatory/$T_{EM}$ cell numbers. In some embodiments, the LFA3 polypeptide molecules disclosed herein, e.g., the variant LFA3-Fc fusion polypeptide molecules, e.g., M1d1 promote elimination and/or suppression of pathogenic T effector cells. In some embodiments, the LFA3 polypeptide molecules disclosed herein, e.g., the variant LFA3-Fc fusion polypeptide molecules, e.g., M1d1, modulate the interaction between CD2 and LFA3, thereby interrupting CD2-mediated T cell co-stimulation. In some embodiments, the LFA3 polypeptide molecules disclosed herein, e.g., the variant LFA3-Fc fusion polypeptide molecules, e.g., M1d1, deplete CD2+ T cells via FcR-mediated antibody dependent cellular cytotoxicity (ADCC). In some embodiments, the LFA3 polypeptide molecules disclosed herein, e.g., the variant LFA3-Fc fusion polypeptide molecules, e.g., M1d1, deplete CD2+ T cells via apoptosis. In some embodiments, the LFA3 polypeptide molecules disclosed herein, e.g., the variant LFA3-Fc fusion polypeptide molecules, e.g., M1d1, decrease the number of $CD2^{high}$ T memory cells ($T_{mem}$), e.g., central memory ($T_{CM}$) and effector memory ($T_{EM}$) T cells, while preserving regulatory T cells (Tregs). In some embodiments, the LFA3 polypeptide molecules disclosed herein, e.g., the variant LFA3-Fc fusion polypeptide molecules, e.g., M1d1, decrease the number of $CD2^{high}T_{mem}$ cells, e.g., central memory ($T_{CM}$) and effector memory ($T_{EM}$) T cells, while preserving regulatory T naïve cells. In some embodiments, the LFA3 polypeptide molecules disclosed herein, e.g., the variant LFA3-Fc fusion polypeptide molecules, e.g., M1d1, increase the Treg/$T_{EM}$ ratio or the Treg/$T_{CM}$ ratio, e.g., in CD4+ and/or CD8+ T cells. In some embodiments, the LFA3 polypeptide molecules disclosed herein, e.g., the variant LFA3-Fc fusion polypeptide molecules, e.g., M1d1, increase the proportion of CD4+ $T_{EM}$ cells expressing PD-1 and/or TIGIT.

Without wishing to be bound by theory, the LFA3 polypeptide molecules disclosed herein, e.g., the variant LFA3-Fc fusion polypeptide molecules, e.g., M1d1, bind to CD2, a cell surface protein expressed most prominently on CD4+ and CD8+ T$_{EM}$ (T effector memory) cells, the cells primarily responsible for beta cell destruction in type 1 Diabetes (T1D). Administration of the LFA3 polypeptide molecules disclosed herein, e.g., the variant LFA3-Fc fusion polypeptide molecules, e.g., M1d1, may lead to extended preservation of endogenous insulin production, reduction in insulin requirements, decrease in the rate of major hypoglycemia, and restoration of β cells in T1D patients.

In some embodiments, the LFA3 polypeptide molecules, e.g., the variant LFA3 polypeptide molecules, of this invention have been engineered to improve their stability and manufacturability relative to the wild type LFA3 sequence. In some embodiments, the LFA3 polypeptide molecules, e.g., the variant LFA3 polypeptide molecules, of this invention have been engineered to increase their binding affinity to CD2 relative to the wild type LFA3 sequence.

In one aspect, the disclosure provides a LFA3 fusion polypeptide molecule comprising a LFA3 domain fused to a second domain. Without wishing to be bound by theory, extending the C-terminal boundary of the LFA3 domain in the LFA3 fusion polypeptide molecule improves one or more activities of the LFA3 fusion polypeptide molecule. For example, extending the C-terminal boundary of the LFA3 domain to include the amino acid residue of Leu, which corresponds to position 93 of wild type LFA3 (e.g., position 93 of SEQ ID NO: 2), or the amino acid sequence of LESLPS (SEQ ID NO: 118), which corresponds to positions 93-98 of wild type LFA3 (e.g., positions 93-98 of SEQ ID NO: 2) improves one or more activities of the LFA3 fusion polypeptide molecule, e.g., increased thermal stability and/or reduced aggregation, e.g., as shown in FIGS. 6B-6D.

Those skilled in the art will recognize or be able to ascertain using no more than routine experimentation, many equivalents to the specific embodiments of the invention described herein. Such equivalents are intended to be encompassed by the following embodiments (E).

E1. An isolated polypeptide molecule (e.g., a fusion polypeptide molecule) that specifically binds to CD2, wherein the polypeptide molecule comprises a LFA3 domain (e.g., a variant LFA3-Fc fusion as described herein) and has one or more of the following properties:

i. Enhanced monomeric expression relative to a polypeptide molecule comprising the amino acid sequence of SEQ ID NO: 120, e.g., showing a percentage of monomers that is more than about 70, 75, 80, 85, 90, 95, 98 or 99%, e.g., as measured using size exclusion chromatography (SEC) and/or methods described in Example 1 with respect to FIG. 3A, ii. Enhanced monomeric expression and reduced multimeric expression relative to a polypeptide molecule comprising the amino acid sequence of SEQ ID NO: 4, e.g., showing a percentage of monomers that is more than about 75, 80, 85, 90, 95, 98 or 99%, a percentage of low molecular weight species (LMWS) that is less than about 10, 8, 6, 4, or 2%, and/or a percentage of high molecular weight species (HMWS) that is less than about 5, 2, or 1%, e.g., as measured using SEC and/or methods described in Example 1 with respect to FIG. 6C, iii. Reduced aggregation propensity under thermal stress relative to a polypeptide molecule comprising the amino acid sequence of SEQ ID NO: 120, e.g., showing a percentage of monomers that is more than about 90, 92, or 95% after incubating at 37.4° C. for 24 hours, and/or showing a percentage of monomers that is more than about 75, 80, or 85% after incubating at 40° C. for 24 hours, e.g., as measured using SEC and/or methods described in Example 1 with respect to FIG. 3D, iv. Reduced aggregation propensity under thermal stress relative to a polypeptide molecule comprising the amino acid sequence of SEQ ID NO: 4, e.g., showing no more than about 5, 10, 15, or 20% increase in HMWS at 40° C., and/or no more than about 5, 10, 15, 20, or 25% increase in HMWS at 50° C., e.g., as measured using SEC and/or methods described in Example 1 with respect to Table 4, v. Reduced aggregation propensity under low pH relative to a polypeptide molecule comprising the amino acid sequence of SEQ ID NO: 4, e.g., showing no more than about 6, 7, 8, or 9% increase in HMWS at low pH for 5 hours, e.g., as measured using SEC and/or methods described in Example 1 with respect to Table 4, vi. Enhanced stability relative to a polypeptide molecule comprising the amino acid sequence of SEQ ID NO: 4, e.g., showing no more than about 0.5, 1, 1.5, or 2% increase in HMMS and/or about 0.5, 1, 2, 3, 4 or 5% increase in LMMS after 2 or 4 weeks of storage at 40° C. as measured using capillary gel electrophoresis (CGE), size exclusion high performance liquid chromatography (SE-HPLC), and/or methods described in Example 4 with respect to FIGS. 30A-30C or FIGS. 31A-31D, vii. Enhanced stability relative to a polypeptide molecule comprising the amino acid sequence of SEQ ID NO: 4, e.g., showing no more than about 0.5, 1, 1.5, or 2% increase in HMMS and/or about 0.5, 1, or 1.5% increase in LMMS after 2, 4 or 6 weeks of storage at 25° C. as measured using SE-HPLC, and/or methods described in Example 4 with respect to FIGS. 32A-32D, viii. Enhanced stability relative to a polypeptide molecule comprising the amino acid sequence of SEQ ID NO: 4, e.g., showing no more than about 0.5, 1, or 1.5% increase in HMMS and/or about 0.5, 1, or 1.5% increase in LMMS after 2, 4 or 6 weeks of storage at 5° C. as measured using SE-HPLC, and/or methods described in Example 4 with respect to FIGS. 33A-33D, ix. Enhanced freeze-thaw stability relative to a polypeptide molecule comprising the amino acid sequence of SEQ ID NO: 4, e.g., showing no more than about 0.5, 1, or 1.5% increase in HMWS after 5 cycles of freeze-thaw, e.g., as measured using SEC and/or methods described in Example 1 with respect to Table 4, x. Increased yield relative to a polypeptide molecule comprising the amino acid sequence of SEQ ID NO: 120, e.g., having a yield that is more than about 5.5, 6, 6.5, or 7 mg per 20 mL Expi293 culture, e.g., as measured using methods described in Example 1 with respect to FIG. 3B, xi. Increased Tm relative to a polypeptide molecule comprising the amino acid sequence of SEQ ID NO: 120, e.g., having a Tm that is more than about 38, 40, 42, or 45° C., e.g., as measured by differential scanning fluorometry (DSF) and/or using methods described in Example 1 with respect to FIG. 3C, xii. Increased Tm relative to a polypeptide molecule comprising the amino acid sequence of SEQ ID NO: 4, e.g., having a Tm that is more than about 40, 45, 50, 55, or 60° C., e.g., as measured by DSF and/or using methods described in Example 1 with respect to FIG. 5B, xiii. Increased Tm relative to a polypeptide molecule comprising the amino acid sequence of SEQ ID NO: 120, e.g., having a Tm that is more than about 40, 45, or 50° C., e.g., as measured by DSF and/or using methods described in Example 1 with respect to FIG. 6D, xiv. Increased Tm relative to a polypeptide molecule comprising the amino acid sequence of SEQ ID NO: 4, e.g., having a Tm that is more than about 45, 50, or 55° C., e.g., as measured by DSF and/or using methods described in Example 1 with respect to FIG. 7D, xv. Increased Tm relative to a polypeptide molecule comprising the amino acid sequence of SEQ ID NO: 4, e.g., having a Tm that is more than about 50 or 60° C., e.g., as measured by differential scanning calorimetry (DSC) and/or using methods described in Example 1 with respect to Table 4, xvi. A Tm1 that is more than about 55, 58, 60, 62, 64 or 66° C. and a Tm2 that is more than about 75, 78, 80, or 82° C. at pH 7.5; a Tm1 that is more than about 55, 58, 60, 62 or 64° C. and a Tm2 that is more than about 75, 78, 80 or 82° C. at pH 5.8; or a Tm1 that is more than 55, 58 or 60° C. and a Tm2 that is more than about 75, 78, or 80° C. at pH 4.5, e.g., as measured by DSC and/or using methods described in Example 4 with respect to Table 13, xvii. Increased Tm relative to a polypeptide molecule comprising the amino acid sequence of SEQ ID NO: 4, e.g., having a Tm that is more than about 50 or 60° C. at pH 7.5 or pH 4.5; having a Tm that is more than about 50 or 62° C. at pH 5.8, e.g., as measured by DSC and/or using methods described in Example 4 with respect to Table 14, xviii. Increased Tm relative to a polypeptide molecule comprising the amino acid sequence of SEQ ID NO: 4, e.g., having a Tm that is more than about 50 or 60° C., e.g., as measured by DSC and FabRICATOR® IdeS and/or using methods described in Example 4 with respect to Table 15, xix. Enhanced binding affinity to CD2 relative to a polypeptide molecule comprising the amino acid sequence of SEQ ID NO: 4, e.g., a $K_D$ for human CD2 that is less than about 1.2, 1, 0.8, 0.6, 0.4, 0.2, 0.1, or 0.08 μM, e.g., as measured by SPR and/or using methods described in Example 1 with respect to FIG. 5A, xx. Enhanced binding affinity to CD2 relative to a polypeptide molecule comprising the amino acid sequence of SEQ ID NO: 4, e.g., a $K_D$ for human CD2 that is less than about 1.3, 1.2, 1.1, or 1 μM, and/or a $K_D$ for cynomolgus CD2 that is less than about 1.4, 1.3, 1.2, 1.1, or 1 μM, e.g., as measured by SPR and/or using methods described in Example 1 with respect to FIG. 7C, xxi. Enhanced binding affinity to CD2-expressing cells relative to a polypeptide molecule comprising the amino acid sequence of SEQ ID NO: 4, e.g., a $K_d$ for binding to CD4 T memory ($T_{mem}$) cells that is no more than about 100, 200, 300, or 400 pM, e.g., as measured using methods described in Example 2 with respect to Table 6, xxii. Enhanced binding affinity to CD2-expressing cells relative to a polypeptide molecule comprising the amino acid sequence of SEQ ID NO: 4, e.g., a calculated IC50 for binding to CD4 memory T cells that is no more than about 300, 400, 500, 600, 700, 800, 1000, 1200 or 1500 pM; a calculated IC50 for binding to CD4+ $T_{EM}$ cells that is no more than about 150, 300, 400, 500, 600, 700, 800, 1000 or 1200 pM; a calculated IC50 for binding to CD4+ $T_{CM}$ cells that is no more than about 100, 200, 300, 400, 500, 600, 700 or 800 pM; a calculated IC50 for binding to CD4 naïve T cells that is no more than about 200, 300, 400, 500, 600, 700, 800, 1000 or 1200 pM; a calculated IC50 for binding to expanded CD4 Treg cells that is no more than about 100, 200, 300, 400 or 500 pM; a calculated IC50 for binding to CD8 memory T cells that is no more than about 100, 200, 300, 400, 500 or 600 pM; and/or a calculated IC50 for binding to CD8 native T cells that is no more than about 300, 400, 500, 600, 700, 800, 1000, 1200, 1500, 1600 or 1700 pM, e.g., as measured using SPR and/or methods described in Example 2 with respect to Table 10 and FIG. 11, xxiii. Enhanced binding affinity to CD2-expressing cells relative to a polypeptide molecule comprising the amino acid sequence of SEQ ID NO: 4, e.g., a calculated $K_d$ for binding to CD4 memory T cells that is no more than about 100, 200, 300, 400, or 500 pM; a calculated $K_d$ for binding to CD4+ $T_{EM}$ cells that is no more than about 100, 200, 300, 400, 500, or 600 pM; a calculated $K_d$ for binding to CD4+ $T_{CM}$ cells that is no more than about 100, 200, 300, 400, or 500 pM; a calculated $K_d$ for binding to CD4 naïve T cells that is no more than about 100, 200, 300, or 400 pM; a calculated $K_d$ for binding to expanded CD4 Treg cells that is no more than about 100, 200, or 300 pM; a calculated $K_d$ for binding to CD8 memory T cells that is no more than about 50, 100, or 150 pM; a calculated $K_d$ for binding to CD8 naïve T cells that is no more than about 50, 100, 200, 300, 400, or 500 pM, e.g., as measured using SPR and/or methods described in Example 2 with respect to Table 10 and FIG. 11, xxiv. Enhanced binding affinity to CD2-expressing cells relative to a polypeptide molecule comprising the amino acid sequence of SEQ ID NO: 4, e.g., a reduced EC50 for binding to cynomolgus CD4+ $T_{EM}$ cells relative to a polypeptide molecule comprising the amino acid sequence of SEQ ID NO: 4, e.g., as measured using SPR and/or methods described in Example 3 with respect to FIGS. 18A and 18B, xxv. Enhanced cytotoxicity against CD2-expressing cells relative to a polypeptide molecule comprising the amino acid sequence of SEQ ID NO: 4, e.g., an EC50 for killing CD4 $T_{mem}$ cells that is no more than about 400, 600, 800, 1000, 1200, 1400 pM, or 1500 pM e.g., as measured using an antibody dependent cellular cytotoxicity (ADCC) assay and/or methods described in Example 5 with respect to Table 17 and FIGS. 12A and 12B, xxvi. Enhanced cytotoxicity against CD2-expressing cells relative to a polypeptide molecule comprising the amino acid sequence of SEQ ID NO: 4, e.g., an EC50 for killing CD8 $T_{mem}$ cells that is no more than about 1, 5, 10, 20, 30, 40, 50 nM e.g., as measured using an antibody dependent cellular cytotoxicity (ADCC) assay and/or methods described in Example 5 with respect to Table 17 and FIG. 12D, xxvii. Enhanced inhibition of allogeneic T cell response, e.g., T cell proliferation and cytokine production, relative to a polypeptide molecule comprising the amino acid sequence of SEQ ID NO: 4, e.g., an IC50 that is no more than about 400, 800, 1200, 1600, 2000, or 2400 pM, e.g., as measured using a mixed lymphocyte reaction (MLR) assay and/or methods described in Example 2 with respect to Table 6 and FIGS. 14A and 14B, xxviii. Enhanced inhibition of allogeneic T cell response, e.g., T cell proliferation and cytokine production, relative to a polypeptide molecule comprising the amino acid sequence of SEQ ID NO: 4, e.g., an IC50 for a mixed lymphocyte reaction (MLR) assay in the absence of NK cells that is no more than about 300, 400, 500, 600, 800, 1000, 1500 or 2000 pM, e.g., as measured using a mixed lymphocyte reaction (MLR) assay and/or methods described in Example 2 with respect to FIGS. 15B and 15C, xxix. Enhanced inhibition of tetanus toxoid recall response relative to a polypeptide molecule comprising the amino acid sequence of SEQ ID NO: 4, e.g., an IC50 for CD4 $T_{mem}$ IFNγ production that is no more than about 1, 2, 5, 10, 15, 20, or 25 nM, e.g., as measured using a tetanus toxoid recall (TTR) assay and/or methods described in Example 2 with respect to Table 6 and FIGS. 16A and 16B, xxx. Slower clearance in vivo relative to a polypeptide molecule comprising the amino acid sequence of SEQ ID NO: 4, e.g., a clearance from central that is no more than about 0.14, 0.16, 0.18, 0.2, or 0.22 mL/hr/kg, e.g., as measured using methods described in Example 2 with respect to Table 11, xxxi. Enhanced purity relative to a polypeptide molecule comprising the amino acid sequence of SEQ ID NO: 4, e.g., a purity of at least about 98% or 99% as measured using capillary gel electrophoresis and/or methods described in Example 1 or 4, or xxxii. Reduced sialic acid modification relative to a polypeptide molecule comprising the amino acid sequence of SEQ ID NO: 4, e.g., a purity of not more than about 20, 18, 16, 14, 12, 10, 9, 8 or 7 nmol sialic acid/nmol polypeptide as measured using capillary gel electrophoresis and/or method described in Example 1 or 4.

E2. The isolated polypeptide molecule of E1, wherein the polypeptide molecule has enhanced monomeric expression relative to a polypeptide molecule comprising the amino acid sequence of SEQ ID NO: 120, e.g., showing a percentage of monomers that is more than about 70, 75, 80, 85, 90, or 95%, e.g., as measured using SEC and/or methods described in Example 1 with respect to FIG. 3A.

E3. The isolated polypeptide molecule of E1 or E2, wherein the polypeptide molecule has enhanced monomeric expression and reduced multimeric expression relative to a polypeptide molecule comprising the amino acid sequence of SEQ ID NO: 4, e.g., showing a percentage of monomers that is more than about 75, 80, 85, 90, or 95%, a percentage of low molecular weight species (LMWS) that is less than about 10, 8, 6, 4, or 2%, and/or a percentage of high molecular weight species (HMWS) that is less than about 5, 2, or 1%, e.g., as measured using SEC and/or methods described in Example 1 with respect to FIG. 6C.

E4. The isolated polypeptide molecule of any one of the preceding embodiments, wherein the polypeptide molecule has reduced aggregation propensity under thermal stress relative to a polypeptide molecule comprising the amino acid sequence of SEQ ID NO: 120, e.g., showing a percentage of monomers that is more than about 90, 92, or 95% after incubating at 37.4° C. for 24 hours, and/or showing a percentage of monomers that is more than about 75, 80, or 85% after incubating at 40° C. for 24 hours, e.g., as measured using SEC and/or methods described in Example 1 with respect to FIG. 3D.

E5. The isolated polypeptide molecule of any one of the preceding embodiments, wherein the polypeptide molecule has reduced aggregation propensity under thermal stress relative to a polypeptide molecule comprising the amino acid sequence of SEQ ID NO: 4, e.g., showing no more than about 5, 10, 15, or 20% increase in HMWS at 40° C., and/or no more than about 5, 10, 15, 20, or 25% increase in HMWS at 50° C., e.g., as measured using SEC and/or methods described in Example 1 with respect to Table 4.

E6. The isolated polypeptide molecule of any one of the preceding embodiments, wherein the polypeptide molecule has reduced aggregation propensity under low pH relative to a polypeptide molecule comprising the amino acid sequence of SEQ ID NO: 4, e.g., showing no more than about 6, 7, 8, or 9% increase in HMWS at low pH for 5 hours, e.g., as measured using SEC and/or methods described in Example 1 with respect to Table 4.

E7. The isolated polypeptide molecule of any one of the preceding embodiments, wherein the polypeptide molecule has enhanced freeze-thaw stability relative to a polypeptide molecule comprising the amino acid sequence of SEQ ID NO: 4, e.g., showing no more than about 0.5, 1, or 1.5% increase in HMWS after 5 cycles of freeze-thaw, e.g., as measured using SEC and/or methods described in Example 1 with respect to Table 4.

E8. The isolated polypeptide molecule of any one of the preceding embodiments, wherein the polypeptide molecule has enhanced stability relative to a polypeptide molecule comprising the amino acid sequence of SEQ ID NO: 4, e.g., showing no more than about 0.5, 1, 1.5, or 2% increase in HMMS and/or about 0.5, 1, 2, 3, 4 or 5% increase in LMMS after 2 or 4 weeks of storage at 40° C. as measured using capillary gel electrophoresis (CGE), size exclusion high performance liquid chromatography (SE-HPLC), and/or methods described in Example 4 with respect to FIGS. 30A-30C or FIGS. 31A-31D.

E9. The isolated polypeptide molecule of any one of the preceding embodiments, wherein the polypeptide molecule has enhanced stability relative to a polypeptide molecule comprising the amino acid sequence of SEQ ID NO: 4, e.g., showing no more than about 0.5, 1, 1.5, or 2% increase in HMMS and/or about 0.5, 1, or 1.5% increase in LMMS after 2, 4 or 6 weeks of storage at 25° C. as measured using SE-HPLC, and/or methods described in Example 4 with respect to FIGS. 32A-32D.

E10. The isolated polypeptide molecule of any one of the preceding embodiments, wherein the polypeptide molecule has enhanced stability relative to a polypeptide molecule comprising the amino acid sequence of SEQ ID NO: 4, e.g., showing no more than about 0.5, 1, or 1.5% increase in HMMS and/or about 0.5, 1, or 1.5% increase in LMMS after 2, 4 or 6 weeks after at 5° C. as measured using SE-HPLC, and/or methods described in Example 4 with respect to FIGS. 33A-33D.

E11. The isolated polypeptide molecule of any one of the preceding embodiments, wherein the polypeptide molecule has increased yield relative to a polypeptide molecule comprising the amino acid sequence of SEQ ID NO: 120, e.g., having a yield that is more than about 5.5, 6, 6.5, or 7 mg per 20 mL Expi293 culture, e.g., as measured using methods described in Example 1 with respect to FIG. 3B.

E12. The isolated polypeptide molecule of any one of the preceding embodiments, wherein the polypeptide molecule has increased Tm relative to a polypeptide molecule comprising the amino acid sequence of SEQ ID NO: 120, e.g., having a Tm that is more than about 38, 40, 42, or 45° C.

E13. The isolated polypeptide molecule of any one of the preceding embodiments, wherein the polypeptide molecule has increased Tm relative to a polypeptide molecule comprising the amino acid sequence of SEQ ID NO: 4, e.g., having a Tm that is more than about 40, 45, 50, 55, or 60° C.

E14. The isolated polypeptide molecule of any one of the preceding embodiments, wherein the polypeptide molecule has increased Tm relative to a polypeptide molecule comprising the amino acid sequence of SEQ ID NO: 120, e.g., having a Tm that is more than about 40, 45, or 50° C., e.g., as measured by DSF and/or using methods described in Example 1 with respect to FIG. 6D.

E15. The isolated polypeptide molecule of any one of the preceding embodiments, wherein the polypeptide molecule has increased Tm relative to a polypeptide molecule comprising the amino acid sequence of SEQ ID NO: 4, e.g., having a Tm that is more than about 45, 50, or 55° C., e.g., as measured by DSF and/or using methods described in Example 1 with respect to FIG. 7D.

E16. The isolated polypeptide molecule of any one of the preceding embodiments, wherein the polypeptide molecule has increased Tm relative to a polypeptide molecule comprising the amino acid sequence of SEQ ID NO: 4, e.g., having a Tm that is more than about 50 or 60° C., e.g., as measured by differential scanning calorimetry (DSC) and/or using methods described in Example 1 with respect to Table 4.

E17. The isolated polypeptide molecule of any one of the preceding embodiments, wherein the polypeptide molecule has Tm1 that is more than about 55, 58, 60, 62, 64 or 66° C. and a Tm2 that is more than about 75, 78, 80, or 82° C. at pH 7.5; a Tm1 that is more than about 55, 58, 60, 62 or 64° C. and a Tm2 that is more than about 75, 78, 80 or 82° C. at pH 5.8; or a Tm1 that is more than about 55, 58 or 60° C. and a Tm2 that is more than about 75, 78, or 80° C. at pH 4.5, e.g., as measured by DSC and/or using methods described in Example 4 with respect to Table 13.

E18. The isolated polypeptide molecule of anyone of the preceding embodiments, wherein the polypeptide molecule has an increased Tm relative to a polypeptide molecule comprising the amino acid sequence of SEQ ID NO: 4, e.g., having a Tm that is more than about 50 or 60° C. at pH 7.5 or pH 4.5; having a Tm that is more than about 50 or 62° C. at pH 5.8, e.g., as measured by DSC and/or using methods described in Example 4 with respect to Table 14.

E19. The isolated polypeptide molecule of any one of the preceding embodiments, wherein the polypeptide molecule has an increased Tm relative to a polypeptide molecule comprising the amino acid sequence of SEQ ID NO: 4, e.g., having a Tm that is more than about 50 or 60° C., e.g., as measured by DSC and FabRICA-TOR® IdeS and/or using methods described in Example 4 with respect to Table 15.

E20. The isolated polypeptide molecule of any one of the preceding embodiments, wherein the polypeptide molecule has enhanced binding affinity to CD2 relative to a polypeptide molecule comprising the amino acid sequence of SEQ ID NO: 4, e.g., a $K_D$ for human CD2 that is less than about 1.2, 1, 0.8, 0.6, 0.4, 0.2, 0.1, or 0.08 μM, e.g., as measured by SPR and/or using methods described in Example 1 with respect to FIG. 5A.

E21. The isolated polypeptide molecule of any one of the preceding embodiments, wherein the polypeptide molecule has enhanced binding affinity to CD2 relative to a polypeptide molecule comprising the amino acid sequence of SEQ ID NO: 4, e.g., a $K_D$ for human CD2 that is less than about 1.3, 1.2, 1.1, or 1 μM, and/or a $K_D$ for cynomolgus CD2 that is less than about 1.4, 1.3, 1.2, 1.1, or 1 μM, e.g., as measured by SPR and/or using methods described in Example 1 with respect to FIG. 7C.

E22. The isolated polypeptide molecule of any one of the preceding embodiments, wherein the polypeptide molecule has enhanced binding affinity to CD2-expressing cells relative to a polypeptide molecule comprising the amino acid sequence of SEQ ID NO: 4, e.g., a $K_d$ for binding to CD4 $T_{mem}$ cells that is no more than about 100, 200, 300, or 400 pM, e.g., as measured using methods described in Example 2 with respect to Table 6.

E23. The isolated polypeptide molecule of any one of the preceding embodiments, wherein the polypeptide molecule has enhanced binding affinity to CD2-expressing cells relative to a polypeptide molecule comprising the amino acid sequence of SEQ ID NO: 4, e.g., a calculated IC50 for binding to CD4 memory T cells that is no more than about 300, 400, 500, 600, 700, 800, 1000, 1200 or 1500 pM; a calculated IC50 for binding to CD4+ $T_{EM}$ cells that is no more than about 150, 300, 400, 500, 600, 700, 800, 1000 or 1200 pM; a calculated IC50 for binding to CD4+ $T_{CM}$ cells that is no more than about 100, 200, 300, 400, 500, 600, 700 or 800 pM; a calculated IC50 for binding to CD4 naïve T cells that is no more than about 200, 300, 400, 500, 600, 700, 800, 1000 or 1200 pM; a calculated IC50 for binding to expanded CD4 Treg cells that is no more than about 100, 200, 300, 400 or 500 pM; a calculated IC50 for binding to CD8 memory T cells that is no more than about 100, 200, 300, 400, 500 or 600 pM; and/or a calculated IC50 for binding to CD8 native T cells that is no more than about 300, 400, 500, 600, 700, 800, 1000, 1200, 1500, 1600 or 1700 pM, e.g., as measured using SPR and/or methods described in Example 2 with respect to Table 10 and FIG. 11.

E24. The isolated polypeptide molecule of any one of the preceding embodiments, wherein the polypeptide molecule has enhanced binding affinity to CD2-expressing cells relative to a polypeptide molecule comprising the amino acid sequence of SEQ ID NO: 4, e.g., a calculated $K_d$ for binding to CD4 memory T cells that is no more than about 100, 200, 300, 400, or 500 pM; a calculated $K_d$ for binding to CD4+ $T_{EM}$ cells that is no more than about 100, 200, 300, 400, 500, or 600 pM; a calculated $K_d$ for binding to CD4+ $T_{CM}$ cells that is no more than about 100, 200, 300, 400, or 500 pM; a calculated $K_d$ for binding to CD4 naïve T cells that is no more than about 100, 200, 300, or 400 pM; a calculated $K_d$ for binding to expanded CD4 Treg cells that is no more than about 100, 200, or 300 pM; a calculated $K_d$ for binding to CD8 memory T cells that is no more than about 50, 100, or 150 pM; a calculated $K_d$ for binding to CD8 naïve T cells that is no more than about 50, 100, 200, 300, 400 or 500 pM, e.g., as measured using SPR and/or methods described in Example 2 with respect to Table 10 and FIG. 11.

E25. The isolated polypeptide molecule of any one of the preceding embodiments, wherein the polypeptide molecule has enhanced binding affinity to CD2-expressing cells relative to a polypeptide molecule comprising the amino acid sequence of SEQ ID NO: 4, e.g., a reduced EC50 for binding to cynomolgus CD4+ $T_{EM}$ cells relative to a polypeptide molecule comprising the amino acid sequence of SEQ ID NO: 4, e.g., as measured using SPR and/or methods described in Example 3 with respect to FIGS. 18A and 18B.

E26. The isolated polypeptide molecule of any one of the preceding embodiments, wherein the polypeptide molecule has enhanced cytotoxicity against CD2-expressing cells relative to a polypeptide molecule comprising the amino acid sequence of SEQ ID NO: 4, e.g., an EC50 for killing CD4 $T_{mem}$ cells that is no more than about 400, 600, 800, 1000, 1200, or 1400 pM, e.g., as measured using an ADCC assay and/or methods described in Example 5 with respect to Table 17 and FIGS. 12A and 12B.

E27. The isolated polypeptide molecule of any one of the preceding embodiments, wherein the polypeptide molecule has enhanced cytotoxicity against CD2-expressing cells relative to a polypeptide molecule comprising the amino acid sequence of SEQ ID NO: 4, e.g., an EC50 for killing CD8 $T_{mem}$ cells that is no more than about 1, 5, 10, 20, 30, 40, or 50 nM e.g., as measured using an antibody dependent cellular cytotoxicity (ADCC) assay and/or methods described in Example 5 with respect to Table 17 and FIG. 12D.

E28. The isolated polypeptide molecule of any one of the preceding embodiments, wherein the polypeptide molecule has enhanced inhibition of allogeneic T cell response, e.g., T cell proliferation and cytokine production, relative to a polypeptide molecule comprising the amino acid sequence of SEQ ID NO: 4, e.g., an IC50 that is no more than about 400, 800, 1200, 1600, 2000, or 2400 pM, e.g., as measured using an MLR assay and/or methods described in Example 2 with respect to Table 6 and FIGS. 14A and 14B.

E29. The isolated polypeptide molecule of any one of the preceding embodiments, wherein the polypeptide molecule has enhanced inhibition of allogeneic T cell response, e.g., T cell proliferation and cytokine production, relative to a polypeptide molecule comprising the amino acid sequence of SEQ ID NO: 4, e.g., an IC50 in the absence of NK cells that is no more than about 300, 400, 500, 600, 800, 1000, 1500 or 2000 pM, e.g., as measured using and MLR assay and/or methods described in Example 2 with respect to FIGS. 15B and 15C.

E30. The isolated polypeptide molecule of any one of the preceding embodiments, wherein the polypeptide molecule has enhanced inhibition of tetanus toxoid recall response relative to a polypeptide molecule comprising the amino acid sequence of SEQ ID NO: 4, e.g., an IC50 for CD4 $T_{mem}$ IFNγ production that is no more than about 1, 2, 5, 10, 15, 20, or 25 nM, e.g., as measured using a TTR assay and/or methods described in Example 2 with respect to Table 6 and FIGS. 16A and 16B.

E31. The isolated polypeptide molecule of any one of the preceding embodiments, wherein the polypeptide molecule has slower clearance in vivo relative to a polypeptide molecule comprising the amino acid sequence of SEQ ID NO: 4, e.g., a clearance from central that is no more than about 0.14, 0.16, 0.18, 0.2, or 0.22 mL/hr/kg, e.g., as measured using methods described in Example 2 with respect to Table 11.

E32. The isolated polypeptide molecule of any one of the preceding embodiments, wherein the polypeptide molecule has enhanced purity relative to a polypeptide molecule comprising the amino acid sequence of SEQ ID NO: 4, e.g., a purity of at least about 98% or 99% as measured using capillary gel electrophoresis and/or methods described in Example 1 or 4.

E33. The isolated polypeptide molecule of any one of the preceding embodiments, wherein the polypeptide molecule has reduced sialic acid modification relative to a polypeptide molecule comprising the amino acid sequence of SEQ ID NO: 4, e.g., a purity of not more than about 20, 18, 16, 14, 12, 10, 9, 8 or 7 nmol sialic acid/nmol polypeptide as measured using capillary gel electrophoresis and/or method described in Example 1 or 4.

E34. The isolated polypeptide molecule of any one of the preceding embodiments, wherein the polypeptide molecule further has one or more of the following properties:
  i. Preferential binding to $CD2^{high}$ $T_{EM}$ cells, e.g., CD4+ and/or CD8+ $T_{EM}$ cells, e.g., in vivo,
  ii. Killing CD2-expressing cells (e.g., CD4+ or CD8+ $T_{CM}$ cells, or CD4+ or CD8+ $T_{EM}$ cells) in the presence of NK cells, e.g., as measured using methods described in Example 2 with respect to FIG. 13A,
  iii. Decreasing CD4+ and/or CD8+ $T_{EM}$ cells, e.g., peripheral CD4+ $T_{EM}$ cells, in vivo, e.g., as measured using methods described in Example 2 with respect to FIG. 20A, iv. Increasing the Treg/$T_{EM}$ ratio, e.g., in CD4+ T cells, in vivo, e.g., as measured using methods described in Example 2 with respect to FIG. 20B, or v. Increasing the Treg/$T_{CM}$ ratio, e.g., in CD4+ and/or CD8+ T cells.

E35. The isolated polypeptide molecule of any one of the preceding embodiments, wherein the polypeptide molecule preferentially binds to $CD2^{high}$ $T_{EM}$ cells, e.g., CD4+ and/or CD8+ $T_{EM}$ cells, e.g., in vivo.

E36. The isolated polypeptide molecule of any one of the preceding embodiments, wherein the polypeptide molecule kills CD2-expressing cells (e.g., CD4+ or CD8+ $T_{CM}$ cells, or CD4+ or CD8+ $T_{EM}$ cells) in the presence of NK cells, e.g., as measured using methods described in Example 2 with respect to FIG. 13A.

E37. The isolated polypeptide molecule of any one of the preceding embodiments, wherein the polypeptide molecule decreases CD4+ and/or CD8+ $T_{EM}$ cells, e.g., peripheral CD4+ $T_{EM}$ cells, in vivo, e.g., as measured using methods described in Example 2 with respect to FIG. 20A.

E38. The isolated polypeptide molecule of any one of the preceding embodiments, wherein the polypeptide molecule increases the Treg/$T_{EM}$ ratio, e.g., in CD4+ T cells, in vivo, e.g., as measured using methods described in Example 2 with respect to FIG. 20B.

E39. The isolated polypeptide molecule of any one of the preceding embodiments, wherein the polypeptide molecule increases the Treg/$T_{CM}$ ratio, e.g., in CD4+ and/or CD8+ T cells.

Alternatively, or in combination with any of the embodiments provided herein (e.g., E1-E39), the polypeptide molecule has one or more of the following features and embodiments.

E40. An isolated polypeptide molecule that specifically binds to CD2, wherein the polypeptide molecule comprises a LFA3 domain, wherein the LFA3 domain comprises the amino acid sequence of SEQ ID NO: 73, or a functional variant of SEQ ID NO: 73 (e.g., a sequence having at least 75%, 80%, 85%, 90%, 95%, or 99% identity thereof), wherein the LFA3 domain does not comprise the amino acid sequence of SEQ ID NO: 3.

E41. An isolated polypeptide molecule that specifically binds to CD2, wherein the polypeptide molecule comprises a LFA3 domain, wherein the LFA3 domain comprises the amino acid sequence of:

(SEQ ID NO: 74)
FSQQIYGVVYGNVTX$_1$HX$_2$PSNVPX$_3$KEX$_4$LX$_5$KKQKDKX$_6$X$_7$EX$_8$ENSE

X$_9$RX$_{10}$FSSFKNRVYX$_{11}$DTVSX$_{12}$SX$_{13}$TIYNLTSSDEDEYEX$_{14}$ESPN

ITDTX$_{15}$KX$_{16}$FLYVX$_{17}$, wherein:

X$_1$ is F, I, L, V, A, or Y,

X$_2$ is F, I, L, V, M, A, or Nle,

X$_3$ is F, I, L, V, Nle, M, or A,

X$_4$ is F, I, L, V, M, A, or Nle,

X$_5$ is W, F, L, C, or Y,

X$_6$ is F, I, L, V, M, A, or Nle,

X$_7$ is A, V, S, L, or I,

X$_8$ is F, I, L, V, Nle, M, or A,

X$_9$ is F, I, L, V, A, or Y,

X$_{10}$ is A, V, S, L, or I,

X$_{11}$ is F, I, L, V, Nle, M, or A,

X$_{12}$ is S, T, A, or G,

X$_{13}$ is F, I, L, V, Nle, M, or A,

X$_{14}$ is M, L, I, or F,

X$_{15}$ is M, L, I, or F,

X$_{16}$ is F, I, L, V, A, or Y, and

X$_{17}$ is absent, L, or LESLPS, or a functional variant of SEQ ID NO: 74 (e.g., a sequence having at least 75%, 80%, 85%, 90%, 95%, or 99% identity thereof), wherein the LFA3 domain does not comprise the amino acid sequence of SEQ ID NO: 3.

E42. An isolated polypeptide molecule that specifically binds to CD2, wherein the polypeptide molecule comprises a LFA3 domain, wherein the LFA3 domain comprises the amino acid sequence of:

(SEQ ID NO: 75)
FSQQIYGVVYGNVTX$_1$HX$_2$PSNVPX$_3$KEX$_4$LX$_5$KKQKDKX$_6$X$_7$EX$_8$ENSE

X$_9$RX$_{10}$FSSFKNRVYX$_{11}$DTVSX$_{12}$SX$_{13}$TIYNLTSSDEDEYEX$_{14}$ESPN

ITDTX$_{15}$KX$_{16}$FLYVX$_{17}$, wherein:

X$_1$ is F, I, L, or V,

X$_2$ is F, I, L, or V,

X$_3$ is F, I, L, or V,

X$_4$ is F, I, L, or V,

X$_5$ is W, F, L, or C,

X$_6$ is F, I, L, or V,

X$_7$ is A, V, S, or L,

X$_8$ is F, I, L, or V,

X$_9$ is F, I, L, or V,

X$_{10}$ is A, V, S, or L,

X$_{11}$ is F, I, L, or V,

X$_{12}$ is S, T, A, or G,

X$_{13}$ is F, I, L, or V,

X$_{14}$ is M, L, I, or F,

X$_{15}$ is M, L, I, or F,

X$_{16}$ is F, I, L, or V, and

X$_{17}$ is absent, L, or LESLPS, or a functional variant of SEQ ID NO: 75 (e.g., a sequence having at least 75%, 80%, 85%, 90%, 95%, or 99% identity thereof), wherein the LFA3 domain does not comprise the amino acid sequence of SEQ ID NO: 3.

E43. An isolated polypeptide molecule that specifically binds to CD2, wherein the polypeptide molecule comprises a LFA3 domain, wherein the LFA3 domain comprises one or more mutations (e.g., a substitution, a deletion, or an addition) at residues 15, 17, 23, 26, 28, 35, 36, 38, 43, 45, 55, 60, 62, 77, 86, or 88 relative to SEQ ID NO: 3.

E44. The isolated polypeptide molecule of E43, wherein the one or more mutations comprise one or more of the following substitutions:
  i. a substitution chosen from F15I, F15L, F15V, F15A, or F15Y,
  ii. a substitution chosen from V17F, V17I, V17L, V17M, V17A, or V17Nle,
  iii. a substitution chosen from L23F, L23I, L23V, L23Nle, L23M, or L23A,
  iv. a substitution chosen from V26F, V26I, V26L, V26M, V26A, or V26Nle,
  v. a substitution chosen from W28F, W28L, W28C, or W28Y,
  vi. a substitution chosen from V35F, V35I, V35L, V35M, V35A, or V35Nle, vii. a substitution chosen from A36V, A36S, A36L, or A36I,
viii. a substitution chosen from L38F, L38I, L38V, L38Nle, L38M, or L38A,
ix. a substitution chosen from F43I, F43L, F43V, F43A, or F43Y,
x. a substitution chosen from A45V, A45S, A45L, or A45I,
xi. a substitution chosen from L55F, L55I, L55V, L55Nle, L55M, or L55A,
xii. a substitution chosen from G60S, G60T, or G60A,
xiii. a substitution chosen from L62F, L62I, L62V, L62Nle, L62M, or L62A,
xiv. a substitution chosen from M77L, M77I, or M77F,
xv. a substitution chosen from M86L, M86I, or M86F, or
xvi. a substitution chosen from F88I, F88L, F88V, F88A, or F88Y.

E45. The isolated polypeptide molecule of E43, wherein the one or more mutations comprise one or more of the following substitutions:
i. a substitution chosen from F15I, F15L, or F15V,
ii. a substitution chosen from V17F, V17I, or V17L,
iii. a substitution chosen from L23F, L23I, or L23V,
iv. a substitution chosen from V26F, V26I, or V26L,
v. a substitution chosen from W28F, W28L, or W28C,
vi. a substitution chosen from V35F, V35I, or V35L,
vii. a substitution chosen from A36V, A36S, or A36L,
viii. a substitution chosen from L38F, L38I, or L38V,
ix. a substitution chosen from F43I, F43L, or F43V,
x. a substitution chosen from A45V, A45S, or A45L,
xi. a substitution chosen from L55F, L55I, or L55V,
xii. a substitution chosen from G60S, G60T, or G60A,
xiii. a substitution chosen from L62F, L62I, L62V,
xiv. a substitution chosen from M77L, M77I, or M77F,
xv. a substitution chosen from M86L, M86I, or M86F, or
xvi. a substitution chosen from F88I, F88L, or F88V.

E46. An isolated polypeptide molecule that specifically binds to CD2, wherein the polypeptide molecule comprises a LFA3 domain, wherein the LFA3 domain comprises the amino acid sequence of SEQ ID NO: 76), or a functional variant of SEQ ID NO: 76 (e.g., a sequence having at least 75%, 80%, 85%, 90%, 95%, or 99% identity thereof), wherein the LFA3 domain does not comprise the amino acid sequence of SEQ ID NO: 3.

E47. An isolated polypeptide molecule that specifically binds to CD2, wherein the polypeptide molecule comprises a LFA3 domain, wherein the LFA3 domain comprises the amino acid sequence of:

(SEQ ID NO: 77)
FSQQIYGVVYGNVTFHVPSNVPLKEVLWKKQKDKVX$_1$EX$_2$ENSEX$_3$RX$_4$

FSSFKNRVYLDTVSGSLTIYNLTSSDEDEYEX$_5$ESPNITDTX$_6$KFFLYV

X$_7$, wherein:

X$_1$ is A, V, S, L, or I,

X$_2$ is F, I, L, V, Nle, M, or A,

X$_3$ is F, I, L, V, A, or Y,

X$_4$ is A, V, S, L, or I,

X$_5$ is M, L, I, or F,

X$_6$ is M, L, I, or F, and

X$_7$ is absent, L, or LESLPS, or a functional variant of SEQ ID NO: 77 (e.g., a sequence having at least 75%, 80%, 85%, 90%, 95%, or 99% identity thereof), wherein the LFA3 domain does not comprise the amino acid sequence of SEQ ID NO: 3.

E48. An isolated polypeptide molecule that specifically binds to CD2, wherein the polypeptide molecule comprises a LFA3 domain, wherein the LFA3 domain comprises the amino acid sequence of:

(SEQ ID NO: 78)
FSQQIYGVVYGNVTFHVPSNVPLKEVLWKKQKDKVX$_1$EX$_2$ENSEX$_3$RX$_4$

FSSFKNRVYLDTVSGSLTIYNLTSSDEDEYEX$_5$ESPNITDTX$_6$KFFLYV

X$_7$, wherein:

X$_1$ is A, V, S, or L,

X$_2$ is F, I, L, or V,

X$_3$ is F, I, L, or V,

X$_4$ is A, V, S, or L,

X$_5$ is M, L, I, or F,

X$_6$ is M, L, I, or F, and

X$_7$ is absent, L, or LESLPS, or a functional variant of SEQ ID NO: 78 (e.g., a sequence having at least 75%, 80%, 85%, 90%, 95%, or 99% identity thereof), wherein the LFA3 domain does not comprise the amino acid sequence of SEQ ID NO: 3.

E49. An isolated polypeptide molecule that specifically binds to CD2, wherein the polypeptide molecule comprises a LFA3 domain, wherein the LFA3 domain comprises the amino acid sequence of:

(SEQ ID NO: 79)
FSQQIYGVVYGNVTFHVPSNVPLKEVLWKKQKDKVX$_1$EX$_2$ENSEX$_3$RX$_4$

FSSFKNRVYLDTVSGSLTIYNLTSSDEDEYEX$_5$ESPNITDTX$_6$KFFLYV

X$_7$, wherein:

X$_1$ is V, L, or A,

X$_2$ is F or L,

X$_3$ is V, I, L, or F,

X$_4$ is A, V, or S,

X$_5$ is M, F, I, or L,

X$_6$ is F, M, I, or L, and

X$_7$ is absent, L, or LESLPS, or a functional variant of SEQ ID NO: 79 (e.g., a sequence having at least 75%, 80%, 85%, 90%, 95%, or 99% identity thereof), wherein the LFA3 domain does not comprise the amino acid sequence of SEQ ID NO: 3.

E50. An isolated polypeptide molecule that specifically binds to CD2, wherein the polypeptide molecule comprises a LFA3 domain, wherein the LFA3 domain comprises the amino acid sequence of:

(SEQ ID NO: 80)
FSQQIYGVVYGNVTFHVPSNVPLKEVLWKKQKDKVX₁EFENSEX₂RX₃FS

SFKNRVYLDTVSGSLTIYNLTSSDEDEYEX₄ESPNITDTX₅KFFLYVX₆, wherein:

X₁ is V or L,

X₂ is V, I, or L,

X₃ is A or V,

X₄ is M or F,

X₅ is F or M, and

X₆ is absent, L, or LESLPS, or a functional variant of SEQ ID NO: 80 (e.g., a sequence having at least 75%, 80%, 85%, 90%, 95%, or 99% identity thereof), wherein the LFA3 domain does not comprise the amino acid sequence of SEQ ID NO: 3.

E51. An isolated polypeptide molecule that specifically binds to CD2, wherein the polypeptide molecule comprises a LFA3 domain, wherein the LFA3 domain comprises the amino acid sequence of:

(SEQ ID NO: 80)
FSQQIYGVVYGNVTFHVPSNVPLKEVLWKKQKDKVX₁EFENSEX₂RX₃FS

SFKNRVYLDTVSGSLTIYNLTSSDEDEYEX₄ESPNITDTX₅KFFLYVX₆, wherein:

X₁ is V or L,

X₂ is V, I, or L,

X₃ is A or V,

X₄ is M or F,

X₅ is F or M, and

X₆ is absent, L, or LESLPS.

E52. An isolated polypeptide molecule that specifically binds to CD2, wherein the polypeptide molecule comprises a LFA3 domain, wherein the LFA3 domain comprises the amino acid sequence of:

(SEQ ID NO: 81)
FSQQIYGVVYGNVTFHVPSNVPLKEVLWKKQKDKVX₁EFENSEX₂RX₃FS

SFKNRVYLDTVSGSLTIYNLTSSDEDEYEX₄ESPNITDTFKFFLYVX₅, wherein:

X₁ is V or L,

X₂ is V, I, or L,

X₃ is A or V,

X₄ is M or F, and

X₅ is absent, L, or LESLPS, or a functional variant of SEQ ID NO: 81 (e.g., a sequence having at least 75%, 80%, 85%, 90%, 95%, or 99% identity thereof), wherein the LFA3 domain does not comprise the amino acid sequence of SEQ ID NO: 3.

E53. An isolated polypeptide molecule that specifically binds to CD2, wherein the polypeptide molecule comprises a LFA3 domain, wherein the LFA3 domain comprises the amino acid sequence of:

(SEQ ID NO: 81)
FSQQIYGVVYGNVTFHVPSNVPLKEVLWKKQKDKVX₁EFENSEX₂RX₃FS

SFKNRVYLDTVSGSLTIYNLTSSDEDEYEX₄ESPNITDTFKFFLYVX₅, wherein:

X₁ is V or L,

X₂ is V, I, or L,

X₃ is A or V,

X₄ is M or F, and

X₅ is absent, L, or LESLPS.

E54. An isolated polypeptide molecule that specifically binds to CD2, wherein the polypeptide molecule comprises a LFA3 domain, wherein the LFA3 domain comprises the amino acid sequence of:

(SEQ ID NO: 82)
FSQQIYGVVYGNVTFHVPSNVPLKEVLWKKQKDKVVEFENSEX₁RX₂FSS

FKNRVYLDTVSGSLTIYNLTSSDEDEYEX₃ESPNITDTFKFFLYVX₄, wherein:

X₁ is V or I,

X₂ is A or V,

X₃ is M or F, and

X₄ is absent, L, or LESLPS, or a functional variant of SEQ ID NO: 82 (e.g., a sequence having at least 75%, 80%, 85%, 90%, 95%, or 99% identity thereof), wherein the LFA3 domain does not comprise the amino acid sequence of SEQ ID NO: 3.

E55. An isolated polypeptide molecule that specifically binds to CD2, wherein the polypeptide molecule comprises a LFA3 domain, wherein the LFA3 domain comprises the amino acid sequence of:

(SEQ ID NO: 82)
FSQQIYGVVYGNVTFHVPSNVPLKEVLWKKQKDKVVEFENSEX₁RX₂FSS

FKNRVYLDTVSGSLTIYNLTSSDEDEYEX₃ESPNITDTFKFFLYVX₄, wherein:

X₁ is V or I,

X₂ is A or V,

X₃ is M or F, and

X₄ is absent, L, or LESLPS.

E56. An isolated polypeptide molecule that specifically binds to CD2, wherein the polypeptide molecule comprises a LFA3 domain, wherein the LFA3 domain comprises an amino acid sequence chosen from SEQ ID NOs: 17-23, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

E57. The isolated polypeptide molecule of E56, further comprising the amino acid residue of Leu or the amino acid sequence of LESLPS (SEQ ID NO: 118).

E58. An isolated polypeptide molecule that specifically binds to CD2, wherein the polypeptide molecule comprises a LFA3 domain, wherein the LFA3 domain comprises an amino acid sequence chosen from SEQ ID NOs: 26-29, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

E59. An isolated polypeptide molecule that specifically binds to CD2, wherein the polypeptide molecule comprises a LFA3 domain, wherein the LFA3 domain comprises the amino acid sequence of SEQ ID NO: 17, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

E60. An isolated polypeptide molecule that specifically binds to CD2, wherein the polypeptide molecule comprises a LFA3 domain, wherein the LFA3 domain comprises the amino acid sequence of SEQ ID NO: 17.

E61. An isolated polypeptide molecule that specifically binds to CD2, wherein the polypeptide molecule comprises a LFA3 domain, wherein the LFA3 domain comprises the amino acid sequence of SEQ ID NO: 18, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

E62. An isolated polypeptide molecule that specifically binds to CD2, wherein the polypeptide molecule comprises a LFA3 domain, wherein the LFA3 domain comprises the amino acid sequence of SEQ ID NO: 18.

E63. An isolated polypeptide molecule that specifically binds to CD2, wherein the polypeptide molecule comprises a LFA3 domain, wherein the LFA3 domain comprises the amino acid sequence of SEQ ID NO: 19, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

E64. An isolated polypeptide molecule that specifically binds to CD2, wherein the polypeptide molecule comprises a LFA3 domain, wherein the LFA3 domain comprises the amino acid sequence of SEQ ID NO: 19.

E65. An isolated polypeptide molecule that specifically binds to CD2, wherein the polypeptide molecule comprises a LFA3 domain, wherein the LFA3 domain comprises the amino acid sequence of SEQ ID NO: 20, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

E66. An isolated polypeptide molecule that specifically binds to CD2, wherein the polypeptide molecule comprises a LFA3 domain, wherein the LFA3 domain comprises the amino acid sequence of SEQ ID NO: 20.

E67. An isolated polypeptide molecule that specifically binds to CD2, wherein the polypeptide molecule comprises a LFA3 domain, wherein the LFA3 domain comprises the amino acid sequence of SEQ ID NO: 21, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

E68. An isolated polypeptide molecule that specifically binds to CD2, wherein the polypeptide molecule comprises a LFA3 domain, wherein the LFA3 domain comprises the amino acid sequence of SEQ ID NO: 21.

E69. An isolated polypeptide molecule that specifically binds to CD2, wherein the polypeptide molecule comprises a LFA3 domain, wherein the LFA3 domain comprises the amino acid sequence of SEQ ID NO: 22, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

E70. An isolated polypeptide molecule that specifically binds to CD2, wherein the polypeptide molecule comprises a LFA3 domain, wherein the LFA3 domain comprises the amino acid sequence of SEQ ID NO: 22.

E71. An isolated polypeptide molecule that specifically binds to CD2, wherein the polypeptide molecule comprises a LFA3 domain, wherein the LFA3 domain comprises the amino acid sequence of SEQ ID NO: 23, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

E72. An isolated polypeptide molecule that specifically binds to CD2, wherein the polypeptide molecule comprises a LFA3 domain, wherein the LFA3 domain comprises the amino acid sequence of SEQ ID NO: 23.

E73. The isolated polypeptide molecule of E59-E72, further comprising the amino acid residue of Leu or the amino acid sequence of LESLPS (SEQ ID NO: 118).

E74. An isolated polypeptide molecule that specifically binds to CD2, wherein the polypeptide molecule comprises a LFA3 domain, wherein the LFA3 domain comprises the amino acid sequence of SEQ ID NO: 26, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

E75. An isolated polypeptide molecule that specifically binds to CD2, wherein the polypeptide molecule comprises a LFA3 domain, wherein the LFA3 domain comprises the amino acid sequence of SEQ ID NO: 26.

E76. An isolated polypeptide molecule that specifically binds to CD2, wherein the polypeptide molecule comprises a LFA3 domain, wherein the LFA3 domain comprises the amino acid sequence of SEQ ID NO: 27, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

E77. An isolated polypeptide molecule that specifically binds to CD2, wherein the polypeptide molecule comprises a LFA3 domain, wherein the LFA3 domain comprises the amino acid sequence of SEQ ID NO: 27.

E78. An isolated polypeptide molecule that specifically binds to CD2, wherein the polypeptide molecule comprises a LFA3 domain, wherein the LFA3 domain comprises the amino acid sequence of SEQ ID NO: 28, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

E79. An isolated polypeptide molecule that specifically binds to CD2, wherein the polypeptide molecule comprises a LFA3 domain, wherein the LFA3 domain comprises the amino acid sequence of SEQ ID NO: 28.

E80. An isolated polypeptide molecule that specifically binds to CD2, wherein the polypeptide molecule comprises a LFA3 domain, wherein the LFA3 domain comprises the amino acid sequence of SEQ ID NO: 29, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

E81. An isolated polypeptide molecule that specifically binds to CD2, wherein the polypeptide molecule comprises a LFA3 domain, wherein the LFA3 domain comprises the amino acid sequence of SEQ ID NO: 29.

E82. An isolated polypeptide molecule that specifically binds to CD2, wherein the polypeptide molecule comprises a LFA3 domain, wherein the LFA3 domain comprises an amino acid sequence chosen from SEQ ID NO: 24 or 25, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

E83. An isolated polypeptide molecule that specifically binds to CD2, wherein the polypeptide molecule comprises a LFA3 domain, wherein the LFA3 domain comprises the amino acid sequence of SEQ ID NO: 24, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

E84. An isolated polypeptide molecule that specifically binds to CD2, wherein the polypeptide molecule comprises a LFA3 domain, wherein the LFA3 domain comprises the amino acid sequence of SEQ ID NO: 24.

E85. An isolated polypeptide molecule that specifically binds to CD2, wherein the polypeptide molecule comprises a LFA3 domain, wherein the LFA3 domain comprises the amino acid sequence of SEQ ID NO: 25, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

E86. An isolated polypeptide molecule that specifically binds to CD2, wherein the polypeptide molecule comprises a LFA3 domain, wherein the LFA3 domain comprises the amino acid sequence of SEQ ID NO: 25.

E87. An isolated polypeptide molecule that specifically binds to CD2, wherein the polypeptide molecule comprises a LFA3 domain, wherein the LFA3 domain comprises an amino acid sequence chosen from SEQ ID NOs: 30-41, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

E88. An isolated polypeptide molecule that specifically binds to CD2, wherein the polypeptide molecule comprises a LFA3 domain, wherein the LFA3 domain comprises the amino acid sequence chosen from SEQ ID NOs: 30-41.

E89. An isolated polypeptide molecule that specifically binds to CD2, wherein the polypeptide molecule comprises a LFA3 domain, wherein the LFA3 domain comprises one or more mutations (e.g., a substitution, a deletion, or an addition) at residues 36, 38, 43, 45, 77, or 86 relative to SEQ ID NO: 3, numbered according to SEQ ID NO: 3.

E90. The isolated polypeptide molecule of E89, wherein the one or more mutations comprise one or more of the following substitutions:
  i. a substitution chosen from A36V, A36S, A36L, or A36I,
  ii. a substitution chosen from L38F, L38I, L38V, L38Nle, L38M, or L38A,
  iii. a substitution chosen from F43I, F43L, F43V, F43A, or F43Y,
  iv. a substitution chosen from A45V, A45S, A45L, or A45I,
  v. a substitution chosen from M77L, M77I, or M77F, or
  vi. a substitution chosen from M86L, M86I, or M86F.

E91. The isolated polypeptide molecule of E89, wherein the one or more mutations comprise one or more of the following substitutions:
  i. a substitution chosen from A36V, A36S, or A36L,
  ii. a substitution chosen from L38F, L38I, or L38V,
  iii. a substitution chosen from F43I, F43L, or F43V,
  iv. a substitution chosen from A45V, A45S, or A45L,
  v. a substitution chosen from M77L, M77I, or M77F, or
  vi. a substitution chosen from M86L, M86I, or M86F.

E92. The isolated polypeptide molecule of E89, wherein the one or more mutations comprise one or more of the following substitutions:
  i. a substitution chosen from A36V or A36L,
  ii. a substitution of L38F,
  iii. a substitution chosen from F43V, F43I, or F43L,
  iv. a substitution chosen from A45V or A45S,
  v. a substitution chosen from M77L, M77I, or M77F, or
  vi. a substitution chosen from M86L, M86I, or M86F.

E93. The isolated polypeptide molecule of E89, wherein the one or more mutations comprise one or more of the following substitutions:
  i. a substitution chosen from A36V or A36L,
  ii. a substitution of L38F,
  iii. a substitution chosen from F43V, F43I, or F43L,
  iv. a substitution of A45V,
  v. a substitution of M77F, or
  vi. a substitution of M86F.

E94. The isolated polypeptide molecule of E89, wherein the one or more mutations comprise one or more of the following substitutions:
  i. a substitution of A36V,
  ii. a substitution of L38F,
  iii. a substitution chosen from F43V or F43I,
  iv. a substitution of A45V,
  v. a substitution of M77F, or
  vi. a substitution of M86F.

E95. The isolated polypeptide molecule of E89, wherein the one or more mutations comprise one or more of the following substitutions:
  i. a substitution of A36V,
  ii. a substitution of L38F,
  iii. a substitution of F43V, or
  iv. a substitution of M86F.

E96. The isolated polypeptide molecule of E89, wherein the mutations comprise the following substitutions: A36V, L38F, F43V and M86F.

E97. The isolated polypeptide molecule of E89, wherein the one or more mutations comprise one or more of the following substitutions:
  i. a substitution of A36V,
  ii. a substitution of L38F, iii. a substitution of F43V,
iv. a substitution of A45V,
v. a substitution of M77F, or
vi. a substitution of M86F.

E98. The isolated polypeptide molecule of E89, wherein the one or more mutations comprise one or more of the following substitutions:
i. a substitution of A36V,
ii. a substitution of L38F,
iii. a substitution of F43I,
iv. a substitution of A45V,
v. a substitution of M77F, or
vi. a substitution of M86F.

E99. The isolated polypeptide molecule of any one of the preceding embodiments, wherein the polypeptide molecule further comprises 1 to 10, e.g., 1 to 6, amino acid residues from the extracellular domain of SEQ ID NO: 2, e.g., amino acid residues 93-187 of SEQ ID NO: 2.

E100. The isolated polypeptide molecule of any one of the preceding embodiments, wherein the polypeptide molecule further comprises one, two, three, four, five, six, seven, eight, nine or ten amino acid residues of LESLPSPTLTCALTNGSIEV (SEQ ID NO: 119).

E101. The isolated polypeptide molecule of any one of the preceding embodiments, wherein the polypeptide molecule further comprises one, two, three, four, five, or all amino acid residues of LESLPS (SEQ ID NO: 118).

E102. The isolated polypeptide molecule of any one of the preceding embodiments, further comprising a second domain, e.g., the polypeptide molecule is a fusion protein molecule.

E103. The isolated polypeptide molecule of E102, wherein the LFA3 domain is linked to the second domain, e.g., through a linker, or without a linker, e.g., the C-terminus of the LFA3 domain is linked to the N-terminus of the second domain, or the N-terminus of the LFA3 domain is linked to the C-terminus of the second domain, optionally wherein the C-terminus of the LFA3 domain is linked to the N-terminus of the second domain without a linker.

E104. The isolated polypeptide molecule of E102 or E103, wherein the second domain is capable of forming a dimer with another second domain, e.g., through an intermolecular disulfide bond.

E105. The isolated polypeptide molecule of any one of E102-E104, wherein:
i. the second domain is capable of mediating antibody-dependent cell-mediated cytotoxicity (ADCC), or
ii. the second domain is capable of binding to and activating CD16-expressing cells, e.g., CD16-expressing NK cells or CD16-expressing macrophages.

E106. The isolated polypeptide molecule of any one of E102-E105, wherein the second domain is an immunoglobulin protein, e.g., a heavy chain constant region, e.g., a human heavy chain constant region, or a functional variant thereof.

E107. The isolated polypeptide molecule of any one of E102-E106, wherein the second domain comprises an Fc region of a heavy chain (e.g., an IgG1, IgG2, IgG3, or IgG4 heavy chain, e.g., a human IgG1 heavy chain) or a functional variant thereof, e.g., wherein the second domain comprises a hinge region, a CH2 region, and a CH3 region, or a functional variant thereof.

E108. The isolated polypeptide molecule of any one of E102-E107, wherein the second domain comprises the amino acid sequence of SEQ ID NO: 16, or a functional variant thereof (e.g., a sequence having at least 75%, 80%, 85%, 90%, 95%, or 99% identity thereof), e.g., wherein the second domain comprises the amino acid sequence of SEQ ID NO: 16.

E109. An isolated polypeptide, or fragment thereof, that specifically binds to CD2 comprising a first domain and a second domain
wherein the first domain comprises a polypeptide comprising an amino acid sequence having at least 75%, 80%, 85%, 90%, 95%, or 99% identity to SEQ ID NO: 26 and wherein the polypeptide does not comprise the amino acid of SEQ ID NO:3; and
wherein the second domain comprises a polypeptide comprising an amino acid sequence having at least 75%, 80%, 85%, 90%, 95%, or 99% identity to SEQ ID NO: 16.

E110. An isolated polypeptide molecule that specifically binds to CD2, wherein the polypeptide molecule comprises the amino acid sequence of SEQ ID NO: 69, or a functional variant thereof (e.g., a sequence having at least 75%, 80%, 85%, 90%, 95%, or 99% identity thereof), wherein the polypeptide molecule does not comprise the amino acid sequence of SEQ ID NO: 4.

E111. An isolated polypeptide molecule that specifically binds to CD2, wherein the polypeptide molecule comprises the amino acid sequence of SEQ ID NO: 69.

E112. An isolated multimeric (e.g., dimeric) protein molecule comprising two or more polypeptide molecules of any one of the preceding embodiments.

E113. An isolated multimeric (e.g., dimeric) protein molecule comprising two or more polypeptide molecules comprising the amino acid sequence of SEQ ID NO: 26, or a functional variant thereof (e.g., a sequence having at least 75%, 80%, 85%, 90%, 95%, or 99% identity thereof), wherein the polypeptide molecule does not comprise the amino acid sequence of SEQ ID NO: 3.

E114. An isolated multimeric (e.g., dimeric) protein molecule comprising two or more polypeptide molecules comprising the amino acid sequence of SEQ ID NO: 26.

E115. An isolated multimeric (e.g., dimeric) protein molecule comprising two or more polypeptide molecules comprising the amino acid sequence of SEQ ID NO: 69, or a functional variant thereof (e.g., a sequence having at least 75%, 80%, 85%, 90%, 95%, or 99% identity thereof), wherein the polypeptide molecule does not comprise the amino acid sequence of SEQ ID NO: 4.

E116. An isolated multimeric (e.g., dimeric) protein molecule comprising two or more polypeptide molecules comprising the amino acid sequence of SEQ ID NO: 69.

E117. A nucleic acid molecule that encodes the polypeptide molecule of any one of E1-E111 or the multimeric protein molecule of any one of E112-E116.

E118. A nucleic acid molecule comprising a nucleotide sequence chosen from SEQ ID NOs: 44-50, 53-56, 122, or 123, or a nucleotide sequence having at least 75%, 80%, 85%, 90%, 95%, or 99% identity thereof, wherein the nucleic acid molecule does not comprise a nucleotide sequence encoding the amino acid sequence of SEQ ID NO: 3.

E119. A nucleic acid molecule comprising a nucleotide sequence chosen from SEQ ID NOs: 44-50, 53-56, 122, or 123.

E120. A nucleic acid molecule comprising the nucleotide sequence of SEQ ID NO: 53, or a nucleotide sequence having at least 75%, 80%, 85%, 90%, 95%, or 99% identity thereof, wherein the nucleic acid molecule does not comprise a nucleotide sequence encoding the amino acid sequence of SEQ ID NO: 3, optionally wherein the nucleic acid molecule comprises the nucleotide sequence of SEQ ID NO: 53.

E121. A nucleic acid molecule comprising the nucleotide sequence of SEQ ID NO: 123, or a nucleotide sequence having at least 75%, 80%, 85%, 90%, 95%, or 99% identity thereof, wherein the nucleic acid molecule does not comprise a nucleotide sequence encoding the amino acid sequence of SEQ ID NO: 4, optionally wherein the nucleic acid molecule comprises the nucleotide sequence of SEQ ID NO: 123.

E122. A vector comprising the nucleic acid molecule of any one of E117-E121.

E123. A host cell comprising the nucleic acid molecule of any one of E117-E121 or the vector of E122.

E124. The host cell of E123, wherein the host cell is a mammalian cell.

E125. The host cell of E124, wherein the host cell is a CHO cell, a COS cell, a HEK-293 cell, an NS0 cell, a PER.C6® cell, or an Sp2.0 cell.

E126. A pharmaceutical composition comprising the polypeptide molecule of any one of E1-E111 or the multimeric protein molecule of any one of E112-E116, and a pharmaceutically acceptable carrier or excipient.

E127. The pharmaceutical composition of E126, further comprising HEPES buffered-saline.

E128. The pharmaceutical composition of E126, wherein the polypeptide molecule of any one of E1-E111 or the multimeric protein molecule of any one of E112-E116 is formulated at a concentration of about 0.015, about 0.15 or about 1.5 mg/mL.

E129. A method of making an isolated polypeptide molecule that specifically binds to CD2, comprising culturing the host cell of any one of E123-E125, under conditions wherein the polypeptide molecule is expressed by the host cell.

E130. The method of E129, further comprising isolating the polypeptide molecule.

E131. The polypeptide molecule produced using the method of E129 or E130.

E132. A method of reducing an activity of CD2, e.g., reducing CD2 signaling, in a subject in need thereof, the method comprising administering to the subject a therapeutically effective amount of the polypeptide molecule of any one of E1-E111, the multimeric protein molecule of any one of E112-E116, or the pharmaceutical composition of any one of E126-E128.

E133. A method of reducing the number of CD2-expressing cells, e.g., CD2-expressing memory T cells, e.g., CD2-expressing $T_{EM}$ cells, e.g., CD2-expressing CD4+ $T_{EM}$ cells or CD8+ $T_{EM}$ cells in a subject in need thereof, the method comprising administering to the subject a therapeutically effective amount of the polypeptide molecule of any one of E1-E111, the multimeric protein molecule of any one of E112-E116, or the pharmaceutical composition of any one of E126-E128.

E134. A method of increasing the Treg/$T_{EM}$ ratio or the Treg/$T_{CM}$ ratio, e.g., in CD4+ and/or CD8+ T cells, in a subject in need thereof, the method comprising administering to the subject a therapeutically effective amount of the polypeptide molecule of any one of E1-E111, the multimeric protein molecule of any one of E112-E116, or the pharmaceutical composition of any one of E126-E128.

E135. A method of disrupting the interaction between CD2 and a naturally-existing LFA3 molecule in a subject in need thereof, the method comprising administering to the subject a therapeutically effective amount of the polypeptide molecule of any one of E1-E111, the multimeric protein molecule of any one of E112-E116, or the pharmaceutical composition of any one of E126-E128.

E136. A method of treating an inflammatory disease, disorder or condition in a subject in need thereof, the method comprising administering to the subject a therapeutically effective amount of the polypeptide molecule of any one of E1-E111, the multimeric protein molecule of any one of E112-E116, or the pharmaceutical composition of any one of E126-E128.

E137. A method of treating an autoimmune disease, disorder or condition in a subject in need thereof, the method comprising administering to the subject a therapeutically effective amount of the polypeptide molecule of any one of E1-E111, the multimeric protein molecule of any one of E112-E116, or the pharmaceutical composition of any one of E126-E128.

E138. A method of treating a subject in need of immunosuppression, the method comprising administering to the subject a therapeutically effective amount of the polypeptide molecule of any one of E1-E111, the multimeric protein molecule of any one of E112-E116, or the pharmaceutical composition of any one of E126-E128.

E139. A method of treating a disease, disorder, or condition associated with or mediated by aberrant memory T cell response in a subject in need thereof, the method comprising administering to the subject a therapeutically effective amount of the polypeptide molecule of any one of E1-E111, the multimeric protein molecule of any one of E112-E116, or the pharmaceutical composition of any one of E126-E128.

E140. The method of any one of E132-E139, wherein the subject is human.

E141. The method of any one of E132-E140, comprising administering the polypeptide molecule, the multimeric protein molecule, or the pharmaceutical composition subcutaneously, intramuscularly, or intravenously.

E142. The method of E141, comprising administering the polypeptide molecule, the multimeric protein molecule, or the pharmaceutical composition subcutaneously.

E143. The method of E141, comprising administering the polypeptide molecule, the multimeric protein molecule, or the pharmaceutical composition intramuscularly.

E144. The method of E141, comprising administering the polypeptide molecule, the multimeric protein molecule, or the pharmaceutical composition intravenously.

E145. The method of any one of E132-E144, wherein the administration of the polypeptide molecule, the multimeric protein molecule, or the pharmaceutical composition has one or more of the following properties:
  i. the polypeptide molecule, the multimeric protein molecule, or the pharmaceutical composition is administered twice a week, once a week, once every two weeks, or once every three weeks, e.g., once a week,
  ii. the polypeptide molecule, the multimeric protein molecule, or the pharmaceutical composition is administered at a dose of about 5-20 mg/week (e.g., 5, 6, 7, 8, 9, 10, 12, 15, 17, or 20 mg/week), e.g., about 7.5 mg/week, iii. the polypeptide molecule, the multimeric protein molecule, or the pharmaceutical composition is administered at a dose of about 0.2-8 mg per injection (e.g., 0.2, 0.5, 1, 1.5, 2, 2.5, 3, 3.5, 4, 4.5, 5, 5.5, 6, 6.5, 7, 7.5, or 8 mg per injection), e.g., between 0.22-7.5 mg per injection or 7.5 mg per injection, iv. the polypeptide molecule, the multimeric protein molecule, or the pharmaceutical composition is administered in about 0.5-2.0 ml solution per injection (e.g., 0.5, 1, or 1.5 ml solution per injection), e.g., about 1 ml solution per injection, or v. the polypeptide molecule, the multimeric protein molecule, or the pharmaceutical composition is administered for one or more courses, e.g., wherein each course consists of 10-14 weeks (e.g., 10, 11, 12, 13, or 14 weeks), e.g., 12 weeks, e.g., wherein two adjoining courses are separated by a 10 to 14 week interval (e.g., a 10, 11, 12, 13, or 14-week interval), e.g., a 12-week interval, optionally wherein: the polypeptide molecule, the multimeric protein molecule, or the pharmaceutical composition is administered subcutaneously at a dose of about 15 mg/week once a week, e.g., wherein the multimeric protein molecule, or the pharmaceutical composition is administered for one or more courses, wherein each course consists of 12 weeks and two adjoining courses are separated by a 12-week interval.

E146. The method of any one of E132-E144, wherein the polypeptide molecule, the multimeric protein molecule, or the pharmaceutical composition, is administered at a dose of about 0.03, about 0.3, about 3, or about 100 mg/kg.

E147. The method of any one of E132-E144, wherein the polypeptide molecule, the multimeric protein molecule, or the pharmaceutical composition is administered in a dose volume of about 2 mL/kg.

E148. The method of any one of E132-E144, wherein the polypeptide molecule, the multimeric protein molecule, or the pharmaceutical composition is administered subcutaneously at a dose of about 7.5 mg/week.

E149. The method of any one of E132-E144, wherein the polypeptide molecule, the multimeric protein molecule, or the pharmaceutical composition, is administered weekly.

E150. The polypeptide molecule of any one of E1-E111, the multimeric protein molecule of any one of E112-E116, or the pharmaceutical composition of any one of E126-E128, for use as a medicament.

E151. The polypeptide molecule of any one of E1-E111, the multimeric protein molecule of any one of E112-E116, or the pharmaceutical composition of any one of E126-E128, for use in reducing the activity of CD2 in a subject.

E152. The polypeptide molecule of any one of E1-E111, the multimeric protein molecule of any one of E112-E116, or the pharmaceutical composition of any one of E126-E128, for use in treating a subject in need of immunosuppression.

E153. The polypeptide molecule of any one of E1-E111, the multimeric protein molecule of any one of E112-E116, or the pharmaceutical composition of any one of E126-E128, for use in treating an autoimmune disease, disorder or condition in a subject.

E154. The method or use of any one of E132-E153, wherein the subject has one or more of the following disease, disorder, or condition: type 1 diabetes, psoriasis, plaque psoriasis, palmoplantaris pustulosis, pustular psoriasis of palms and soles, pustulosis palmaris et plantaris, pustulosis of palms and soles, atopic dermatitis, lichen planus, graft-versus-host disease (GVHD), vitiligo, *Pityriasis rubra pilaris*, transplantation (e.g., organ transplantation, e.g., kidney transplantation), psoriatic arthritis, a disease, disorder, or condition requiring allogeneic hematopoietic stem cell transplantation, thalassemia, sickle cell disease, glanzmann thrombasthenia, Wiskott-Aldrich syndrome, chronic-granulomatous disease, severe congenital neutropenia, leukocyte adhesion deficiency, Schwachman-Diamond syndrome, Diamond-Blackfan anemia, Fanconi anemia, Dyskeratosis-congenita, Chediak-Higashi syndrome, aplastic anemia, alopecia areata, and T cell lymphoma (e.g., cutaneous T-cell lymphoma or peripheral T-cell non-Hodgkin's lymphoma).

E155. The method or use of any one of E132-E153, wherein the subject has one or more of the following disease, disorder, or condition: diabetes mellitus (e. g. Type I diabetes mellitus or insulin dependent diabetes mellitus); juvenile onset diabetes; inflammatory responses such as inflammatory skin diseases including psoriasis and dermatitis (e. g. atopic dermatitis); dermatomyositis; systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; gastritis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); multiple sclerosis; Reynaud's syndrome; autoimmune thyroiditis; allergic encephalomyelitis; Sjogren's syndrome; and immune responses associated with acute and delayed hypersensitivity mediated by cytokines and T-lymphocytes typically found in tuberculosis, sarcoidosis, polymyositis, granulomatosis and vasculitis; Wegener's disease; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; vitiligo; Reiter's disease; stiff-person syndrome; Bechet disease; giant cell arteritis; immune complex nephritis; IgA nephropathy; IgM polyneuropathies; immune thrombocytopenic purpura (ITP) or autoimmune thrombocytopenia and autoimmune hemolytic diseases; Hashimoto's thyroiditis; autoimmune hepatitis; autoimmune hemophilia; autoimmune lymphoproliferative syndrome (ALPS); autoimmune uveoretinitis; Guillain-Barre syndrome; Goodpasture's syndrome; mixed connective tissue disease; autoimmune-associated infertility; polyarteritis nodosa; alopecia areata; idiopathic myxedema; graft versus host disease; muscular dystrophy (Duchenne, Becker, Myotonic, Limb-girdle, Facioscapulohumeral, Congenital, Oculopharyngeal, Distal, Emery-Dreifuss); and an inflammatory non-immune disease, such as a heart disease or a brain disease.

E156. The method or use of any one of E132-E153, wherein:
i. the subject has diabetes,
ii. the subject has type 1 diabetes (T1D),
iii. the subject has new onset T1D,
iv. the subject has new onset T1D with residual β cell function,
v. the subject is diagnosed for new onset T1D for less than 100 days),
vi. the subject is a T1D patient in the pre-diabetes stage,
vii. the subject has stage 2 T1D, e.g., the subject exhibits dysglycemia, has a presymptomatic disease, and/or is positive for at least two T1D-associated autoantibodies,
viii. the subject has stage 3 T1D, e.g., the subject exhibits hyperglycemia, has a symptomatic disease, and/or is positive for at least two T1D-associated autoantibodies, or
ix. the subject is positive for one or more T1D-associated autoantibodies.

E157. The method or use of any one of E132-E156, further comprising administering to the subject a second therapy, optionally wherein the second therapy promotes the activity of Tregs or increases the number of Tregs, optionally wherein the second therapy comprises IL-2.

E158. The method or use of E156, wherein the subject has diabetes, e.g., type 1 diabetes, e.g., new onset type 1 diabetes, and the second therapy comprises insulin.

E159. A method of detecting CD2 in a sample, tissue, or cell using the polypeptide molecule of any one of E1-E111, the multimeric protein molecule of any one of E112-E116, or the pharmaceutical composition of any one of E126-E128, comprising contacting the sample, tissue or cell with the polypeptide molecule, multimeric protein molecule, or pharmaceutical composition, and detecting the polypeptide molecule, multimeric protein molecule, or pharmaceutical composition.

E160. A kit comprising the polypeptide molecule of any one of E1-E111, the multimeric protein molecule of any one of E112-E116, or the pharmaceutical composition of any one of E126-E128.

E161. An isolated polypeptide molecule, or functional variant thereof, that specifically binds to CD2,
wherein the polypeptide molecule comprises an amino acid sequence having at least about 75%, 80%, 85%, 90%, 95%, 98% or 99% identity to the amino acid sequence of SEQ ID NO: 69, and
wherein the polypeptide molecule does not comprise the amino acid sequence of SEQ ID NO: 4.

E162. The isolated polypeptide molecule, or functional variant thereof, of E161,
wherein the polypeptide molecule comprises an amino acid sequence having at least 90% identity to the amino acid sequence of SEQ ID NO: 69, and
wherein the polypeptide molecule does not comprise the amino acid sequence of SEQ ID NO: 4.

E163. The isolated polypeptide molecule of E161 or E162, wherein the polypeptide molecule comprises the amino acid sequence of SEQ ID NO: 69.

E164. An isolated polypeptide, or functional variant thereof, that specifically binds to CD2, comprising an LFA3 domain comprising an amino acid sequence having at least about 75%, 80%, 85%, 90%, 95%, or 99% identity to an amino acid sequence selected from the group consisting of SEQ ID NOs: 17-41, and wherein the LFA3 domain does not comprise the amino acid sequence of SEQ ID NO: 3.

E165. The isolated polypeptide, or functional variant thereof, of E164, wherein the amino acid sequence is SEQ ID NO: 17, 18, 19, 20, 21, 22 or 23 and wherein the LFA3 domain further comprises the amino acid residue of Leu or the amino acid sequence of LESLPS (SEQ ID NO: 118).

E166. The isolated polypeptide, or functional variant thereof, of E164, wherein the LFA3 domain comprises an amino acid sequence having at least 90% identity to SEQ ID NO: 26, and wherein the LFA3 domain does not comprise the amino acid sequence of SEQ ID NO: 3.

E167. The isolated polypeptide of E164 or E166, wherein the LFA3 domain comprises the amino acid sequence of SEQ ID NO: 26.

E168. An isolated polypeptide, or functional variant thereof, comprising an LFA3 domain,
wherein the LFA3 domain comprises the amino acid sequence of SEQ ID NO: 3 with one or more mutations at residues 36, 38, 43 and 86, numbered according to SEQ ID NO: 3.

E169. The isolated polypeptide, or functional variant thereof, of E168, wherein the LFA3 domain further comprises the amino acid residue of Leu or the amino acid sequence of LESLPS (SEQ ID NO: 118).

E170. The isolated polypeptide, or functional variant thereof, of E168 or E169, wherein the one or more mutations at residues 36, 38, 43 and 86 numbered according to SEQ ID NO: 3 are A36V, L38F, F43V and M86F.

E171. The isolated polypeptide, or functional variant thereof, of anyone of E164-E170, further comprising a second domain,
wherein the second domain comprises an immunoglobulin protein, e.g., a heavy chain constant region, e.g., a human heavy chain constant region, or a functional variant thereof;
wherein the second domain comprises an Fc region of a heavy chain (e.g., a human IgG1 heavy chain) or a functional variant thereof; or
wherein the second domain comprises a hinge region, a CH2 region, and a CH3 region, or a functional variant thereof.

E172. The isolated polypeptide, or functional variant thereof, of anyone of E164-E171, further comprising a second domain wherein the second domain comprises an Fc domain comprising an amino acid sequence having at least about 75%, 80%, 85%, 90%, 95%, or 99% identity to SEQ ID NO: 16.

E173. The isolated polypeptide, or functional variant thereof, of E172, wherein the second domain comprises an Fc domain comprising the amino acid sequence of SEQ ID NO: 16.

E174. The isolated polypeptide, or functional variant thereof, of anyone of E171-E173, further comprising a linker, wherein the linker links the N-terminus of the second domain to the C-terminus of the LFA3 domain.

E175. The isolated polypeptide, or functional variant thereof, of anyone of E171-E174, wherein:
i. the second domain is capable of forming a dimer with another second domain, e.g., through an intermolecular disulfide bond, and/or
ii. the second domain is capable of mediating antibody-dependent cell-mediated cytotoxicity (ADCC).

E176. The isolated polypeptide, or functional variant thereof, of anyone of E171-E175,
wherein the LFA3 domain comprises a polypeptide comprising an amino acid sequence having at least 90% identity to SEQ ID NO: 26, and wherein the polypeptide does not comprise the amino acid sequence of SEQ ID NO: 3; and
wherein the Fc domain comprises a polypeptide comprising an amino acid sequence having at least 90% identity to SEQ ID NO: 16.

E177. The isolated polypeptide, or functional variant thereof, of anyone of E171-E175,
wherein the polypeptide or functional variant thereof comprises the amino acid sequence of SEQ ID NO: 4, and
wherein the amino acid sequence comprises one or more mutations at residues 36, 38, 43, 86, 92, 228 and 230 numbered according to SEQ ID NO: 4.

E178. The isolated polypeptide, or fragment thereof, of E177, wherein the one or more mutations at residues 36, 38, 43, 86, 92, 228 and 230 numbered according to SEQ ID NO: 4 are A36V, L38F, F43V, M86F, V92_D93insL, D228E and L230M.

E179. An isolated polypeptide molecule that binds, e.g., specifically binds, to CD2, wherein the polypeptide molecule comprises a LFA3 domain and has one or more of the following properties:
  i. Enhanced monomeric expression demonstrated by a percentage of monomer that is about 70, 75, 80, 85, 90 or 95% higher relative to a polypeptide molecule comprising the amino acid sequence of SEQ ID NO: 120 as measured using size exclusion chromatography,
  ii. Enhanced monomeric expression and reduced multimeric expression demonstrated by a percentage of monomer that is more than about 75, 80, 85, 90, or 95%, a percentage of low molecular weight species (LMWS) that is less than about 10, 8, 6, 4, or 2%, and/or a percentage of high molecular weight species (HMWS) that is less than 5, 2, or 1% relative to a polypeptide molecule comprising the amino acid sequence of SEQ ID NO: 4, as measured using size exclusion chromatography,
  iii. Reduced aggregation propensity under thermal stress demonstrated by a percentage of monomer that is more than about 90, 92, or 95% after incubating at 37.4° C. for 24 hours, and/or showing a percentage of monomer that is more than about 75, 80, or 85% after incubating at 40° C. for 24 hours relative to a polypeptide molecule comprising the amino acid sequence of SEQ ID NO: 120, as measured using size exclusion chromatography,
  iv. Reduced aggregation propensity under thermal stress demonstrated by no more than about 5, 10, 15, or 20% increase in HMWS at 40° C., and/or no more than about 5, 10, 15, 20, or 25% increase in HMWS at 50° C. relative to a polypeptide molecule comprising the amino acid sequence of SEQ ID NO: 4, as measured using size exclusion chromatography,
  v. Reduced aggregation propensity under low pH demonstrated by no more than about 6, 7, 8, or 9% increase in HMWS at low pH for 5 hours relative to a polypeptide molecule comprising the amino acid sequence of SEQ ID NO: 4, as measured using size exclusion chromatography,
  vi. Enhanced stability as demonstrated by no more than about 0.5, 1, 1.5, or 2% increase in HMMS and/or about 0.5, 1, 2, 3, 4 or 5% increase in LMMS after 2 or 4 weeks of storage at 40° C. relative to a polypeptide molecule comprising the amino acid sequence of SEQ ID NO: 4, as measured using capillary gel electrophoresis (CGE) or size exclusion high performance liquid chromatography (SE-HPLC),
  vii. Enhanced stability relative to a polypeptide molecule comprising the amino acid sequence of SEQ ID NO: 4, e.g., showing no more than about 0.5, 1, 1.5, or 2% increase in HMMS and/or about 0.5, 1, or 1.5% increase in LMMS after 2, 4 or 6 weeks of storage at 25° C. as measured using SE-HPLC,
  viii. Enhanced stability relative to a polypeptide molecule comprising the amino acid sequence of SEQ ID NO: 4, e.g., showing no more than about 0.5, 1, or 1.5% increase in HMMS and/or about 0.5, 1, or 1.5% increase in LMMS after 2, 4 or 6 weeks of storage at 5° C. as measured using SE-HPLC,
  ix. Enhanced freeze-thaw stability demonstrated by no more than about 0.5, 1, or 1.5% increase in HMWS after 5 cycles of freeze-thaw relative to a polypeptide molecule comprising the amino acid sequence of SEQ ID NO: 4, as measured using size exclusion chromatography,
  x. Increased yield as demonstrated by a yield that is more than about 5.5, 6, 6.5, or 7 mg per 20 mL Expi293 culture relative to a polypeptide molecule comprising the amino acid sequence of SEQ ID NO: 120,
  xi. Increased Tm demonstrated by a Tm that is more than about 38, 40, 42, 45 or 50° C. relative to a polypeptide molecule comprising the amino acid sequence of SEQ ID NO: 120, as measured by differential scanning fluorometry (DSF),
  xii. Increased Tm as demonstrated by a Tm that is more than about 40, 45, 50, 55, or 60° C. relative to a polypeptide molecule comprising the amino acid sequence of SEQ ID NO: 4, as measured by DSF,
  xiii. Increased Tm as demonstrated by a Tm that is more than about 50 or 60° C. relative to a polypeptide molecule comprising the amino acid sequence of SEQ ID NO: 4, as measured by differential scanning calorimetry (DSC),
  xiv. A Tm1 that is more than about 55, 58, 60, 62, 64 or 66° C. and a Tm2 that is more than about 75, 78, 80, or 82° C. at pH 7.5; a Tm1 that is more than about 55, 58, 60, 62 or 64° C. and a Tm2 that is more than about 75, 78, 80 or 82° C. at pH 5.8; or a Tm1 that is more than about 55, 58 or 60° C. and a Tm2 that is more than about 75, 78, or 80° C. at pH 4.5 as measured by DSC,
  xv. Increased Tm as demonstrated by a Tm that is more than about 50 or 60° C. at pH 7.5 or pH 4.5 or a Tm that is more than about 50 or 62° C. at pH 5.8 relative to a polypeptide molecule comprising the amino acid sequence of SEQ ID NO: 4, as measured by DSC,
  xvi. Increased Tm as demonstrated by a Tm that is more than about 50 or 60° C. relative to a polypeptide molecule comprising the amino acid sequence of SEQ ID NO: 4 as measured by DSC and FabRICATOR® IdeS,
  xvii. Enhanced binding affinity to CD2 as demonstrated by a $K_D$ for human CD2 that is less than about 1.2, 1, 0.8, 0.6, 0.4, 0.2, 0.1, or 0.08 μM relative to a polypeptide molecule comprising the amino acid sequence of SEQ ID NO: 4, as measured by SPR, xviii. Enhanced binding affinity to CD2 as demonstrated by a $K_D$ for human CD2 that is less than about 1.3, 1.2, 1.1, or 1 μM, and/or a $K_D$ for cynomolgus CD2 that is less than 1.4, 1.3, 1.2, 1.1, or 1 μM relative to a polypeptide molecule comprising the amino acid sequence of SEQ ID NO: 4, as measured by SPR, xix. Enhanced binding affinity to CD2-expressing cells as demonstrated by a $K_d$ for binding to CD4 $T_{mem}$ cells that is no more than about 100, 200, 300, or 400 pM relative to a polypeptide molecule comprising the amino acid sequence of SEQ ID NO: 4, as measured using SPR, xx. Enhanced binding affinity to CD2-expressing cells as demonstrated by a calculated IC50 for binding to CD4 memory T cells that is no more than about 300, 400, 500, 600, 700, 800, 1000, 1200 or 1500 pM; a calculated IC50 for binding to CD4+ $T_{EM}$ cells that is no more than about 150, 300, 400, 500, 600, 700, 800, 1000 or 1200 pM; a calculated IC50 for binding to CD4+ $T_{CM}$ cells that is no more than about 100, 200, 300, 400, 500, 600, 700 or 800 pM; a calculated IC50 for binding to CD4 naïve T cells that is no more than about 200, 300, 400, 500, 600, 700, 800, 1000 or 1200 pM; a calculated IC50 for binding to expanded CD4 Treg cells that is no more than about 100, 200, 300, 400 or 500 pM; a calculated IC50 for binding to CD8 memory T cells that is no more than about 100, 200, 300, 400, 500 or 600 pM; and/or a calculated IC50 for binding to CD8 native T cells that is no more than about 300, 400, 500, 600, 700, 800, 1000, 1200, 1500, 1600 or 1700 pM, e.g., as measured using SPR and/or methods described in Example 2 with respect to Table 10 and FIG. 11, relative to a polypeptide molecule comprising the amino acid sequence of SEQ ID NO: 4, as measured by SPR, xxi. Enhanced binding affinity to CD2-expressing cells as demonstrated by a calculated $K_d$ for binding to CD4 memory T cells that is no more than about 100, 200, 300, 400, or 500 pM; a calculated $K_d$ for binding to CD4+ $T_{EM}$ cells that is no more than about 100, 200, 300, 400, 500, or 600 pM; a calculated $K_d$ for binding to CD4+ $T_{CM}$ cells that is no more than about 100, 200, 300, 400, or 500 pM; a calculated $K_d$ for binding to CD4 naïve T cells that is no more than about 100, 200, 300 or 400 pM; a calculated $K_d$ for binding to expanded CD4 Treg cells that is no more than about 100, 200 or 300 pM; a calculated $K_d$ for binding to CD8 memory T cells that is no more than about 50, 100 or 150 pM; a calculated $K_d$ for binding to CD8 naïve T cells that is no more than about 50, 100, 200, 300, 400, or 500 pM relative to a polypeptide molecule comprising the amino acid sequence of SEQ ID NO: 4, as measured by SPR, xxii. Enhanced binding affinity to CD2-expressing cells as demonstrated by a reduced EC50 for binding to cynomolgus CD4+ $T_EM$ cells relative to a polypeptide molecule comprising the amino acid sequence of SEQ ID NO: 4, as measured by SPR, xxiii. Enhanced cytotoxicity against CD2-expressing cells as demonstrated by an EC50 for killing CD4 $T_{mem}$ cells that is no more than about 400, 600, 800, 1000, 1200, or 1400 pM relative to a polypeptide molecule comprising the amino acid sequence of SEQ ID NO: 4, as measured using an antibody dependent cellular cytotoxicity (ADCC) assay, xxiv. Enhanced cytotoxicity against CD2-expressing cells as demonstrated by an EC50 for killing CD8 $T_{mem}$ cells that is no more than about 1, 5, 10, 20, 30, 40, or 50 nM relative to a polypeptide molecule comprising the amino acid sequence of SEQ ID NO: 4, as measured using an antibody dependent cellular cytotoxicity (ADCC) assay, xxv. Enhanced inhibition of allogeneic T cell response, wherein the allogeneic T cell response is T cell proliferation and/or cytokine production, as demonstrated by an IC50 for a mixed lymphocyte reaction (MLR) assay that is no more than about 400, 800, 1200, 1600, 2000, or 2400 pM relative to a polypeptide molecule comprising the amino acid sequence of SEQ ID NO: 4, xxvi. Enhanced inhibition of allogeneic T cell response, wherein the allogenic T cell response is T cell proliferation and/or cytokine production, as demonstrated by an IC50 for a mixed lymphocyte reaction (MLR) assay in the absence of NK cells that is no more than about 330, 400, 500, 600, 800, 1000, 1500 or 2000 pM relative to a polypeptide molecule comprising the amino acid sequence of SEQ ID NO: 4, xxvii. Enhanced inhibition of tetanus toxoid recall response as demonstrated by an IC50 for CD4 $T_{mem}$ IFNγ production that is no more than about 1, 2, 5, 10, 15, 20, or 25 nM relative to a polypeptide molecule comprising the amino acid sequence of SEQ ID NO: 4, as measured in a tetanus toxoid recall (TTR) assay, xxviii. Slower clearance in vivo as demonstrated by a clearance from central that is no more than about 0.14, 0.16, 0.18, 0.2, or 0.22 mL/hr/kg relative to a polypeptide molecule comprising the amino acid sequence of SEQ ID NO: 4, as measured by PK/PD studies, and/or xxix. Enhanced purity of at least about 98% or 99% relative to a polypeptide molecule comprising the amino acid sequence of SEQ ID NO: 4, as measured using capillary gel electrophoresis.

E180. An isolated nucleic acid encoding the isolated polypeptide, or functional variant thereof, of any one of E161-E179.

E181. The isolated nucleic acid of E180, comprising a nucleic acid sequence having at least about 75%, 80%, 85%, 90%, 95%, 98% identity to SEQ ID NO: 43, 53 and/or 123.

E182. The isolated nucleic acid of E180 or E181, comprising the nucleic acid sequence of SEQ ID NO: 43, 53 and/or 123.

E183. A vector comprising the nucleic acid of anyone of E180-E182.

E184. A host cell comprising the nucleic acid of anyone of E180-E182 or the vector of E183.

E185. The host cell of E184, wherein the host cell is a mammalian cell selected from the group consisting of an Expi293 cell, an ExpiCHO cell, a CHO cell, a COS cell, a HEL-293 cell, an NSO cell, a PER.C6 cell, or an SP2.0 cell.

E186. The host cell of E184 or E185, wherein the host cell is an Expi293 cell or an ExpiCHO cell.

E187. A pharmaceutical composition comprising the polypeptide molecule of any one of E161-E179 and a pharmaceutically acceptable carrier or excipient.

E188. The pharmaceutical composition of E187, comprising 7.5 mg of the polypeptide molecule of any one of E161-E179 and HEPES buffered saline.

E189. A method of making an isolated polypeptide molecule that specifically binds to CD2, comprising culturing the host cell of any one of E184-E186, under conditions wherein the polypeptide molecule is expressed by the host cell.

E190. The method of E189, further comprising isolating the polypeptide molecule.

E191. The isolated polypeptide of any one of E161-E179, or the pharmaceutical composition of E187 or E188, for use in treating a subject in need of immunosuppression.

E192. Use of the isolated polypeptide of any one of E161-E179 or the pharmaceutical composition of E187 or E188, for treating an immune disease, disorder or condition.

E193. A method for treating or preventing an immune disease, disorder or condition mediated by CD2 in a human subject in need thereof, said method comprising administering to the subject an effective amount of the pharmaceutical composition of E187 or E188, wherein said disease, disorder or condition is selected from the group consisting of: type 1 diabetes, psoriasis, plaque psoriasis, palmoplantaris pustulosis, pustular psoriasis of palms and soles, pustulosis palmaris et plantaris, pustulosis of palms and soles, atopic dermatitis, lichen planus, graft-versus-host disease (GVHD), vitiligo, Pityriasis rubra pilaris, transplantation (e.g., organ transplantation, e.g., kidney transplantation), psoriatic arthritis, a disease, disorder, or condition requiring allogeneic hematopoietic stem cell transplantation, thalassemia, sickle cell disease, glanzmann thrombasthenia, Wiskott-Aldrich syndrome, chronic-granulomatous disease, severe congenital neutropenia, leukocyte adhesion deficiency, Schwachman-Diamond syndrome, Diamond-Blackfan anemia, Fanconi anemia, Dyskeratosis-congenita, Chediak-Higashi syndrome, aplastic anemia, alopecia areata, and T cell lymphoma (e.g., cutaneous T-cell lymphoma or peripheral T-cell non-Hodgkin's lymphoma).

E194. The method of E193, wherein said disease is diabetes, e.g., type 1 diabetes (T1D), e.g., new onset T1D, e.g., new onset T1D with residual β cell function (e.g., the subject is diagnosed for less than 100 days), e.g., stage 2 or stage 3 T1D.

E195. Use of the isolated polypeptide of anyone of E161-E179 in the manufacture of a medicament for treating an immune disease, disorder or condition.

E196. A method of detecting CD2 in a sample, tissue, or cell using the isolated polypeptide or functional variant thereof, of any one of E161-E179, comprising contacting the sample, tissue or cell with the polypeptide or functional variant thereof, and detecting the polypeptide or functional variant thereof.

E197. The method or use of E132-E153, wherein the subject has psoriatic arthritis.

BRIEF DESCRIPTION OF THE DRAWINGS

The foregoing summary, as well as the following detailed description of the invention, will be better understood when read in conjunction with the appended drawings. For the purpose of illustrating the invention there are shown in the drawings embodiment(s). It should be understood, however, that the invention is not limited to the precise arrangements and instrumentalities shown.

FIG. 1: Structure-based library design for first generation stability (S) and affinity+stability (AS) yeast display libraries. 16 core (S and AS library) and 15 contact residues (AS library) residues were mutated to 4-6 chemically similar residues. The residues shown in FIG. 1 are numbered according to SEQ ID NO: 2.

FIGS. 2A-2D: Frequency of amino acid variation in clones identified from yeast display libraries identified 6 hotspot positions. FIG. 2A is a graph showing six hotspot residues identified. These six residues are numbered according to SEQ ID NO: 2. In FIG. 2B, the LFA3 residues targeted in the libraries are shown in bold, and the six hotspot residues are shown in bold and underlined. FIG. 2C is a graph showing frequency of amino acid variation in the six hotspot positions. FIG. 2D is a table showing the designing of the 6 recombinant variants M1-M6. The amino acid residues in the hotspot positions are specified for each variant.

FIGS. 5A and 5B: Exemplary characterization of high affinity LFA3 variants. Clones were assessed for binding affinity to recombinant CD2 in a Biacore assay (SPR) (FIG. 5A) and thermal stability by DSF (FIG. 5B). "LFA3-WT" refers to LFA3-Fc WT. "LFA3-Pfe" refers to WT LFA3-Pfe.

FIGS. 7A-7D: Domain boundary variants M1-d1 (also referred to as "M1d1") and M1-d3 (also referred to as "M1d3") affinity for human and cyno CD2 and thermal stability (DSF).

FIGS. 8A-8D: Design and characterization of M7-d1. Shown in FIGS. 8B, 8C, and 8D are exemplary results from SEC analysis, thermal stability analysis, and affinity analysis, respectively. "LFA3-WT" in FIG. 8C and "WT" in FIG. 8D refer to LFA3-Fc WT. "LFA3-Pfe" in FIG. 8C refers to WT LFA3-Pfe.

FIG. 11: Exemplary LFA3-Fc binding to primary human T cell populations using competitive binding assay with an anti-CD2 antibody. Assay was run in triplicate and mean±st. dev. is plotted. "WT" refers to LFA3-Fc WT.

FIG. 13A: Target cells (CD4 memory cells) were incubated with 250 nM protein. Mean of triplicate wells±st. dev. for 1 of 5 donors is shown. Target cells (CD4 naïve, CD4 memory, or B cells) were incubated with 100 nM LFA3-Fc WT (FIG. 13B) or LFA3-Fc M1d1 (FIG. 13C) and NK cells (effector cells) at various effector to target cell ratios. Mean of triplicate wells±st. dev. for 1 donor is shown. "WT" refers to LFA3-Fc WT.

FIG. 19: Experimental design of cynomolgus monkey repeat dose PK/PD study 17MA057.

FIG. 21: LFA3-Fc M1d1 treatment has greater impact on memory T cells. Exemplary data is plotted as fold change compared to pre-dose cell counts. Mean+/−SEM of 4 animals is shown.

FIG. 24: Proposed mechanisms of action of LFA3-Fc.

FIG. 25A depicts CD2 expression in CD4 effector memory ("EM") cells.

FIG. 25B depicts CD2 expression in CD4 central memory ("CM") cells. Data are expressed as the geometric mean florescence intensity (gMFI) of n=2 donor+/−SD. KLRG1=killer-cell lectin like receptor G1; TIGIT=T cell immunoreceptor with Ig and ITIM domains.

FIG. 26A and FIG. 26B represent two donors analyzed on two different days. Data are expressed as the geometric mean florescence intensity (gMFI)+/−SD. CCR7=C—C chemokine receptor type 7; PD1=Programmed cell death protein 1; TH=T helper; Tfh=T follicular helper; Tregs=T regulatory cells.

FIGS. 32A-32D: Exemplary size exclusion high performance liquid chromatography (SE-HPLC) analysis of LFA3-Fc M1d1 and LFA3-Fc WT formulated in Tris buffer pH 7.5 (FIG. 32A), histidine buffer pH 5.8 (FIG. 32B) or glutamate buffer pH 4.5 (FIG. 32C) at time 0 and following storage at 25° C. for 2, 4 or 6 weeks. The percentage of low molecular mass species (LMMS) (FIG. 32D) and high molecular mass species (HMMS) (FIG. 32A-32C) was quantified.

DETAILED DESCRIPTION

Figure 3A:
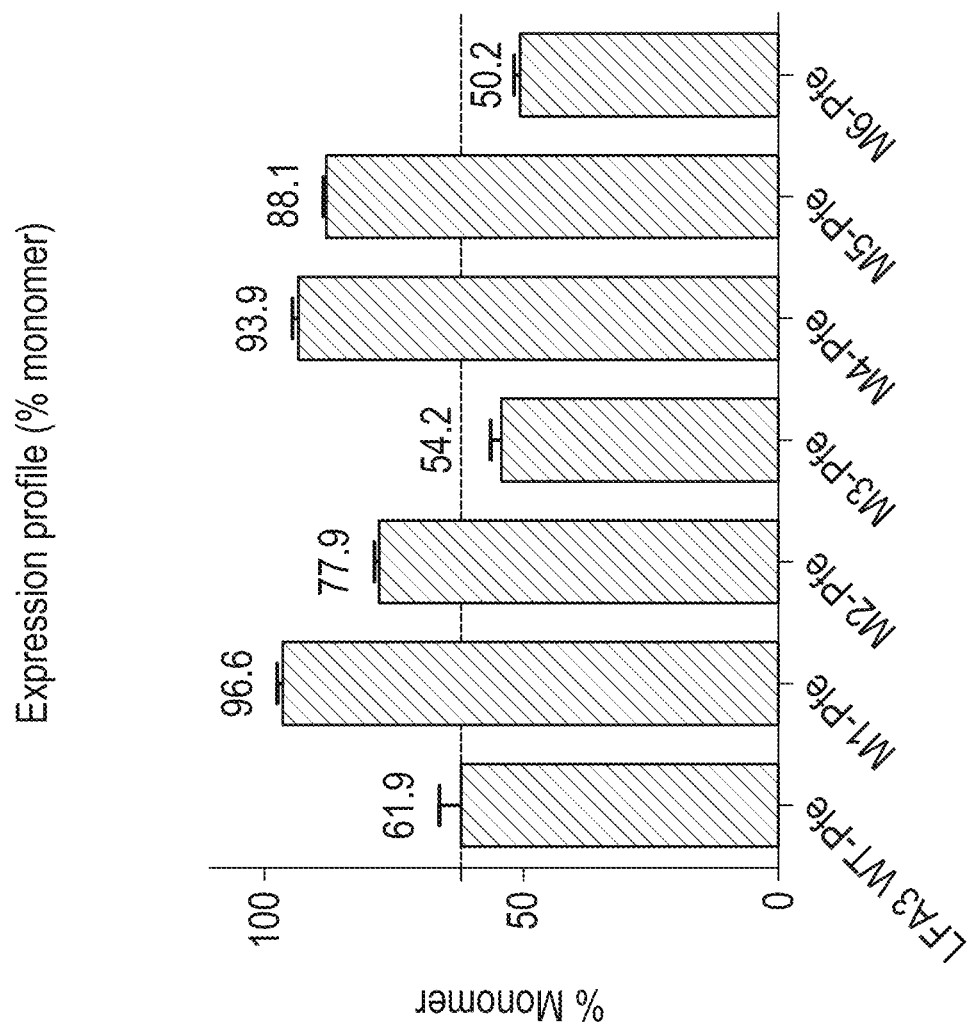
FIGS. 3A-3D: Exemplary graphs depicting molecular assessment of wild-type LFA3 (LFA3 WT) and M1-M6 variant Fc fusion proteins. "LFA3 WT-Pfe" and "WT-Pfe" refer to WT LFA3-Pfe.

Disclosed herein are LFA3 polypeptide molecules, e.g., variant LFA3 polypeptide molecules, e.g., variant LFA3 fusion polypeptide molecules, e.g., variant LFA3-Fc fusion polypeptide molecules, that bind to CD2, inhibit an activity of CD2, and/or depleting CD2-expressing cells. Methods of making LFA3 polypeptide molecules, compositions comprising these LFA3 polypeptide molecules, and methods of using these LFA3 polypeptide molecules are provided.

In some embodiments, the LFA3 polypeptide molecules of the invention have enhanced stability and manufacturability properties relative to wild-type LFA3 polypeptide molecules. In some embodiments, the LFA3 polypeptide molecules (e.g., variant LFA3-Fc fusion proteins) of the invention have increased binding affinity to CD2 relative to wild-type LFA3 polypeptide molecules (e.g., wild type LFA3-Fc fusion proteins). In some embodiments, the LFA3 polypeptide molecules (e.g., variant LFA3-Fc fusion proteins) of the invention show enhanced cytotoxicity against CD2-expressing cells relative to wild-type LFA3 polypeptide molecules (e.g., wild type LFA3-Fc fusion proteins). In some embodiments, the LFA3 polypeptide molecules (e.g., variant LFA3-Fc fusion proteins) of the invention exhibit enhanced inhibition of allogeneic T cell response relative to wild-type LFA3 polypeptide molecules (e.g., wild type LFA3-Fc fusion proteins). In some embodiments, the LFA3 polypeptide molecules (e.g., variant LFA3-Fc fusion proteins) of the invention show a slower clearance in vivo relative to wild-type LFA3 polypeptide molecules (e.g., wild type LFA3-Fc fusion proteins).

Polynucleotides encoding LFA3 polypeptide molecules are provided. Host cells that express LFA3 polypeptide molecules are provided. Methods of treatment using LFA3 polypeptide molecules are provided. In one embodiment, such methods include methods of treating an inflammatory disease, disorder, or condition. In one embodiment, such methods include methods of treating diseases in need of immune suppression, including, but not limited to, autoimmune diseases. In one embodiment, such methods include methods of treating an inflammatory non-immune disease, such as a heart disease or a brain disease.

The section headings used herein are for organizational purposes only and are not to be construed as limiting the subject matter described.

All references cited herein, including patent applications, patent publications, and Genbank Accession numbers are herein incorporated by reference, as if each individual reference were specifically and individually indicated to be incorporated by reference in its entirety.

The techniques and procedures described or referenced herein are generally well understood and commonly employed using conventional methodology by those skilled in the art, such as, for example, the widely utilized methodologies described in Sambrook et al, Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds); Gene Transfer Vectors for Mammalian Cells (J. M. Miller and M. P. Calos, eds., 1987); PCR: The Polymerase Chain Reaction, (Mullis et al, eds., 1994); Current Protocols in Immunology (J. E. Coligan et al, eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999)); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993); and updated versions thereof.

LFA3 polypeptide molecules (e.g., variant LFA3 fusion polypeptide molecules) can be used in the prevention, treatment, and/or amelioration of diseases, disorders or conditions including, but not limited to, type 1 diabetes, psoriasis, plaque psoriasis, palmoplantaris pustulosis, pustular psoriasis of palms and soles, pustulosis palmaris et plantaris, pustulosis of palms and soles, atopic dermatitis, lichen planus, graft-versus-host disease (GVHD), vitiligo, *Pityriasis rubra pilaris*, transplantation (e.g., organ transplantation, e.g., kidney transplantation), psoriatic arthritis, a disease, disorder, or condition requiring allogeneic hematopoietic stem cell transplantation, thalassemia, sickle cell disease, glanzmann thrombasthenia, Wiskott-Aldrich syndrome, chronic-granulomatous disease, severe congenital neutropenia, leukocyte adhesion deficiency, Schwachman-Diamond syndrome, Diamond-Blackfan anemia, Fanconi anemia, Dyskeratosis-congenita, Chediak-Higashi syndrome, aplastic anemia, alopecia areata, and T cell lymphoma (e.g., cutaneous T-cell lymphoma or peripheral T-cell non-Hodgkin's lymphoma). Additional exemplary diseases, disorders or conditions are: diabetes mellitus (e. g. Type I diabetes mellitus or insulin dependent diabetes mellitus); juvenile onset diabetes; inflammatory responses such as inflammatory skin diseases including psoriasis and dermatitis (e. g. atopic dermatitis); dermatomyositis; systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; gastritis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); multiple sclerosis; Reynaud's syndrome; autoimmune thyroiditis; allergic encephalomyelitis; Sjogren's syndrome; and immune responses associated with acute and delayed hypersensitivity mediated by cytokines and T-lymphocytes typically found in tuberculosis, sarcoidosis, polymyositis, granulomatosis and vasculitis; Wegener's disease; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; vitiligo; Reiter's disease; stiff-person syndrome; Bechet disease; giant cell arteritis; immune complex nephritis; IgA nephropathy; IgM polyneuropathies; immune thrombocytopenic purpura (ITP) or autoimmune thrombocytopenia and autoimmune hemolytic diseases; Hashimoto's thyroiditis; autoimmune hepatitis; autoimmune hemophilia; autoimmune lymphoproliferative syndrome (ALPS); autoimmune uveoretinitis; Guillain-Barre syndrome; Goodpasture's syndrome; mixed connective tissue disease; autoimmune-associated infertility; polyarteritis nodosa; alopecia areata; idiopathic myxedema; graft versus host disease; muscular dystrophy (Duchenne, Becker, Myotonic, Limb-girdle, Facioscapulohumeral, Congenital, Oculopharyngeal, Distal, Emery-Dreifuss); and an inflammatory non-immune disease, such as a heart disease or a brain disease.

I. Definitions

The present invention may be understood more readily by reference to the following detailed description of exemplary embodiments of the invention and the examples included therein.

Unless otherwise defined, all technical and scientific terms used herein have the same meaning as commonly understood by one of ordinary skill in the art to which this invention belongs. In case of conflict, the present specification, including definitions, will control.

Further, unless otherwise required by context or expressly indicated, singular terms shall include pluralities and plural terms shall include the singular.

It is understood that aspect and embodiments of the invention described herein include "consisting" and/or "consisting essentially of" aspects and embodiments. As used herein, the singular form "a", "an", and "the" includes plural references unless indicated otherwise.

In this application, the use of "or" means "and/or" unless expressly stated or understood by one skilled in the art. In the context of a multiple dependent claim, the use of "or" refers back to more than one preceding independent or dependent claim.

"About" or "approximately," when used in connection with a measurable numerical variable, refers to the indicated value of the variable and to all values of the variable that are within the experimental error of the indicated value (e.g. within the 95% confidence interval for the mean) or within 10 percent of the indicated value, whichever is greater. Numeric ranges are inclusive of the numbers defining the range.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10.

Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

It is to be understood that the terminology used herein is for the purpose of describing particular embodiments only and is not intended to be limiting. In this specification and in the claims that follow, reference will be made to a number of terms that shall be defined to have the following meanings.

The term "isolated molecule" (where the molecule is, for example, a polypeptide or a polynucleotide) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well-known in the art. Molecule purity or homogeneity may be assayed by a number of means well-known in the art. For example, the purity of a polypeptide sample may be assayed using polyacrylamide gel electrophoresis and staining of the gel to visualize the polypeptide using techniques well-known in the art. For certain purposes, higher resolution may be provided by using HPLC or other means well-known in the art for purification.

As used herein, "substantially pure" means an object species is the predominant species present (i.e., on a molar basis it is more abundant than any other individual species in the composition), and preferably a substantially purified fraction is a composition wherein the object species (e.g., a glycoprotein) comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species. In certain embodiments a substantially pure material is at least 50% pure (i.e., free from contaminants), more preferably, at least 90% pure, more preferably, at least 95% pure, yet more preferably, at least 98% pure, and most preferably, at least 99% pure.

The term "identity," as known in the art, refers to a relationship between the sequences of two or more polypeptide molecules or two or more nucleic acid molecules, as determined by comparing the sequences. In the art, "identity" also means the degree of sequence relatedness between polypeptide or nucleic acid molecule sequences, as the case may be, as determined by the match between strings of nucleotide or amino acid sequences. "Identity" measures the percent of identical matches between two or more sequences with gap alignments addressed by a particular mathematical model of computer programs (i. e. "algorithms").

The term "similarity" is a related concept, but in contrast to "identity", refers to a measure of similarity which includes both identical matches and conservative substitution matches. Since conservative substitutions apply to polypeptides and not nucleic acid molecules, similarity only deals with polypeptide sequence comparisons. If two polypeptide sequences have, for example, 10 out of 20 identical amino acids, and the remainder are all non-conservative substitutions, then the percent identity and similarity would both be 50%. If in the same example, there are 5 more positions where there are conservative substitutions, then the percent identity remains 50%, but the percent similarity would be 75% (15 out of 20). Therefore, in cases where there are conservative substitutions, the degree of similarity between two polypeptide sequences will be higher than the percent identity between those two sequences.

Polypeptide "fragments" or "portions" according to the invention may be made by truncation, e.g. by removal of one or more amino acids from the N and/or C-terminal ends of a polypeptide. Up to 10, up to 20, up to 30, up to 40 or more amino acids may be removed from the N and/or C terminal in this way. Fragments may also be generated by one or more internal deletions.

A variant molecule may comprise 1, 2, 3, 4, 5, up to 10, up to 20, up to 30 or more amino acid substitutions and/or deletions and/or insertions from the specific sequences and fragments discussed above. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Insertion" variants may comprise the insertion of individual amino acids, insertion of small groups of amino acids such as 2, 3, 4 or 5 amino acids, or insertion of larger amino acid regions, such as the insertion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows.

Substitution variants have at least one amino acid residue in the molecule removed and a different residue inserted in its place. Exemplary conservative substitutions are shown in Table 1 under the heading of "conservative substitutions." Additional substitutions denominated "exemplary substitutions" below, or as further described below in reference to amino acid classes, may be introduced and the products screened.

TABLE 1

Amino Acids and Substitutions

| Original Residue | Conservative Substitutions | Exemplary Substitutions |
| --- | --- | --- |
| alanine Ala (A) | Val (V) | Val (V); Leu (L); Ile (I) |
| arginine Arg (R) | Lys (K) | Lys (K); Gln (Q); Asn (N) |
| asparagine Asn (N) | Gln (Q) | Gln (Q); His (H); Asp (D), Lys (K); Arg (R) |
| aspartic acid Asp (D) | Glu (E) | Glu (E); Asn (N) |
| cysteine Cys (C) | Ser (S) | Ser (S); Ala (A) |
| glutamine Gln (Q) | Asn (N) | Asn (N); Glu (E) |
| glutamic Glu (E) | Asp (D) | Asp (D); Gln (Q) |
| glycine Gly (G) | Ala (A) | Ala (A) |
| histidine His (H) | Arg (R) | Asn (N); Gln (Q); Lys (K); Arg (R) |
| isoleucine Ile (I) | Leu (L) | Leu (L); Val (V); Met (M); Ala (A); Phe (F); Norleucine (Nle) |
| leucine Leu (L) | Ile (I) | Norleucine (Nle); Ile (I); Val (V); Met (M); Ala (A); Phe (F) |
| lysine Lys (K) | Arg (R) | Arg (R); Gln (Q); Asn (N) |
| methionine Met (M) | Leu (L) | Leu (L); Phe (F); Ile (I) |
| phenylalanine Phe (F) | Tyr (Y) | Leu (L); Val (V); Ile (I); Ala (A); Tyr (Y) |
| proline Pro (P) | Ala (A) | Ala (A) |
| serine Ser (S) | Thr (T) | Thr (T) |
| threonine Thr (T) | Ser (S) | Ser (S) |
| tryptophan Trp (W) | Tyr (Y) | Tyr (Y); Phe (F) |
| tyrosine Tyr (Y) | Phe (F) | Trp (W); Phe (F); Thr (T); Ser (S) |
| valine Val (V) | Leu (L) | Ile (I); Leu (L); Met (M); Phe (F); Ala (A); Norleucine (Nle) |

Substantial modifications in the biological properties of the molecule are accomplished by selecting substitutions that differ significantly in their effect on maintaining (a) the structure of the polypeptide backbone in the area of the substitution, for example, as a beta-sheet or helical conformation, (b) the charge or hydrophobicity of the molecule at the target site, or (c) the bulk of the side chain. Naturally occurring residues are divided into groups based on common side-chain properties:
   i. Non-polar: Norleucine, Met, Ala, Val, Leu, Ile;
   ii. Polar without charge: Cys, Ser, Thr, Asn, Gln;
   iii. Acidic (negatively charged): Asp, Glu;
   iv. Basic (positively charged): Lys, Arg;
   v. Residues that influence chain orientation: Gly, Pro; and
   vi. Aromatic: Trp, Tyr, Phe, His.

Non-conservative substitutions are made by exchanging a member of one of these classes for another class.

One type of substitution, for example, that may be made is to change one or more cysteines in the molecule, which may be chemically reactive, to another residue, such as, without limitation, alanine or serine. For example, there can be a substitution of a non-canonical cysteine. In some embodiments, the cysteine is canonical. Any cysteine residue not involved in maintaining the proper conformation of the molecule also may be substituted, generally with serine, to improve the oxidative stability of the molecule and prevent aberrant cross-linking. Conversely, cysteine bond(s) may be added to the molecule to improve its stability.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', F(ab')$_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. A diabody may include a non-covalent dimer of single-chain Fv (scFv) fragment that consists of the heavy chain variable ($V_H$) and light chain variable ($V_L$) regions connected by a small peptide linker. In another embodiment, a diabody is single-chain (Fv)$_2$ in which two scFv fragments are covalently linked to each other. A triabody is, for example, a single-chain (Fv)$_2$ in which three scFv fragments are covalently linked to each other.

An antibody includes an antibody of any class, such as IgG, IgA, or IgM (or subclass thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$ and IgA$_2$. The heavy-chain constant regions that correspond to the different classes of immunoglobulins are called alpha, delta, epsilon, gamma, and mu, respectively. The subunit structures and three-dimensional configurations of different classes of immunoglobulins are well-known.

A molecule that "preferentially binds" or "specifically binds" (used interchangeably herein) to a target is a term well understood in the art, and methods to determine such specific or preferential binding are also well-known in the art. A molecule is said to exhibit "specific binding" or "preferential binding" if it reacts or associates more frequently, more rapidly, with greater duration and/or with greater affinity with a particular cell or substance than it does with alternative cells or substances. A molecule "specifically binds" or "preferentially binds" to a target if it binds with greater affinity, avidity, more readily, and/or with greater duration than it binds to other substances. Also, a molecule "specifically binds" or "preferentially binds" to a target if it binds with greater affinity, avidity, more readily, and/or with greater duration to that target in a sample than it binds to other substances present in the sample. For example, a molecule that specifically or preferentially binds to CD2 is a molecule that binds CD2 with greater affinity, avidity, more readily, and/or with greater duration than it binds to a non-CD2 protein. It is also understood by reading this definition, for example, that a molecule which specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specific binding" or "preferential binding" includes a compound, e.g., a protein, a nucleic acid, and the like, which recognizes and binds to a specific molecule, but does not substantially recognize or bind other molecules in a sample. For instance, a molecule which recognizes and binds to a cognate ligand or binding partner (e.g., a LFA3 polypeptide molecule that binds CD2) in a sample, but does not substantially recognize or bind other molecules in the sample, specifically binds to that cognate ligand or binding partner. Thus, under designated assay conditions, the specified binding moiety binds preferentially to a particular target molecule and does not bind in a significant amount to other components present in a test sample.

A variety of assay formats may be used to select a molecule that specifically binds a target of interest. For example, solid-phase ELISA immunoassay, immunoprecipitation, Biacore™ (GE Healthcare, Piscataway, NJ), KinExA, fluorescence-activated cell sorting (FACS), Octet™ (FortdBio, Inc., Menlo Park, CA) and Western blot analysis are among many assays that may be used to identify a molecule that specifically reacts with an antigen or a receptor, or ligand binding portion thereof, that specifically binds with a cognate ligand or binding partner. Typically, a specific or selective reaction will be at least twice the background signal or noise, e.g., more than 10 times background, e.g., more than 50 times background, e.g., more than 100 times background, e.g., more than 500 times background, e.g., more than 1000 times background, e.g., more than 10,000 times background.

The term "binding affinity" is herein used as a measure of the strength of a noncovalent interaction between two molecules, e.g., a polypeptide molecule, and its target. The term "binding affinity" is used to describe monovalent interactions (intrinsic activity).

Additionally, to determine the binding affinity of LFA3 polypeptide molecules to CD2-expressing cells, cell binding experiments can be performed to determine the apparent affinity. The apparent affinity of polypeptide molecule binding to cells expressing the target can be calculated as the $EC_{50}$ of equilibrium binding titration curves in which the geometric mean fluorescence intensity (gMFI) of the target binding population is quantified by flow cytometry.

Binding affinity between two molecules, e.g. a polypeptide molecule and its target, through a monovalent interaction may be quantified by determination of the dissociation constant ($K_D$). In turn, $K_D$ can be determined by measurement of the kinetics of complex formation and dissociation using, e.g., the surface plasmon resonance (SPR) method (Biacore). The rate constants corresponding to the association and the dissociation of a monovalent complex are referred to as the association rate constants $k_a$ (or $k_{on}$ and dissociation rate constant $k_d$ (or $k_{off}$), respectively. $K_D$ is related to $k_a$ and $k_d$ through the equation $K_D=k_d/k_a$. The value of the dissociation constant can be determined directly by well-known methods and can be computed even for complex mixtures by methods such as those, for example, set forth in Caceci et al. (1984, Byte 9: 340-362). For example, the $K_D$ may be established using a double-filter nitrocellulose filter binding assay such as that disclosed by Wong & Lohman (1993, Proc. Natl. Acad. Sci. USA 90: 5428-5432). Other standard assays to evaluate the binding ability of ligands towards target antigens are known in the art, including for example, ELISAs, Western blots, RIAs, and flow cytometry analysis, and other assays exemplified elsewhere herein. The binding kinetics and binding affinity of the molecule also can be assessed by standard assays known in the art, such as Surface Plasmon Resonance (SPR), e.g. by using a Biacore™ system, or KinExA.

A competitive binding assay can be conducted in which the binding of the molecule to the target is compared to the binding of the target by another ligand of that target, such as an antibody or a soluble receptor that otherwise binds the target. The concentration at which 50% inhibition occurs is known as the $K_i$. Under ideal conditions, the $K_i$ is equivalent to $K_D$. The $K_i$ value will never be less than the $K_D$, so measurement of $K_i$ can conveniently be substituted to provide an upper limit for $K_D$.

Following the above definition, binding affinities associated with different molecular interactions, e.g., comparison of the binding affinity of different molecules for a given target, may be compared by comparison of the $K_D$ values for the individual molecule/target complexes. $K_D$ values for binding partners can be determined using methods well established in the art. One method for determining the $K_D$ is by using surface plasmon resonance, typically using a biosensor system such as a Biacore® system.

Similarly, the specificity of an interaction may be assessed by determination and comparison of the $K_D$ value for the interaction of interest, e.g., a specific interaction between a molecule and a target, with the $K_D$ value of an interaction not of interest, e.g., a control molecule known not to bind the target.

As stated previously elsewhere herein, specific binding may be assessed with reference to binding of the molecule to a control molecule that is not the target. This comparison may be made by comparing the ability of the molecule to bind to the target and to a control molecule. This comparison may be made as described above in an assessment of $K_D$ or $K_i$. The control molecule used in such a comparison may be any molecule that is not the target. Preferably, the control molecule is not identical to the target. Preferably the control molecule is not a fragment of the target. The control molecule used to determine specific binding may be unrelated in structure or function to the target. For example, the control molecule may be an unrelated material or accompanying material in the environment. The control molecule used to determine specific binding may be a molecule involved in the same in vivo pathway as the target, i.e., CD2. By ensuring that the molecule of the invention has specificity for CD2 over another such molecule, unwanted in vivo cross-reactivity may be avoided.

The molecule of the invention may retain the ability to bind to some molecules that are related to the target.

Alternatively, the molecule of the invention may have specificity for a particular target molecule. For example, it may bind to one target molecule as described herein, but may not bind, or may bind with significantly reduced affinity to a different target molecule as described herein. For example, a mature human CD2 may be used as the target, but the molecule that binds to that target may be unable to bind to or may bind with lesser affinity to, e.g. other CD2 proteins from other species, such as other mammalian CD2. In some embodiments, the molecule binds to both human and cynomolgus CD2.

A "fusion" protein or "fusion" molecule is a protein wherein a first polypeptide is operably linked, e.g., directly or indirectly, to a second polypeptide. In some embodiments, the LFA3 polypeptide molecule disclosed herein is a fusion protein comprising a LFA3 domain operably linked to a second polypeptide.

An "Fc fusion" protein or "Fc fusion" molecule is a protein wherein one or more polypeptides are operably linked, e.g., directly or indirectly, to an Fc polypeptide. An Fc fusion comprises the Fc region of an immunoglobulin with a fusion partner. In some embodiments, the LFA3 polypeptide molecule disclosed herein is an Fc fusion protein comprising a LFA3 domain operably linked to an Fc polypeptide.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As known in the art, a "constant region" of an antibody refers to the constant region of the antibody light chain or the constant region of the antibody heavy chain, either alone or in combination.

The terms "IgG Fc region", "Fc region", "Fc domain" and "FC", as interchangeably used herein refer to the portion of an IgG molecule that correlates to a crystallizable fragment obtained by papain digestion of an IgG molecule. As used herein, the terms relate to the constant region of an antibody excluding the first constant region immunoglobulin domain and further relates to portions of that region. Thus, Fc refers to the last two constant region immunoglobulin domains of IgA, IgD, and IgG, and the last three constant region immunoglobulin domains of IgE and IgM, and the flexible hinge N-terminal to these domains, or portions thereof. For IgA and IgM, Fc may include the J chain. For IgG, Fc comprises immunoglobulin domains Cγ2 and Cγ3 (C gamma 2 and C gamma 3) and the hinge between Cγ1 (C gamma 1) and Cγ2 (C gamma 2). Although the boundaries of the Fc region may vary, the human IgG heavy chain Fc region is usually defined to comprise residues C226 or P230 to its carboxyl-terminus, wherein the numbering is according to the EU index of Edelman et al., 1969, Proc. Natl. Acad. Sci. USA 63(1):78-85 as described in Kabat et al., 1991. Typically, the Fc domain comprises from about amino acid residue 236 to about 447 of the human IgG1 constant domain. An exemplary human wild type IgG1 Fc domain amino acid sequence is set forth in SEQ ID NO:31. Fc polypeptide may refer to this region in isolation, or this region in the context of an antibody, or an antigen-binding portion thereof, or Fc fusion protein.

The heavy chain constant domain comprises the Fc region and further comprises the CH1 domain and hinge as well as the CH2 and CH3 (and, optionally, CH4 of IgA and IgE) domains of the IG heavy chain.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain and can be assessed using various assays known in the art for evaluating such effector functions.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification.

"Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (IT AM) in its cytoplasmic domain Inhibiting receptor FcγRIIB contains an immunoreceptor tyrosine-based inhibition motif (ITIM) in its cytoplasmic domain, (see, e.g., Daeron, Annu. Rev. Immunol. 15:203-234 (1997)). FcRs are reviewed, for example, in Ravetch and Kinet, Annu. Rev. Immunol 9:457-92 (1991); Capel et ah, Immunomethods 4:25-34 (1994); and de Haas et ah, J. Lab. Clin. Med. 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et ah, J. Immunol. 117:587 (1976) and Kim et ah, J. Immunol. 24:249 (1994)) and regulation of homeostasis of immunoglobulins. Methods of measuring binding to FcRn are known (see, e.g., Ghetie and Ward., Immunol. Today 18(12):592-598 (1997); Ghetie et ah, Nature Biotechnology, 15(7):637-640 (1997); Hinton et ah, J. Biol. Chem. 279(8):6213-6216 (2004); WO 2004/92219 (Hinton et al).

"Effector functions" refer to biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, macrophages, cytotoxic T cells, and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. Proc. Natl. Acad. Sci. (USA) 95:652-656 (1998). Additional antibodies with altered Fc region amino acid sequences and increased or decreased ADCC activity are described, e.g., in U.S. Pat. Nos. 7,923,538, and 7,994,290.

A molecule (e.g., an Fc fusion) having an "enhanced ADCC activity" refers to a molecule that is more effective at mediating ADCC in vitro or in vivo compared to a reference molecule, wherein the molecule and the reference molecule differ in at least one structural aspect, and when the amounts of such molecule and reference molecule used in the assay are essentially the same. In some embodiments, ADCC activity will be determined using the in vitro ADCC assay as herein disclosed, but other assays or methods for determining ADCC activity, e.g. in an animal model etc., are contemplated. In some embodiments, a molecule with enhanced ADCC activity has enhanced affinity for Fc gamma RIIIA. In some embodiments, a molecule with enhanced ADCC activity has enhanced affinity for Fc gamma RIIIA (V158). In some embodiments, a molecule with enhanced ADCC activity has enhanced affinity for Fc gamma RIIIA (F158).

A molecule (e.g., an Fc fusion) with "altered" FcR binding affinity or ADCC activity is one which has either enhanced or diminished FcR binding activity and/or ADCC activity compared to a reference molecule, wherein the molecule and the reference molecule differ in at least one structural aspect. A molecule that "displays increased binding" to an FcR binds at least one FcR with better affinity than the reference molecule. A molecule that "displays decreased binding" to an FcR, binds at least one FcR with lower affinity than the reference molecule. Such molecules that display decreased binding to an FcR may possess little or no appreciable binding to an FcR, e.g., 0-20 percent binding to the FcR compared to a native sequence IgG Fc region.

"Enhanced affinity for Fc gamma RIIIA" refers to a molecule (e.g., an Fc fusion) that has greater affinity for Fc gamma RIIIA (also referred to, in some instances, as CD 16a) than a reference molecule, wherein the molecule and the reference molecule differ in at least one structural aspect. Any suitable method for determining affinity for Fc gamma RIIIA may be used. In some embodiments, affinity for Fc gamma RIIIA is determined by a method described herein. In some embodiments, a molecule with enhanced affinity for Fc gamma RIIIA has enhanced ADCC activity. In some embodiments, a molecule with enhanced affinity for Fc gamma RIIIA has enhanced affinity for Fc gamma RIIIA (V158). In some embodiments, a molecule with enhanced affinity for Fc gamma RIIIA has enhanced affinity for Fc gamma RIIIA(F158).

L-fucose, also referred to as 6-deoxy-L-galactose, is a monosaccharide that is a component of some N- and O-linked glycans and glycolipids in animals. See Becker and Lowe, Glycobiology 13:41R-51R (2003). Fucose is typically added as a terminal modification to glycans, including glycans attached to blood group antigens, selectins and antibodies. Fucose can be attached to glycans via α(1,2)-, α(1,3)-, α(1,4)- and α(1,6)-linkages by specific fucosyltransferases. α(1,2)-fucose linkages are typically associated with the H-blood group antigens. α(1,3)- and α(1,4)-fucose linkages are associated with modification of LewisX antigens. α(1,6)-fucose linkages are associated with N-linked GlcNAc molecules, such as those on antibodies.

The carbohydrate moieties of the present invention will be described with reference to commonly used nomenclature for the description of oligosaccharides. A review of carbohydrate chemistry which uses this nomenclature is found in Hubbard and Ivatt (1981) Ann. Rev. Biochem. 50:555-583. This nomenclature includes, for instance, Man, which represents mannose; GlcNAc, which represents 2-N-acetylglucosamine; Gal which represents galactose; Fuc for fucose; and Glc, which represents glucose. Sialic acids are described by the shorthand notation NeuNAc, for 5-N-acetylneuraminic acid, and NeuNGc for 5-glycolylneuraminic acid (IUB-IUPAC Joint Commission on Biochemical Nomenclature, 1982, J. Biol. Chem. 257: 3347-3351; (1982) J. Biol. Chem. 257: 3352).

The carbohydrate structures of the present invention occur on the protein expressed as N-linked oligosaccharides. "N-linked glycosylation" refers to the attachment of the carbohydrate moiety via GlcNAc to an asparagine residue in a polypeptide chain. The N-linked carbohydrates all contain a common Man 1-6(Man1-3)Manβ1-4GcNAcβ1-4GlcNAcβ-R core structure. Therefore, in the core structure described, R represents an asparagine residue of the produced glycoprotein. The sequence of the protein produced will contain an asparagine-X-serine, asparagine-X-threonine, and asparagine-X-cysteine, wherein X is any amino acid except proline (Asn-Xaa-Ser/Thr). "O-linked" carbohydrates, by contrast are characterized by a common core structure, which is the GalNAc attached to the hydroxyl group of a threonine or serine but no consensus sequence is required. Of the N-linked carbohydrates the most important are the "complex" N-linked carbohydrates such as the "biantennary" structures described herein.

The skilled artisan will recognize that the glycoprotein immunoglobulin G (IgG) is associated with three types of complex biantennary structures containing zero, one or two galactose residues (Wormland et al., 1997, Biochemistry 36:1370-1380) commonly known as G0, G1 and G2, respectively. With respect to human antibody molecules of the IgG class each has an N-linked oligosaccharide attached at the amide side chain of Asn 297 of the β-4 bend of the inner face of the CH2 domain of the Fc region (Beale and Feinstein, 1976, Q. Rev. Biophys. 9:253-259; Jefferis et al., 1995, Immunol. Letts. 44:111-117). The oligosaccharide moiety attached at Asn 297 of the IgG CH2 domain is of the complex biantennary type having the identified hexasaccharide core structure and variable outer sugar residues (see Jefferis et al., 1997, supra; Wyss and Wagner, 1996, Current Opinions in Biotech. 7:409-416). The core structure (GlcNAc2Man3GlcNAc) is typical of biantennary oligosaccharides and is represented schematically in FIG. 1.

Since each core structure may have a bisecting N-acetylglucoseamine, core fucose and either galactose or sialic acid outer saccharides, there are a total of 36 structurally unique oligosaccharides which may occupy the Asn 297 site (Jefferis and Lund, supra). It will also be recognized that within a particular CH2 domain, glycosylation at Asn 297 may be asymmetric owing to different oligosaccharide chains attached at either Asn 297 residue within the two chain Fc domain. For example, while the heavy chain synthesized within a single antibody-secreting cell may be homogeneous in its amino acid sequence, it is generally differentially glycosylated resulting in a large number of structurally unique Ig glycoforms.

The major types of complex oligosaccharide structures, also referred to as "glycoforms," found in the CH2 domain of the IgG are depicted in International Patent Publication No. WO 99/22764 at page 7.

According to the present invention G0 refers to a biantennary structure wherein no terminal sialic acids (NeuAcs) or Gals are present, G1 refers to a biantennary structure having one Gal and no NeuAcs and G2 refers to a biantennary structure with two terminal Gals and no NeuAcs. See, e.g., FIG. 2, depicting exemplary structures of G0, G1, G-1 and G2.

"Afucosylated" molecule (e.g., an Fc fusion) or a molecule (e.g., an Fc fusion) "lacking fucose" refers to an IgG1 or IgG3 isotype molecule (e.g., an Fc fusion) that lacks fucose in its constant region glycosylation. Glycosylation of human IgG1 or IgG3 occurs at Asn297 as core fucosylated biantennary complex oligosaccharide glycosylation terminated with up to 2 Gal residues. In some embodiments, an afucosylated antibody lacks fucose at Asn297. These structures are designated as G0, G1 (a 1,6 or a 1,3) or G2 glycan residues, depending on the amount of terminal Gal residues. See, e.g., Raju, T. S., BioProcess Int. 1: 44-53 (2003). CHO type glycosylation of antibody Fc is described, e.g., in Routier, F. FL, Glycoconjugate J. 14: 201-207 (1997).

In some embodiments, the "fucosyl" or "afucosylated", as used interchangeably herein, molecule (e.g., an Fc fusion) refers to a molecule (e.g., an Fc fusion) that has been glycoengineered to lack core fucose. Molecule (e.g., Fc fusions) with reduced fucose content in glycan moieties have increased affinity to FcγRIIIa (CD16), and as a result, possess enhanced activity-dependent cellular cytotoxicity (ADCC) activity. Afucosyl molecules (e.g., Fc fusions) can be produced using the Potelligent® CHOK1SV cell line (Lonza Biologics), which lacks both alleles of the gene responsible for fucose addition (α1,6-fucosyltransferase). Afucosyl or reduced fusose molecules (e.g., Fc fusions) can also be generated by modifying the oligosaccharide biosynthesis activities in various ways. For example, overexpression of N-acetylglucosamine-transferase III (GnTIII) in the Golgi apparatus of the production cell line generates bisected oligosaccharide structures associated with the Fc constant region of the molecule and suppresses fucosylation. In such expression systems, the level of GnTIII expression correlates with the generation of afucosylated IgG1 glycoforms and resulting enhanced ADCC activity. Fucosylation can also be decreased in cell culture by use of sugar analogs, such as, but not limited to, fucose analogs as described in WO 2012/019165. Thus, afucosylated, or reduced fucose, molecules (e.g., Fc fusions) can be produced using a wide variety of methods well-known in the art.

In some embodiments, an afucosylated molecule (e.g., an Fc fusion) has enhanced affinity for Fc gamma RIIIA. In some embodiments, an afucosylated molecule (e.g., an Fc fusion) has enhanced affinity for Fc gamma RIIIA(V158). In some embodiments, an afucosylated molecule (e.g., an Fc fusion) has enhanced affinity for Fc gamma RIIIA(F158).

"Glycoform" refers to a complex oligosaccharide structure comprising linkages of various carbohydrate units. Such structures are described in, e.g., Essentials of Glycobiology Varki et al., eds., Cold Spring Harbor Laboratory Press, Cold Spring Harbor, NY (1999), which also provides a review of standard glycobiology nomenclature. Such glycoforms include, but are not limited to, G2, G1, G0, G-1, and G-2 (see, e.g., International Patent Publication No. WO 99/22764).

"Glycosylation pattern" is defined as the pattern of carbohydrate units that are covalently attached to a protein (e.g., the glycoform) as well as to the site(s) to which the glycoform(s) are covalently attached to the peptide backbone of a protein, more specifically to an immunoglobulin protein.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., J. Immunol. Methods 202: 163 (1996), may be performed. Antibodies with altered Fc region amino acid sequences and increased or decreased C1q binding capability are described, e.g., in U.S. Pat. No. 6,194,551 B 1, U.S. Pat. Nos. 7,923,538, 7,994,290 and WO 1999/51642. See also, e.g., Idusogie et al, J.

As used herein, the terms "wild-type amino acid" and "wild-type sequence" refer to a sequence of amino or nucleic acids that occurs naturally within a certain population (e.g., human, mouse, rats, cell, etc.).

"Lymphocyte function-associated antigen 3" or "LFA3," used interchangeably herein, also referred to in the art as "CD58" is a member of the immunoglobulin superfamily. The term LFA3 includes LFA3 homologs and orthologs, including human, cynomolgus monkey, rat, rabbit, and mouse, among others. As used herein, "LFA3" refers to a mammalian LFA3, such as human, rat or mouse, as well as non-human primate, bovine, ovine, or porcine LFA3. A non-limiting example of LFA3 is human LFA3 (see, e.g., UniProtKB Accession Number P19256, SEQ ID NO: 2). The term "LFA3" also encompasses fragments, variants, isoforms, and other homologs of such LFA3 molecules. Variant LFA3 molecules will generally be characterized by having the same type of activity as naturally occurring LFA3, such as the ability to bind CD2.

A "LFA3 domain" refers to a fragment of LFA3, or a variant thereof. In some embodiments, the LFA3 domain is no more than 100, 110, 120, 130, 140, 150, 160, 170, or 180 amino acids in length. In some embodiments, the LFA3 domain is derived from the first extracellular domain of LFA3. In some embodiments, the LFA3 domain comprises no more than 6, 10, 15, 20, or 30 amino acid mutations (e.g., substitutions, additions, or deletions) relative to the wild type LFA3 sequence.

"CD2," also referred to in the art as "erythrocyte receptor," "LFA-3 receptor," "rosette receptor," or "T-cell surface antigen T11/Leu-5" is a molecule expressed on cells such as T cells and NK cells. The term CD2 includes CD2 homologs and orthologs, including human, cynomolgus monkey, rat, rabbit, and mouse, among others. As used herein, "CD2" refers to a mammalian CD2, such as human, rat or mouse, as well as non-human primate, bovine, ovine, or porcine CD2. A non-limiting example of CD2 is human CD2 (see, e.g., UniProtKB Accession Number P06729, SEQ ID NO: 121). The term "CD2" also encompasses fragments, variants, isoforms, and other homologs of such CD2 molecules. Variant CD2 molecules will generally be characterized by having the same type of activity as naturally occurring CD2.

(SEQ ID NO: 121)
KEITNALETWGALGQDINLDIPSFQMSDDIDDIKWEKTSDKKKIAQFRKE

KETFKEKDTYKLFKNGTLKIKHLKTDDQDIYKVSIYDTKGKNVLEKIFDL

KIQERVSKPKISWTCINTTLTCEVMNGTDPELNLYQDGKHLKLSQRVITH

KWTTSLSAKFKCTAGNKVSKESSVEPVSCPEKGLDIYLIIGICGGGSLLM

VFVALLVFYITKRKKQRSRRNDEELETRAHRVATEERGRKPHQIPASTPQ

NPATSQHPPPPGHRSQAPSHRPPPPGHRVQHQPQKRPPAPSGTQVHQQK

GPPLPRPRVQPKPPHGAAENSLSPSSN.

As outlined elsewhere herein, certain positions of a polypeptide molecule can be altered. By "position" as used herein is meant a location in the sequence of a protein. Positions may be numbered sequentially, or according to an established format, for example the EU index and Kabat index can be used to number amino acid residues of an antibody.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR₂ ("amidate"), P(O)R, P(O)OR', CO or CH₂ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected and/or transformed in vivo with a polynucleotide of this invention.

Host cells may be prokaryotic cells or eukaryotic cells. Exemplary eukaryotic cells include mammalian cells, such as primate or non-primate animal cells; fungal cells, such as yeast; plant cells; and insect cells.

Any host cell susceptible to cell culture, and to expression of protein or polypeptides, may be utilized in accordance with the present invention. In certain embodiments, the host cell is mammalian. Mammalian cell lines available as hosts for expression are well-known in the art and include many immortalized cell lines available from the American Type Culture Collection (ATCC). Nonlimiting exemplary mammalian cells include, but are not limited to, NS0 cells, HEK 293 and Chinese hamster ovary (CHO) cells, and their derivatives, such as 293-6E and CHO DG44 cells, CHO DXB11, and Potelligent® CHOK1SV cells (BioWa/Lonza, Allendale, NJ). Mammalian host cells also include, but are not limited to, human cervical carcinoma cells (HeLa, ATCC CCL 2), baby hamster kidney (BHK, ATCC CCL 10) cells, monkey kidney cells (COS), and human hepatocellular carcinoma cells (e.g., Hep G2). Other non-limiting examples of mammalian cells that may be used in accordance with the present invention include human retinoblasts (PER.C6®; CruCell, Leiden, The Netherlands); monkey kidney CV1 line transformed by SV40 (COS-7, ATCC CRL 1651); human embryonic kidney line 293 (HEK 293) or 293 cells subcloned for growth in suspension culture (Graham et al., 1977, J. Gen Virol. 36:59); mouse sertoli cells (TM4, Mather, 1980, Biol. Reprod. 23:243-251); monkey kidney cells (CV1 ATCC CCL 70); African green monkey kidney cells (VERO-76, ATCC CRL-1 587); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., 1982, Annals N.Y. Acad. Sci. 383:44-68); MRC 5 cells; FS4 cells; a human hepatoma line (Hep G2); and numerous myeloma cell lines, including, but not limited to, BALB/c mouse myeloma line (NS0/1, ECACC No: 85110503), NS0 cells and Sp2/0 cells.

Additionally, any number of commercially and non-commercially available cell lines that express polypeptides or proteins may be utilized in accordance with the present invention. One skilled in the art will appreciate that different cell lines might have different nutrition requirements and/or might require different culture conditions for optimal growth and polypeptide or protein expression, and will be able to modify conditions as needed.

The invention includes any eukaryotic expression system known in the art or disclosed herein for production of proteins of interest, such as expression in an insect cell system, a yeast expression system, or a mammalian cell system, such as, but not limited to, CHO cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

By the term "leader peptide" or "leader sequence" or "leader signal sequence", as used interchangeably herein, is meant any nucleic acid sequence, or amino acid sequence encoded thereby, that may be present on the 5' end of a nucleic acid molecule and/or at or near the N-terminus of a polypeptide, that when present may mediate the transport of the polypeptide to an organelle of destination, including, but not limited to, the secretion of the polypeptide from a cell. Such leader sequences include, but are not limited to, nucleic acid sequences comprising, e.g., (SEQ ID NO: 42)
<u>ATGGGCTGGTCCTGTATCATCCTCTTTCTGGTGGCCACAGCTACCGGAGT</u>

<u>GCATAGC</u>,
and (SEQ ID NO: 130)
ATGGTTGCTGGGAGCGACGCGGGGCGGGCCCTGGGGGTCCTCAGCGTGGT

CTGCCTGCTGCACTGCTTTGGITTTCATCAGCTGT, and amino acid sequences encoded thereby, such as, but not limited to, mgwsciilflvatatgvhs (SEQ ID NO: 15), and mvagsdagralgvlsvvcllhcfgfisc (SEQ ID NO: 129). The invention encompasses these and any other leader signals (nucleic and amino acid sequences) known in the art or to be identified which can result in the transport of a polypeptide to the desired organelle, e.g., the endoplasmic reticulum, and/or secreted from the cell. Generally, the signal peptide is removed from the mature polypeptide.

As used herein, "treatment" is an approach for obtaining beneficial or desired clinical results. For purposes of this invention, beneficial or desired clinical results include, but are not limited to, one or more of the following: improved survival rate (reduced mortality), reduction in inflammatory response to the disease, reduction in the amount of tissue fibrosis, improvement in the appearance of the disease lesions, limitation of the pathological lesions to focal sites, decreased extent of damage from the disease, decreased duration of the disease, and/or reduction in the number, extent, or duration of symptoms related to the disease. The term includes the administration of the compounds or agents of the present invention to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

"Ameliorating" means a lessening or improvement of one or more symptoms as compared to not administering a LFA3 polypeptide molecule. "Ameliorating" also includes shortening or reduction in duration of a symptom.

As used herein, an "effective dosage" or "effective amount" of drug, compound, or pharmaceutical composition is an amount sufficient to affect any one or more beneficial or desired results. In more specific aspects, an effective amount prevents, alleviates or ameliorates symptoms of disease or infection, and/or prolongs the survival of the subject being treated. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing one or more symptoms of a disease, disorder or condition, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals (e.g., cows, pigs, horses, chickens, etc.), sport animals, pets, primates, horses, dogs, cats, mice and rats. In certain embodiments, the subject has an autoimmune disease, disorder or condition, such as type 1 diabetes or psoriatic arthritis. In certain embodiments, the subject is in need of immunosuppression therapy.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, PA, 1990; and Remington, The Science and Practice of Pharmacy 20th Ed. Mack Publishing, 2000).

Exemplary methods and materials are described herein, although methods and materials similar or equivalent to those described herein can also be used in the practice or testing of the present invention. The materials, methods, and examples are illustrative only and not intended to be limiting.

II. LFA3 Variants

The present invention relates to LFA3 variants, e.g., human LFA3 variants that bind to human CD2. In some embodiments, the LFA3 variants contain one or more mutations that enhance their stability and manufacturability properties. In some embodiments, the LFA3 variants contain one or more mutations that increase their binding affinity to CD2. In some embodiments, the LFA3 variants (e.g., variant LFA3-Fc fusion proteins) contain one or more mutations that enhance cytotoxicity against CD2-expressing cells. In some embodiments, the LFA3 variants (e.g., variant LFA3-Fc fusion proteins) contain one or more mutations that enhance inhibition of allogeneic T cell response. In some embodiments, the LFA3 variants contain one or more mutations that lead to a slower clearance of the molecules in vivo. Exemplary sequences of wild type LFA3 and LFA3 variants, including LFA3-Fc fusion proteins, are provided in Table 2 and Table 3.

In other embodiments, where the engineered Fc polypeptide comprises a C-terminal lysine (K) amino acid residue (e.g., human IgG1 heavy chain comprises a terminal lysine), one skilled in the art would understand that the lysine residue may be clipped resulting in a fusion protein lacking the C-terminal lysine residue. Thus, in some embodiments, the Fc fusion protein comprising an engineered Fc polypeptide comprises a polypeptide where the terminal lysine otherwise present is not present.

TABLE 2

Exemplary amino acid sequences of wild type LFA3 and LFA3 variants.

| SEQ ID NO | Description | Sequence |
|---|---|---|
| SEQ ID NO: 1 | Human LFA3 isoform 1 (P19256) with signal peptide (underlined, italic) | *mvagsdagralgvlsvvcilhcfgfisc*FSQQIYG VVYGNVTFHVPSNVPLKEVLWKKQKDKVAELENSE FRAFSSFKNRVYLDTVSGSLTIYNLTSSDEDEYEM ESPNITDTMKFFLYVLESLPSPTLTCALTNGSIEV QCMIPEHYNSHRGLIMYSWDCPMEQCKRNSTSIYF KMENDLPQKIQCTLSNPLFNTTSSIILTTCIPSSG HSRHRYALIPIPLAVITTCIVLYMNGILKCDRKPD RTNSN |
| SEQ ID NO: 2 | Human LFA3 isoform 1 (P19256) without signal peptide | FSQQIYGVVYGNVTFHVPSNVPLKEVLWKKQKDKV AELENSEFRAFSSFKNRVYLDTVSGSLTIYNLTSS DEDEYEMESPNITDTMKFFLYVLESLPSPTLTCAL TNGSIEVQCMIPEHYNSHRGLIMYSWDCPMEQCKR NSTSIYFKMENDLPQKIQCTLSNPLFNTTSSIILT TCIPSSGHSRHRYALIPIPLAVITTCIVLYMNGIL KCDRKPDRTNSN |

TABLE 2-continued

Exemplary amino acid sequences of
wild type LFA3 and LFA3 variants.

| SEQ ID NO | Description | Sequence |
| --- | --- | --- |
| SEQ ID NO: 3 | Human LFA3 isoform 1 domain 1 | FSQQIYGVVYGNVTFHVPSNVPLKEVLWKKQKDKV AELENSEFRAFSSFKNRVYLDTVSGSLTIYNLTSS DEDEYEMESPNITDTMKFFLYV |
| SEQ ID NO: 4 | WT LFA3-Fc (also referred to as "LFA3-Fc WT") | FSQQIYGVVYGNVTFHVPSNVPLKEVLWKKQKDKV AELENSEFRAFSSFKNRVYLDTVSGSLTIYNLTSS DEDEYEMESPNITDTMKFFLYVdkthtcppcpape llggpsvflfppkpkdtlmisrtpevtcyvvdvsh edpevkfnwyydgvevhnaktkpreeqynstyrvy syltylhqdwingkeykckysnkalpapiektisk akgqprepqvytlppsrdeltknqvsltclykgfy psdiavewesngqpennykttppyldsdgsfflys kltvdksrwqqgnyfscsvmhealhnhytqkslsl spgk |
| SEQ ID NO: 120 | WT LFA3-Pfe | FSQQIYGVVYGNVTFHVPSNVPLKEVLWKKQKDKV AELENSEFRAFSSFKNRVYLDTVSGSLTIYNLTSS DEDEYEMESPNITDTMKFFLYVdkthtcppcpape llggpsvflfppkpkdtlmisrtpevtcyvvdvsh edpevkfnwyydgvevhnaktkpreeqynstyrvy syltylhqdwingkeykckysnkalpapiektisk akgqprepqvytlppsreemtknqvsltclykgfy psdiavewesngqpennykttppyldsdgsfflys kltvdksrwqqgnyfscsvmhealhnhytqkslsl spg |
| SEQ ID NO: 15 | Leader sequence of LFA3-Fc fusion proteins | mgwsciilflvatatgvhs |
| SEQ ID NO: 16 | Hinge-Pfe (human IgG1 Fc) | dkthtcppcpapellggpsvflfppkpkdtlmisr tpevtcyvvdyshedpevkfnwyydgvevhnaktk preeqynstyryysyltylhqdwingkeykckvsn kalpapiektiskakgqprepqvytlppsreemtk nqvsltclvkgfypsdiavewesngqpennykttp pyldsdgsfflyskltvdksrwqqgnyfscsvmhe alhnhytqkslslspg |
| SEQ ID NO: 17 | M1 | FSQQIYGVVYGNVTFHVPSNVPLKEVLWKKQKDKV VEFENSEVRAFSSFKNRVYLDTVSGSLTIYNLTSS DEDEYEMESPNITDTFKFFLYV |
| SEQ ID NO: 18 | M2 | FSQQIYGVVYGNVTFHVPSNVPLKEVLWKKQKDKV VEFENSEVRAFSSFKNRVYLDTVSGSLTIYNLTSS DEDEYEFESPNITDTFKFFLYV |
| SEQ ID NO: 19 | M3 | FSQQIYGVVYGNVTFHVPSNVPLKEVLWKKQKDKV VEFENSEVRVFSSFKNRVYLDTVSGSLTIYNLTSS DEDEYEMESPNITDTFKFFLYV |
| SEQ ID NO: 20 | M4 | FSQQIYGVVYGNVTFHVPSNVPLKEVLWKKQKDKV VEFENSEVRVFSSFKNRVYLDTVSGSLTIYNLTSS DEDEYEFESPNITDTFKFFLYV |
| SEQ ID NO: 21 | M5 | FSQQIYGVVYGNVTFHVPSNVPLKEVLWKKQKDKV VEFENSEIRVFSSFKNRVYLDTVSGSLTIYNLTSS DEDEYEFESPNITDTFKFFLYV |
| SEQ ID NO: 22 | M6 | FSQQIYGVVYGNVTFHVPSNVPLKEVLWKKQKDKV LEFENSELRVFSSFKNRVYLDTVSGSLTIYNLTSS DEDEYEFESPNITDTFKFFLYV |
| SEQ ID NO: 23 | M7 | FSQQIYGVVYGNVTFHVPSNVPLKEVLWKKQKDKV VEFENSEVRAFSSFKNRVYLDTVSGSLTIYNLTSS DEDEYEMESPNITDTMKFFLYV |
| SEQ ID NO: 24 | d1 | FSQQIYGVVYGNVTFHVPSNVPLKEVLWKKQKDKV AELENSEFRAFSSFKNRVYLDTVSGSLTIYNLTSS DEDEYEMESPNITDTMKFFLYVL |
| SEQ ID NO: 25 | d3 | FSQQIYGVVYGNVTFHVPSNVPLKEVLWKKQKDKV AELENSEFRAFSSFKNRVYLDTVSGSLTIYNLTSS DEDEYEMESPNITDTMKFFLYVLESLPS |

TABLE 2-continued

Exemplary amino acid sequences of wild type LFA3 and LFA3 variants.

| SEQ ID NO | Description | Sequence |
| --- | --- | --- |
| SEQ ID NO: 26 | M1d1 | FSQQIYGVVYGNVTFHVPSNVPLKEVLWKKQKDKV VEFENSEVRAFSSFKNRVYLDTVSGSLTIYNLTSS DEDEYEMESPNITDTFKFFLYVL |
| SEQ ID NO: 27 | M1d3 | FSQQIYGVVYGNVTFHVPSNVPLKEVLWKKQKDKV VEFENSEVRAFSSFKNRVYLDTVSGSLTIYNLTSS DEDEYEMESPNITDTFKFFLYVLESLPS |
| SEQ ID NO: 28 | M4d1 | FSQQIYGVVYGNVTFHVPSNVPLKEVLWKKQKDKV VEFENSEVRVFSSFKNRVYLDTVSGSLTIYNLTSS DEDEYEFESPNITDTFKFFLYVL |
| SEQ ID NO: 29 | M7d1 | FSQQIYGVVYGNVTFHVPSNVPLKEVLWKKQKDKV VEFENSEVRAFSSFKNRVYLDTVSGSLTIYNLTSS DEDEYEMESPNITDTMKFFLYVL |
| SEQ ID NO: 30 | CM1d1 | FSQQIYGVVYGNVTFHVPSNVPLKEVLWKKQKDKV VEFENSEVRAFSSFKNRVYLDTVSGSLTIYNLTSS DEDEYEMESRNGGPDFKFFLYVL |
| SEQ ID NO: 31 | CM2d1 | FSQQIYGVVYGNVTFHVPSNVPLKEVLWKKQKDKV VEFENSEVRAFSSFKNRVYLDTVSGSLTIYNLTSS DEDEYEMESRNPYRRFKFFLYVL |
| SEQ ID NO: 32 | CM3d1 | FSQQIYGVVYGNVTFHVPSNVPLKEVLWKKQKDKV VEFENSEVRAFSSFKNRVYLDTVSGSLTIYNLTSS DEDEYEMESRNPYRDFKFFLYVL |
| SEQ ID NO: 33 | CM4d1 | FSQQIYGVVYGNVTFHVPSNVPLKEVLWKKQKDKV VEFENSEVRAFSSFKNRVYLDTVSGSLTIYNLTSS DEDEYEMESWNGGPDFKFFLYVL |
| SEQ ID NO: 34 | CM5d1 | FSQQIYGVVYGNVTFHVPSNVPLKEVLWKKQKDKV VEFENSEVRAFSSFKNRVYLDTVSGSLTIYNLTSS DEDEYEMESWNPYRRFKFFLYVL |
| SEQ ID NO: 35 | CM6d1 | FSQQIYGVVYGNVTFHVPSNVPLKEVLWKKQKDKV VEFENSEVRAFSSFKNRVYLDTVSGSLTIYNLTSS DEDEYEMESWNPYRDFKFFLYVL |
| SEQ ID NO: 36 | M11d1 | FSQQIYGVVYGNVTFHVPSNVPLKEVLWKKQKDKV VEFENSEVRAFSSFKNRVYLDTVSGSLTIYNLTSS DEDEYEMEGRYPYESFKFFLYVL |
| SEQ ID NO: 37 | M12d1 | FSQQIYGVVYGNVTFHVPSNVPLKEVLWKKQKDKV VEFENSEVRVFSSFKNRVYLDTVSGSLTIYNLTSS DEDEYEFESWEPGREFKFFLYVL |
| SEQ ID NO: 38 | M13d1 | FSQQIYGVVYGNVTFHVPSNVPLKEVLWKKQKDKV VEFENSEVRAFSSFKNRVYLDTVSGSLTIYNLTSS DEDEYEMEARYPYRQFKFFLYVL |
| SEQ ID NO: 39 | M14d1 | FSQQIYGVVYGNVTFHVPSNVPLKEVLWKKQKDKV VEFENSEVRAFSSFKNRVYLDTVSGSLTIYNLTSS DEDEYEMEMRNGGPDFKFFLYVL |
| SEQ ID NO: 40 | M15d1 | FSQQIYGVVYGNVTFHVPSNVPLKEVLWKKQKDKV VEFENSEVRAFSSFKNRVYLDTVSGSLTIYNLTSS DEDEYEMEARDGGPDFKFFLYVL |
| SEQ ID NO: 41 | M16d1 | FSQQIYGVVYGNVTFHVPSNVPLKEVLWKKQKDKV VEFENSEVRAFSSFKNRVYLDTVSGSLTIYNLTSS DEDEYEMESWSPYKAFKFFLYVL |
| SEQ ID NO: 69 | M1d1 LFA3-Fc fusion protein (also referred to as "LFA3-Fc M1d1", "M1d1" or "M1d1-Pfe") | FSQQIYGVVYGNVTFHVPSNVPLKEVLWKKQKDKV VEFENSEVRAFSSFKNRVYLDTVSGSLTIYNLTSS DEDEYEMESPNITDTFKFFLYVLdkthtcppcpap ellggpsyflfppkpkdtlmisrtpeytcyyydys hedpeykfnwyydgveyhnakttkpreeqynstyry ysyltylhqdwhigkeykckysnkalpapiektis kakgqprepqyytlppsreemtknqysltclykgf ypsdiayewesngqpennykttppyldsdgsffly skltydksrwqqgnyfscsymhealhnhytqksls lspg |

TABLE 2-continued

Exemplary amino acid sequences of wild type LFA3 and LFA3 variants.

| SEQ ID NO | Description | Sequence |
| --- | --- | --- |
| SEQ ID NO: 70 | Contact library consensus #1 | FSQQIYGVVYGNVTFHVPSNVPLKX$_1$VX$_2$WX$_3$KQ X$_4$X$_5$X$_6$VAX$_7$LX$_8$N$_5$X$_9$FX$_{10}$AX$_{11}$X$_{12}$SFKNRV YLDTVSGSLTIYNLTSSDEDEYEMESX$_{13}$NX$_{14}$T X$_{15}$TMKFFLYVX$_{16}$, wherein: X$_1$ is any amino acid, X$_2$ is any amino acid, X$_3$ is any amino acid, X$_4$ is any amino acid, X$_5$ is any amino acid, X$_6$ is any amino acid, X$_7$ is any amino acid, X$_8$ is any amino acid, X$_9$ is any amino acid, X$_{10}$ is any amino acid, X$_{11}$ is any amino acid, X$_{12}$ is any amino acid, X$_{13}$ is any amino acid, X$_{14}$ is any amino acid, X$_{15}$ is any amino acid, and X$_{16}$ is absent, L, or LESLPS |
| SEQ ID NO: 71 | Contact library consensus #2 | FSQQIYGVVYGNVTFHVPSNVPLKX$_1$VX$_2$WX$_3$KQ X$_4$X$_5$X$_6$VAX$_7$LX$_8$NSX$_9$FX$_{10}$AX$_{11}$X$_{12}$SFKNRV YLDTVSGSLTIYNLTSSDEDEYEMESX$_{13}$NX$_{14}$T X$_{15}$TMKFFLYVX$_{16}$, wherein: X$_1$ is D, E, N, K, Q, or H, X$_2$ is F, I, L, V, Nle, M, or A, X$_3$ is K, R, M, T, Q, or N, X$_4$ is K, R, M, T, Q, or N, X$_5$ is D, E, N, K, Q, or H, X$_6$ is K, R, M, T, Q, or N, X$_7$ is D, E, N, K, Q, or H, X$_8$ is D, E, N, K, Q, or H, X$_9$ is D, E, N, K, Q, or H, X$_{10}$ is K, R, M, T, Q, or N, X$_{11}$ is F, Y, L, H, I, N, V, D, A, or Y, X$_{12}$ is S, T, A, or G, X$_{13}$ is P, L, H, R, or A, X$_{14}$ is F, I, L, V, M, A, or Nle, X$_{15}$ is D, E, N, K, Q, or H, and X$_{16}$ is absent, L, or LESLPS |
| SEQ ID NO: 72 | Contact library consensus #3 | FSQQIYGVVYGNVTFHVPSNVPLKX$_1$VX$_2$WX$_3$KQ X$_4$X$_5$X$_6$VAX$_7$LX$_8$N$_5$X$_9$FX$_{10}$AX$_{11}$X$_{12}$SFKNRV YLDTV$_5$G$_5$LTIYNLTSSDEDEYEMESX$_{13}$NX$_{14}$T X$_{15}$TMKFFLYVX$_{16}$, wherein: X$_1$ is D, E, N, K, Q, or H, X$_2$ is F, I, L, or V, X$_3$ is K, R, M, or T, X$_4$ is K, R, M, or T, X$_5$ is D, E, N, K, Q, or H, X$_6$ is K, R, M, or T, X$_7$ is D, E, N, K, Q, or H, X$_8$ is D, E, N, K, Q, or H, X$_9$ is D, E, N, K, Q, or H, X$_{10}$ is K, R, M, or T, X$_{11}$ is F, Y, L, H, I, N, V, or D, X$_{12}$ is S, T, A, or G, X$_{13}$ is P, L, H, or R, X$_{14}$ is F, I, L, or V, X$_{15}$ is D, E, N, K, Q, or H, and X$_{16}$ is absent, L, or LESLPS |
| SEQ ID NO: 73 | Core library consensus #1 | FSQQIYGVVYGNVTX$_1$HX$_2$PSNVPX$_3$KEX$_4$LX$_5$K KQKDKX$_6$X$_7$EX$_8$ENSEX$_9$RX$_{10}$FSSFKNRVYX$_{11}$ DTVSX$_{12}$SX$_{13}$TIYNLTSSDEDEYEX$_{14}$ESPNIT DTX$_{15}$KX$_{16}$FLYVX$_{17}$, wherein: X$_1$ is any amino acid, X$_2$ is any amino acid, X$_3$ is any amino acid, X$_4$ is any amino acid, X$_5$ is any amino acid, X$_6$ is any amino acid, |

TABLE 2-continued

Exemplary amino acid sequences of wild type LFA3 and LFA3 variants.

| SEQ ID NO | Description | Sequence |
|---|---|---|
| | | $X_7$ is any amino acid,<br>$X_8$ is any amino acid,<br>$X_9$ is any amino acid,<br>$X_{10}$ is any amino acid,<br>$X_{11}$ is any amino acid,<br>$X_{12}$ is any amino acid,<br>$X_{13}$ is any amino acid,<br>$X_{14}$ is any amino acid,<br>$X_{15}$ is any amino acid,<br>$X_{16}$ is any amino acid, and<br>$X_{17}$ is absent, L, or LESLPS |
| SEQ ID NO: 74 | Core library consensus #2 | FSQQIYGVVYGNVTX$_1$HX$_2$PSNVPX$_3$KEX$_4$LX$_5$K<br>KQKDKX$_6$X$_7$EX$_8$ENSEX$_9$RX$_{10}$FSSFKNRVYX$_{11}$<br>DTVSX$_{12}$SX$_{13}$TIYNLTSSDEDEYEX$_{14}$ESPNIT<br>DTX$_{15}$KX$_{16}$FLYVX$_{17}$, wherein:<br>$X_1$ is F, I, L, V, A, or Y,<br>$X_2$ is F, I, L, V, M, A, or Nle,<br>$X_3$ is F, I, L, V, Nle, M, or A,<br>$X_4$ is F, I, L, V, M, A, or Nle,<br>$X_5$ is W, F, L, C, or Y,<br>$X_6$ is F, I, L, V, M, A, or Nle,<br>$X_7$ is A, V, S, L, or I,<br>$X_8$ is F, I, L, V, Nle, M, or A,<br>$X_9$ is F, I, L, V, A, or Y,<br>$X_{10}$ is A, V, S, L, or I,<br>$X_{11}$ is F, I, L, V, Nle, M, or A,<br>$X_{12}$ is S, T, A, or G,<br>$X_{13}$ is F, I, L, V, Nle, M, or A,<br>$X_{14}$ is M, L, I, or F,<br>$X_{15}$ is M, L, I, or F,<br>$X_{16}$ is F, I, L, V, A, or Y, and<br>$X_{17}$ is absent, L, or LESLPS |
| SEQ ID NO: 75 | Core library consensus #3 | FSQQIYGVVYGNVTX$_1$HX$_2$PSNVPX$_3$KEX$_4$LX$_5$K<br>KQKDKX$_6$X$_7$EX$_8$ENSEX$_9$RX$_{10}$FSSFKNRVYX$_{11}$<br>DTVSX$_{12}$SX$_{13}$TIYNLTSSDEDEYEX$_{14}$ESPNIT<br>DTX$_{15}$KX$_{16}$FLYVX$_{17}$, wherein:<br>$X_1$ is F, I, L, or V,<br>$X_2$ is F, I, L, or V,<br>$X_3$ is F, I, L, or V,<br>$X_4$ is F, I, L, or V,<br>$X_5$ is W, F, L, or C,<br>$X_6$ is F, I, L, or V,<br>$X_7$ is A, V, S, or L,<br>$X_8$ is F, I, L, or V,<br>$X_9$ is F, I, L, or V,<br>$X_{10}$ is A, V, S, or L,<br>$X_{11}$ is F, I, L, or V,<br>$X_{12}$ is S, T, A, or G,<br>$X_{13}$ is F, I, L, or V,<br>$X_{14}$ is M, L, I, or F,<br>$X_{15}$ is M, L, I, or F,<br>$X_{16}$ is F, I, L, or V, and<br>$X_{17}$ is absent, L, or LESLPS |
| SEQ ID NO: 76 | Hotspot consensus #1 | FSQQIYGVVYGNVTFHVPSNVPLKEVLWKKQKDKV<br>X$_1$EX$_2$ENSEX$_3$RX$_4$FSSFKNRVYLDTVSGSLTIYN<br>LTSSDEDEYEX$_5$ESPNITDTX$_6$KFFLYVX$_7$,<br>wherein:<br>$X_1$ is any amino acid,<br>$X_2$ is any amino acid,<br>$X_3$ is any amino acid,<br>$X_4$ is any amino acid,<br>$X_5$ is any amino acid,<br>$X_6$ is any amino acid, and<br>$X_7$ is absent, L, or LESLPS |
| SEQ ID NO: 77 | Hotspot consensus #2 | FSQQIYGVVYGNVTFHVPSNVPLKEVLWKKQKDKV<br>X$_1$EX$_2$ENSEX$_3$RX$_4$FSSFKNRVYLDTVSGSLTIYN<br>LTSSDEDEYEX$_5$ESPNITDTX$_6$KFFLYVX$_7$,<br>wherein:<br>$X_1$ is A, V, S, L, or I,<br>$X_2$ is F, I, L, V, Nle, M, or A,<br>$X_3$ is F, I, L, V, A, or Y, |

TABLE 2-continued

Exemplary amino acid sequences of wild type LFA3 and LFA3 variants.

| SEQ ID NO | Description | Sequence |
|---|---|---|
| | | $X_4$ is A, V, S, L, or I, |
| | | $X_5$ is M, L, I, or F, |
| | | $X_6$ is M, L, I, or F, and |
| | | $X_7$ is absent, L, or LESLPS |
| SEQ ID NO: 78 | Hotspot consensus #3 | FSQQIYGVVYGNVTFHVPSNVPLKEVLWKKQKDKV$X_1$E$X_2$ENSE$X_3$R$X_4$FSSFKNRVYLDTVSGSLTIYNLTSSDEDEYE$X_5$ESPNITDT$X_6$KFFLYV$X_7$, wherein: <br> $X_1$ is A, V, S, or L, <br> $X_2$ is F, I, L, or V, <br> $X_3$ is F, I, L, or V, <br> $X_4$ is A, V, S, or L, <br> $X_5$ is M, L, I, or F, <br> $X_6$ is M, L, I, or F, and <br> $X_7$ is absent, L, or LESLPS |
| SEQ ID NO: 79 | Hotspot consensus #4 | FSQQIYGVVYGNVTFHVPSNVPLKEVLWKKQKDKV$X_1$E$X_2$ENSE$X_3$R$X_4$FSSFKNRVYLDTVSGSLTIYNLTSSDEDEYE$X_5$ESPNITDT$X_6$KFFLYV$X_7$, wherein: <br> $X_1$ is V, L, or A, <br> $X_2$ is F or L, <br> $X_3$ is V, I, L, or F, <br> $X_4$ is A, V, or S, <br> $X_5$ is M, F, I, or L, <br> $X_6$ is F, M, I, or L, and <br> $X_7$ is absent, L, or LESLPS |
| SEQ ID NO: 80 | Hotspot consensus #5 | FSQQIYGVVYGNVTFHVPSNVPLKEVLWKKQKDKV$X_1$EFENSE$X_2$R$X_3$FSSFKNRVYLDTVSGSLTIYNLTSSDEDEYE$X_4$ESPNITDT$X_5$KFFLYV$X_6$, wherein: <br> $X_1$ is V or L, <br> $X_2$ is V, I, or L, <br> $X_3$ is A or V, <br> $X_4$ is M or F, <br> $X_5$ is F or M, and <br> $X_6$ is absent, L, or LESLPS |
| SEQ ID NO: 81 | Hotspot consensus #6 | FSQQIYGVVYGNVTFHVPSNVPLKEVLWKKQKDKV$X_1$EFENSE$X_2$R$X_3$FSSFKNRVYLDTVSGSLTIYNLTSSDEDEYE$X_4$ESPNITDTFKFFLYV$X_5$, wherein: <br> $X_1$ is V or L, <br> $X_2$ is V, I, or L, <br> $X_3$ is A or V, <br> $X_4$ is M or F, and <br> $X_5$ is absent, L, or LESLPS |
| SEQ ID NO: 82 | Hotspot consensus #7 | FSQQIYGVVYGNVTFHVPSNVPLKEVLWKKQKDKVVEFENSE$X_1$R$X_2$FSSFKNRVYLDTVSGSLTIYNLTSSDEDEYE$X_3$ESPNITDTFKFFLYV$X_4$, wherein: <br> $X_1$ is V or I, <br> $X_2$ is A or V, <br> $X_3$ is M or F, and <br> $X_4$ is absent, L, or LESLPS |
| SEQ ID NO: 83 | LFA3 wild type loop region | SPNITDT |
| SEQ ID NO: 84 | Loop consensus #1 | $X_1X_2X_3X_4X_5X_6X_7$, wherein: <br> $X_1$ is S, G, A, M, or T, <br> $X_2$ is R, W, P, or A, <br> $X_3$ is N, Y, S, E, D, Q, H, K, or R <br> $X_4$ is P, G, I, L, V, M, A, F, or Nle, <br> $X_5$ is Y, G, T, or S, <br> $X_6$ is R, E, K, P, D, or N, and <br> $X_7$ is R, D, S, Q, A, E, T, or S |

TABLE 2-continued

Exemplary amino acid sequences of wild type LFA3 and LFA3 variants.

| SEQ ID NO | Description | Sequence |
|---|---|---|
| SEQ ID NO: 85 | Loop consensus #2 | $X_1X_2X_3X_4X_5X_6X_7$, wherein:<br>$X_1$ is S, G, A, or M,<br>$X_2$ is R, W, or P,<br>$X_3$ is N, Y, S, E, or D,<br>$X_4$ is P, G, or I,<br>$X_5$ is Y, G, or T,<br>$X_6$ is R, E, K, P, or D, and<br>$X_7$ is R, D, S, Q, A, E, or T |
| SEQ ID NO: 86 | Loop consensus #3 | $X_1X_2X_3X_4X_5X_6X_7$, wherein:<br>$X_1$ is S, G, A, or M,<br>$X_2$ is R or W,<br>$X_3$ is N, Y, S, E, or D,<br>$X_4$ is P or G,<br>$X_5$ is Y or G,<br>$X_6$ is R, E, K, or P, and<br>$X_7$ is R, D, S, Q, A, or E |
| SEQ ID NO: 87 | Loop consensus #4 | $SX_1NX_2X_3X_4X_5$, wherein:<br>$X_1$ is R, W, P, or A,<br>$X_2$ is P, G, I, L, V, M, A, F, or Nle,<br>$X_3$ is Y, G, T, or S,<br>$X_4$ is R, P, D, or N, and<br>$X_5$ is R, D, T, or S |
| SEQ ID NO: 88 | Loop consensus #5 | $SX_1NX_2X_3X_4X_5$, wherein:<br>$X_1$ is R, W, or P,<br>$X_2$ is P, G, or I,<br>$X_3$ is Y, G, or T,<br>$X_4$ is R, P, or D, and<br>$X_5$ is R, D, or T |
| SEQ ID NO: 89 | Loop consensus #6 | $SX_1NX_2X_3X_4X_5$, wherein:<br>$X_1$ is R or W,<br>$X_2$ is P or G,<br>$X_3$ is Y or G,<br>$X_4$ is R or P, and<br>$X_5$ is R or D |
| SEQ ID NO: 90 | Loop consensus #7 | $X_1X_2X_3X_4X_5X_6X_7$, wherein:<br>$X_1$ is S, G, A, M, or T,<br>$X_2$ is R, W, P, or A,<br>$X_3$ is N, Y, S, E, D, Q, H, K, or R,<br>$X_4$ is P, G, I, L, V, M, A, F, or Nle,<br>$X_5$ is Y, G, T, or S,<br>$X_6$ is R, E, K, P, D, or N, and<br>$X_7$ is D, S, Q, A, E, T, or S |
| SEQ ID NO: 91 | Loop consensus #8 | $X_1X_2X_3X_4X_5X_6X_7$, wherein:<br>$X_1$ is S, G, A, or M,<br>$X_2$ is R, W, or P,<br>$X_3$ is N, Y, S, E, or D,<br>$X_4$ is P, G, or I,<br>$X_5$ is Y, G, or T,<br>$X_6$ is R, E, K, P, or D, and<br>$X_7$ is D, S, Q, A, E, or T |
| SEQ ID NO: 92 | Loop consensus #9 | $X_1X_2X_3X_4X_5X_6X_7$, wherein:<br>$X_1$ is S, G, A, or M,<br>$X_2$ is R or W,<br>$X_3$ is N, Y, S, E, or D,<br>$X_4$ is P or G,<br>$X_5$ is Y or G,<br>$X_6$ is R, E, K, or P, and<br>$X_7$ is D, S, Q, A, or E |
| SEQ ID NO: 93 | Loop consensus #10 | FSQQIYGVVYGNVTFHVPSNVPLKEVLWKKQKDKV$X_1EX_2ENSEX_3RX_4FSSFKNRVYLDTVSGSLTIYN$LTSSDEDEYEX_5EX_6X_7X_8X_9X_{10}X_{11}X_{12}X_{13}KF$FLYVX_{14}$, wherein:<br>$X_1$ is V, L, or A, |

TABLE 2-continued

Exemplary amino acid sequences of wild type LFA3 and LFA3 variants.

| SEQ ID NO | Description | Sequence |
|---|---|---|
| | | $X_2$ is F or L, <br> $X_3$ is V, I, L, or F, <br> $X_4$ is A, V, or S, <br> $X_5$ is M, F, I, or L, <br> $X_6$ is S, G, A, or M, <br> $X_7$ is R or W, <br> $X_8$ is N, Y, S, E, or D, <br> $X_9$ is P or G, <br> $X_{10}$ is Y or G, <br> $X_{11}$ is R, E, K, or P, <br> $X_{12}$ is R, D, S, Q, A, or E, <br> $X_{13}$ is F, M, I, or L, and <br> $X_{14}$ is absent, L, or LESLPS |
| SEQ ID NO: 94 | Loop consensus #11 | FSQQIYGVVYGNVTFHVPSNVPLKEVLWKKQKDKV $X_1EX_2ENSEX_3RX_4FSSFKNRVYLDTVSGSLTIYN$ LTSSDEDEYEX$_5$EX$_6$X$_7$X$_8$X$_9$X$_{10}$X$_{11}$X$_{12}$X$_{13}$KF FLYVX$_{14}$, wherein: <br> $X_1$ is V or A, <br> $X_2$ is F or L, <br> $X_3$ is V, I, or F, <br> $X_4$ is A or V, <br> $X_5$ is M or F, <br> $X_6$ is S, G, A, or M, <br> $X_7$ is R or W, <br> $X_8$ is N, Y, S, E, or D, <br> $X_9$ is P or G, <br> $X_{10}$ is Y or G, <br> $X_{11}$ is R, E, K, or P, <br> $X_{12}$ is R, D, S, Q, A, or E, <br> $X_{13}$ is F or M, and <br> $X_{14}$ is absent, L, or LESLPS |
| SEQ ID NO: 95 | Loop consensus #12 | FSQQIYGVVYGNVTFHVPSNVPLKEVLWKKQKDKV VEFENSEVRX$_1$FSSFKNRVYLDTVSGSLTIYNLTS SDEDEYEX$_2$EX$_3$X$_4$X$_5$X$_6$X$_7$X$_8$X$_9$FKFFLYVX$_{10}$, wherein: <br> $X_1$ is any amino acid, <br> $X_2$ is any amino acid, <br> $X_3$ is any amino acid, <br> $X_4$ is any amino acid, <br> $X_5$ is any amino acid, <br> $X_6$ is any amino acid, <br> $X_7$ is any amino acid, <br> $X_8$ is any amino acid, <br> $X_9$ is any amino acid, and <br> $X_{10}$ is absent, L, or LESLPS |
| SEQ ID NO: 96 | Loop consensus #13 | FSQQIYGVVYGNVTFHVPSNVPLKEVLWKKQKDKV VEFENSEVRX$_1$FSSFKNRVYLDTVSGSLTIYNLTS SDEDEYEX$_2$EX$_3$X$_4$X$_5$X$_6$X$_7$X$_8$X$_9$FKFFLYVX$_{10}$, wherein: <br> $X_1$ is A, V, L, or I, <br> $X_2$ is M, F, L, or I, <br> $X_3$ is S, G, A, M, or T, <br> $X_4$ is R, W, P, or A, <br> $X_5$ is N, Y, S, E, D, Q, H, K, or R, <br> $X_6$ is P, G, I, L, V, M, A, F, or Nle, <br> $X_7$ is Y, G, T, or S, <br> $X_8$ is R, E, K, P, D, or N, <br> $X_9$ is R, D, S, Q, A, E, T, or S <br> $X_{10}$ is absent, L, or LESLPS |
| SEQ ID NO: 97 | Loop consensus #14 | FSQQIYGVVYGNVTFHVPSNVPLKEVLWKKQKDKV VEFENSEVRX$_1$FSSFKNRVYLDTVSGSLTIYNLTS SDEDEYEX$_2$EX$_3$X$_4$X$_5$X$_6$X$_7$X$_8$X9FKFFLYVX$_{10}$, wherein: <br> $X_1$ is A or V, <br> $X_2$ is M or F, <br> $X_3$ is S, G, A, or M, <br> $X_4$ is R, W, or P, <br> $X_5$ is N, Y, S, E, or D, <br> $X_6$ is P, G, or I, |

TABLE 2-continued

Exemplary amino acid sequences of
wild type LFA3 and LFA3 variants.

| SEQ ID NO | Description | Sequence |
|---|---|---|
| | | $X_7$ is Y, G, or T,<br>$X_8$ is R, E, K, P, or D,<br>$X_9$ is R, D, S, Q, A, E, or T, and<br>$X_{10}$ is absent, L, or LESLPS |
| SEQ ID NO: 98 | Loop consensus #15 | FSQQIYGVVYGNVTFHVPSNVPLKEVLWKKQKDKV VEFENSEVRX$_1$FSSFKNRVYLDTVSGSLTIYNLTS SDEDEYEX$_2$EX$_3$X$_4$X$_5$X$_6$X$_7$X$_8$X$_9$FKFFLYVX$_{10}$,<br>wherein:<br>$X_1$ is A or V,<br>$X_2$ is M or F,<br>$X_3$ is S, G, A, or M,<br>$X_4$ is R or W,<br>$X_5$ is N, Y, S, E, or D,<br>$X_6$ is P or G,<br>$X_7$ is Y or G,<br>$X_8$ is R, E, K, or P,<br>$X_9$ is R, D, S, Q, A, or E, and<br>$X_{10}$ is absent, L, or LESLPS |
| SEQ ID NO: 99 | Loop consensus #16 | FSQQIYGVVYGNVTFHVPSNVPLKEVLWKKQKDKV VEFENSEVRAFSSFKNRVYLDTVSGSLTIYNLTSS DEDEYEMESX$_1$NX$_2$X$_3$X$_4$X$_5$FKFFLYVX$_6$,<br>wherein:<br>$X_1$ is any amino acid,<br>$X_2$ is any amino acid,<br>$X_3$ is any amino acid,<br>$X_4$ is any amino acid,<br>$X_5$ is any amino acid, and<br>$X_6$ is absent, L, or LESLPS |
| SEQ ID NO: 100 | Loop consensus #17 | FSQQIYGVVYGNVTFHVPSNVPLKEVLWKKQKDKV VEFENSEVRAFSSFKNRVYLDTVSGSLTIYNLTSS DEDEYEMESX$_1$NX$_2$X$_3$X$_4$X$_5$FKFFLYVX$_6$,<br>wherein:<br>$X_1$ is R, W, P, or A,<br>$X_2$ is P, G, I, L, V, M, A, F, or Nle,<br>$X_3$ is Y, G, T, or S,<br>$X_4$ is R, P, D, or N,<br>$X_5$ is R, D, T, or S, and<br>$X_6$ is absent, L, or LESLPS |
| SEQ ID NO: 101 | Loop consensus #18 | FSQQIYGVVYGNVTFHVPSNVPLKEVLWKKQKDKV VEFENSEVRAFSSFKNRVYLDTVSGSLTIYNLTSS DEDEYEMESX$_1$NX$_2$X$_3$X$_4$X$_5$FKFFLYVX$_6$,<br>wherein:<br>$X_1$ is R, W, or P,<br>$X_2$ is P, G, or I,<br>$X_3$ is Y, G, or T,<br>$X_4$ is R, P, or D,<br>$X_5$ is R, D, or T, and<br>$X_6$ is absent, L, or LESLPS |
| SEQ ID NO: 102 | Loop consensus #19 | FSQQIYGVVYGNVTFHVPSNVPLKEVLWKKQKDKV VEFENSEVRAFSSFKNRVYLDTVSGSLTIYNLTSS DEDEYEMESX$_1$NX$_2$X$_3$X$_4$X$_5$FKFFLYVX$_6$,<br>wherein:<br>$X_1$ is R or W,<br>$X_2$ is P or G,<br>$X_3$ is Y or G,<br>$X_4$ is R or P,<br>$X_5$ is R or D, and<br>$X_6$ is absent, L, or LESLPS |
| SEQ ID NO: 103 | Loop consensus #20 | FSQQIYGVVYGNVTFHVPSNVPLKEVLWKKQKDKV VEFENSEVRX$_1$FSSFKNRVYLDTVSGSLTIYNLTS SDEDEYEX$_2$EX$_3$X$_4$X$_5$X$_6$X$_7$X$_8$X$_9$FKFFLYVX$_{10}$,<br>wherein:<br>$X_1$ is A, V, L, or I,<br>$X_2$ is M, F, L, or I,<br>$X_3$ is S, G, A, M, or T,<br>$X_4$ is R, W, P, or A,<br>$X_5$ is N, Y, S, E, D, Q, H, K, or R, |

TABLE 2-continued

Exemplary amino acid sequences of wild type LFA3 and LFA3 variants.

| SEQ ID NO | Description | Sequence |
|---|---|---|
| | | $X_6$ is P, G, I, L, V, M, A, F, or Nle,<br>$X_7$ is Y, G, T, or $_5$,<br>$X_8$ is R, E, K, P, D, or N,<br>$X_9$ is D, S, Q, A, E, T, or S, and<br>$X_{10}$ is absent, L, or LESLPS |
| SEQ ID NO: 104 | Loop consensus #21 | FSQQIYGVVYGNVTFHVPSNVPLKEVLWKKQKDKV VEFENSEVRX$_1$FSSFKNRVYLDTVSGSLTIYNLTS SDEDEYEX$_2$EX$_3$X$_4$X$_5$X$_6$X$_7$X$_8$X$_9$FKFFLYVX$_{10}$, wherein:<br>$X_1$ is A or V,<br>$X_2$ is M or F,<br>$X_3$ is S, G, A, or M,<br>$X_4$ is R, W, or P,<br>$X_5$ is N, Y, S, E, or D,<br>$X_6$ is P, G, or I,<br>$X_7$ is Y, G, or T,<br>$X_8$ is R, E, K, P, or D,<br>$X_9$ is D, S, Q, A, E, or T, and<br>$X_{10}$ is absent, L, or LESLPS |
| SEQ ID NO: 105 | Loop consensus #22 | FSQQIYGVVYGNVTFHVPSNVPLKEVLWKKQKDKV VEFENSEVRX$_1$FSSFKNRVYLDTVSGSLTIYNLTS SDEDEYEX$_2$EX$_3$X$_4$X$_5$X$_6$X$_7$X$_8$X$_9$FKFFLYVX$_{10}$, wherein:<br>$X_1$ is A or V,<br>$X_2$ is M or F,<br>$X_3$ is S, G, A, or M,<br>$X_4$ is R or W,<br>$X_5$ is N, Y, S, E, or D,<br>$X_6$ is P or G,<br>$X_7$ is Y or G,<br>$X_8$ is R, E, K, or P,<br>$X_9$ is D, S, Q, A, or E, and<br>$X_{10}$ is absent, L, or LESLPS |
| SEQ ID NO: 106 | CM1d1 loop | SRNGGPD |
| SEQ ID NO: 107 | CM2d1 loop | SRNPYRR |
| SEQ ID NO: 108 | CM3d1 loop | SRNPYRD |
| SEQ ID NO: 109 | CM4d1 loop | SWNGGPD |
| SEQ ID NO: 110 | CM5d1 loop | SWNPYRR |
| SEQ ID NO: 111 | CM6d1 loop | SWNPYRD |
| SEQ ID NO: 112 | ML1d1 loop | GRYPYES |
| SEQ ID NO: 113 | ML2d1 loop | SWEPGRE |
| SEQ ID NO: 114 | ML3d1 loop | ARYPYRQ |
| SEQ ID NO: 115 | ML4d1 loop | MRNGGPD |
| SEQ ID NO: 116 | ML5d1 loop | ARDGGPD |
| SEQ ID NO: 117 | ML6d1 loop | SWSPYKA |
| SEQ ID NO: 118 | C-terminal boundary | LESLPS |
| SEQ ID NO: 119 | C-terminal boundary | LESLPSPTLTCALTNGSIEV |
| SEQ ID NO: 128 | IgG1 Fc domain | dkthtcppcpapellggpsvflfppkpkdtlmisr tpevtcyvvdvshedpevkfnwyydgvevhnaktk preeqynstyryysyltylhqdwingkeykckvsn kalpapiektiskakgqprepqvytlppsrdeltk |

TABLE 2-continued

Exemplary amino acid sequences of
wild type LFA3 and LFA3 variants.

| SEQ ID NO | Description | Sequence |
| --- | --- | --- |
| | | nqvsltclykgfypsdiavewesngqpennykapp
yldsdgsfflyskltydksrwqqgnyfscsvmhea
lhnhytqkslslspgk |
| SEQ ID NO: 129 | leader | *mvagsdagralgvlsvvcllhcfgfisc* |

TABLE 3

Exemplary nucleotide sequences of
wild type LFA3 and LFA3 variants.

| SEQ ID NO | Description | Sequence |
| --- | --- | --- |
| SEQ ID NO: 42 | Leader sequence of LFA3-Fc fusion proteins | *ATGGGCTGGTCCTGTATCATCCTCTTTCTGGTGGCC
ACAGCTACCGGAGTGCATAGC* |
| SEQ ID NO: 43 | Hinge-Pfe | GACAAAACTCACACATGCCCACCGTGCCCAGCACCT
GAACTCCTGGGGGGACCGTCAGTCTTCCTCTTCCCC
CCAAAACCCAAGGACACCCTCATGATCTCCCGGACC
CCTGAGGTCACATGCGTGGTGGTGGACGTGAGCCAC
GAAGACCCTGAGGTCAAGTTCAACTGGTACGTGGAC
GGCGTGGAGGTGCATAATGCCAAGACAAAGCCGCGG
GAGGAGCAGTACAACAGCACGTACCGTGTGGTCAGC
GTCCTCACCGTCCTGCACCAGGACTGGCTGAATGGC
AAGGAGTACAAGTGCAAGGTCTCCAACAAAGCCCTC
CCAGCCCCCATCGAGAAAACCATCTCCAAAGCCAAA
GGGCAGCCCCGAGAACCACAGGTGTACACCCTGCCC
CCATCCCGGGAAGAGATGACCAAGAACCAGGTCAGC
CTGACCTGCCTGGTCAAAGGCTTCTATCCCAGCGAC
ATCGCCGTGGAGTGGGAGAGCAATGGGCAGCCGGAG
AACAACTACAAGACCACGCCTCCCGTGTTGGACTCC
GACGGCTCCTTCTTCCTCTACAGCAAGCTCACCGTG
GACAAGAGCAGGTGGCAGCAGGGGAACGTCTTCTCA
TGCTCCGTGATGCATGAGGCTCTGCACAACCACTAC
ACGCAGAAGAGCCTCTCCCTGTCTCCGGGT |
| SEQ ID NO: 44 | M1 | TTTTCACAGCAGATTTACGGTGTTGTTTACGGTAAT
GTGACTTTTCACGTTCCGAGTAACGTTCCTTTGAAG
GAAGTCTTATGGAAAAAACAAAAAGATAAAGTTGTA
GAATTTGAGAATAGTGAGGTTAGGGCATTTAGTTCA
TTTAAGAATAGGGTCTATTTGGATACTGTATCCGGT
TCTTTGACCATTTATAATTTAACAAGTAGTGATGAA
GACGAGTACGAAATGGAGTCCCTAATATTACAGAC
ACATTCAAGTTTTTTTTGTACGTT |
| SEQ ID NO: 45 | M2 | TTTTCACAGCAGATTTACGGTGTTGTTTACGGTAAT
GTGACTTTTCACGTTCCGAGTAACGTTCCTTTGAAG
GAAGTCTTATGGAAAAAACAAAAAGATAAAGTTGTA
GAATTTGAGAATAGTGAGGTTAGGGCATTTAGTTCA
TTTAAGAATAGGGTCTATTTGGATACTGTATCCGGT
TCTTTGACCATTTATAATTTAACAAGTAGTGATGAA
GACGAGTACGAATTCGAGTCCCTAATATTACAGAC
ACATTCAAGTTTTTTTTGTACGTT |
| SEQ ID NO: 46 | M3 | TTTTCACAGCAGATTTACGGTGTTGTTTACGGTAAT
GTGACTTTTCACGTTCCGAGTAACGTTCCTTTGAAG
GAAGTCTTATGGAAAAAACAAAAAGATAAAGTTGTA
GAATTTGAGAATAGTGAGGTTAGGGTATTTAGTTCA
TTTAAGAATAGGGTCTATTTGGATACTGTATCCGGT
TCTTTGACCATTTATAATTTAACAAGTAGTGATGAA
GACGAGTACGAAATGGAGTCCCTAATATTACAGAC
ACATTCAAGTTTTTTTTGTACGTT |
| SEQ ID NO: 47 | M4 | TTTTCACAGCAGATTTACGGTGTTGTTTACGGTAAT
GTGACTTTTCACGTTCCGAGTAACGTTCCTTTGAAG
GAAGTCTTATGGAAAAAACAAAAAGATAAAGTTGTA
GAATTTGAGAATAGTGAGGTTAGGGTATTTAGTTCA
TTTAAGAATAGGGTCTATTTGGATACTGTATCCGGT
TCTTTGACCATTTATAATTTAACAAGTAGTGATGAA |

TABLE 3-continued

Exemplary nucleotide sequences of wild type LFA3 and LFA3 variants.

| SEQ ID NO | Description | Sequence |
|---|---|---|
| | | GACGAGTACGAATTCGAGTCCCTAATATTACAGAC<br>ACATTCAAGTTTTTTTGTACGTT |
| SEQ ID NO: 48 | M5 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAGATAAAGTTGTA<br>GAATTTGAGAATAGTGAGATTAGGGTATTTAGTTCA<br>TTTAAGAATAGGGTCTATTTGGATACTGTATCCGGT<br>TCTTTGACCATTTATAATTTAACAAGTAGTGATGAA<br>GACGAGTACGAATTCGAGTCCCTAATATTACAGAC<br>ACATTCAAGTTTTTTTGTACGTT |
| SEQ ID NO: 49 | M6 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAGATAAAGTTTTA<br>GAATTTGAGAATAGTGAGCTTAGGGTATTTAGTTCA<br>TTTAAGAATAGGGTCTATTTGGATACTGTATCCGGT<br>TCTTTGACCATTTATAATTTAACAAGTAGTGATGAA<br>GACGAGTACGAATTCGAGTCCCTAATATTACAGAC<br>ACATTCAAGTTTTTTTGTACGTT |
| SEQ ID NO: 50 | M7 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAGATAAAGTTGTA<br>GAATTTGAGAATAGTGAGGTTAGGGCATTTAGTTCA<br>TTTAAGAATAGGGTCTATTTGGATACTGTATCCGGT<br>TCTTTGACCATTTATAATTTAACAAGTAGTGATGAA<br>GACGAGTACGAAATGGAGTCCCTAATATTACAGAC<br>ACAATGAAGTTTTTTTGTACGTT |
| SEQ ID NO: 51 | d1 | TTTTCCCAACAAATATATGGTGTTGTGTATGGGAAT<br>GTAACTTTCCATGTACCAAGCAATGTGCCTTTAAAA<br>GAGGTCCTATGGAAAAAACAAAAGGATAAAGTTGCA<br>GAACTGGAAAATTCTGAATTCAGAGCTTTCTCATCT<br>TTTAAAAATAGGGTTTATTTAGACACTGTGTCAGGT<br>AGCCTCACTATCTACAACTTAACATCATCAGATGAA<br>GATGAGTATGAAATGGAATCGCCAAATATTACTGAT<br>ACCATGAAGTTCTTTCTTTATGTCCTC |
| SEQ ID NO: 52 | d3 | TTTTCCCAACAAATATATGGTGTTGTGTATGGGAAT<br>GTAACTTTCCATGTACCAAGCAATGTGCCTTTAAAA<br>GAGGTCCTATGGAAAAAACAAAAGGATAAAGTTGCA<br>GAACTGGAAAATTCTGAATTCAGAGCTTTCTCATCT<br>TTTAAAAATAGGGTTTATTTAGACACTGTGTCAGGT<br>AGCCTCACTATCTACAACTTAACATCATCAGATGAA<br>GATGAGTATGAAATGGAATCGCCAAATATTACTGAT<br>ACCATGAAGTTCTTTCTTTATGTCCTTGAGAGTCTG<br>CCCAGC |
| SEQ ID NO: 53 | M1d1 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAGATAAAGTTGTA<br>GAATTTGAGAATAGTGAGGTTAGGGCATTTAGTTCA<br>TTTAAGAATAGGGTCTATTTGGATACTGTATCCGGT<br>TCTTTGACCATTTATAATTTAACAAGTAGTGATGAA<br>GACGAGTACGAAATGGAGTCCCTAATATTACAGAC<br>ACATTCAAGTTTTTTTGTACGTTCTC |
| SEQ ID NO: 54 | M1d3 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAGATAAAGTTGTA<br>GAATTTGAGAATAGTGAGGTTAGGGCATTTAGTTCA<br>TTTAAGAATAGGGTCTATTTGGATACTGTATCCGGT<br>TCTTTGACCATTTATAATTTAACAAGTAGTGATGAA<br>GACGAGTACGAAATGGAGTCCCTAATATTACAGAC<br>ACATTCAAGTTTTTTTGTACGTTCTTGAGAGTCTG<br>CCCAGC |
| SEQ ID NO: 55 | M4d1 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAGATAAAGTTGTA<br>GAATTTGAGAATAGTGAGGTTAGGGTATTTAGTTCA<br>TTTAAGAATAGGGTCTATTTGGATACTGTATCCGGT<br>TCTTTGACCATTTATAATTTAACAAGTAGTGATGAA |

TABLE 3-continued

Exemplary nucleotide sequences of wild type LFA3 and LFA3 variants.

| SEQ ID NO | Description | Sequence |
|---|---|---|
| | | GACGAGTACGAATTCGAGTCCCTAATATTACAGAC<br>ACATTCAAGTTTTTTTGTACGTTCTC |
| SEQ ID NO: 56 | M7d1 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAGATAAAGTTGTA<br>GAATTTGAGAATAGTGAGGTTAGGGCATTTAGTTCA<br>TTTAAGAATAGGGTCTATTTGGATACTGTATCCGGT<br>TCTTTGACCATTTATAATTTAACAAGTAGTGATGAA<br>GACGAGTACGAAATGGAGTCCCTAATATTACAGAC<br>ACAATGAAGTTTTTTTGTACGTTCTC |
| SEQ ID NO: 57 | CM1d1 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAGATAAAGTTGTA<br>GAATTTGAGAATAGTGAGGTTAGGGCATTTAGTTCA<br>TTTAAGAATAGGGTCTATTTGGATACTGTATCCGGT<br>TCTTTGACCATTTATAATTTAACAAGTAGTGATGAA<br>GACGAGTACGAAATGGAGTCCAGGAATGGTGGACCT<br>GATTTCAAGTTTTTTTGTACGTTTTG |
| SEQ ID NO: 58 | CM2d1 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAGATAAAGTTGTA<br>GAATTTGAGAATAGTGAGGTTAGGGCATTTAGTTCA<br>TTTAAGAATAGGGTCTATTTGGATACTGTATCCGGT<br>TCTTTGACCATTTATAATTTAACAAGTAGTGATGAA<br>GACGAGTACGAAATGGAGTCCAGGAATCCTTATAGA<br>AGGTTCAAGTTTTTTTGTACGTTTTG |
| SEQ ID NO: 59 | CM3d1 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAGATAAAGTTGTA<br>GAATTTGAGAATAGTGAGGTTAGGGCATTTAGTTCA<br>TTTAAGAATAGGGTCTATTTGGATACTGTATCCGGT<br>TCTTTGACCATTTATAATTTAACAAGTAGTGATGAA<br>GACGAGTACGAAATGGAGTCCAGGAATCCTTATAGA<br>GACTTCAAGTTTTTTTGTACGTTTTG |
| SEQ ID NO: 60 | CM4d1 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAGATAAAGTTGTA<br>GAATTTGAGAATAGTGAGGTTAGGGCATTTAGTTCA<br>TTTAAGAATAGGGTCTATTTGGATACTGTATCCGGT<br>TCTTTGACCATTTATAATTTAACAAGTAGTGATGAA<br>GACGAGTACGAAATGGAGTCCTGGAATGGTGGACCT<br>GATTTCAAGTTTTTTTGTACGTTTTG |
| SEQ ID NO: 61 | CM5d1 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAGATAAAGTTGTA<br>GAATTTGAGAATAGTGAGGTTAGGGCATTTAGTTCA<br>TTTAAGAATAGGGTCTATTTGGATACTGTATCCGGT<br>TCTTTGACCATTTATAATTTAACAAGTAGTGATGAA<br>GACGAGTACGAAATGGAGTCCTGGAATCCTTATAGA<br>AGGTTCAAGTTTTTTTGTACGTTTTG |
| SEQ ID NO: 62 | CM6d1 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAGATAAAGTTGTA<br>GAATTTGAGAATAGTGAGGTTAGGGCATTTAGTTCA<br>TTTAAGAATAGGGTCTATTTGGATACTGTATCCGGT<br>TCTTTGACCATTTATAATTTAACAAGTAGTGATGAA<br>GACGAGTACGAAATGGAGTCCTGGAATCCTTATAGA<br>GACTTCAAGTTTTTTTGTACGTTTTG |
| SEQ ID NO: 63 | M11d1 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAGATAAAGTTGTA<br>GAATTTGAGAATAGTGAGGTTAGGGCATTTAGTTCA<br>TTTAAGAATAGGGTCTATTTGGATACTGTATCCGGT<br>TCTTTGACCATTTATAATTTAACAAGTAGTGATGAA<br>GACGAGTACGAAATGGAGGGTCGGTATCCGTATGAG<br>TCGTTCAAGTTTTTTTGTACGTTTTG |

TABLE 3-continued

Exemplary nucleotide sequences of wild type LFA3 and LFA3 variants.

| SEQ ID NO | Description | Sequence |
| --- | --- | --- |
| SEQ ID NO: 64 | M12d1 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAAGATAAAGTTGTA<br>GAATTTGAGAATAGTGAGGTTAGGGTATTTAGTTCA<br>TTTAAGAATAGGGTCTATTTGGATACTGTATCCGGT<br>TCTTTGACCATTTATAATTTAACAAGTAGTGATGAA<br>GACGAGTACGAATTCGAGAGTTGGGAGCCTGGGAGG<br>GAGTTCAAGTTTTTTTTGTACGTTTTG |
| SEQ ID NO: 65 | M13d1 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAAGATAAAGTTGTA<br>GAATTTGAGAATAGTGAGGTTAGGGCATTTAGTTCA<br>TTTAAGAATAGGGTCTATTTGGATACTGTATCCGGT<br>TCTTTGACCATTTATAATTTAACAAGTAGTGATGAA<br>GACGAGTACGAAATGGAGGCTCGGTATCCTTATCGG<br>CAGTTCAAGTTTTTTTTGTACGTTTTG |
| SEQ ID NO: 66 | M14d1 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAAGATAAAGTTGTA<br>GAATTTGAGAATAGTGAGGTTAGGGCATTTAGTTCA<br>TTTAAGAATAGGGTCTATTTGGATACTGTATCCGGT<br>TCTTTGACCATTTATAATTTAACAAGTAGTGATGAA<br>GACGAGTACGAAATGGAGATGCGGAATGGTGGTCCT<br>GATTTCAAGTTTTTTTTGTACGTTTTG |
| SEQ ID NO: 67 | M15d1 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAAGATAAAGTTGTA<br>GAATTTGAGAATAGTGAGGTTAGGGCATTTAGTTCA<br>TTTAAGAATAGGGTCTATTTGGATACTGTATCCGGT<br>TCTTTGACCATTTATAATTTAACAAGTAGTGATGAA<br>GACGAGTACGAAATGGAGGCGCGGGATGGGGGTCCT<br>GATTTCAAGTTTTTTTTGTACGTTTTG |
| SEQ ID NO: 68 | M16d1 | TTTTCACAGCAGATTTACGGTGTTGTTTACGGTAAT<br>GTGACTTTTCACGTTCCGAGTAACGTTCCTTTGAAG<br>GAAGTCTTATGGAAAAAACAAAAAGATAAAGTTGTA<br>GAATTTGAGAATAGTGAGGTTAGGGCATTTAGTTCA<br>TTTAAGAATAGGGTCTATTTGGATACTGTATCCGGT<br>TCTTTGACCATTTATAATTTAACAAGTAGTGATGAA<br>GACGAGTACGAAATGGAGTCGTGGTCTCCTTATAAG<br>GCGTTCAAGTTTTTTTTGTACGTTTTG |
| SEQ ID NO: 122 | LFA3-Fc M1-d1 nucleotide (including leader sequence, underline and italics) | *ATGGGCTGGTCCTGTATCATCCTCTTTCTGGTGGCC*<br>*ACAGCTACCGGAGTGCATAGC*TTTTCACAGCAGATT<br>TACGGTGTTGTTTACGGTAATGTGACTTTTCACGTT<br>CCGAGTAACGTTCCTTTGAAGGAAGTCTTATGGAAA<br>AAACAAAAAGATAAAGTTGTAGAATTTGAGAATAGT<br>GAGGTTAGGGCATTTAGTTCATTTAAGAATAGGGTC<br>TATTTGGATACTGTATCCGGTTCTTTGACCATTTAT<br>AATTTAACAAGTAGTGATGAAGACGAGTACGAAATG<br>GAGTCCCCTAATATTACAGACACATTCAAGTTTTTT<br>TTGTACGTTCTCGACAAAACTCACACATGCCCACCG<br>TGCCCAGCACCTGAACTCCTGGGGGGACCGTCAGTC<br>TTCCTCTTCCCCCCAAAACCCAAGGACACCCTCATG<br>ATCTCCCGGACCCCTGAGGTCACATGCGTGGTGGTG<br>GACGTGAGCCACGAAGACCCTGAGGTCAAGTTCAAC<br>TGGTACGTGGACGGCGTGGAGGTGCATAATGCCAAG<br>ACAAAGCCGCGGGAGGAGCAGTACAACAGCACGTAC<br>CGTGTGGTCAGCGTCCTCACCGTCCTGCACCAGGAC<br>TGGCTGAATGGCAAGGAGTACAAGTGCAAGGTCTCC<br>AACAAAGCCCTCCCAGCCCCCATCGAGAAAACCATC<br>TCCAAAGCCAAAGGGCAGCCCCGAGAACCACAGGTG<br>TACACCCTGCCCCCATCCCGGGAAGAGATGACCAAG<br>AACCAGGTCAGCCTGACCTGCCTGGTCAAAGGCTTC<br>TATCCCAGCGACATCGCCGTGGAGTGGGAGAGCAAT<br>GGGCAGCCGGAGAACAACTACAAGACCACGCCTCCC<br>GTGTTGGACTCCGACGGCTCCTTCTTCCTCTACAGC<br>AAGCTCACCGTGGACAAGAGCAGGTGGCAGCAGGGG<br>AACGTCTTCTCATGCTCCGTGATGCATGAGGCTCTG<br>CACAACCACTACACGCAGAAGAGCCTCTCCCTGTCT<br>CCGGGT |

TABLE 3-continued

Exemplary nucleotide sequences of wild type LFA3 and LFA3 variants.

| SEQ ID NO | Description | Sequence |
|---|---|---|
| SEQ ID NO: 123 | LFA3-Fc M1-d1 nucleotide (also referred to as "LFA3-Fc M1d1", "M1d1", "M1-d1" or "M1d1-Pfe") (without leader sequence) | TTTTCACAGCAGATTTACGGTGTTGTTTACGGTAAT GTGACTTTTCACGTTCCGAGTAACGTTCCTTTGAAG GAAGTCTTATGGAAAAAACAAAAGATAAAGTTGTA GAATTTGAGAATAGTGAGGTTAGGGCATTTAGTTCA TTTAAGAATAGGGTCTATTTGGATACTGTATCCGGT TCTTTGACCATTTATAATTTAACAAGTAGTGATGAA GACGAGTACGAAATGGAGTCCCCTAATATTACAGAC ACATTCAAGTTTTTTTTGTACGTTCTCGACAAAACT CACACATGCCCACCGTGCCCAGCACCTGAACTCCTG GGGGGACCGTCAGTCTTCCTCTTCCCCCCAAAACCC AAGGACACCCTCATGATCTCCCGGACCCCTGAGGTC ACATGCGTGGTGGTGGACGTGAGCCACGAAGACCCT GAGGTCAAGTTCAACTGGTACGTGGACGGCGTGGAG GTGCATAATGCCAAGACAAAGCCGCGGGAGGAGCAG TACAACAGCACGTACCGTGTGGTCAGCGTCCTCACC GTCCTGCACCAGGACTGGCTGAATGGCAAGGAGTAC AAGTGCAAGGTCTCCAACAAAGCCCTCCCAGCCCCC ATCGAGAAAACCATCTCCAAAGCCAAAGGGCAGCCC CGAGAACCACAGGTGTACACCCTGCCCCCATCCCGG GAAGAGATGACCAAGAACCAGGTCAGCCTGACCTGC CTGGTCAAAGGCTTCTATCCCAGCGACATCGCCGTG GAGTGGGAGAGCAATGGGCAGCCGGAGAACAACTAC AAGACCACGCCTCCCGTGTTGGACTCCGACGGCTCC TTCTTCCTCTACAGCAAGCTCACCGTGGACAAGAGC AGGTGGCAGCAGGGGAACGTCTTCTCATGCTCCGTG ATGCATGAGGCTCTGCACAACCACTACACGCAGAAG AGCCTCTCCCTGTCTCCGGGT |
| SEQ ID NO: 124 | LFA3-Fc WT (including leader, underlined) | *ATGGTTGCTGGGAGCGACGCGGGGCGGGCCCTGGGG GTCCTCAGCGTGGTCTGCCTGCTGCACTGCMGGTTT CATCAGCTGT*VTTTCCCAACAAATATATGGTGTTGT GTATGGGAATGTAACTTTCCATGTACCAAGCAATGT GCCTTTAAAAGAGGTCCTATGGAAAAAACAAAAGGA TAAAGTTGCAGAACTGGAAAATTCTGAATTCAGAGC TTTCTCATCTTTTAAAAATAGGGTTTATTTAGACAC TGTGTCAGGTAGCCTCACTATCTACAACTTAACATC ATCAGATGAAGATGAGTATGAAATGGAATCGCCAAA TATTACTGATACCATGAAGTTCTTTCTTTATGTCGA CAAAACTCACACATGCCCACCGTGCCCAGCACCTGA ACTCCTGGGGGGACCGTCAGTCTTCCTCTTCCCCCC AAAACCCAAGGACACCCTCATGATCTCCCGGACCCC TGAGGTCACATGCGTGGTGGTGGACGTGAGCCACGA AGACCCTGAGGTCAAGTTCAACTGGTACGTGGACGG CGTGGAGGTGCATAATGCCAAGACAAAGCCGCGGGA GGAGCAGTACAACAGCACGTACCGTGTGGTCAGCGT CCTCACCGTCCTGCACCAGGACTGGCTGAATGGCAA GGAGTACAAGTGCAAGGTCTCCAACAAAGCCCTCCC AGCCCCCATCGAGAAAACCATCTCCAAAGCCAAAGG GCAGCCCCGAGAACCACAGGTGTACACCCTGCCCCC ATCCCGGGATGAGCTGACCAAGAACCAGGTCAGCCT GACCTGCCTGGTCAAAGGCTTCTATCCCAGCGACAT CGCCGTGGAGTGGGAGAGCAATGGGCAGCCGGAGAA CAACTACAAGACCACGCCTCCCGTGTTGGACTCCGA CGGCTCCTTCTTCCTCTACAGCAAGCTCACCGTGGA CAAGAGCAGGTGGCAGCAGGGGAACGTCTTCTCATG CTCCGTGATGCATGAGGCTCTGCACAACCACTACAC GCAGAAGAGCCTCTCCCTGTCTCCGGGTAAA |
| SEQ ID NO: 125 | LFA3-Fc WT (no leader) | TTTTCCCAACAAATATATGGTGTTGTGTATGGGAAT GTAACTTTCCATGTACCAAGCAATGTGCCTTTAAAA GAGGTCCTATGGAAAAAACAAAAGGATAAAGTTGCA GAACTGGAAAATTCTGAATTCAGAGCTTTCTCATCT TTTAAAAATAGGGTTTATTTAGACACTGTGTCAGGT AGCCTCACTATCTACAACTTAACATCATCAGATGAA GATGAGTATGAAATGGAATCGCCAAATATTACTGAT ACCATGAAGTTCTTTCTTTATGTCGACAAAACTCAC ACATGCCCACCGTGCCCAGCACCTGAACTCCTGGGG GGACCGTCAGTCTTCCTCTTCCCCCCAAAACCCAAG GACACCCTCATGATCTCCCGGACCCCTGAGGTCACA TGCGTGGTGGTGGACGTGAGCCACGAAGACCCTGAG GTCAAGTTCAACTGGTACGTGGACGGCGTGGAGGTG CATAATGCCAAGACAAAGCCGCGGGAGGAGCAGTAC AACAGCACGTACCGTGTGGTCAGCGTCCTCACCGTC CTGCACCAGGACTGGCTGAATGGCAAGGAGTACAAG TGCAAGGTCTCCAACAAAGCCCTCCCAGCCCCCATC |

TABLE 3-continued

Exemplary nucleotide sequences of wild type LFA3 and LFA3 variants.

| SEQ ID NO | Description | Sequence |
|---|---|---|
| | | GAGAAAACCATCTCCAAAGCCAAAGGGCAGCCCCGA<br>GAACCACAGGTGTACACCCTGCCCCATCCCGGGAT<br>GAGCTGACCAAGAACCAGGTCAGCCTGACCTGCCTG<br>GTCAAAGGCTTCTATCCCAGCGACATCGCCGTGGAG<br>TGGGAGAGCAATGGGCAGCCGGAGAACAACTACAAG<br>ACCACGCCTCCCGTGTTGGACTCCGACGGCTCCTTC<br>TTCCTCTACAGCAAGCTCACCGTGGACAAGAGCAGG<br>TGGCAGCAGGGGAACGTCTTCTCATGCTCCGTGATG<br>CATGAGGCTCTGCACAACCACTACACGCAGAAGAGC<br>CTCTCCCTGTCTCCGGGTAAA |
| SEQ ID NO: 126 | LFA3 WT domain | TTTTCCCAACAAATATATGGTGTTGTGTATGGGAAT<br>GTAACTTTCCATGTACCAAGCAATGTGCCTTTAAAA<br>GAGGTCCTATGGAAAAAACAAAAGGATAAAGTTGCA<br>GAACTGGAAAATTCTGAATTCAGAGCTTTCTCATCT<br>TTTAAAAATAGGGTTTATTTAGACACTGTGTCAGGT<br>AGCCTCACTATCTACAACTTAACATCATCAGATGAA<br>GATGAGTATGAAATGGAATCGCCAAATATTACTGAT<br>ACCATGAAGTTCTTTCTTTATGTC |
| SEQ ID NO: 127 | IgG1 Fc domain | GACAAAACTCACACATGCCCACCGTGCCCAGCACCT<br>GAACTCCTGGGGGGACCGTCAGTCTTCCTCTTCCCC<br>CCAAAACCCAAGGACACCCTCATGATCTCCCGGACC<br>CCTGAGGTCACATGCGTGGTGGTGGACGTGAGCCAC<br>GAAGACCCTGAGGTCAAGTTCAACTGGTACGTGGAC<br>GGCGTGGAGGTGCATAATGCCAAGACAAAGCCGCGG<br>GAGGAGCAGTACAACAGCACGTACCGTGTGGTCAGC<br>GTCCTCACCGTCCTGCACCAGGACTGGCTGAATGGC<br>AAGGAGTACAAGTGCAAGGTCTCCAACAAAGCCCTC<br>CCAGCCCCCATCGAGAAAACCATCTCCAAAGCCAAA<br>GGGCAGCCCCGAGAACCACAGGTGTACACCCTGCCC<br>CCATCCCGGGATGAGCTGACCAAGAACCAGGTCAGC<br>CTGACCTGCCTGGTCAAAGGCTTCTATCCCAGCGAC<br>ATCGCCGTGGAGTGGGAGAGCAATGGGCAGCCGGAG<br>AACAACTACAAGACCACGCCTCCCGTGTTGGACTCC<br>GACGGCTCCTTCTTCCTCTACAGCAAGCTCACCGTG<br>GACAAGAGCAGGTGGCAGCAGGGGAACGTCTTCTCA<br>TGCTCCGTGATGCATGAGGCTCTGCACAACCACTAC<br>ACGCAGAAGAGCCTCTCCCTGTCTCCGGGTAAA |
| SEQ ID NO: 130 | leader | *ATGGTTGCTGGGAGCGACGCGGGGCGGGCCCTGGGG<br>GTCCTCAGCGTGGTCTGCCTGCTGCACTGCTTTGGT<br>TTCATCAGCTGT* |

The amino acid sequence of M1d1 LFA3-Fc fusion protein is provided as SEQ ID NO: 69. The four non-native amino acid substitutions (A36V, L38F, F43V, and M86F) are in bold and underlined. The C-terminal residue of the LFA3 domain (L93) is marked by double underline. The four predicted N-linked glycosylation sites (N12, N66, N81, and N170) are marked by dotted underline.

(SEQ ID NO: 69)
FSQQIYGVVYCNVTFHVPSNVPLKEVLWKKQKDKVVEFENSEVRAFSSFK

NRVYLDTVSGSLTIYNLTSSDEDEYEMESENITDTFKFFLYVLDKTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSREEMTKNQVSLTCLVKGFYPSDI

AVEWESNGQPENNYKTTPPVLDSDGSFFLYSKLTVDKSRWQQGNVFSCSV

MHEALHNHYTQKSLSLSPG

In one aspect, additional polypeptide molecule includes one or more of the following embodiments.

A1. An isolated polypeptide molecule that specifically binds to CD2, wherein the polypeptide molecule comprises a LFA3 domain, wherein the LFA3 domain comprises the amino acid sequence of SEQ ID NO: 70, or a functional variant of SEQ ID NO: 70 (e.g., a sequence having at least 75%, 80%, 85%, 90%, 95%, or 99% identity thereof), wherein the LFA3 domain does not comprise the amino acid sequence of SEQ ID NO: 3.

A2. An isolated polypeptide molecule that specifically binds to CD2, wherein the polypeptide molecule comprises a LFA3 domain, wherein the LFA3 domain comprises the amino acid sequence of:

(SEQ ID NO: 71)
FSQQIYGVVYGNVTFHVPSNVPLKX$_1$VX$_2$WX$_3$KQX$_4$X$_5$X$_6$VAX$_7$LX$_8$NS

X$_9$FX$_{10}$AX$_{11}$X$_{12}$SFKNRVYLDTVSGSLT$_1$YNLTSSDEDEYEMESX$_{13}$N

X$_{14}$TX$_{15}$TMKFFLYVX$_{16}$, wherein:

X$_1$ is D, E, N, K, Q, or H,

X$_2$ is F, I, L, V, Nle, M, or A,

X$_3$ is K, R, M, T, Q, or N,

-continued

X$_4$ is K, R, M, T, Q, or N,

X$_5$ is D, E, N, K, Q, or H,

X$_6$ is K, R, M, T, Q, or N,

X$_7$ is D, E, N, K, Q, or H,

X$_8$ is D, E, N, K, Q, or H,

X$_9$ is D, E, N, K, Q, or H,

X$_{10}$ is K, R, M, T, Q, or N,

X$_{11}$ is F, Y, L, H, I, N, V, D, A, or Y,

X$_{12}$ is S, T, A, or G,

X$_{13}$ is P, L, H, R, or A,

X$_{14}$ is F, I, L, V, M, A, or Nle,

X$_{15}$ is D, E, N, K, Q, or H, and

X$_{16}$ is absent, L, or LESLPS, or a functional variant of SEQ ID NO: 71 (e.g., a sequence having at least 75%, 80%, 85%, 90%, 95%, or 99% identity thereof), wherein the LFA3 domain does not comprise the amino acid sequence of SEQ ID NO: 3.

A3. An isolated polypeptide molecule that specifically binds to CD2, wherein the polypeptide molecule comprises a LFA3 domain, wherein the LFA3 domain comprises the amino acid sequence of:

(SEQ ID NO: 72)
FSQQIYGVVYGNVTFHVPSNVPLKX$_1$VX$_2$WX$_3$KQX$_4$X$_5$X$_6$VAX$_7$LX$_8$NS

X$_9$FX$_{10}$AX$_{11}$X$_{12}$SFKNRVYLDTVSGSLTIYNLTSSDEDEYEMESX$_{13}$N

X$_{14}$TX$_{15}$TMKFFLYVX$_{16}$, wherein:

$X_1$ is D, E, N, K, Q, or H, $X_2$ is F, I, L, or V, $X_3$ is K, R, M, or T, $X_4$ is K, R, M, or T, $X_5$ is D, E, N, K, Q, or H, $X_6$ is K, R, M, or T, $X_7$ is D, E, N, K, Q, or H, $X_8$ is D, E, N, K, Q, or H, $X_9$ is D, E, N, K, Q, or H, $X_{10}$ is K, R, M, or T, $X_{11}$ is F, Y, L, H, I, N, V, or D, $X_{12}$ is S, T, A, or G, $X_{13}$ is P, L, H, or R, $X_{14}$ is F, I, L, or V, $X_{15}$ is D, E, N, K, Q, or H, and $X_{16}$ is absent, L, or LESLPS, or a functional variant of SEQ ID NO: 72 (e.g., a sequence having at least 75%, 80%, 85%, 90%, 95%, or 99% identity thereof), wherein the LFA3 domain does not comprise the amino acid sequence of SEQ ID NO: 3.

A4. An isolated polypeptide molecule that specifically binds to CD2, wherein the polypeptide molecule comprises a LFA3 domain, wherein the LFA3 domain comprises one or more mutations (e.g., a substitution, a deletion, or an addition) at residues 25, 27, 29, 32, 33, 34, 37, 39, 42, 44, 46, 47, 80, 82, or 84 relative to SEQ ID NO: 3, numbered according to SEQ ID NO: 3, e.g., wherein the LFA3 domain comprises SEQ ID NO: 3 with one or more mutations (e.g., a substitution, a deletion, or an addition) at residues 25, 27, 29, 32, 33, 34, 37, 39, 42, 44, 46, 47, 80, 82, or 84 relative to SEQ ID NO: 3.

A5. The isolated polypeptide molecule of A4, wherein the one or more mutations comprise one or more of the following substitutions:

i. a substitution chosen from E25D, E25N, E25K, E25Q, or E25H,
ii. a substitution chosen from L27F, L27I, L27V, L27Nle, L27M, or L27A,
iii. a substitution chosen from K29R, K29M, K29T, K29Q, or K29N,
iv. a substitution chosen from K32R, K32M, K32T, K32Q, or K32N,
v. a substitution chosen from D33E, D33N, D33K, D33Q, or D33H,
vi. a substitution chosen from K34R, K34M, K34T, K34Q, or K34N,
vii. a substitution chosen from E37D, E37N, E37K, E37Q, or E37H,
viii. a substitution chosen from E39D, E39N, E39K, E39Q, or E39H,
ix. a substitution chosen from E42D, E42N, E42K, E42Q, or E42H,
x. a substitution chosen from R44K, R44M, R44T, R44Q, or R44N,
xi. a substitution chosen from F46Y, F46L, F46H, F46I, F46N, F46V, F46D, F46A, or F46Y,
xii. a substitution chosen from S47T, S47A, or S47G,
xiii. a substitution chosen from P80L, P80H, P80R, or P80A,
xiv. a substitution chosen from 182F, 182L, 182V, 182M, 182A, or J82Nle, or
xv. a substitution chosen from D84E, D84N, D84K, D84Q, or D84H.

A6. The isolated polypeptide molecule of A4, wherein the one or more mutations comprise one or more of the following substitutions:

i. a substitution chosen from E25D, E25N, E25K, E25Q, or E25H,
ii. a substitution chosen from L27F, L27I, or L27V,
iii. a substitution chosen from K29R, K29M, or K29T,
iv. a substitution chosen from K32R, K32M, or K32T,
v. a substitution chosen from D33E, D33N, D33K, D33Q, or D33H,
vi. a substitution chosen from K34R, K34M, or K34T,
vii. a substitution chosen from E37D, E37N, E37K, E37Q, or E37H,
viii. a substitution chosen from E39D, E39N, E39K, E39Q, or E39H,
ix. a substitution chosen from E42D, E42N, E42K, E42Q, or E42H,
x. a substitution chosen from R44K, R44M, or R44T,
xi. a substitution chosen from F46Y, F46L, F46H, F46I, F46N, F46V, or F46D,
xii. a substitution chosen from S47T, S47A, or S47G,
xiii. a substitution chosen from P80L, P80H, or P80R,
xiv. a substitution chosen from 182F, 182L, or 182V, or xv. a substitution chosen from D84E, D84N, D84K, D84Q, or D84H.

A7. An isolated polypeptide molecule that specifically binds to CD2, wherein the polypeptide molecule comprises a LFA3 domain, wherein the LFA3 domain comprises the amino acid sequence of: $X_1X_2X_3X_4X_5X_6X_7$, wherein:

(SEQ ID NO: 84)

$X_1$ is S, G, A, M, or T, $X_2$ is R, W, P, or A, $X_3$ is N, Y, S, E, D, Q, H, K, or R $X_4$ is P, G, I, L, V, M, A, F, or Nle, $X_5$ is Y, G, T, or S, $X_6$ is R, E, K, P, D, or N, and $X_7$ is R, D, S, Q, A, E, T, or S, or a functional variant of SEQ ID NO: 84 (e.g., a sequence having at least 75%, 80%, 85%, 90%, 95%, or 99% identity thereof), wherein the LFA3 domain does not comprise the amino acid sequence of SPNITDT (SEQ ID NO: 83).

A8. An isolated polypeptide molecule that specifically binds to CD2, wherein the polypeptide molecule comprises a LFA3 domain, wherein the LFA3 domain comprises the amino acid sequence of: $X_1X_2X_3X_4X_5X_6X_7$, wherein:

(SEQ ID NO: 85)

$X_1$ is S, G, A, or M, $X_2$ is R, W, or P, $X_3$ is N, Y, S, E, or D, $X_4$ is P, G, or I, $X_5$ is Y, G, or T, $X_6$ is R, E, K, P, or D, and $X_7$ is R, D, S, Q, A, E, or T, or a functional variant of SEQ ID NO: 85 (e.g., a sequence having at least 75%, 80%, 85%, 90%, 95%, or 99% identity thereof), wherein the LFA3 domain does not comprise the amino acid sequence of SEQ ID NO: 83.

A9. An isolated polypeptide molecule that specifically binds to CD2, wherein the polypeptide molecule comprises a LFA3 domain, wherein the LFA3 domain comprises the amino acid sequence of: $X_1X_2X_3X_4X_5X_6X_7$, wherein:

(SEQ ID NO: 86)

$X_1$ is S, G, A, or M, $X_2$ is R or W, $X_3$ is N, Y, S, E, or D, $X_4$ is P or G, $X_5$ is Y or G, $X_6$ is R, E, K, or P, and $X_7$ is R, D, S, Q, A, or E, or a functional variant of SEQ ID NO: 86 (e.g., a sequence having at least 75%, 80%, 85%, 90%, 95%, or 99% identity thereof), wherein the LFA3 domain does not comprise the amino acid sequence of SEQ ID NO: 83.

A10. An isolated polypeptide molecule that specifically binds to CD2, wherein the polypeptide molecule comprises a LFA3 domain, wherein the LFA3 domain comprises the amino acid sequence of: $X_1X_2X_3X_4X_5X_6X_7$, wherein:

(SEQ ID NO: 86)

$X_1$ is S, G, A, or M, $X_2$ is R or W, $X_3$ is N, Y, S, E, or D, $X_4$ is P or G, $X_5$ is Y or G, $X_6$ is R, E, K, or P, and $X_7$ is R, D, S, Q, A, or E.

A11. An isolated polypeptide molecule that specifically binds to CD2, wherein the polypeptide molecule comprises a LFA3 domain, wherein the LFA3 domain comprises the amino acid sequence of: $SX_1NX_2X_3X_4X_5$, wherein:

(SEQ ID NO: 87)

$X_1$ is R, W, P, or A, $X_2$ is P, G, I, L, V, M, A, F, or Nle, $X_3$ is Y, G, T, or S, $X_4$ is R, P, D, or N, and $X_5$ is R, D, T, or S, or a functional variant of SEQ ID NO: 87 (e.g., a sequence having at least 75%, 80%, 85%, 90%, 95%, or 99% identity thereof), wherein the LFA3 domain does not comprise the amino acid sequence of SEQ ID NO: 83.

A12. An isolated polypeptide molecule that specifically binds to CD2, wherein the polypeptide molecule comprises a LFA3 domain, wherein the LFA3 domain comprises the amino acid sequence of: $SX_1NX_2X_3X_4X_5$, wherein:

(SEQ ID NO: 88)

$X_1$ is R, W, or P, $X_2$ is P, G, or I, $X_3$ is Y, G, or T, $X_4$ is R, P, or D, and $X_5$ is R, D, or T, or a functional variant of SEQ ID NO: 88 (e.g., a sequence having at least 75%, 80%, 85%, 90%, 95%, or 99% identity thereof), wherein the LFA3 domain does not comprise the amino acid sequence of SEQ ID NO: 83.

A13. An isolated polypeptide molecule that specifically binds to CD2, wherein the polypeptide molecule comprises a LFA3 domain, wherein the LFA3 domain comprises the amino acid sequence of: $SX_1NX_2X_3X_4X_5$, wherein:

(SEQ ID NO: 89)
$X_1$ is R or W, $X_2$ is P or G, $X_3$ is Y or G, $X_4$ is R or P, and $X_5$ is R or D, or a functional variant of SEQ ID NO: 89 (e.g., a sequence having at least 75%, 80%, 85%, 90%, 95%, or 99% identity thereof), wherein the LFA3 domain does not comprise the amino acid sequence of SEQ ID NO: 83.

A14. An isolated polypeptide molecule that specifically binds to CD2, wherein the polypeptide molecule comprises a LFA3 domain, wherein the LFA3 domain comprises the amino acid sequence of: $SX_1NX_2X_3X_4X_5$, wherein:

(SEQ ID NO: 89)
$X_1$ is R or W, $X_2$ is P or G, $X_3$ is Y or G, $X_4$ is R or P, and $X_5$ is R or D.

A15. An isolated polypeptide molecule that specifically binds to CD2, wherein the polypeptide molecule comprises a LFA3 domain, wherein the LFA3 domain comprises the amino acid sequence of: $X_1X_2X_3X_4X_5X_6X_7$, wherein:

(SEQ ID NO: 90)
$X_1$ is S, G, A, M, or T, $X_2$ is R, W, P, or A, $X_3$ is N, Y, S, E, D, Q, H, K, or R $X_4$ is P, G, I, L, V, M, A, F, or Nle, $X_5$ is Y, G, T, or S, $X_6$ is R, E, K, P, D, or N, and $X_7$ is D, S, Q, A, E, T, or S, or a functional variant of SEQ ID NO: 90 (e.g., a sequence having at least 75%, 80%, 85%, 90%, 95%, or 99% identity thereof), wherein the LFA3 domain does not comprise the amino acid sequence of SEQ ID NO: 83.

A16. An isolated polypeptide molecule that specifically binds to CD2, wherein the polypeptide molecule comprises a LFA3 domain, wherein the LFA3 domain comprises the amino acid sequence of: $X_1X_2X_3X_4X_5X_6X_7$, wherein:

(SEQ ID NO: 91)
$X_1$ is S, G, A, or M, $X_2$ is R, W, or P, $X_3$ is N, Y, S, E, or D, $X_4$ is P, G, or I, $X_5$ is Y, G, or T, $X_6$ is R, E, K, P, or D, and $X_7$ is D, S, Q, A, E, or T, or a functional variant of SEQ ID NO: 91 (e.g., a sequence having at least 75%, 80%, 85%, 90%, 95%, or 99% identity thereof), wherein the LFA3 domain does not comprise the amino acid sequence of SEQ ID NO: 83.

A17. An isolated polypeptide molecule that specifically binds to CD2, wherein the polypeptide molecule comprises a LFA3 domain, wherein the LFA3 domain comprises the amino acid sequence of: $X_1X_2X_3X_4X_5X_6X_7$, wherein:

(SEQ ID NO: 92)
$X_1$ is S, G, A, or M, $X_2$ is R or W, $X_3$ is N, Y, S, E, or D, $X_4$ is P or G, $X_5$ is Y or G, $X_6$ is R, E, K, or P, and $X_7$ is D, S, Q, A, or E, or a functional variant of SEQ ID NO: 92 (e.g., a sequence having at least 75%, 80%, 85%, 90%, 95%, or 99% identity thereof), wherein the LFA3 domain does not comprise the amino acid sequence of SEQ ID NO: 83.

A18. An isolated polypeptide molecule that specifically binds to CD2, wherein the polypeptide molecule comprises a LFA3 domain, wherein the LFA3 domain comprises the amino acid sequence of: $X_1X_2X_3X_4X_5X_6X_7$, wherein:

(SEQ ID NO: 92)
$X_1$ is S, G, A, or M, $X_2$ is R or W, $X_3$ is N, Y, S, E, or D, $X_4$ is P or G, $X_5$ is Y or G, $X_6$ is R, E, K, or P, and $X_7$ is D, S, Q, A, or E.

A19. An isolated polypeptide molecule that specifically binds to CD2, wherein the polypeptide molecule comprises a LFA3 domain, wherein the LFA3 domain comprises the amino acid sequence of:

```
                                              (SEQ ID NO: 93)
FSQQIYGVVYGNVTFHVPSNVPLKEVLWKKQKDKVX₁EX₂ENSEX₃RX₄

FSSFKNRVYLDTVSGSLTIYNLTSSDEDEYEX₅EX₆X₇X₈X₉X₁₀X₁₁

X₁₂X₁₃KFFLYVX₁₄,
wherein:

X₁ is V, L, or A,

X₂ is F or L,

X₃ is V, I, L, or F,

X₄ is A, V, or S,

X₅ is M, F, I, or L,

X₆ is S, G, A, or M,

X₇ is R or W,

X₈ is N, Y, S, E, or D,

X₉ is P or G,

X₁₀ is Y or G,

X₁₁ is R, E, K, or P,

X₁₂ is R, D, S, Q, A, or E,

X₁₃ is F, M, I, or L,
and

X₁₄ is absent, L, or LESLPS,
``` or a functional variant of SEQ ID NO: 93 (e.g., a sequence having at least 75%, 80%, 85%, 90%, 95%, or 99% identity thereof), wherein the LFA3 domain does not comprise the amino acid sequence of SEQ ID NO: 3.

A20. An isolated polypeptide molecule that specifically binds to CD2, wherein the polypeptide molecule comprises a LFA3 domain, wherein the LFA3 domain comprises the amino acid sequence of:

```
                                              (SEQ ID NO: 93)
FSQQIYGVVYGNVTFHVPSNVPLKEVLWKKQKDKVX₁EX₂ENSEX₃RX₄

FSSFKNRVYLDTVSGSLTIYNLTSSDEDEYEX₅EX₆X₇X₈X₉X₁₀X₁₁

X₁₂X₁₃KFFLYVX₁₄,
wherein:

X₁ is V, L, or A,

X₂ is F or L,

X₃ is V, I, L, or F,

X₄ is A, V, or S,

X₅ is M, F, I, or L,

X₆ is S, G, A, or M,

X₇ is R or W,

X₈ is N, Y, S, E, or D,

X₉ is P or G,

X₁₀ is Y or G,

X₁₁ is R, E, K, or P,

X₁₂ is R, D, S, Q, A, or E,

X₁₃ is F, M, I, or L,
and

X₁₄ is absent, L, or LESLPS.
```

A21. An isolated polypeptide molecule that specifically binds to CD2, wherein the polypeptide molecule comprises a LFA3 domain, wherein the LFA3 domain comprises the amino acid sequence of:

```
                                              (SEQ ID NO: 94)
FSQQIYGVVYGNVTFHVPSNVPLKEVLWKKQKDKVX₁EX₂ENSEX₃RX₄

FSSFKNRVYLDTVSGSLTIYNLTSSDEDEYEX₅EX₆X₇X₈X₉X₁₀X₁₁

X₁₂X₁₃KFFLYVX₁₄,
wherein:

X₁ is V or A,

X₂ is F or L,

X₃ is V, I, or F,

X₄ is A or V,

X₅ is M or F,

X₆ is S, G, A, or M,

X₇ is R or W,

X₈ is N, Y, S, E, or D,

X₉ is P or G,

X₁₀ is Y or G,

X₁₁ is R, E, K, or P,

X₁₂ is R, D, S, Q, A, or E,

X₁₃ is F or M,
and

X₁₄ is absent, L, or LESLPS,
``` or a functional variant of SEQ ID NO: 94 (e.g., a sequence having at least 75%, 80%, 85%, 90%, 95%, or 99% identity thereof), wherein the LFA3 domain does not comprise the amino acid sequence of SEQ ID NO: 3.

A22. An isolated polypeptide molecule that specifically binds to CD2, wherein the polypeptide molecule comprises a LFA3 domain, wherein the LFA3 domain comprises the amino acid sequence of:

```
                                              (SEQ ID NO: 94)
FSQQIYGVVYGNVTFHVPSNVPLKEVLWKKQKDKVX₁EX₂ENSEX₃RX₄

FSSFKNRVYLDTVSGSLTIYNLTSSDEDEYEX₅EX₆X₇X₈X₉X₁₀X₁₁

X₁₂X₁₃KFFLYVX₁₄,
wherein:

X₁ is V or A,

X₂ is F or L,

X₃ is V. I, or F,

X₄ is A or V,

X₅ is M or F,

X₆ is S, G, A, or M,
```

-continued $X_7$ is R or W, $X_8$ is N, Y, S, E, or D, $X_9$ is P or G, $X_{10}$ is Y or G, $X_{11}$ is R, E, K, or P, $X_{12}$ is R, D, S, Q, A, or E, $X_{13}$ is F or M,
and $X_{14}$ is absent, L, or LESLPS.

A23. An isolated polypeptide molecule that specifically binds to CD2, wherein the polypeptide molecule comprises a LFA3 domain, wherein the LFA3 domain comprises the amino acid sequence of SEQ ID NO: 95, or a functional variant of SEQ ID NO: 95 (e.g., a sequence having at least 75%, 80%, 85%, 90%, 95%, or 99% identity thereof), wherein the LFA3 domain does not comprise the amino acid sequence of SEQ ID NO: 3.

A24. An isolated polypeptide molecule that specifically binds to CD2, wherein the polypeptide molecule comprises a LFA3 domain, wherein the LFA3 domain comprises the amino acid sequence of:

(SEQ ID NO: 96)
FSQQIYGVVYGNVTFHVPSNVPLKEVLWKKQKDKVVEFENSEVRX$_1$FSSF

KNRVYLDTVSGSLTIYNLTSSDEDEYEX$_2$EX$_3$X$_4$X$_5$X$_6$X$_7$X$_8$X$_9$FKFFLY

VX$_{10}$,
wherein:

$X_1$ is A, V, L, or I, $X_2$ is M, F, L, or I, $X_3$ is S, G, A, M, or T, $X_4$ is R, W, P, or A, $X_5$ is N, Y, S, E, D, Q, H, K, or R, $X_6$ is P, G, I, L, V, M, A, F, or Nle, $X_7$ is Y, G, T, or S, $X_8$ is R, E, K, P, D, or N, $X_9$ is R, D, S, Q, A, E, T, or S $X_{10}$ is absent, L, or LESLPS, or a functional variant of SEQ ID NO: 96 (e.g., a sequence having at least 75%, 80%, 85%, 90%, 95%, or 99% identity thereof), wherein the LFA3 domain does not comprise the amino acid sequence of SEQ ID NO: 3.

A25. An isolated polypeptide molecule that specifically binds to CD2, wherein the polypeptide molecule comprises a LFA3 domain, wherein the LFA3 domain comprises the amino acid sequence of:

(SEQ ID NO: 97)
FSQQIYGVVYGNVTFHVPSNVPLKEVLWKKQKDKVVEFENSEVRX$_1$

FSSFKNRVYLDTVSGSLTIYNLTSSDEDEYEX$_2$EX$_3$X$_4$X$_5$X$_6$X$_7$X$_8$X$_9$

FKFFLYVX$_{10}$, wherein:
$X_1$ is A or V,
$X_2$ is M or F,
$X_3$ is S, G, A, or M,
$X_4$ is R, W, or P,
$X_5$ is N, Y, S, E, or D,
$X_6$ is P, G, or I,
$X_7$ is Y, G, or T,
$X_8$ is R, E, K, P, or D,
$X_9$ is R, D, S, Q, A, E, or T,
and
$X_{10}$ is absent, L, or LESLPS, or a functional variant of SEQ ID NO: 97 (e.g., a sequence having at least 75%, 80%, 85%, 90%, 95%, or 99% identity thereof), wherein the LFA3 domain does not comprise the amino acid sequence of SEQ ID NO: 3.

A26. An isolated polypeptide molecule that specifically binds to CD2, wherein the polypeptide molecule comprises a LFA3 domain, wherein the LFA3 domain comprises the amino acid sequence of:

(SEQ ID NO: 98)
FSQQIYGVVYGNVTFHVPSNVPLKEVLWKKQKDKVVEFENSEVRX$_1$

FSSFKNRVYLDTVSGSLTIYNLTSSDEDEYEX$_2$EX$_3$X$_4$X$_5$X$_6$X$_7$X$_8$X$_9$

FKFFLYVX$_{10}$,
wherein:
$X_1$ is A or V,
$X_2$ is M or F,
$X_3$ is S, G, A, or M,
$X_4$ is R or W,
$X_5$ is N, Y, S, E, or D,
$X_6$ is P or G,
$X_7$ is Y or G,
$X_8$ is R, E, K, or P,
$X_9$ is R, D, S, Q, A, or E,
and
$X_{10}$ is absent, L, or LESLPS, or a functional variant of SEQ ID NO: 98 (e.g., a sequence having at least 75%, 80%, 85%, 90%, 95%, or 99% identity thereof), wherein the LFA3 domain does not comprise the amino acid sequence of SEQ ID NO: 3.

A27. An isolated polypeptide molecule that specifically binds to CD2, wherein the polypeptide molecule comprises a LFA3 domain, wherein the LFA3 domain comprises the amino acid sequence of:

(SEQ ID NO: 98)
FSQQIYGVVYGNVTFHVPSNVPLKEVLWKKQKDKVVEFENSEVRX$_1$

FSSFKNRVYLDTVSGSLTIYNLTSSDEDEYEX$_2$EX$_3$X$_4$X$_5$X$_6$X$_7$X$_8$X$_9$

FKFFLYVX$_{10}$,
wherein:
$X_1$ is A or V,
$X_2$ is M or F,
$X_3$ is S, G, A, or M,
$X_4$ is R or W,
$X_5$ is N, Y, S, E, or D,
$X_6$ is P or G,
$X_7$ is Y or G,
$X_8$ is R, E, K, or P,
$X_9$ is R, D, S, Q, A, or E,
and
$X_{10}$ is absent, L, or LESLPS.

A28. An isolated polypeptide molecule that specifically binds to CD2, wherein the polypeptide molecule comprises a LFA3 domain, wherein the LFA3 domain comprises the amino acid sequence of:

(SEQ ID NO: 99)
FSQQIYGVVYGNVTFHVPSNVPLKEVLWKKQKDKVVEFENSEVR

AFSSFKNRVYLDTVSGSLTIYNLTSSDEDEYEMESX$_1$NX$_2$X$_3$X$_4$

X$_5$FKFFLYVX$_6$,
wherein:
X$_1$ is any amino acid,
X$_2$ is any amino acid,
X$_3$ is any amino acid,
X$_4$ is any amino acid,
X$_5$ is any amino acid,
and
X$_6$ is absent, L, or LESLPS, or a functional variant of SEQ ID NO: 99 (e.g., a sequence having at least 75%, 80%, 85%, 90%, 95%, or 99% identity thereof), wherein the LFA3 domain does not comprise the amino acid sequence of SEQ ID NO: 3.

A29. An isolated polypeptide molecule that specifically binds to CD2, wherein the polypeptide molecule comprises a LFA3 domain, wherein the LFA3 domain comprises the amino acid sequence of:

(SEQ ID NO: 100)
FSQQIYGVVYGNVTFHVPSNVPLKEVLWKKQKDKVVEFENSE

VRAFSSFKNRVYLDTVSGSLTIYNLTSSDEDEYEMESX$_1$

NX$_2$X$_3$X$_4$X$_5$FKFFLYVX$_6$,
wherein:
X$_1$ is R, W, P, or A,
X$_2$ is P, G, I, L, V, M, A, F, or Nle,
X$_3$ is Y, G, T, or S,
X$_4$ is R, P, D, or N,
X$_5$ is R, D, T, or S,
and
X$_6$ is absent, L, or LESLPS, or a functional variant of SEQ ID NO: 100 (e.g., a sequence having at least 75%, 80%, 85%, 90%, 95%, or 99% identity thereof), wherein the LFA3 domain does not comprise the amino acid sequence of SEQ ID NO: 3.

A30. An isolated polypeptide molecule that specifically binds to CD2, wherein the polypeptide molecule comprises a LFA3 domain, wherein the LFA3 domain comprises the amino acid sequence of:

(SEQ ID NO: 101)
FSQQIYGVVYGNVTFHVPSNVPLKEVLWKKQKDKVVEFEN

SEVRAFSSFKNRVYLDTVSGSLTIYNLTSSDEDEYEM

ESX$_1$NX$_2$X$_3$X$_4$X$_5$FKFFLYVX$_6$,
wherein:
X$_1$ is R, W, or P,
X$_2$ is P, G, or I,
X$_3$ is Y, G, or T,
X$_4$ is R, P, or D,
X$_5$ is R, D, or T,
and
X$_6$ is absent, L, or LESLPS, or a functional variant of SEQ ID NO: 101 (e.g., a sequence having at least 75%, 80%, 85%, 90%, 95%, or 99% identity thereof), wherein the LFA3 domain does not comprise the amino acid sequence of SEQ ID NO: 3.

A31. An isolated polypeptide molecule that specifically binds to CD2, wherein the polypeptide molecule comprises a LFA3 domain, wherein the LFA3 domain comprises the amino acid sequence of:

(SEQ ID NO: 102)
FSQQIYGVVYGNVTFHVPSNVPLKEVLWKKQKDKVVEFENSEV

RAFSSFKNRVYLDTVSGSLTIYNLTSSDEDEYEMES

X$_1$NX$_2$X$_3$X$_4$X$_5$FKFFLYVX$_6$,
wherein:
X$_1$ is R or W,
X$_2$ is P or G,
X$_3$ is Y or G,
X$_4$ is R or P,
X$_5$ is R or D,
and
X$_6$ is absent, L, or LESLPS, or a functional variant of SEQ ID NO: 102 (e.g., a sequence having at least 75%, 80%, 85%, 90%, 95%, or 99% identity thereof), wherein the LFA3 domain does not comprise the amino acid sequence of SEQ ID NO: 3.

A32. An isolated polypeptide molecule that specifically binds to CD2, wherein the polypeptide molecule comprises a LFA3 domain, wherein the LFA3 domain comprises the amino acid sequence of:

(SEQ ID NO: 102)
FSQQIYGVVYGNVTFHVPSNVPLKEVLWKKQKDKVVEFENSE

VRAFSSFKNRVYLDTVSGSLTIYNLTSSDEDEYEMES

X$_1$NX$_2$X$_3$X$_4$X$_5$FKFFLYVX$_6$,
wherein:
X$_1$ is R or W,
X$_2$ is P or G,
X$_3$ is Y or G,
X$_4$ is R or P,
X$_5$ is R or D,
and
X$_6$ is absent, L, or LESLPS.

A33. An isolated polypeptide molecule that specifically binds to CD2, wherein the polypeptide molecule comprises a LFA3 domain, wherein the LFA3 domain comprises the amino acid sequence of:

(SEQ ID NO: 103)
FSQQIYGVVYGNVTFHVPSNVPLKEVLWKKQKDKVVEFENSEV

RX$_1$FSSFKNRVYLDTVSGSLTIYNLTSSDEDEYE

X$_2$EX$_3$X$_4$X$_5$X$_6$X$_7$X$_8$X$_9$FKFFLYVX$_{10}$,
wherein:
X$_1$ is A, V, L, or I,
X$_2$ is M, F, L, or I,
X$_3$ iS S, G, A, M, or T,
X$_4$ is R, W, P, or A,
X$_5$ is N, Y, S, E, D, Q, H, K, or R,
X$_6$ is P, G, I, L, V, M, A, F, or Nle,
X$_7$ is Y, G, T, or S,
X$_8$ is R, E, K, P, D, or N,
X$_9$ is D, S, Q, A, E, T, or S,
and
X$_{10}$ is absent, L, or LESLPS, or a functional variant of SEQ ID NO: 103 (e.g., a sequence having at least 75%, 80%, 85%, 90%, 95%, or 99% identity thereof), wherein the LFA3 domain does not comprise the amino acid sequence of SEQ ID NO: 3.

A34. An isolated polypeptide molecule that specifically binds to CD2, wherein the polypeptide molecule comprises a LFA3 domain, wherein the LFA3 domain comprises the amino acid sequence of:

```
                                              (SEQ ID NO: 104)
FSQQIYGVVYGNVTFHVPSNVPLKEVLWKKQKDKVVEFENSE

VRX₁FSSFKNRVYLDTVSGSLTIYNLTSSDEDEYE

X₂EX₃X₄X₅X₆X₇X₈X₉FKFFLYVX₁₀,
wherein:
X₁ is A or V,
X₂ is M or F,
X₃ is S, G, A, or M,
X₄ is R, W, or P,
X₅ is N, Y, S, E, or D,
X₆ is P, G, or I,
X₇ is Y, G, or T,
X₈ is R, E, K, P, or D,
X₉ is D, S, Q, A, E, or T,
and
X₁₀ is absent, L, or LESLPS,
``` or a functional variant of SEQ ID NO: 104 (e.g., a sequence having at least 75%, 80%, 85%, 90%, 95%, or 99% identity thereof), wherein the LFA3 domain does not comprise the amino acid sequence of SEQ ID NO: 3.

A35. An isolated polypeptide molecule that specifically binds to CD2, wherein the polypeptide molecule comprises a LFA3 domain, wherein the LFA3 domain comprises the amino acid sequence of:

```
                                              (SEQ ID NO: 105)
FSQQIYGVVYGNVTFHVPSNVPLKEVLWKKQKDKVVEFEN

SEVRX₁FSSFKNRVYLDTVSGSLTIYNLTSSDEDEYE

X₂EX₃X₄X₅X₆X₇X₈X₉FKFFLYVX₁₀,
wherein:
X₁ is A or V,
X₂ is M or F,
X₃ is S, G, A, or M,
X₄ is R or W,
X₅ is N, Y, S, E, or D,
X₆ is P or G,
X₇ is Y or G,
X₈ is R, E, K, or P,
X₉ is D, S, Q, A, or E,
and
X₁₀ is absent, L, or LESLPS,
``` or a functional variant of SEQ ID NO: 104 (e.g., a sequence having at least 75%, 80%, 85%, 90%, 95%, or 99% identity thereof), wherein the LFA3 domain does not comprise the amino acid sequence of SEQ ID NO: 3.

A36. An isolated polypeptide molecule that specifically binds to CD2, wherein the polypeptide molecule comprises a LFA3 domain, wherein the LFA3 domain comprises the amino acid sequence of:

```
                                              (SEQ ID NO: 105)
FSQQIYGVVYGNVTFHVPSNVPLKEVLWKKQKDKVVEFEN

SEVRX₁FSSFKNRVYLDTVSGSLTIYNLTSSDED

EYEX₂EX₃X₄X₅X₆X₇X₈X₉FKFFLYVX₁₀,
wherein:
X₁ is A or V,
X₂ is M or F,
X₃ is S, G, A, or M,
X₄ is R or W,
X₅ is N, Y, S, E, or D,
X₆ is P or G,
X₇ is Y or G,
X₈ is R, E, K, or P,
X₉ is D, S, Q, A, or E,
and
X₁₀ is absent, L, or LESLPS.
```

A37. An isolated polypeptide molecule that specifically binds to CD2, wherein the polypeptide molecule comprises a LFA3 domain, wherein the LFA3 domain comprises an amino acid sequence chosen from SEQ ID NOs: 106-117, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A38. An isolated polypeptide molecule that specifically binds to CD2, wherein the polypeptide molecule comprises a LFA3 domain, wherein the LFA3 domain comprises the amino acid sequence of SEQ ID NO: 106, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A39. An isolated polypeptide molecule that specifically binds to CD2, wherein the polypeptide molecule comprises a LFA3 domain, wherein the LFA3 domain comprises the amino acid sequence of SEQ ID NO: 106.

A40. An isolated polypeptide molecule that specifically binds to CD2, wherein the polypeptide molecule comprises a LFA3 domain, wherein the LFA3 domain comprises the amino acid sequence of SEQ ID NO: 107, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A41. An isolated polypeptide molecule that specifically binds to CD2, wherein the polypeptide molecule comprises a LFA3 domain, wherein the LFA3 domain comprises the amino acid sequence of SEQ ID NO: 107.

A42. An isolated polypeptide molecule that specifically binds to CD2, wherein the polypeptide molecule comprises a LFA3 domain, wherein the LFA3 domain comprises the amino acid sequence of SEQ ID NO: 108, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A43. An isolated polypeptide molecule that specifically binds to CD2, wherein the polypeptide molecule comprises a LFA3 domain, wherein the LFA3 domain comprises the amino acid sequence of SEQ ID NO: 108.

A44. An isolated polypeptide molecule that specifically binds to CD2, wherein the polypeptide molecule comprises a LFA3 domain, wherein the LFA3 domain comprises the amino acid sequence of SEQ ID NO: 109, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A45. An isolated polypeptide molecule that specifically binds to CD2, wherein the polypeptide molecule comprises a LFA3 domain, wherein the LFA3 domain comprises the amino acid sequence of SEQ ID NO: 109.

A46. An isolated polypeptide molecule that specifically binds to CD2, wherein the polypeptide molecule comprises a LFA3 domain, wherein the LFA3 domain comprises the amino acid sequence of SEQ ID NO: 110, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A47. An isolated polypeptide molecule that specifically binds to CD2, wherein the polypeptide molecule comprises a LFA3 domain, wherein the LFA3 domain comprises the amino acid sequence of SEQ ID NO: 110.

A48. An isolated polypeptide molecule that specifically binds to CD2, wherein the polypeptide molecule comprises a LFA3 domain, wherein the LFA3 domain comprises the amino acid sequence of SEQ ID NO: 111, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A49. An isolated polypeptide molecule that specifically binds to CD2, wherein the polypeptide molecule comprises a LFA3 domain, wherein the LFA3 domain comprises the amino acid sequence of SEQ ID NO: 111.

A50. An isolated polypeptide molecule that specifically binds to CD2, wherein the polypeptide molecule comprises a LFA3 domain, wherein the LFA3 domain comprises the amino acid sequence of SEQ ID NO: 112, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A51. An isolated polypeptide molecule that specifically binds to CD2, wherein the polypeptide molecule comprises a LFA3 domain, wherein the LFA3 domain comprises the amino acid sequence of SEQ ID NO: 112.

A52. An isolated polypeptide molecule that specifically binds to CD2, wherein the polypeptide molecule comprises a LFA3 domain, wherein the LFA3 domain comprises the amino acid sequence of SEQ ID NO: 113, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A53. An isolated polypeptide molecule that specifically binds to CD2, wherein the polypeptide molecule comprises a LFA3 domain, wherein the LFA3 domain comprises the amino acid sequence of SEQ ID NO: 113.

A54. An isolated polypeptide molecule that specifically binds to CD2, wherein the polypeptide molecule comprises a LFA3 domain, wherein the LFA3 domain comprises the amino acid sequence of SEQ ID NO: 114, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A55. An isolated polypeptide molecule that specifically binds to CD2, wherein the polypeptide molecule comprises a LFA3 domain, wherein the LFA3 domain comprises the amino acid sequence of SEQ ID NO: 114.

A56. An isolated polypeptide molecule that specifically binds to CD2, wherein the polypeptide molecule comprises a LFA3 domain, wherein the LFA3 domain comprises the amino acid sequence of SEQ ID NO: 115, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A57. An isolated polypeptide molecule that specifically binds to CD2, wherein the polypeptide molecule comprises a LFA3 domain, wherein the LFA3 domain comprises the amino acid sequence of SEQ ID NO: 115.

A58. An isolated polypeptide molecule that specifically binds to CD2, wherein the polypeptide molecule comprises a LFA3 domain, wherein the LFA3 domain comprises the amino acid sequence of SEQ ID NO: 116, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A59. An isolated polypeptide molecule that specifically binds to CD2, wherein the polypeptide molecule comprises a LFA3 domain, wherein the LFA3 domain comprises the amino acid sequence of SEQ ID NO: 116.

A60. An isolated polypeptide molecule that specifically binds to CD2, wherein the polypeptide molecule comprises a LFA3 domain, wherein the LFA3 domain comprises the amino acid sequence of SEQ ID NO: 117, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A61. An isolated polypeptide molecule that specifically binds to CD2, wherein the polypeptide molecule comprises a LFA3 domain, wherein the LFA3 domain comprises the amino acid sequence of SEQ ID NO: 117.

A62. An isolated polypeptide molecule that specifically binds to CD2, wherein the polypeptide molecule comprises a LFA3 domain, wherein the LFA3 domain comprises an amino acid sequence chosen from SEQ ID NOs: 30-41, or a functional variant thereof (e.g., a sequence having at least 75%, 80%, 85%, 90%, 95%, or 99% identity thereof), wherein the LFA3 domain does not comprise the amino acid sequence of SEQ ID NO: 3.

A63. An isolated polypeptide molecule that specifically binds to CD2, wherein the polypeptide molecule comprises a LFA3 domain, wherein the LFA3 domain comprises the amino acid sequence of SEQ ID NO: 30, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A64. An isolated polypeptide molecule that specifically binds to CD2, wherein the polypeptide molecule comprises a LFA3 domain, wherein the LFA3 domain comprises the amino acid sequence of SEQ ID NO: 30.

A65. An isolated polypeptide molecule that specifically binds to CD2, wherein the polypeptide molecule comprises a LFA3 domain, wherein the LFA3 domain comprises the amino acid sequence of SEQ ID NO: 31, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A66. An isolated polypeptide molecule that specifically binds to CD2, wherein the polypeptide molecule comprises a LFA3 domain, wherein the LFA3 domain comprises the amino acid sequence of SEQ ID NO: 31.

A67. An isolated polypeptide molecule that specifically binds to CD2, wherein the polypeptide molecule comprises a LFA3 domain, wherein the LFA3 domain comprises the amino acid sequence of SEQ ID NO: 32, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A68. An isolated polypeptide molecule that specifically binds to CD2, wherein the polypeptide molecule comprises a LFA3 domain, wherein the LFA3 domain comprises the amino acid sequence of SEQ ID NO: 32.

A69. An isolated polypeptide molecule that specifically binds to CD2, wherein the polypeptide molecule comprises a LFA3 domain, wherein the LFA3 domain comprises the amino acid sequence of SEQ ID NO: 33, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A70. An isolated polypeptide molecule that specifically binds to CD2, wherein the polypeptide molecule comprises a LFA3 domain, wherein the LFA3 domain comprises the amino acid sequence of SEQ ID NO: 33.

A71. An isolated polypeptide molecule that specifically binds to CD2, wherein the polypeptide molecule comprises a LFA3 domain, wherein the LFA3 domain comprises the amino acid sequence of SEQ ID NO: 34, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A72. An isolated polypeptide molecule that specifically binds to CD2, wherein the polypeptide molecule comprises a LFA3 domain, wherein the LFA3 domain comprises the amino acid sequence of SEQ ID NO: 34.

A73. An isolated polypeptide molecule that specifically binds to CD2, wherein the polypeptide molecule comprises a LFA3 domain, wherein the LFA3 domain comprises the amino acid sequence of SEQ ID NO: 35, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A74. An isolated polypeptide molecule that specifically binds to CD2, wherein the polypeptide molecule comprises a LFA3 domain, wherein the LFA3 domain comprises the amino acid sequence of SEQ ID NO: 35.

A75. An isolated polypeptide molecule that specifically binds to CD2, wherein the polypeptide molecule comprises a LFA3 domain, wherein the LFA3 domain comprises the amino acid sequence of SEQ ID NO: 36, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A76. An isolated polypeptide molecule that specifically binds to CD2, wherein the polypeptide molecule comprises a LFA3 domain, wherein the LFA3 domain comprises the amino acid sequence of SEQ ID NO: 36.

A77. An isolated polypeptide molecule that specifically binds to CD2, wherein the polypeptide molecule comprises a LFA3 domain, wherein the LFA3 domain comprises the amino acid sequence of SEQ ID NO: 37, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A78. An isolated polypeptide molecule that specifically binds to CD2, wherein the polypeptide molecule comprises a LFA3 domain, wherein the LFA3 domain comprises the amino acid sequence of SEQ ID NO: 37.

A79. An isolated polypeptide molecule that specifically binds to CD2, wherein the polypeptide molecule comprises a LFA3 domain, wherein the LFA3 domain comprises the amino acid sequence of SEQ ID NO: 38, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A80. An isolated polypeptide molecule that specifically binds to CD2, wherein the polypeptide molecule comprises a LFA3 domain, wherein the LFA3 domain comprises the amino acid sequence of SEQ ID NO: 38.

A81. An isolated polypeptide molecule that specifically binds to CD2, wherein the polypeptide molecule comprises a LFA3 domain, wherein the LFA3 domain comprises the amino acid sequence of SEQ ID NO: 39, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A82. An isolated polypeptide molecule that specifically binds to CD2, wherein the polypeptide molecule comprises a LFA3 domain, wherein the LFA3 domain comprises the amino acid sequence of SEQ ID NO: 39.

A83. An isolated polypeptide molecule that specifically binds to CD2, wherein the polypeptide molecule comprises a LFA3 domain, wherein the LFA3 domain comprises the amino acid sequence of SEQ ID NO: 40, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A84. An isolated polypeptide molecule that specifically binds to CD2, wherein the polypeptide molecule comprises a LFA3 domain, wherein the LFA3 domain comprises the amino acid sequence of SEQ ID NO: 40.

A85. An isolated polypeptide molecule that specifically binds to CD2, wherein the polypeptide molecule comprises a LFA3 domain, wherein the LFA3 domain comprises the amino acid sequence of SEQ ID NO: 41, or a functional variant thereof (e.g., a sequence having at least 75%, 80%, 85%, 90%, 95%, or 99% identity thereof), wherein the LFA3 domain does not comprise the amino acid sequence of SEQ ID NO: 83.

A86. An isolated polypeptide molecule that specifically binds to CD2, wherein the polypeptide molecule comprises a LFA3 domain, wherein the LFA3 domain comprises the amino acid sequence of SEQ ID NO: 41.

A87. An isolated polypeptide molecule that specifically binds to CD2, wherein the polypeptide molecule comprises a LFA3 domain, wherein the LFA3 domain comprises one or more mutations (e.g., a substitution, a deletion, or an addition) at residues 79, 80, 81, 82, 83, 84, or 85 relative to SEQ ID NO: 3, numbered according to SEQ ID NO: 3, e.g., wherein the LFA3 domain comprises SEQ ID NO: 3 with one or more mutations (e.g., a substitution, a deletion, or an addition) at residues 79, 80, 81, 82, 83, 84, or 85 relative to SEQ ID NO: 3, numbered according to SEQ ID NO: 3.

In some embodiments, the LFA3 polypeptide molecules of the invention comprise a LFA3 domain, wherein the LFA3 domain is any LFA3 variant sequence disclosed herein (e.g., any LFA3 variant sequence disclosed in Table 2). In some embodiments, the LFA3 domain is no more than 100, 110, 120, 130, 140, 150, 160, 170, or 180 amino acids in length. In some embodiments, the LFA3 domain is 92 amino acids in length. In some embodiments, the LFA3 domain is 93 amino acids in length. In some embodiments, the LFA3 domain is 98 amino acids in length. In some embodiments, the LFA3 domain is derived from the first extracellular domain of LFA3. In some embodiments, the LFA3 domain comprises no more than 6, 10, 15, 20, or 30 amino acid mutations (e.g. substitutions, additions, or deletions) relative to the wild type LFA3 sequence. In some embodiments, the LFA3 domain comprises 5 amino acid substitutions relative to the wild type LFA3 sequence.

The LFA3 polypeptide molecules of the invention may be made by any method known in the art. General techniques for production of recombinant proteins are known in the art and/or are described herein.

Following initial identification, the activity of a candidate LFA3 polypeptide molecule can be further confirmed and refined by bioassays, known to test the targeted biological activities. In some embodiments, an in vitro cell assay is used to further characterize a candidate LFA3 polypeptide molecule. For example, bioassays can be used to screen candidates directly. Some of the methods for identifying and characterizing LFA3 polypeptide molecules are described in detail in the Examples.

In certain embodiments, the LFA3 polypeptide molecule described herein comprises an Fc domain. The Fc domain can be derived from IgA (e.g., IgA1 or IgA2), IgG, IgE, or IgG (e.g., IgG1, IgG2, IgG3, or IgG4). In some embodiments, the Fc domain is an IgG1 Fc domain. In some embodiments, an IgG1 Fc domain comprises the amino acid sequence of SEQ ID NO:16.

In one aspect, the invention disclose a LFA3 polypeptide molecule (e.g., a variant LFA3 fusion polypeptide molecule) having one or more of the following properties: (a) enhanced monomeric expression relative to a wild type LFA3 sequence, (b) reduced multimeric expression relative to a wild type LFA3 sequence, (c) reduced aggregation propensity under thermal stress relative to a wild type LFA3 sequence, (d) reduced aggregation propensity under low pH relative to a wild type LFA3 sequence, (e) enhanced freeze-thaw stability relative to a wild type LFA3 sequence, (f) increased yield relative to a wild type LFA3 sequence, (g) increased melting temperature (Tm) relative to a wild type LFA3 sequence.

In some embodiments, the LFA3 polypeptide molecule (e.g., a variant LFA3 fusion polypeptide molecule) of the invention shows a percentage of monomers that is more than about 70, 75, 80, 85, 90, 95, 98 or 99%, e.g., as measured using size exclusion chromatography (SEC) and/or methods described in Example 1 with respect to FIG. 3A. In some embodiments, the LFA3 polypeptide molecule (e.g., a variant LFA3 fusion polypeptide molecule) of the invention shows a percentage of monomers that is more than about 75, 80, 85, 90, 95, 98 or 99%, a percentage of low molecular weight species (LMWS) that is less than about 10, 8, 6, 4, or 2%, and/or a percentage of high molecular weight species (HMWS) that is less than about 5, 2, or 1%, e.g., as measured using SEC and/or methods described in Example 1 with respect to FIG. 6C.

Figure 3B:
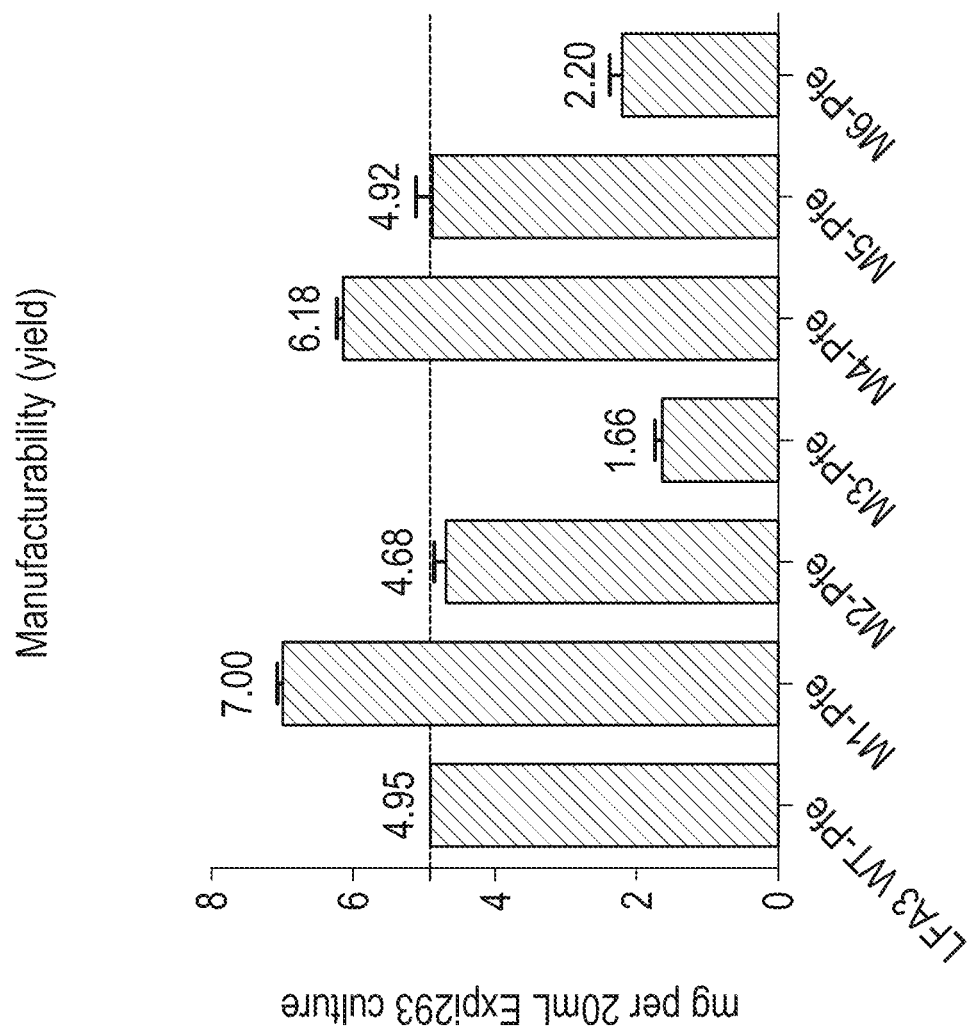
Figure 3C:
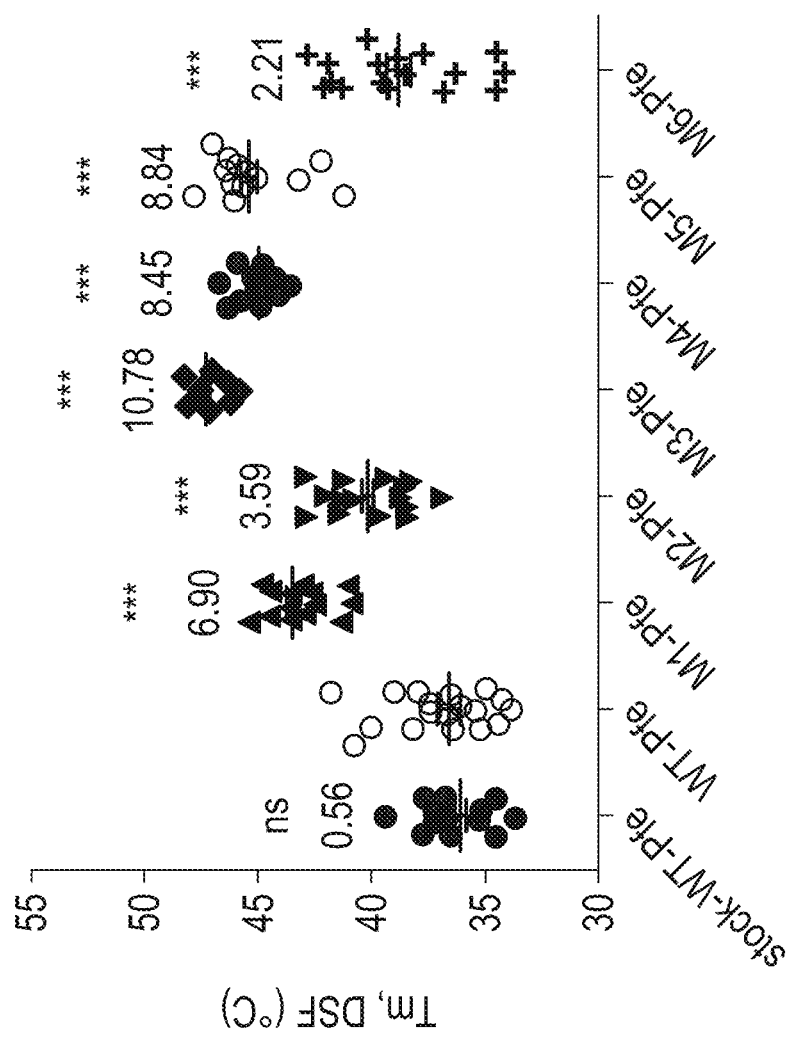
Figure 3D:
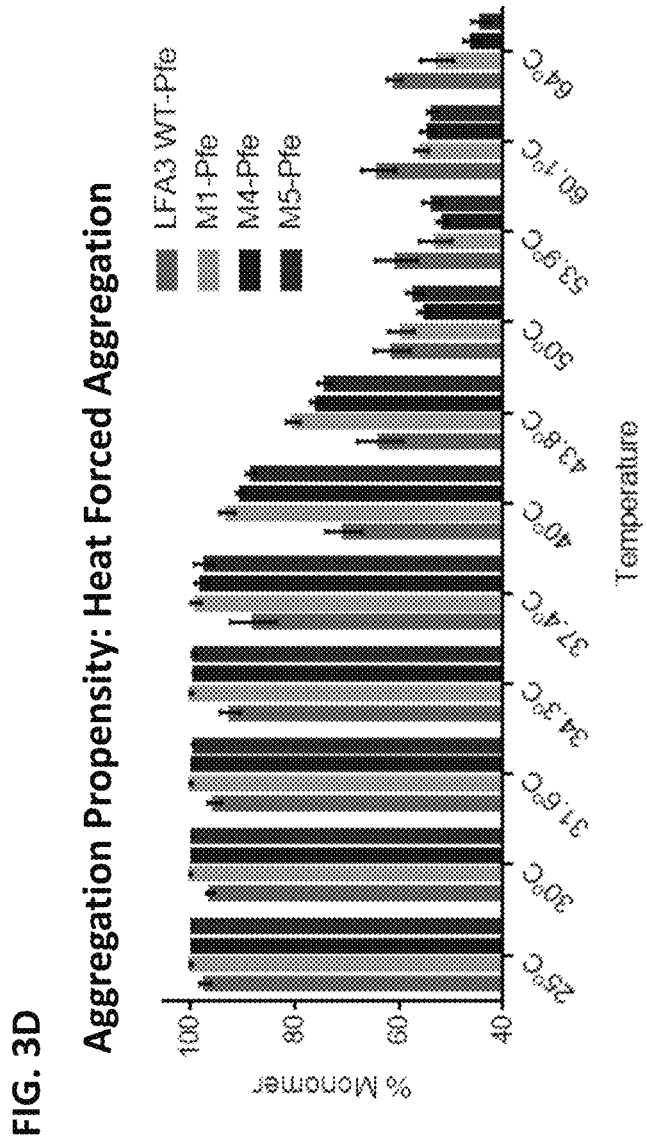

In some embodiments, the LFA3 polypeptide molecule (e.g., a variant LFA3 fusion polypeptide molecule) of the invention shows a percentage of monomers that is more than about 90, 92, or 95% after incubating at 37.4° C. for 24 hours, and/or showing a percentage of monomers that is more than about 75, 80, or 85% after incubating at 40° C. for 24 hours, e.g., as measured using SEC and/or methods described in Example 1 with respect to FIG. 3D. In some embodiments, the LFA3 polypeptide molecule (e.g., a variant LFA3 fusion polypeptide molecule) of the invention shows no more than about 5, 10, 15, or 20% increase in HMWS at 40° C., and/or no more than about 5, 10, 15, 20, or 25% increase in HMWS at 50° C., e.g., as measured using SEC and/or methods described in Example 1 with respect to Table 4.

In some embodiments, the LFA3 polypeptide molecule (e.g., a variant LFA3 fusion polypeptide molecule) of the invention shows no more than about 6, 7, 8, or 9% increase in HMWS at low pH for 5 hours, e.g., as measured using SEC and/or methods described in Example 1 with respect to Table 4.

In some embodiments, the LFA3 polypeptide molecule (e.g., a variant LFA3 fusion polypeptide molecule) of the invention shows no more than about 0.5, 1, or 1.5% increase in HMWS after 5 cycles of freeze-thaw, e.g., as measured using SEC and/or methods described in Example 1 with respect to Table 4.

Figure 30C:
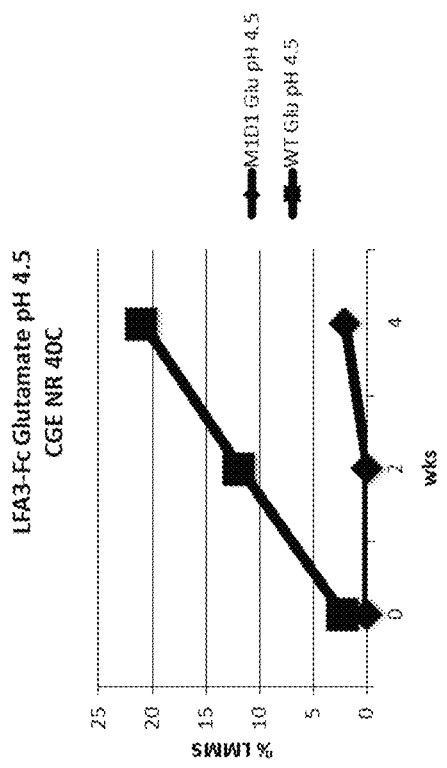
FIGS. 30A-30C: Exemplary non-reduced (NR) capillary gel electrophoresis (CGE) analysis of LFA3-Fc M1d1 and LFA3-Fc WT formulated in Tris buffer pH 7.5 (FIG. 30A), histidine buffer pH 5.8 (FIG. 30B) or glutamate buffer pH 4.5 (FIG. 30C) at time 0 and following storage at 40° C. for 2 or 4 weeks. The percentage of low molecular mass species (LMMS) was quantified.
Figure 30A:
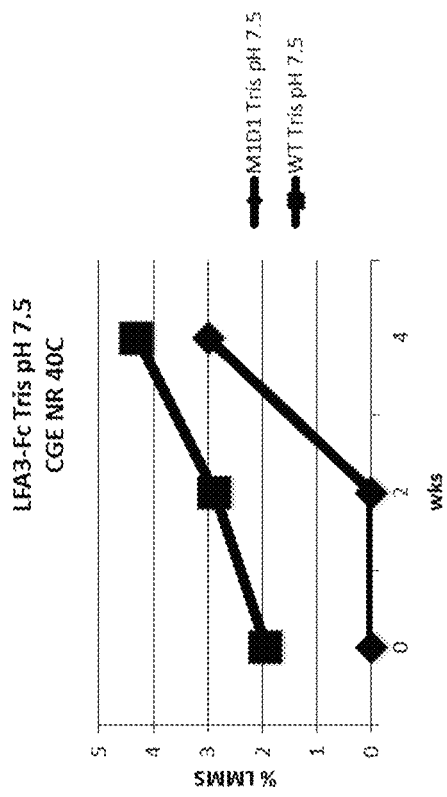
Figure 30B:
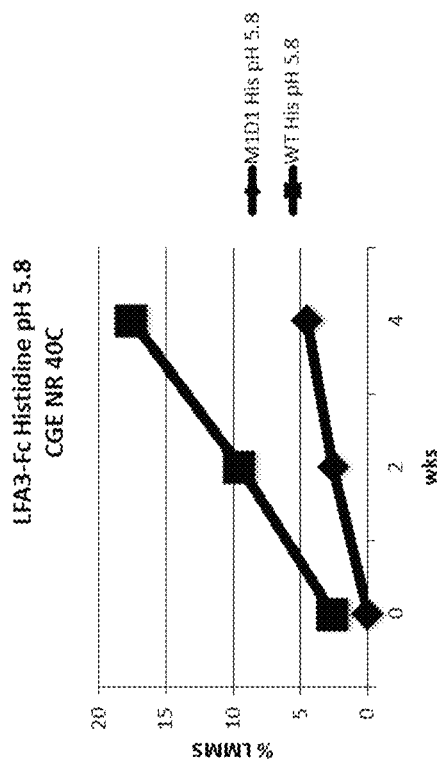

In some embodiments, the LFA3 polypeptide molecule (e.g., a variant LFA3 fusion polypeptide molecule of the invention shows no more than a about 0.5, 1, 1.5, or 2% increase in HMMS and/or about 0.5, 1, 2, 3, 4 or 5% increase in LMMS after 2 or 4 weeks of storage at 40° C., e.g., as measured using capillary gel electrophoresis (CGE), size exclusion high performance liquid chromatography (SE_HPLC), and/or methods described in Example 3 with respect to FIGS. 30A-30C and/or FIGS. 31A-31D.

In some embodiments, the LFA3 polypeptide molecule (e.g., a variant LFA3 fusion polypeptide molecule of the invention shows no more than a about 0.5, 1, 1.5, or 2% increase in HMMS and/or about 0.5, 1, or 1.5% increase in LMMS after 2, 4 or 6 weeks of storage at 25° C., e.g., as measured using SE-HPLC methods described in Example 3 with respect to FIGS. 32A-32D.

In some embodiments, the LFA3 polypeptide molecule (e.g., a variant LFA3 fusion polypeptide molecule of the invention shows no more than about 0.5, 1, or 1.5% increase in HMMS and/or about 0.5, 1, or 1.5% increase in LMMS after 2, 4 or 6 weeks of storage at 5° C., e.g., as measured using SE-HPLC methods described in Example 3 with respect to FIGS. 33A-33D.

In some embodiments, the LFA3 polypeptide molecule (e.g., a variant LFA3 fusion polypeptide molecule) of the invention has a yield that is more than about 5.5, 6, 6.5, or 7 mg per 20 mL Expi293 culture, e.g., as measured using methods described in Example 1 with respect to FIG. 3B.

In some embodiments, the LFA3 polypeptide molecule (e.g., a variant LFA3 fusion polypeptide molecule) of the invention has a Tm that is more than about 38, 40, 42, or 45° C., e.g., as measured by differential scanning fluorometry (DSF) and/or using methods described in Example 1 with respect to FIG. 3C. In some embodiments, the LFA3 polypeptide molecule (e.g., a variant LFA3 fusion polypeptide molecule) of the invention has a Tm that is more than about 40, 45, 50, 55, or 60° C., e.g., as measured by DSF and/or using methods described in Example 1 with respect to FIG. 5B. In some embodiments, the LFA3 polypeptide molecule (e.g., a variant LFA3 fusion polypeptide molecule) of the invention has a Tm that is more than about 40, 45, or 50° C., e.g., as measured by DSF and/or using methods described in Example 1 with respect to FIG. 6D. In some embodiments, the LFA3 polypeptide molecule (e.g., a variant LFA3 fusion polypeptide molecule) of the invention has a Tm that is more than about 45, 50, or 55° C., e.g., as measured by DSF and/or using methods described in Example 1 with respect to FIG. 7D. In some embodiments, the LFA3 polypeptide molecule (e.g., a variant LFA3 fusion polypeptide molecule) of the invention has a Tm that is more than about 50 or 60° C., e.g., as measured by differential scanning calorimetry (DSC) and/or using methods described in Example 1 with respect to Table 4.

In some embodiments, the LFA3 polypeptide molecule (e.g., a variant LFA3 fusion polypeptide molecule) of the invention has a Tm1 that is more than about 55, 58, 60, 62, 64 or 66° C. and a Tm2 that is more than about 75, 78, 80, or 82° C. at pH 7.5; a Tm1 that is more than about 55, 58, 60, 62 or 64° C. and a Tm2 that is more than about 75, 78, 80 or 82° C. at pH 5.8; or a Tm1 that is more than 55, 58 or 60° C. and a Tm2 that is more than about 75, 78, or 80° C. at pH 4.5, e.g., as measured by DSC and/or using methods described in Example 4 with respect to Table 13.

In some embodiments, the LFA3 polypeptide molecule (e.g., a variant LFA3 fusion polypeptide molecule) of the invention has an increased Tm relative to a polypeptide molecule comprising the amino acid sequence of SEQ ID NO: 4, e.g., having a Tm that is more than about 50 or 60° C. at pH 7.5 or pH 4.5; having a Tm that is more than about 50 or 62° C. at pH 5.8, e.g., as measured by DSC and/or using methods described in Example 4 with respect to Table 14, In some embodiments, the LFA3 domain of the LFA3 polypeptide molecule (e.g., a variant LFA3 fusion polypeptide molecule) of the invention has an increased Tm relative to a polypeptide molecule comprising the amino acid sequence of SEQ ID NO: 4, e.g., having a Tm that is more than about 50 or 60° C., e.g., as measured by DSC and FabRICATOR® IdeS and/or using methods described in Example 4 with respect to Table 15.

The invention disclose a LFA3 polypeptide molecule (e.g., a variant LFA3 fusion polypeptide molecule) that binds to CD2 and mediates at least one detectable activity selected from the following: (a) binds to CD2+ cells, e.g., CD2-expressing CD4 $T_{mem}$ cells or CD2-expressing CD8 $T_{mem}$ cells, (b) reduces the interaction between CD2 and a naturally occurring LFA3, (c) mediates cytotoxicity against CD2-expressing cells, e.g., CD2-expressing CD4 $T_{mem}$ cells or CD2-expressing CD8 $T_{mem}$ cells, e.g., in the presence of NK cells, (d) decreases CD4+ and/or CD8+ $T_{EM}$ cells, (e) increases the Treg/$T_{EM}$ ratio, e.g., in CD4+ and/or CD8+ T cells, (f) increases the Treg/$T_{CM}$ ratio, e.g., in CD4+ and/or CD8+ T cells, (g) inhibits allogeneic T cell response, e.g., T cell proliferation and cytokine production, and (h) inhibits tetanus toxoid recall response. $T_{mem}$ cells include, for example, central memory ($T_{CM}$) and effector memory ($T_{EM}$) T cells.

In one aspect, the invention includes a LFA3 polypeptide molecule (e.g., a variant LFA3 fusion polypeptide molecule) that binds to cells expressing human or cynomolgus monkey CD2 with high apparent affinity but does not bind cells expressing rodent CD2. Apparent affinity binding can be assessed using flow cytometry to detect binding to cells expressing the target protein (e.g., CD2). The cells can be transiently or stably transfected with a nucleic acid encoding CD2. Alternatively, the cells can be cells that naturally express CD2 on their surface. Regardless of the sources of CD2+ cells, the binding of the LFA3 polypeptide molecule to the cells can be readily assessed using a variety of art-recognized methods. The LFA3 polypeptide molecule binds human or cyno CD2, but does not detectably bind, or bind to a much lesser extent, rodent CD2.

In one aspect, the LFA3 polypeptide molecule (e.g., a variant LFA3 fusion polypeptide molecule) of the invention binds to recombinant human CD2 with an affinity that is less than 1.3, 1.2, 1.1, or 1 µM, e.g., as measured by SPR described in the Examples. In some embodiments, the LFA3 polypeptide molecule (e.g., a variant LFA3 fusion polypeptide molecule) of the invention binds to recombinant human CD2 with an affinity of about 1.08 µM.

In one aspect, the LFA3 polypeptide molecule (e.g., a variant LFA3 fusion polypeptide molecule) of the invention binds to recombinant cynomolgus CD2 with an affinity that is less than 1.4, 1.3, 1.2, 1.1, or 1 µM, e.g., as measured by SPR described in the Examples. In some embodiments, the LFA3 polypeptide molecule (e.g., a variant LFA3 fusion polypeptide molecule) of the invention binds to recombinant cynomolgus CD2 with an affinity of about 1.06 µM.

In one aspect, disclosed herein is a LFA3 polypeptide molecule (e.g., a variant LFA3 fusion polypeptide molecule) that binds to CD2-expressing cells, e.g., CD4 $T_{mem}$ cells, with a $K_d$ that is no more than 100, 200, 300, or 400 pM. In some embodiments, the LFA3 polypeptide molecule (e.g., a variant LFA3 fusion polypeptide molecule) binds to CD2-expressing cells, e.g., CD4 $T_{mem}$ cells, with a $K_d$ of about 94 pM.

In one aspect, the LFA3 polypeptide molecule (e.g., a variant LFA3 fusion polypeptide molecule) of the invention binds to CD4 memory T cells with a calculated IC50 that is no more than about 300, 400, 500, 500, 700, 800, 1000, 1200 or 1500 pM. In some embodiments, the LFA3 polypeptide molecule (e.g., a variant LFA3 fusion polypeptide molecule) of the invention binds to CD4 memory T cells with a calculated IC50 of about 1.18E-10 M. In some embodiments, the LFA3 polypeptide molecule (e.g., a variant LFA3 fusion polypeptide molecule) of the invention binds to CD4 memory T cells with an average calculated IC50 of about 307 pM.

In one aspect, the LFA3 polypeptide molecule (e.g., a variant LFA3 fusion polypeptide molecule) of the invention binds to CD4+ $T_{EM}$ cells with a calculated IC50 that is no more than about 150, 300, 400, 500, 600, 700, 800, 1000 or 1200 pM. In some embodiments, the LFA3 polypeptide molecule (e.g., a variant LFA3 fusion polypeptide molecule) of the invention binds to CD4+ $T_{EM}$ cells with a calculated IC50 of about 150 pM.

In one aspect, the LFA3 polypeptide molecule (e.g., a variant LFA3 fusion polypeptide molecule) of the invention binds to CD4+ $T_{CM}$ cells with a calculated IC50 that is no more than about 100, 200, 300, 400, 500, 600, 700 or 800 pM. In some embodiments, the LFA3 polypeptide molecule (e.g., a variant LFA3 fusion polypeptide molecule) of the invention binds to CD4+ $T_{CM}$ cells with a calculated IC50 of about 110 pM.

In one aspect, the LFA3 polypeptide molecule (e.g., a variant LFA3 fusion polypeptide molecule) of the invention binds to CD4 naïve T cells with a calculated IC50 that is no more than about 200, 300, 400, 500, 600, 700, 800, 1000 or 1200 pM. In some embodiments, the LFA3 polypeptide molecule (e.g., a variant LFA3 fusion polypeptide molecule) of the invention binds to CD4 naïve T cells with a calculated IC50 of about 1.44E-10M. In some embodiments, the LFA3 polypeptide molecule (e.g., a variant LFA3 fusion polypeptide molecule) of the invention binds to CD4 naïve T cells with an average calculated IC50 of about 180 pM.

In one aspect, the LFA3 polypeptide molecule (e.g., a variant LFA3 fusion polypeptide molecule) of the invention binds to expanded CD4 Treg cells with a calculated IC50 that is no more than about 100, 200, 300, 400 or 500 pM. In some embodiments, the LFA3 polypeptide molecule (e.g., a variant LFA3 fusion polypeptide molecule) of the invention binds to expanded CD4 Treg cells with a calculated IC50 of about 8.54E-11M. In some embodiments, the LFA3 polypeptide molecule (e.g., a variant LFA3 fusion polypeptide molecule) of the invention binds to expanded CD4 Treg cells with a calculated IC50 of about 90 pM.

In one aspect, the LFA3 polypeptide molecule (e.g., a variant LFA3 fusion polypeptide molecule) of the invention binds to CD8 memory T cells with a calculated IC50 that is no more than about 100, 200, 300, 400, 500 or 600 pM. In some embodiments, the LFA3 polypeptide molecule (e.g., a variant LFA3 fusion polypeptide molecule) of the invention binds to CD8 memory T cells with a calculated IC50 of about 120 pM.

In one aspect, the LFA3 polypeptide molecule (e.g., a variant LFA3 fusion polypeptide molecule) of the invention binds to CD8 native T cells with a calculated IC50 that is no more than about 300, 400, 500, 600, 700, 800, 1000, 1200, 1500, 1600 or 1700 pM. In some embodiments, the LFA3 polypeptide molecule (e.g., a variant LFA3 fusion polypeptide molecule) of the invention binds to CD8 native T cells with a calculated IC50 of about 9.49E-11M. In some embodiments, the LFA3 polypeptide molecule (e.g., a variant LFA3 fusion polypeptide molecule) of the invention binds to CD8 native T cells with an average calculated IC50 of about 300 pM.

In one aspect, the LFA3 polypeptide molecule (e.g., a variant LFA3 fusion polypeptide molecule) of the invention binds to CD4 memory T cells with a calculated $K_d$ that is no more than about 100, 200, 300, 400, or 500 pM. In some embodiments, the LFA3 polypeptide molecule (e.g., a variant LFA3 fusion polypeptide molecule) of the invention binds to CD4 memory T cells with a calculated $K_d$ of about 67 pM. In some embodiments, the LFA3 polypeptide molecule (e.g., a variant LFA3 fusion polypeptide molecule) of the invention binds to CD4 memory T cells with an average calculated $K_d$ of about 94 pM.

In one aspect, the LFA3 polypeptide molecule (e.g., a variant LFA3 fusion polypeptide molecule) of the invention binds to CD4+ $T_{EM}$ cells with a calculated $K_d$ that is no more than about 100, 200, 300, 400, 500, or 600 pM. In some embodiments, the LFA3 polypeptide molecule (e.g., a variant LFA3 fusion polypeptide molecule) of the invention binds to CD4+ $T_{EM}$ cells with a calculated $K_d$ of about 79 pM.

In one aspect, the LFA3 polypeptide molecule (e.g., a variant LFA3 fusion polypeptide molecule) of the invention binds to CD4+ $T_{CM}$ cells with a calculated $K_d$ that is no more than about 100, 200, 300, 400, or 500 pM. In some embodiments, the LFA3 polypeptide molecule (e.g., a variant LFA3 fusion polypeptide molecule) of the invention binds to CD4+ $T_{CM}$ cells with a calculated $K_d$ of about 64 pM.

In one aspect, the LFA3 polypeptide molecule (e.g., a variant LFA3 fusion polypeptide molecule) of the invention binds to CD4 naïve T cells with a calculated $K_d$ that is no more than about 100, 200, 300, or 400 pM. In some embodiments, the LFA3 polypeptide molecule (e.g., a variant LFA3 fusion polypeptide molecule) of the invention binds to CD4 naïve T cells with a calculated $K_d$ of about 61 pM. In some embodiments, the LFA3 polypeptide molecule (e.g., a variant LFA3 fusion polypeptide molecule) of the invention binds to CD4 naïve T cells with an average calculated $K_d$ of about 54 pM.

In one aspect, the LFA3 polypeptide molecule (e.g., a variant LFA3 fusion polypeptide molecule) of the invention binds to expanded CD4 Treg cells with a calculated $K_d$ that is no more than about 100, 200, or 300 pM. In some embodiments, the LFA3 polypeptide molecule (e.g., a variant LFA3 fusion polypeptide molecule) of the invention binds to expanded CD4 Treg cells with a calculated $K_d$ of about 58 pM.

In one aspect, the LFA3 polypeptide molecule (e.g., a variant LFA3 fusion polypeptide molecule) of the invention binds to CD8 memory T cells with a calculated $K_d$ that is no more than about 50, 100, or 150 pM. In some embodiments, the LFA3 polypeptide molecule (e.g., a variant LFA3 fusion polypeptide molecule) of the invention binds to CD8 memory T cells with a calculated $K_d$ of about 31 pM.

In one aspect, the LFA3 polypeptide molecule (e.g., a variant LFA3 fusion polypeptide molecule) of the invention binds to CD8 native T cells with a calculated $K_d$ that is no more than about 50, 100, 200, 300, 400, or 500 pM. In some embodiments, the LFA3 polypeptide molecule (e.g., a variant LFA3 fusion polypeptide molecule) of the invention binds to CD8 native T cells with a calculated $K_d$ of about 30 pM. In some embodiments, the LFA3 polypeptide molecule (e.g., a variant LFA3 fusion polypeptide molecule) of the invention binds to CD8 native T cells with a calculated $K_d$ of about 98 pM.

In one aspect, the invention provides a LFA3 polypeptide molecule (e.g., a variant LFA3 fusion polypeptide molecule) that mediates cytotoxicity against CD2-expressing cells, e.g., CD4 $T_{mem}$ cells, with an EC50 that is no more than about 400, 600, 800, 1000, 1200, 1400, or 1500 pM. In some embodiments, the LFA3 polypeptide molecule (e.g., a variant LFA3 fusion polypeptide molecule) of this invention mediates cytotoxicity against CD2-expressing cells, e.g., CD4 $T_{mem}$ cells, with an EC50 of about 348 pM.

In one aspect, the invention provides a LFA3 polypeptide molecule (e.g., a variant LFA3 fusion polypeptide molecule) that mediates cytotoxicity against CD2-expressing cells, e.g., CD8 $T_{mem}$ cells, with an EC50 that is no more than about 1, 5, 10, 20, 30, 40 or 50 nM. In some embodiments, the LFA3 polypeptide molecule (e.g., a variant LFA3 fusion polypeptide molecule) of this invention mediates cytotoxicity against CD2-expressing cells, e.g., CD8 $T_{mem}$ cells, with an EC50 of about 0.716 nM.

In one aspect, the invention provides a LFA3 polypeptide molecule (e.g., a variant LFA3 fusion polypeptide molecule) that mediates cytotoxicity against CD2-expressing cells, e.g., CD4 $T_{non-mem}$ cells, with an EC50 that is no more than about 1200, 1500, 1800, 2000, 2500, 3000, 3500, 4000 pM. In some embodiments, the LFA3 polypeptide molecule (e.g., a variant LFA3 fusion polypeptide molecule) of this invention mediates cytotoxicity against CD2-expressing cells, e.g., CD4 $T_{non-mem}$ cells, with an EC50 of about 1256 pM.

In one aspect, the invention provides a LFA3 polypeptide molecule (e.g., a variant LFA3 fusion polypeptide molecule) that mediates cytotoxicity against CD2-expressing cells, e.g., CD8 $T_{non-mem}$ cells, with an EC50 that is no more than about 1, 5, 10, 20, 30, 40 or 50 nM. In some embodiments, the LFA3 polypeptide molecule (e.g., a variant LFA3 fusion polypeptide molecule) of this invention mediates cytotoxicity against CD2-expressing cells, e.g., CD8 $T_{non-mem}$ cells, with an EC50 of about 0.787 nM.

The invention includes a LFA3 polypeptide molecule (e.g., a variant LFA3 fusion polypeptide molecule) that binds to CD2 and suppresses an immune response, e.g., a T cell-mediated immune response. There are many assays known in the art to determine the inhibition of an immune response, e.g., a T cell-mediated immune response. One such assay is mixed lymphocyte reaction (MLR) assay described in the Examples. In some embodiments, the LFA3 polypeptide molecule (e.g., a variant LFA3 fusion polypeptide molecule) of this invention can inhibit the allogenic response with an IC50 that is no more than about 400, 800, 1200, 1600, 2000, or 2400 pM. In some embodiments, the LFA3 polypeptide molecule (e.g., a variant LFA3 fusion polypeptide molecule) of this invention can inhibit the allogenic response with an IC50 of about 302 pM. Another assay is tetanus toxoid recall response assay described in the Examples. In some embodiments, the LFA3 polypeptide molecule (e.g., a variant LFA3 fusion polypeptide molecule) of this invention can inhibit IFNγ production of CD4 memory T cells in a tetanus toxoid recall response assay with an IC50 that is no more than about 5, 10, 15, 20, or 25 nM. In some embodiments, the LFA3 polypeptide molecule (e.g., a variant LFA3 fusion polypeptide molecule) of this invention can inhibit IFNγ production of CD4 memory T cells in a tetanus toxoid recall response assay with an IC50 of about 1.342 nM.

In one aspect, the invention provides a LFA3 polypeptide molecule (e.g., a variant LFA3 fusion polypeptide molecule) that shows a clearance from central that is no more than 0.14, 0.16, 0.18, 0.2, or 0.22 mL/hr/kg, e.g., as measured using methods described in Example 2 with respect to Table 11. In some embodiments, the LFA3 polypeptide molecule (e.g., a variant LFA3 fusion polypeptide molecule) shows a clearance from central that is about 0.11 mL/hr/kg.

In one aspect, the invention provides a LFA3 polypeptide molecule (e.g., a variant LFA3 fusion polypeptide molecule) that shows enhanced purity relative to a polypeptide molecule comprising the amino acid sequence of SEQ ID NO: 4, e.g., a purity of at least about 98% or 99% as measured using capillary gel electrophoresis. In some embodiments, the LFA3 polypeptide molecule (e.g., a variant LFA3 fusion polypeptide molecule) is about 99% pure.

In one aspect, the invention provides a LFA3 polypeptide molecule (e.g., a variant LFA3 fusion polypeptide molecule) that shows reduced sialic acid modification relative to a polypeptide molecule comprising the amino acid sequence of SEQ ID NO: 4, e.g., a purity of not more than about 20, 18, 16, 14, 12, 10, 9, 8 or 7 nmol sialic acid/nmol polypeptide as measured using capillary gel electrophoresis. In some embodiments, the LFA3 polypeptide molecule (e.g., a variant LFA3 fusion polypeptide molecule) is comprises about 14 nmol sialic acid/nmol polypeptide. In some embodiments, the LFA3 polypeptide molecule (e.g., a variant LFA3 fusion polypeptide molecule) is comprises about 9 nmol sialic acid/nmol polypeptide.

The invention encompasses a LFA3 polypeptide molecule (e.g., a variant LFA3 fusion polypeptide molecule) that exhibits at least 1, 2, 3, 4, 5, 6, 7, 8, 9, 10, or more, e.g., all, of the above discussed biological activities.

III. LFA3 Polypeptide Molecule Expression and Production

Nucleic Acids Encoding LFA3 Polypeptide Molecules

The invention also provides polynucleotides encoding any of the polypeptide molecules described herein. The invention also provides a method of making any of the polynucleotides described herein. Polynucleotides can be made and expressed by procedures known in the art.

The sequence of a desired polypeptide molecule, and nucleic acid encoding such polypeptide molecule, or portion thereof, can be determined using standard sequencing techniques. A nucleic acid sequence encoding a desired polypeptide molecule may be inserted into various vectors (such as cloning and expression vectors) for recombinant production and characterization.

In one aspect, the invention provides polynucleotides encoding any of the following polypeptides disclosed herein: human LFA3 isoform 1, human LFA3 isoform 1 domain 1, LFA3-Fc WT, LFA3-Pfe WT, human IgG2 Fc, M1, M2, M3, M4, M5, M6, M7, d1, d3, M1d1, M1d3, M4d1, M7d1, CM1d1, CM2d1, CM3d1, CM4d1, CM5d1, CM6d1, ML1d1, ML2d1, ML3d1, ML4d1, ML5d1, ML6d1 and LFA3-Fc M1d1. In some embodiments, a polynucleotide encoding an amino acid sequence above, encodes an amino acid sequence at least 91%, 92%, 93%, 94%, 95%, 96%, 97%, 98%, or 99%, and more preferably identical to, the amino acid sequence of a polypeptide molecule disclosed herein.

The invention provides polynucleotides encoding one or more proteins comprising an amino acid sequence selected from the group consisting of SEQ ID NOs: 15-41, 69, 120 and 128. In some embodiments, a polynucleotide encoding an amino acid sequence encodes an amino acid sequence at least 91%, 92%, 93%, 94%, 95%, 96%, 97%, 98%, or 99%, and more preferably identical to, the amino acid sequence of SEQ ID NO: 26 or SEQ ID Nos: 16 and 69.

The invention provides polynucleotides comprising a nucleic acid sequence selected from the group consisting of SEQ ID NOs: 42-68 and 122-127. The invention provides a polynucleotide comprising the nucleic acid sequence as set forth in SEQ ID NO: 44. The invention provides a polynucleotide comprising the nucleic acid sequence as set forth in SEQ ID NO: 53. The invention provides a polynucleotide comprising the nucleic acid sequence as set forth in SEQ ID NO: 122. The invention provides a polynucleotide comprising the nucleic acid sequence as set forth in SEQ ID NO: 123. The invention provides a polynucleotide comprising the nucleic acid sequence as set forth in SEQ ID NO: 43. The invention provides a polynucleotide comprising the nucleic acid sequence as set forth in SEQ ID NOs: 43 and 53.

The invention provides cells comprising one or more nucleic acid molecules selected from the group consisting of SEQ ID NOs: 42-68 and 122-127. The invention provides cells comprising a polynucleotide comprising the nucleic acid sequence as set forth in SEQ ID NO: 44. The invention provides cells comprising a polynucleotide comprising the nucleic acid sequence as set forth in SEQ ID NO: 53. The invention provides cells comprising a polynucleotide comprising the nucleic acid sequence as set forth in SEQ ID NO: 122. The invention provides cells comprising a polynucleotide comprising the nucleic acid sequence as set forth in SEQ ID NO: 123. The invention provides cells comprising a polynucleotide comprising the nucleic acid sequence as set forth in SEQ ID NO: 43. The invention provides cells comprising a polynucleotide comprising the nucleic acid sequence as set forth in SEQ ID NOs: 43 and 53.

In another aspect, the invention provides polynucleotides and variants thereof encoding LFA3 polypeptide molecules, wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific nucleic acid sequences disclosed herein. In some embodiments, the invention provides polynucleotides and variants thereof, encoding LFA3 polypeptide molecules, wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to SEQ ID NO: 123 or SEQ ID NOs: 43 and 53. These amounts are not meant to be limiting, and increments between the recited percentages are specifically envisioned as part of the disclosure.

The invention provides polypeptides encoded by the nucleic acid molecules described herein.

Polynucleotides complementary to any such sequences are also encompassed by the present disclosure. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present disclosure, and a polynucleotide may, but need not, be linked to other molecules and/or support materials.

Polynucleotides may comprise a native sequence (i.e., an endogenous sequence that encodes a polypeptide molecule) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. In some embodiments, variants exhibit at least about 70% identity, in some embodiments, at least about 80% identity, in some embodiments, at least about 90% identity, and in some embodiments, at least about 95% identity to a polynucleotide sequence that encodes a native polypeptide molecule. These amounts are not meant to be limiting and increments between the recited percentages are specifically envisioned as part of the disclosure.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, WI), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J., 1990, Unified Approach to Alignment and Phylogenes pp. 626-645 Methods in Enzymology vol. 183, Academic Press, Inc., San Diego, CA; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, CA; Wilbur, W. J. and Lipman, D. J., 1983, Proc. Natl. Acad. Sci. USA 80:726-730.

In some embodiments, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native polypeptide molecule.

Suitable "moderately stringent conditions" include pre-washing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present disclosure. Further, alleles of the genes comprising the polynucleotide sequences provided herein are within the scope of the present disclosure. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this disclosure can be obtained using chemical synthesis, recombinant methods, or PCR. Methods of chemical polynucleotide synthesis are well-known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well-known within the art. See, e.g., Sambrook et al., 1989.

Alternatively, PCR allows reproduction of DNA sequences. PCR technology is well-known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well-known to those of skill in the art, as set forth in Sambrook et al., 1989, for example.

In some embodiments, a first vector comprises a polynucleotide that encodes an LFA3 polypeptide, for example M1d1, and a second vector comprises a polynucleotide that encodes a heavy chain Fc region from, for example IgG1. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the LFA3 polypeptide, for example M1d1, and the vector encoding the heavy chain Fc domain from, for example IgG1, is used. In some embodiments, a mass ratio of 1:2 for the vector encoding the LFA3 polypeptide, for example M1d1, and the vector encoding the heavy chain Fc from, for example IgG1 is used.

Vectors

In some embodiments, a vector is selected that is optimized for expression of polypeptides in CHO or CHO-derived cells, or in NSO cells. Exemplary such vectors are described, e.g., in Running Deer et al, Biotechnol. Prog. 20:880-889 (2004).

Suitable cloning and expression vectors can include a variety of components, such as promoter, enhancer, and other transcriptional regulatory sequences. The vector may also be constructed to allow for subsequent cloning of an antibody variable domain into different vectors. Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratgene, and Invitrogen. Expression vectors are further provided. Expression vectors generally are replicable polynucleotide constructs that contain a polynucleotide according to the disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest and/or the polynucleotides themselves, can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Host Cells

The LFA3 polypeptide molecule may be made recombinantly using a suitable host cell. A nucleic acid encoding the LFA3 polypeptide molecule can be cloned into an expression vector, which can then be introduced into a host cell, such as E. coli cell, a yeast cell, an insect cell, a simian COS cell, a Chinese hamster ovary (CHO) cell, or a myeloma cell where the cell does not otherwise produce an immunoglobulin protein, to obtain the synthesis of the LFA3 polypeptide molecule in the recombinant host cell. Preferred host cells include a CHO cell, a Human embryonic kidney HEK-293 cell, or an Sp2.0 cell, among many cells well-known in the art. Methods of chemical synthesis for proteins and peptides are known in the art and are commercially available.

In various embodiments, the LFA3 polypeptide molecule may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E and Expi293 cells; CHO cells, including CHO-S, DG44. Lec13 CHO cells, ExpiCHO and FUT8 CHO cells; PER.C6® cells (Crucell); and NSO cells. In some embodiments, the LFA3 polypeptide molecule may be expressed in yeast. See, e.g., U.S. Publication No. US 2006/0270045 A1. In some embodiments, a particular eukaryotic host cell is selected based on its ability to make desired post-translational modifications to the LFA3 polypeptide molecule. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., Molecular Cloning, A Laboratory Manual, 3rd ed. Cold Spring Harbor Laboratory Press (2001). Nucleic acids may be transiently or stably transfected in the desired host cells, according to any suitable method.

LFA3 polypeptide molecules may be purified by any suitable method. Such methods include, but are not limited to, the use of affinity matrices or hydrophobic interaction chromatography, e.g., a Protein A, Protein G, or Protein A/G. Hydrophobic interactive chromatography, for example, a butyl or phenyl column, may also suitable for purifying some polypeptides. Many methods of purifying polypeptides are known in the art.

In some embodiments, the LFA3 polypeptide molecule is produced in a cell-free system. Non-limiting exemplary cell-free systems are described, e.g., in Sitaraman et al., Methods Mol. Biol. 498: 229-44 (2009); Spirin, Trends Biotechnol. 22: 538-45 (2004); Endo et al, Biotechnol. Adv. 21: 695-713 (2003).

IV. Uses and Medical Therapies

In some aspects, the invention provides for therapeutic methods using a LFA3 polypeptide molecule, wherein the therapeutic methods comprise administering a therapeutically effective amount of a pharmaceutical composition comprising the LFA3 polypeptide molecule.

The applicable diseases, disorders or conditions include, but are not limited to, type 1 diabetes, psoriasis, plaque psoriasis, palmoplantaris pustulosis, pustular psoriasis of palms and soles, pustulosis palmaris et plantaris, pustulosis of palms and soles, atopic dermatitis, lichen planus, graft-versus-host disease (GVHD), vitiligo, *Pityriasis rubra pilaris*, transplantation (e.g., organ transplantation, e.g., kidney transplantation), psoriatic arthritis, a disease, disorder, or condition requiring allogeneic hematopoietic stem cell transplantation, thalassemia, sickle cell disease, glanzmann thrombasthenia, Wiskott-Aldrich syndrome, chronic-granulomatous disease, severe congenital neutropenia, leukocyte adhesion deficiency, Schwachman-Diamond syndrome, Diamond-Blackfan anemia, Fanconi anemia, Dyskeratosis-congenita, Chediak-Higashi syndrome, aplastic anemia, alopecia areata, and T cell lymphoma (e.g., cutaneous T-cell lymphoma or peripheral T-cell non-Hodgkin's lymphoma).

Additional diseases, disorders or conditions include, but are not limited to, diabetes mellitus (e. g. Type I diabetes mellitus or insulin dependent diabetes mellitus); juvenile onset diabetes; inflammatory responses such as inflammatory skin diseases including psoriasis and dermatitis (e. g. atopic dermatitis); dermatomyositis; systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; gastritis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); multiple sclerosis; Reynaud's syndrome; autoimmune thyroiditis; allergic encephalomyelitis; Sjogren's syndrome; and immune responses associated with acute and delayed hypersensitivity mediated by cytokines and T-lymphocytes typically found in tuberculosis, sarcoidosis, polymyositis, granulomatosis and vasculitis; Wegener's disease; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; vitiligo; Reiter's disease; stiff-person syndrome; Bechet disease; giant cell arteritis; immune complex nephritis; IgA nephropathy; IgM polyneuropathies; immune thrombocytopenic purpura (ITP) or autoimmune thrombocytopenia and autoimmune hemolytic diseases; Hashimoto's thyroiditis; autoimmune hepatitis; autoimmune hemophilia; autoimmune lymphoproliferative syndrome (ALPS); autoimmune uveoretinitis; Guillain-Barre syndrome; Goodpasture's syndrome; mixed connective tissue disease; autoimmune-associated infertility; polyarteritis nodosa; alopecia areata; idiopathic myxedema; graft versus host disease; muscular dystrophy (Duchenne, Becker, Myotonic, Limb-girdle, Facioscapulohumeral, Congenital, Oculopharyngeal, Distal, Emery-Dreifuss); and an inflammatory non-immune disease, such as a heart disease or a brain disease.

The LFA3 polypeptide molecules of the present invention may also be used to detect and/or measure CD2, or CD2-expressing cells in a sample, e.g., for diagnostic purposes. For example, a LFA3 polypeptide molecule may be used to diagnose a condition or disease characterized by aberrant expression (e.g., over-expression, under-expression, lack of expression, etc.) of CD2. Exemplary diagnostic assays for CD2 may comprise, e.g., contacting a sample, obtained from a patient, with a LFA3 polypeptide molecule of the invention, wherein the LFA3 polypeptide molecule is labeled with a detectable label or reporter molecule.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, HEPES (4-(2-hydroxyethyl)-1-piperazineethanesulfonic acid) buffered saline, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, PA, 1990; and Remington, The Science and Practice of Pharmacy, 20th Ed., Mack Publishing, 2000).

V. Compositions

The disclosure also provides pharmaceutical compositions comprising an effective amount of a LFA3 polypeptide molecule described herein. Examples of such compositions, as well as how to formulate, are also described herein. In some embodiments, the composition comprises one or more LFA3 polypeptide molecules.

The composition used in the present disclosure can further comprise pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, HEPES and other organic acids. In some embodiments, compositions comprising LFA3 polypeptides provided herein, for example LFA3-Fc M1d1, include HEPES-buffered saline. In some embodiments, a concentration of a HEPES buffer is about 10 mM, about 20 mM, about 30 mM, about 40 mM, about 50 mM, about 60 mM, about 70 mM, about 80 mM, about 90 mM, about 100 mM. In some embodiments, a concentration of HEPES buffer is 20 mM. Additional acceptable carriers, excipients or stabilizers include antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutically acceptable excipients are further described herein.

The LFA3 polypeptide molecules and compositions thereof can also be used in conjunction with other agents that serve to enhance and/or complement the effectiveness of the agents.

The disclosure also provides compositions, including pharmaceutical compositions, comprising any of the polynucleotides of the disclosure. In some embodiments, the composition comprises an expression vector comprising a polynucleotide encoding the LFA3 polypeptide molecule as described herein. In other embodiments, the composition comprises an expression vector comprising a polynucleotide encoding any of the LFA3 polypeptide molecules described herein.

Pharmaceutical compositions of the disclosure also can be administered in combination therapy, such as, combined with other agents. For example, the combination therapy can include the LFA3 polypeptide molecule of the present disclosure combined with at least one other therapy, wherein the therapy may be surgery, immunotherapy, or drug therapy.

The pharmaceutical compounds of the disclosure may include one or more pharmaceutically acceptable salts. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be suitable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

A pharmaceutical composition of the present disclosure may be prepared, packaged, or sold in a formulation suitable for ophthalmic administration. Such formulations may, for example, be in the form of eye drops including, for example, a 0.1%-1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the disclosure are known in the art and described, for example in Remington's Pharmaceutical Sciences, Genaro, ed., Mack Publishing Co., Easton, PA (1985), which is incorporated herein by reference.

In some embodiments, the LFA3 polypeptide molecule of this invention can be formulated for subcutaneous injection. In some embodiments, the LFA3 polypeptide molecule of this invention can be formulated for intramuscular injection.

In some embodiments, the LFA3 polypeptide, for example LFA3-Fc M1d1, is formulated at a concentration of about 0.01-2.0 mg/mL. In some embodiments, the LFA3 polypeptide, for example LFA3-Fc M1d1, is formulation at a concentration of about 0.01, about 0.02, about 0.05, about 0.1, about 0.2, about 0.3, about 0.4, about 0.5, about 0.6, about 0.7, about 0.8, about 0.9, about 1.0, about 1.2, about 1.5, about 1.8 or about 2.0 mg/mL. In some embodiments, the LFA3 polypeptide, for example LFA3-Fc M1d1, is formulated at a concentration of about 0.015 mg/mL. In some embodiments, the LFA3 polypeptide, for example LFA3-Fc M1d1, is formulated at a concentration of about 0.15 mg/mL. In some embodiments, the LFA3 polypeptide, for example LFA3-Fc M1d1, is formulated at a concentration of about 1.5 mg/mL. In some embodiments, the LFA3 polypeptide, for example LFA3-Fc M1d1, is formulated at a concentration of about 10, about 20, about 30, about 40 or about 50 mg/mL.

In some embodiments, the LFA3 polypeptide molecule of this invention can be formulated as a dose of about 0.2-8 mg per injection (e.g., 0.2, 0.5, 1, 1.5, 2, 2.5, 3, 3.5, 4, 4.5, 5, 5.5, 6, 6.5, 7, 7.5, or 8 mg per injection), e.g., between 0.22-7.5 mg per injection. In some embodiments, the LFA3 polypeptide molecule of this invention can be formulated in about 0.5-1.5 ml solution per injection (e.g., 0.5, 1, or 1.5 ml solution per injection), e.g., about 1 ml solution per injection.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In one embodiment the compositions of the disclosure are pyrogen-free formulations which are substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food and Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight it is advantageous to remove even trace amounts of endotoxin. In one embodiment, endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg. In another embodiment, endotoxin and pyrogen levels in the composition are less than about 10 EU/mg, or less than about 5 EU/mg, or less than about 1 EU/mg, or less than about 0.1 EU/mg, or less than about 0.01 EU/mg, or less than about 0.001 EU/mg.

In one embodiment, the disclosure comprises administering a composition wherein said administration is oral, parenteral, intramuscular, intranasal, vaginal, rectal, lingual, sublingual, buccal, intrabuccal, intravenous, cutaneous, subcutaneous or transdermal. In some embodiments, a composition comprising an LFA3 polypeptide, for example, LFA3-Fc M1d1, is administered intravenously. In another embodiment the disclosure further comprises administering a composition in combination with other therapies, such as surgery, chemotherapy, hormonal therapy, biological therapy, immunotherapy or radiation therapy. In some embodiments, the other therapy is hematopoietic stem cell transplantation, e.g., allogeneic hematopoietic stem cell transplantation.

VI. Dosing/Administration

To prepare pharmaceutical or sterile compositions including a LFA3 polypeptide molecule of the disclosure, the LFA3 polypeptide molecule is mixed with a pharmaceutically acceptable carrier or excipient. Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N. Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY;

Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, 1996, Antibody Therapy, Bios Scientific Pub. Ltd, Oxfordshire, UK; Kresina (ed.), 1991, Monoclonal Antibodies, Cytokines and Arthritis, Marcel Dekker, New York, N.Y.; Bach (ed.), 1993, Monoclonal Antibodies and Peptide Therapy in Autoimmune Diseases, Marcel Dekker, New York, N. Y.; Baert, et al., 2003, New Engl. J. Med. 348:601-608; Milgrom, et al., 1999, New Engl. J. Med. 341:1966-1973; Slamon, et al., 2001, New Engl. J. Med. 344:783-792; Beniaminovitz, et al., 2000, New Engl. J. Med. 342:613-619; Ghosh, et al., 2003, New Engl. J. Med. 348:24-32; Lipsky, et al., 2000, New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well-known in the medical arts.

Compositions comprising LFA3 polypeptide molecules of the disclosure can be administered twice a week, once a week, once every two weeks, or once every three weeks. In some embodiments, the LFA3 polypeptide molecule of the invention, or pharmaceutical composition thereof, is administered once a week.

In some embodiments, the LFA3 polypeptide molecule of the invention, or pharmaceutical composition thereof, is administered at a dose of about 5-20 mg/week (e.g., 5, 6, 7, 8, 9, 10, 12, 15, 17, or 20 mg/week). In some embodiments, the LFA3 polypeptide molecule of the invention, or pharmaceutical composition thereof, is administered at a dose of about 15 mg/week. In some embodiments, the LFA3 polypeptide molecule of the invention, or pharmaceutical composition thereof, is administered at a dose of about 7.5 mg/week.

In some embodiments, the LFA3 polypeptide molecule of the invention, or pharmaceutical composition thereof, is administered at a dose of about 0.2-8 mg per injection (e.g., 0.2, 0.5, 1, 1.5, 2, 2.5, 3, 3.5, 4, 4.5, 5, 5.5, 6, 6.5, 7, 7.5, or 8 mg per injection). In some embodiments, the LFA3 polypeptide molecule of the invention, or pharmaceutical composition thereof, is administered at a dose between 0.22-7.5 mg per injection. In some embodiments, the LFA3 polypeptide molecule of the invention, for example LFA3-Fc M1d1, or pharmaceutical composition thereof, is administered at a dose of about 7.5 mg per injection.

In some embodiments, the LFA3 polypeptide of the invention (for example LFA3-Fc M1d1), or pharmaceutical composition thereof, is administered at a dose of about 0.01 to 10 mg/kg. In some embodiments, the LFA3 polypeptide of the invention (for example LFA3-Fc M1d1), or pharmaceutical composition thereof, is administered at a dose of about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, about 1.0, about 2.0, about 3.0, about 4.0, about 5.0, about 6.0, about 7.0, about 8.0, about 9.0 or about 10.0 mg/kg. In some embodiments, the LFA polypeptide of the invention (for example LFA3-Fc M1d1), or pharmaceutical composition thereof, is administered at a dose of about 0.03 mg/kg. In some embodiments, the LFA polypeptide of the invention (for example LFA3-Fc M1d1), or pharmaceutical composition thereof, is administered at a dose of about 0.3 mg/kg. In some embodiments, the LFA polypeptide of the invention (for example LFA3-Fc M1d1), or pharmaceutical composition thereof, is administered at a dose of about 3.0 mg/kg. In some embodiments, the LFA polypeptide of the invention (for example LFA3-Fc M1d1), or pharmaceutical composition thereof, is administered at a dose of about 25, about 50, about 75 or about 100 mg/kg.

In some embodiments, the LFA3 polypeptide molecule of the invention, or pharmaceutical composition thereof, is administered in about 0.5-1.5 ml solution per injection (e.g., 0.5, 1, or 1.5 ml solution per injection). In some embodiments, the LFA3 polypeptide molecule of the invention, or pharmaceutical composition thereof, is administered in about 1 mL solution per injection.

In some embodiments, the LFA3 polypeptide molecule of the invention (for example LFA3-Fc M1d1), or pharmaceutical composition thereof, is administered at a dose volume of about 0.5 to 5 mL/kg. In some embodiments, the LFA3 polypeptide molecule of the invention (for example LFA3-Fc M1d1), or pharmaceutical composition thereof, is administered at a dose volume of about 0.5, about 1.0, about 1.5, about 2.0, about 2.5, about 3.0, about 3.5, about 4.0, about 4.5 or about 5.0 mL/kg. In some embodiments, the LFA3 polypeptide molecule of the invention (for example LFA3-Fc M1d1), or pharmaceutical composition thereof, is administered at a dose volume of about 2.0 mL/kg.

In some embodiments, the LFA3 polypeptide molecule of the invention, or pharmaceutical composition thereof, is administered for one or more (e.g., 1, 2, 3, 4, or more) courses, e.g., wherein each course consists of 10-14 weeks (e.g., 10, 11, 12, 13, or 14 weeks), e.g., 12 weeks, e.g., wherein two adjoining courses are separated by a 10 to 14 week interval (e.g., a 10, 11, 12, 13, or 14-week interval), e.g., a 12-week interval.

In some embodiments, the LFA3 polypeptide molecule of the invention, or pharmaceutical composition thereof, is administered subcutaneously at a dose of about 15 mg/week once a week, e.g., wherein the LFA3 polypeptide molecule of the invention, or pharmaceutical composition thereof, is administered for one or more (e.g., 1, 2, 3, 4, or more) courses, wherein each course consists of 12 weeks and two adjoining courses are separated by a 12-week interval.

An effective amount for a particular patient may vary depending on factors such as the condition being treated, the overall health of the patient, the method route and dose of administration and the severity of side effects (see, e.g., Maynard, et al., 1996, A Handbook of SOPs for Good Clinical Practice, Interpharm Press, Boca Raton, Fla.; Dent, 2001, Good Laboratory and Good Clinical Practice, Urch Publ, London, UK).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., 1983, Biopolymers 22:547-556; Langer, et al., 1981, J. Biomed. Mater. Res. 15: 167-277; Langer, 1982, Chem. Tech. 12:98-105; Epstein, et al., 1985, Proc. Natl. Acad. Sci. USA 82:3688-3692; Hwang, et al., 1980, Proc. Natl. Acad. Sci. USA 77:4030-4034; U.S. Pat. Nos. 6,350,466 and 6,316,024). Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety. In one embodiment, the LFA3 polypeptide molecule, or pharmaceutical composition thereof, of the disclosure is administered using Alkermes AIR™ pulmonary drug delivery technology (Alkermes, Inc., Cambridge, Mass.).

A composition of the present disclosure may also be administered via one or more routes of administration using one or more of a variety of methods known in the art. As will be appreciated by the skilled artisan, the route and/or mode of administration will vary depending upon the desired results. Selected routes of administration for polypeptide molecules of the disclosure include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the disclosure can be administered via a non-parenteral route, such as a topical, epidermal or mucosal route of administration, for example, intranasally, orally, vaginally, rectally, sublingually or topically.

If the LFA3 polypeptide molecules of the disclosure are administered in a controlled release or sustained release system, a pump may be used to achieve controlled or sustained release (see, Langer, supra; Sefton, 1987, CRC Crit. Ref. Biomed. Eng. 14:20; Buchwald et al., 1980, Surgery 88:501; Saudek et al., 1989, N. Engl. J. Med. 321:514).

Polymeric materials can be used to achieve controlled or sustained release of the therapies of the disclosure (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. ScL Rev. Macromol. Chem. 23:61; see also Levy et al, 1985, Science 11225:190; During et al., 19Z9, Ann. Neurol. 25:351; Howard et al, 1989, J. Neurosurg. 71: 105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), polyvinyl alcohol), polyacrylamide, polyethylene glycol), polylactides (PLA), polyoeactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer, 1990, Science 249:1527-1533. Any technique known to one of skill in the art can be used to produce sustained release formulations comprising one or more polypeptide molecules of the disclosure or conjugates thereof. See, e.g., U.S. Pat. No. 4,526,938, International Patent Publication Nos. WO 91/05548, WO 96/20698, Ning et al., 1996, "Intratumoral Radioimmunotheraphy of a Human Colon Cancer Xenograft Using a Sustained-Release Gel," Radiotherapy and Oncology 59:179-189, Song et al., 1995, "Antibody Mediated Lung Targeting of Long-Circulating Emulsions," PDA Journal of Pharmaceutical Science and Technology 50:372-397, Cleek et ah, 1997, "Biodegradable Polymeric Carriers for a bFGF Antibody for Cardiovascular Application," Pro. M1. Symp. Control. Rel. Bioact. Mater. 24:853-854, and Lam et al., 1997, "Microencapsulation of Recombinant Humanized Monoclonal Antibody for Local Delivery," Proc. M1. Symp. Control Rel. Bioact. Mater. 24:759-160, each of which is incorporated herein by reference in their entirety.

If the LFA3 polypeptide molecule of the disclosure is administered topically, it can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising the LFA3 polypeptide molecules are administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are well-known in the art (see, e.g., Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams and Wilkins, Phila., Pa.; Chabner and Longo (eds.) (2001) Cancer Chemotherapy and Biotherapy, Lippincott, Williams and Wilkins, Phila., Pa.). An effective amount of therapeutic may decrease the symptoms by at least 10 percent; by at least 20 percent; at least about 30 percent; at least 40 percent, or at least 50 percent.

In one embodiment, the LFA3 polypeptide molecules of the disclosure can be co-administered with compositions for treating autoimmune diseases and disorders, including, but not limited to, adriamycin, azathiopurine, busulfan, cyclophosphamide, cyclosporine A, Cytoxan, fludarabine, 5-fluorouracil, methotrexate, mycophenolate mofetil, 6-mercaptopurine, a corticosteroid, a nonsteroidal anti-inflammatory, sirolimus (rapamycin), and tacrolimus (FK-506). In alternative embodiments, the immunomodulatory or immunosuppressive agent is an antibody selected from the group consisting of muromonab-CD3, alemtuzumab (Campath®), basiliximab, daclizumab, muromonab (OKT3®), rituximab, anti-thymocyte globulin and IVIg, and others, which are known to persons skilled in the art.

In one embodiment, the LFA3 polypeptide molecules of the disclosure can be co-administered with compositions for treating diabetes, including, but not limited to, biguanides (e.g., buformin, metformin, and phenform), hormones and analogs thereof (amylin, insulin, insulin aspart, insulin detemir, insulin glargine, insulin glulisine, insulin lispro, liraglutide, and pramlintide), sulfonylurea derivatives (acetohexamide, carbutamide, chlorpropamide, glibornuride, gliclazide, glimepiride, glipizide, gliquidone, glisoxepid, glyburide, glybuthiazole, glybuzole, glyhexamide, glymidine, tolazamide, tolbutamide, and tolcyclamide), thiazolidinediones (pioglitazone, rosiglitazone, and troglitazone), acarbose, exenatide, miglitol, mitiglinide, muraglitazar, nateglinide, repaglinide, sitagliptin, tesaglitazar, vildagliptin, and voglibose.

In certain embodiments, the LFA3 polypeptide molecules of the disclosure can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade, 1989, J. Clin. Pharmacol. 29:685). Exemplary targeting moieties include folate or biotin (see, e.g., U.S. Pat. No. 5,416,016); mannosides (Umezawa et al., Biochem. Biophys. Res. Commun. 153: 1038); antibodies (P. G. Bloeman et al., 1995, FEBS Lett. 357: 140; M. Owais et al., 1995, Antimicrob. Agents Chemother. 39: 180); surfactant protein A receptor (Briscoe et al. (1995) Am. J. Physiol. 1233: 134); p 120 (Schreier et al. (1994) J. Biol. Chem. 269:9090); see also K. Keinanen; M. L. Laukkanen, 1994, FEBS Lett. 346:123; Killion; Fidler, 1994; Immunomethods 4:273.

The disclosure provides protocols for the administration of pharmaceutical composition comprising LFA3 polypeptide molecules of the disclosure alone or in combination with other therapies to a subject in need thereof. The therapies (e.g., prophylactic or therapeutic agents) of the combination therapies of the present disclosure can be administered concomitantly or sequentially to a subject. The therapy (e.g., prophylactic or therapeutic agents) of the combination therapies of the present disclosure can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising LFA3 polypeptide molecules of the disclosure are administered to a subject in a sequence and within a time interval such that the LFA3 polypeptide molecules of the disclosure can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

VII. Kits

The disclosure also provides kits comprising any or all of the polypeptide molecules described herein. Kits of the disclosure include one or more containers comprising a LFA3 polypeptide molecule described herein and instructions for use in accordance with any of the methods of the disclosure described herein. Generally, these instructions comprise a description of administration of the polypeptide molecule for the above described therapeutic treatments. In some embodiments, kits are provided for producing a single-dose administration unit. In certain embodiments, the kit can contain both a first container having a dried protein and a second container having an aqueous formulation. In certain embodiments, kits containing an applicator, e.g., single and multi-chambered pre-filled syringes (e.g., liquid syringes and lyosyringes), are included.

The instructions relating to the use of a LFA3 polypeptide molecule generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a LFA3 polypeptide molecule of the disclosure. The container may further comprise a second pharmaceutically active agent.

Kits may optionally provide additional components such as buffers and interpretive information. Normally, the kit comprises a container and a label or package insert(s) on or associated with the container.

The disclosure also provides diagnostic kits comprising any or all of the polypeptide molecules described herein. The diagnostic kits are useful for, for example, detecting the presence of CD2 in a sample. In some embodiments, a diagnostic kit can be used to identify an individual with a latent disease, disorder or condition that may put them at risk of developing CD2-mediated disease, disorder or condition or a CD2 deficiency disease, disorder or condition. In some embodiments, a diagnostic kit can be used to detect the presence and/or level of CD2 in an individual suspected of having a CD2 mediated disease or a CD2 deficiency disease, disorder or condition.

Diagnostic kits of the disclosure include one or more containers comprising a LFA3 polypeptide molecule described herein and instructions for use in accordance with any of the methods of the disclosure described herein. Generally, these instructions comprise a description of use of the LFA3 polypeptide molecule to detect the presence of CD2 in individuals at risk for, or suspected of having, a CD2 mediated disease or a CD2 deficiency disease, disorder or condition. In some embodiments, an exemplary diagnostic kit can be configured to contain reagents such as, for example, a LFA3 polypeptide molecule, a negative control sample, a positive control sample, and directions for using the kit.

VIII. Equivalents

The foregoing description and following Examples detail certain specific embodiments of the disclosure and describes the best mode contemplated by the inventors. It will be appreciated, however, that no matter how detailed the foregoing may appear in text, the disclosure may be practiced in many ways and the disclosure should be construed in accordance with the appended claims and any equivalents thereof.

Although the disclosed teachings have been described with reference to various applications, methods, kits, and compositions, it will be appreciated that various changes and modifications can be made without departing from the teachings herein and the claimed disclosure below. The following examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

IX. General Teachings

It is to be understood that this invention is not limited to specific synthetic methods of making that may of course vary. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Sambrook and Russell, Molecular Cloning: A Laboratory Manual, 3rd. ed., Cold Spring Harbor Laboratory Press, Cold Spring Harbor, NY (2001); Ausubel et al., Current Protocols in Molecular Biology, John Wiley & Sons, N Y (2002); Harlow and Lane Using Antibodies: A Laboratory Manual, Cold Spring Harbor Laboratory Press, Cold Spring Harbor, NY (1998); Coligan et al., Short Protocols in Protein Science, John Wiley & Sons, N Y (2003); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Enzymatic reactions and purification techniques are performed according to manufacturer's specifications, as commonly accomplished in the art or as described herein. The nomenclatures used in connection with, and the laboratory procedures and techniques of, analytical chemistry, biochemistry, immunology, molecular biology, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

EXAMPLES

The disclosure is further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Example 1: Stability and Affinity Maturation of LFA3 Via Yeast Display

Methods:

Protein Expression and Purification

Human LFA3 variants with a C-terminal hinge-Pfe Fc were cloned into mammalian expression vector pRY19 and used to transiently transfect Expi293 (ThermoFisher) and ExpiCHO (ThermoFisher) cells using the ExpiFectamine 293 Transfection Kit (ThermoFisher #A14525) and the ExpiCHO Expression System Kit (ThermoFisher #A29133), respectively, according to manufacturer's instructions. After 4-7 days of expression, protein was harvested and purified by Protein A affinity column using the MabSelectSuRe resin (GE Healthcare #17-5438-01) followed by size exclusion chromatography (SEC) using a Superdex200 13100 Increase column (GE Healthcare).

For large scale expression, CHO SSI pooled stable cell lines were generated. LFA3-Fc M1-d1 and M1-d3 containing supernatant was filtered and captured on MabSelect SuRe LX resin. Eluted protein was neutralized and passed over a SP column in flow-through mode as a polishing step. For the wild-type (WT) LFA3-Fc protein, the monomeric fraction was purified using SEC. Process impurities were measured using commercial assay kits for residual Protein A, host cell proteins (HCP), and DNA.

Yeast Surface Display of Human LFA3

The N-terminal Ig-domain of human LFA3 (Residues 1-93), for example the polypeptide of SEQ ID NO: 24, was displayed on the surface of *S. cerevisiae* strain BJ5465 using either the pRNYD2 or pRNYDG vectors (Pfizer). Both vectors display LFA3 with an N-terminal V5 epitope tag, and the C-terminus of LFA3 is fused to Muc3 and a membrane anchoring region. Whereas the pRNYD2 vector uses the transmembrane region of Axl2 to anchor LFA3 onto the surface of yeast, pRNYDG utilizes the GPI linker. Surface display of active LFA3 was confirmed by V5 epitope staining and CD2 binding via flow cytometry (data not shown). It was found that the pRNYDG system displays LFA3 much more efficiently and to much higher expression levels on yeast surface compared to the pRNYD2 system.

$1^{st}$ Generation Library Designs and Construction

Based on the crystal structure of wild-type human LFA3: CD2 complex (Wang, et al (1999) Cell 97, 791-803), 15 contact residues and 16 inward-facing, hydrophobic 'core' residues of LFA3 were chosen to be randomized using overlap extension PCR and the following PCR primers with degenerate codons. Two libraries were constructed: 1—S (stability library), which contained randomization of only the 'core' residues; and 2—AS (affinity & stability library), which contained randomization of both the contact and the 'core' residues. It has been reported that on-yeast expression level correlates with thermal stability of recombinant proteins (Shusta, et al (1999) Journal of molecular biology 292, 949-956). Therefore, these 1 generation libraries were constructed on the pRNYD2 display platform with lower surface expression to increase the range of the thermal stability of LFA3 that can be improved.

PCR Primers for Contact Residues:

Glu25=VAK, Leu27=NTT, Lys29=ANG, Lys32=ANG, Asp33=VAM, Lys34=ANG, Glu37=VAK, Glu39=VAM, Gu42=VAK, Arg44=ANG, Phe46=NWT, Ser47=RST, Pro80=CNT, Ile82=NTT, Asp84=VAM

```
                                              (SEQ ID NO: 5)
5'-gagtaacgttcctttgaagVAKgtcNTTtggANG aaacaaANGVAMANGgtggcagaattagagaatag-3'

(SEQ ID NO: 6)
5'-gaaaaaacaaaaagataaagtggcaVAKttaVAMaat agtVAKtttANGgctNWTRSTtcatttaagaatagggtc-3'

(SEQ ID NO: 7)
5'-gtacgaaatggagtccCNTaatNTTacaVAMacaat gaagttttttttgtac-3'
```

PCR Primers for 'Core' Residues:
Phe15=NTT, Val17=NTT, Leu23=NTT, Val26=NTT, Trp28=TKS, Va35=NTT, Ala36=KYA, Leu38=NTT, Phe43=NTT, Ala45=KYA, Leu55=NTT, Gly60=RST, Leu62=NTT, Met77=WTS, Met86=WTS, Phe88=NTT

```
                                              (SEQ ID NO: 8)
5'-gtttacggtaatgtgactNTTcacNTTccgagtaacgacct NTTaaggaaNTTtttaTKSaaaaaacaaaaagataaagtg-3'

(SEQ ID NO: 9)
5'-cttatggaaaaaacaaaaagataaaNTTKYAgaaNTT gagaatagtgagNTTaggKYAtttagttcatttaagaatag-3'

(SEQ ID NO: 10)
5'-catttaagaatagggtctatNTTgatactgtatccRSTtc tNTTaccatttataatttaacaagtag-3'

(SEQ ID NO: 11)
5'-gatgaagacgagtacgaaWTSgagtcccctaatattacaga cacaWTSaagNTTttttttgtacgttttggg-3'
```

For constructing the AS library, LFA3 gene fragments containing randomization of the contact and the 'core' residues were amplified separately and mixed together with ApaI/NcoI double-digested pRNYD2 vector prior to electroporation. Electroporation, rescue and expansion of the yeast libraries were performed as described previously (Chao, et al (2006) Nature protocols 1, 755-768). The final AS and S libraries contained approximately 1.5×10$^8$ and 1.3×10$^8$ transformants, respectively.

1$^{st}$ Generation Selections

On-yeast expression of LFA3 variants was induced at 20° C. for all rounds of selections, and library selections were conducted by varying two selective parameters: 1—on-yeast heat denaturation was applied to improve thermal stability; and 2—concentration of CD2 was either maintained or lowered to retain or improve affinity. A total of 4 rounds of selections were performed for each library.

S Library Selections:

For S library selections, ligand (hCD2-biotin) was kept at a constant concentration of 1 µM whereas increasing heat exposure was applied through the selection rounds to enrich for the most thermal stable clones while maintaining wild-type like affinity for CD2. The selection strategy was adapted from previously reported approach for evolving protein stability on yeast (Shusta, et al (2000) Nature biotechnology 18, 754-759). For round 1, approximately 2.0× 10$^9$ cells, without additional heat exposure, were incubated with hCD2-biotin for 1 h at 4° C. and washed twice with PBE (PBS, pH 7.4+0.5% (w/v) BSA+2 mM EDTA, pH 8.0). The library was subsequently stained with 1:50 Streptavidin-PE (SA-PE, Life Technologies #S21388) for 15 min, washed twice, and finally, labeled with 1:10 paramagnetic anti-PE microbeads (Miltenyi #130-048-801) for 20 min, all at 4° C. The library was selected using MACS LS columns (Miltenyi #130-042-401) and QuadroMACS Separator (Miltenyi #130-090-976) according to manufacturer's instructions. For rounds 2-4, 1.0×10$^8$ cells in PBE were exposed to [20 min @ 46° C.], [30 min @ 46° C.] and [20 min @46° C.+10 min @ 50° C.], respectively, using a heat block (Eppendorf). After heat denaturation, the libraries were stained with 1 µM hCD2-biotin for 1 h at 4° C., washed twice, and co-labeled with SA-PE (for detecting hCD2 binding) and anti-V5-FITC (for detecting LFA3 variant expression) for 10 min at 4° C. Library selection was performed by two-color FACS, sorting the CD2+V5+ double-positive population using a SH800 sorter (Sony).

AS Library Selections:

For AS library selections, hCD2-biotin concentration was lowered and increasing heat exposure was applied through the selection rounds to enrich for the most thermal stable with the highest affinity clones. The criteria and modality of selection rounds for AS library were essentially the same as those for the S library described above with one modification: for rounds 2-4, instead of staining the library with 1 µM ligand, the AS library was stained with 40 nM hCD2-biotin for 1 h at 4° C.

At the conclusion of the selections, 100 µl of post-round-4 S and AS libraries were used to extract library DNA using the Zymoprep™ Yeast Plasmid Miniprep II Kit (Zymo Research #D2004), according to manufacturer's instructions. The extracted DNA was transformed into chemically competent TOP10 E. coli and plated to sequence the individual clones.

2$^{nd}$ Generation 'Loop' Library Design and Construction

To further improve the affinity of LFA3 variants, a 2$^{nd}$ generation library was constructed by using WT and 3 of the 1' generation variants (M1, M4 and M5) as templates for overlap extension PCR, and randomizing the FG loop with the following degenerate primers. Since the FG loop is the region of the LFA3:CD2 interface that has the least charge/surface complementarity, the rationale for this design is to completely randomize the loop in order to optimize the binding energetics. The 'Loop' library was constructed on the pRNYDG display platform for optimal surface expression in order to avoid preferential selection of high expressing clones that are not necessarily high affinity.

PCR Primers for Loop Residues:
Ser79=NNK, Pro80=NNK, Asn81=NNK, Ile82=NNK, Thr83=NNK, Asp84=NNK, Ser85=NNK

```
Based on WT template:
                                              (SEQ ID NO: 12)
5'-gaagacgagtacgaaatggagNNKNNKNNKNNKNNKNNKNNK atgaagttttttttgtacgttttg-3'

Based on M1 template:
                                              (SEQ ID NO: 13)
5'-gaagacgagtacgaaatggagNNKNNKNNKNNKNNKNNKNNK ttcaagttttttttgtacgttgg-3'

Based on M4 or M5 templates:
                                              (SEQ ID NO: 14)
5'-gaagacgagtacgaattcgagNNKNNKNNKNNKNNKNNKNNK ttcaagttttttttgtacgttg-3'
```

Electroporation, rescue and expansion of the yeast libraries were performed as described previously (Chao, et al (2006) Nature protocols 1, 755-768). The final library contained approximately $2.9 \times 10^8$ transformants.

2$^{nd}$ Generation Selection

A total of 6 rounds of selection, with increasing selective pressure on affinity but not stability, were performed on the Loop library to enrich for the highest affinity LFA3 variants. For the initial round of selection, $3 \times 10^9$ cells were selected with 50 nM monomeric hCD2-biotin via MACS using a similar procedure as described for round 1 of the 1$^{st}$ generation libraries. Subsequent rounds utilized a kinetic selection strategy (Boder, et al (1997) Nature biotechnology 15, 553-557) to enrich for clones with the slowest off-rates. Briefly, the kinetic selection strategy involved staining $1 \times 10^8$ yeast with 250 nM monomeric hCD2-biotin for 1 h at room temperature, washing twice with PBE, competing with 1 µM monomeric unbiotinylated hCD2 at room temperature for increasing amount of time, washing twice with PBE and, finally, enriching with either MACS or two-color FACS. The lengths of competition for rounds 2-6 were 10, 20, 40, 80 and 80 min, respectively. The selection modality was MACS for rounds 2-3 and FACS for round 4-6.

At the conclusion of the selections, individual clones were sequenced as described above for 1$^t$ generation selections.

On-Yeast Titrations

To assess affinity for CD2 on-yeast, serial dilutions of hCD2-biotin were incubated with LFA3-expressing yeast for 1 h at 4° C. with shaking. Unbound hCD2-biotin was removed by washing twice with 200 µl PBE. The hCD2-biotin-labeled yeast were incubated with 1:100 SA-PE for 15 min at 4° C. with shaking and washed again twice with PBE. Samples were analyzed on an Accuri C6 flow cytometer (BD Biosciences). Data represent the mean fluorescence intensity, and points were fitted to sigmoidal dose-response curves using Prism 6 (Graphpad).

On-yeast protein thermal stability was assessed using previously published approach, with some modifications (Orr, et al (2003) Biotechnology progress 19, 631-638). Briefly, LFA3-expressing yeast in PBE were heated at the indicated temperatures between 30-70° C. for 15 min then cooled to 4° C. using a Tetrad 2 Peltier Thermal Cycler (BioRad). The yeast was incubated with 500 nM hCD2-biotin for 1 h, washed twice with PBE, and then stained with 1:100 SA-PE for 15 min at 4° C. Samples were analyzed on an Accuri C6 flow cytometer. Data represent the mean fluorescence intensity normalized to the maximal binding for each LFA3 variant, and points were fitted to sigmoidal dose-response curves using Prism 6.

Stability Assessments

Differential Scanning Fluorometry (DSF)

Experiments were conducted with a ViiA 7 Real-Time PCR system (Thermo Fisher) and Protein Thermal Shift Dye Kit (Thermo Fisher #4461146) according to manufacturer's instructions. Briefly, 0.8-1 mg/ml LFA3 variants were mixed with 1:1000 dilution of the dye in PBS. Samples (20 µl reaction volume) were distributed across a MicroAmp Optical 96-well reaction plate (Applied Biosystems #N8010560), avoiding the sides of the plate, and sealed with an optical adhesive cover (Applied Biosystems #4360954). Viia 7 Real-Time PCR system was programmed to increase temperature from 25° C. to 99° C. at a rate of 0.05° C./s. The melting temperatures of LFA3-Pfe variants were quantified by measuring the temperature corresponding to the first transition of the melting curve on the ViiA 7 software, and points were plotted using Prism 6.

Heat Forced Aggregation

LFA3-Pfe variants at 1 mg/ml in PBS, pH 7.2 were heated at the indicated temperatures (20 µl/reaction) for 24 h using a Tetrad 2 Peltier Thermal Cycler (BioRad). To assess the level of heat-induced aggregation, 15 µl/sample was loaded onto YMC-Pack Diol-200 (YMC) column for size exclusion chromatography (SEC) analysis. The resulting chromatograms were used to quantify % high molecular weight species (HMMS), % dimer and % monomer as functions of temperature.

Low-pH Hold

LFA3-Pfe variants at 1.5 mg/ml in PBS, pH 7.2 were mixed with 10% (v/v) of either 0.4 M Glycine, pH 2.7 or PBS, pH 7.2 (i.e. 5 µl of glycine or PBS was added to 50 µl of protein) and incubated at room temperature for 5 h. The samples were neutralized with 4.55% (v/v) of either 0.25 M Tris Base, pH 7.4 or PBS (i.e. 2.5 µl of neutralization buffer was added to 55 µl of sample). To assess the level of low-pH-induced aggregation, 25 µl/sample was loaded onto YMC-Pack Diol-200 (YMC) column for size exclusion chromatography (SEC) analysis. The resulting chromatograms were used to quantify % high molecular weight species (HMMS), % dimer and % monomer as functions of temperature.

Freeze-Thaw and Shaking Stability

Freeze-thaw stability was assessed by freezing the material at −80° C. or −20° C. for ≥30 minutes, thawing at 5° C. for ≥30 minutes, and vortexing. The process is repeated for 5 cycles and samples assessed by analytical SEC. For shaking stability, samples were subjected to shaking for 24 hours at 300 rpm (with and without PS80) and inspected for soluble aggregation and precipitation.

Thermostability (Differential Scanning Calorimetry)

Thermostability by DSC was assessed using a MicroCal VP-Capillary DSC, scanning from 10-110° C. at a rate of 60° C./hr. Samples were diluted in buffer to 1 mg/ml.

Protein Analytics

Capillary Gel Electrophoresis (cGE)

Samples were diluted to 1 mg/ml. Non-reduced samples were treated with iodoacetamide (JAM) and reduced samples were treated with DTT. Analysis was performed using the cGE LabChip HT Antibody Express 200 method (Perkin Elmer).

Analytical SEC

SEC-HPLC analysis was performed using a YMC-Pack Diol-200 chromatography (YMC America) column.

Viscosity

Viscosity was measured using RheoSense m-VROC viscometer. Protein was formulated in histidine sucrose EDTA buffer pH5.8 and viscosity measured at concentrations up to 150 mg/ml.

Protein Characterization

Affinity-Capture Self-Interaction Nanoparticle Spectroscopy (AC-SINS)

AC-SINS assay was performed using coated gold nanoparticles coated with anti-human IgG. Samples at 50 µg/ml in PBS where mixed with coated nanoparticles and incubated for 2 hours. Samples are transferred to a UV transparent plate and absorbance measured from 450 to 650 nm.

FcRn Chromatography

Biotinylated human FcRn was captured on streptavidin resin and packed into a column. 50 µg of sample was injected onto the column and a linear elution gradient from pH 5.5 to 8.8 applied. The relative elution time compared to a control mAb and peak width at 50% peak height was recorded.

Polyreactivity ELISA

ELISA plates were coated with 10 µg/ml dsDNA or 5 µg/ml insulin overnight. Plates were blocked with ELISA buffer (PBS, 0.05% Tween-20, 1 mM EDTA), and test proteins applied using 4-fold serial dilutions starting from 1 µg/ml. Binding was detected using a HRP-conjugated goat anti-human IgG.

In Silico Immunogenicity

In silico immunogenicity was assessed using EpiVax ISPRI web-based screening toolkit.

Binding Affinity Analysis

The affinity of LFA3-Fc variants binding to recombinant CD2 was determined by surface plasmon resonance using a Biacore T200 instrument (GE Healthcare, Piscataway, NJ). Biotinylated CD2 protein was captured on a streptavidin (SA) coated Biacore sensor chip (Series S Sensor Chip SA, BR100531, GE Healthcare) at low coupling densities. Experiments were performed at 25° C. using a 30 µl/min flow rate in 0.01 M HEPES pH 7.4, 0.15 M NaCl and 0.005% v/v surfactant P20 (HBS-P) buffer. LFA3-Fc variants were injected over the surface for 2 minutes and the dissociation monitored for a further 5 minutes, or 10 minutes for the higher affinity clones. No regeneration was required. Data was analyzed using the Biacore T200 Evaluation software, the signal from the adjacent control flow cell with only streptavidin immobilized was background subtracted along with buffer only injections for each antibody. An equilibrium binding model was used to calculate affinity constants ($K_d$).

Results

Structure based design was used to construct yeast display libraries based on the first extracellular domain of human LFA3 (FIG. 1). The AS and S libraries were estimated to contain ~1.5×10$^8$ and ~1.3×10$^8$ transformants respectively. Sequence analysis of the naïve libraries confirmed approximately 6-7 mutations per clones in each library.

Libraries were exposed to increasing amounts of heat exposure post induction, and decreasing concentrations of the CD2 ligand for the AS library. After four rounds of selection, individual clones were sequenced and 6 hot spot residues identified: A36, L38, F43, A45, M77, and M86 (FIGS. 2A and 2B). Based on the most frequent residues observed in these six positions (FIG. 2C), 6 recombinant variants were designed (M1→M6) (FIG. 2D) and expressed as Fc fusion proteins in mammalian cells. M1 to M6 Fc fusion proteins comprise a variant LFA3 extracellular domain (SEQ ID NOs: 17-22, respectively) fused to a human IgG1 Fc region (SEQ ID NO: 16) (Table 2). The human IgG1 Fc region SEQ ID NO: 16 is also referred to as "Pfe" in the figures and throughout the applications. The corresponding nucleotide sequences are provided in Table 3.

In the studies described in Example 1 and Example 2, M1 to M6 Fc fusion proteins as well as other variant LFA3-Fc fusion proteins were compared with wild type LFA3-Fc fusion proteins. Two reference wild type LFA3-Fc fusion proteins were used in the studies, both of which comprise a wild-type first extracellular domain of human LFA3 fused to a human IgG1 Fc region. The first reference molecule is referred to as "WT LFA3-Fc" or "LFA3-Fc WT" (SEQ ID NO: 4), which was generated based on the published sequence of alefacept. This reference molecule was disclosed in U.S. Pat. No. 5,547,853, herein incorporated by reference in its entirety. The second reference molecule is referred to as "WT LFA3-Pfe" (SEQ ID NO: 120), which comprises the same wild-type first extracellular domain of human LFA3 as WT LFA3-Fc, but has a slightly different human IgG1 Fc region. In some embodiments, LFA3-Fc WT (SEQ ID NO: 4) and/or WT LFA3-Pfe (SEQ ID NO: 120) include a carboxy terminal lysine residue. In some embodiments, SEQ ID NO: 4 and/or SEQ ID NO: 120 do not include a carboxy terminal lysine residue. In some embodiments, SEQ ID NO: 128 does not include a carboxy terminal lysine residue.

LFA3 variant Fc fusion proteins were characterized to assess the stability and potential manufacturability attributes of the recombinant proteins. Variants were ranked based of their monomeric expression, overall yield, thermal stability, and propensity to aggregate under thermal stress (FIGS. 3A-3D). Variants M1, M4, and M5 were identified to have the most desirable properties based on this analysis.

Figure 4:
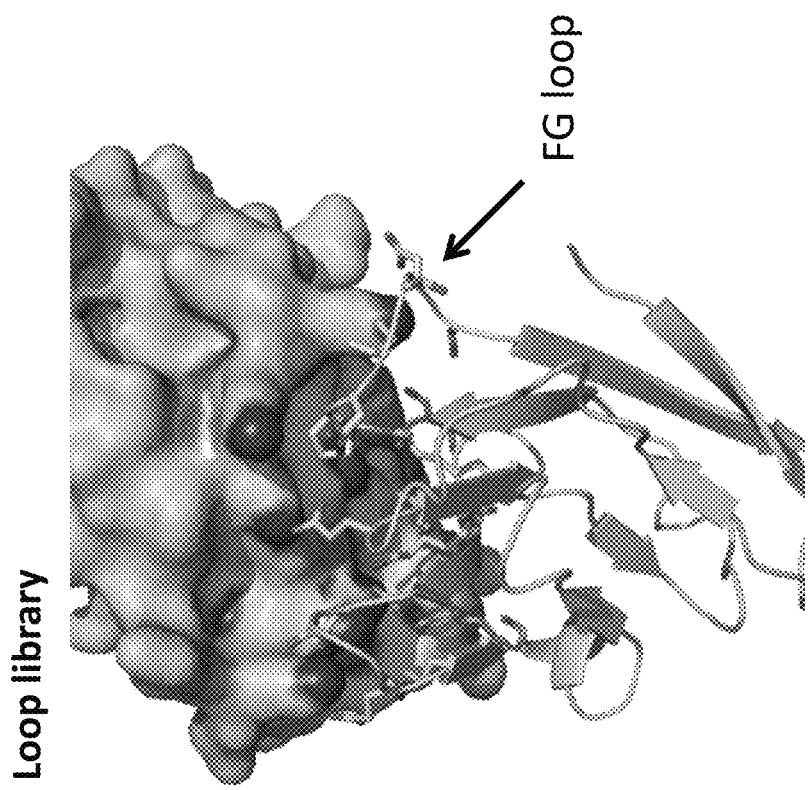
FIG. 4: Structure-based design of FG loop library to identify clones with increased binding affinity. Shown in the table in FIG. 4 are residues targeted for mutagenesis in the second-generation library. The residue positions are numbered according to SEQ ID NO: 2.

A second-generation library was designed to identify clones with increased binding affinity for CD2. This library mutated 7 residues on the FG loop of LFA3 using wild-type, M1, M4, and M5 variants as the template (FIG. 4). Based on sequence analysis, 12 variant LFA3-Fc fusion proteins were designed and expressed in mammalian cells for further analysis (CM1d1→CM6d1 and ML1d1→ML6d1). CM1d1 to CM6d1 Fc fusion proteins a variant LFA3 extracellular domain (SEQ ID NOs: 30-35, respectively) fused to a human IgG1 Fc region (SEQ ID NO: 16) (Table 2). Similarly, ML1d1 to ML6d1 Fc fusion proteins comprise a variant LFA3 extracellular domain (SEQ ID NOs: 36-41, respectively) fused to a human IgG1 Fc region (SEQ ID NO: 16) (Table 2). The corresponding nucleotide sequences are provided in Table 3.

Figure 5B:
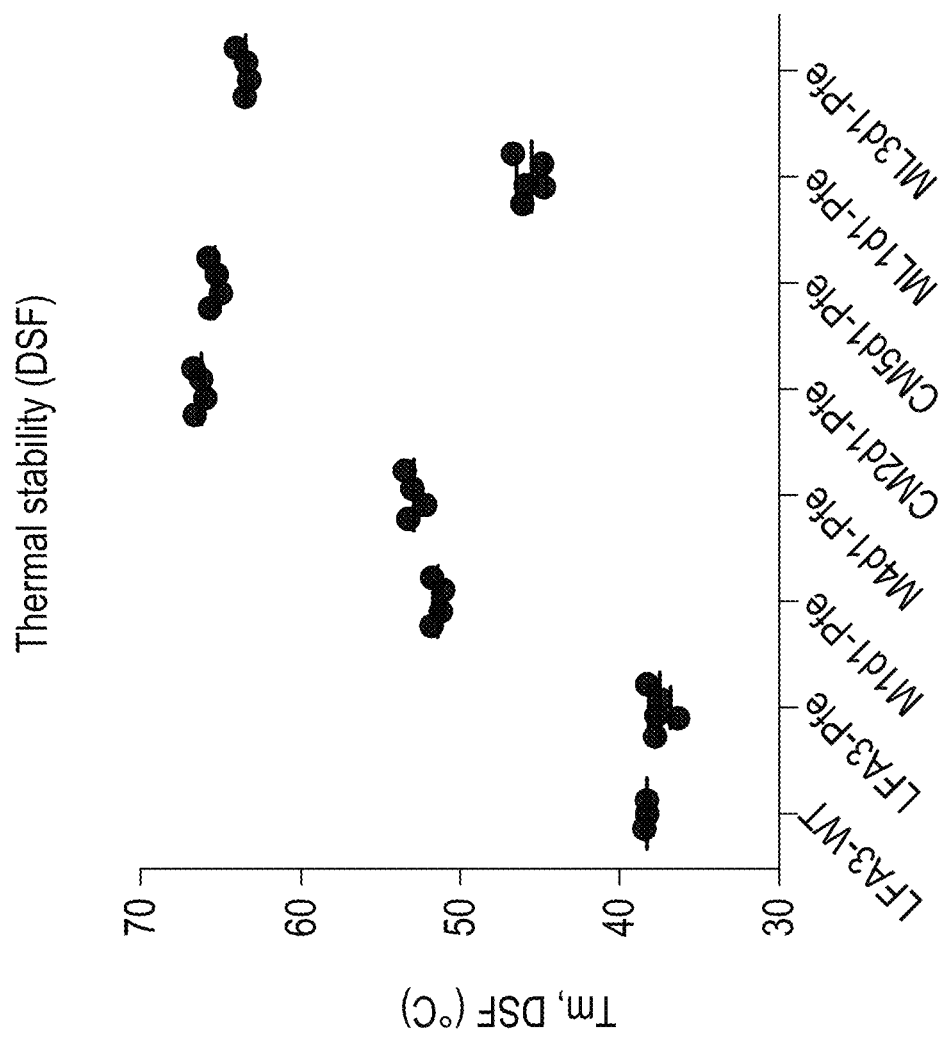

The clones identified from the second-generation Loop library were expressed as Fc fusion proteins and assessed for thermal stability using a differential scanning fluorometry (DSF) (FIG. 5B) and binding affinity to recombinant CD2 protein by SPR using a Biacore binding assay (FIG. 5A). The highest affinity clones assessed had apparent affinities in the range of 60-100 nM (FIG. 5A). The highest affinity clones assessed had an affinity increase of ~20-fold compared to the parental WT LFA3-Fc protein and 10-fold over the M1d1-Pfe (also referred to as "LFA3-Fc M1d1") and M4d1-Pfe variants (FIG. 5A). Variants CM2d1-Pfe, CM5d1-Pfe, and ML3d1-Pfe have increased thermostability by DSF compared to the wild type constructs (WT LFA3-Fc and WT LFA3-Pfe) as well as the parental variant constructs (M1d1-Pfe and M4d1-Pfe) (FIG. 5B).

Figure 6A:
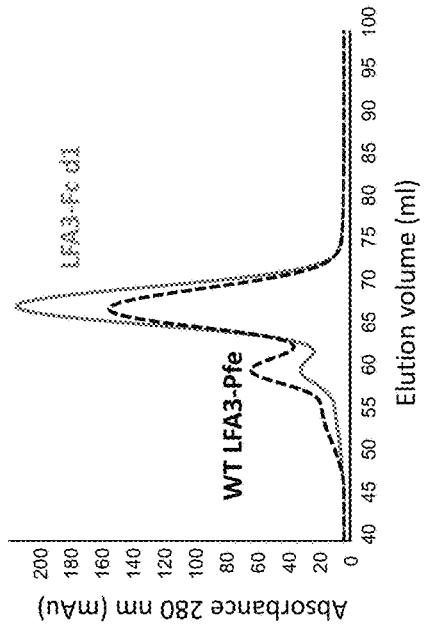
FIGS. 6A-6D: Rational design of domain boundary variant d1. Exemplary characterization of LFA3-Fc proteins containing an additional endogenous leucine residue (d1) for monomeric expression and thermal stability with either a wild-type LFA3 sequence (LFA3-Fc d1) or the stability M-variants (M1-d1 (also referred to as "M1d1") and M4-d1 (also referred to as "M4d1")). "WT" in FIG. 6C refers to LFA3-Fc WT. "Pfe" in FIG. 6D refers to WT LFA3-Pfe.
Figure 6B:
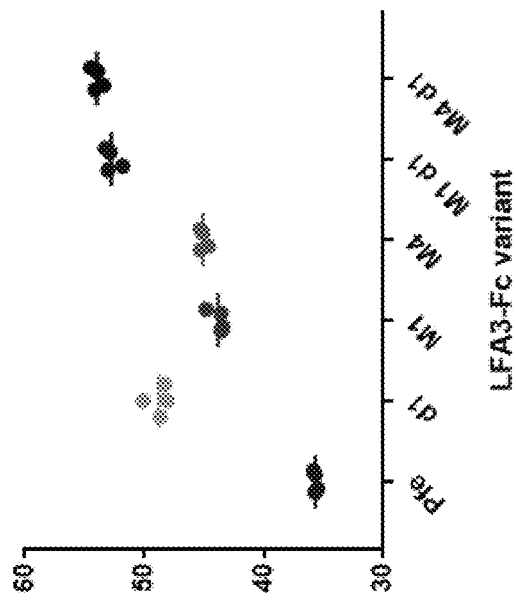
Figure 6C:
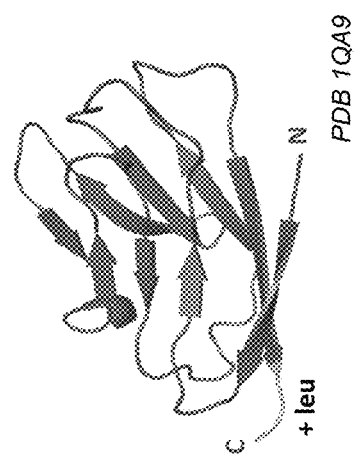
Figure 6D:
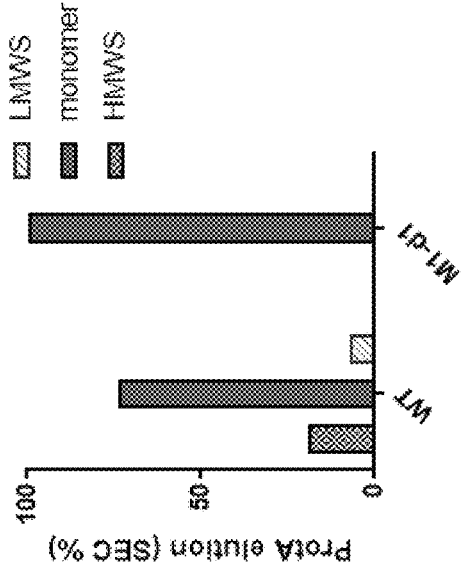

Rational design based on structural analysis was used to extend the c-terminal boundary of the LFA3 domain included in the expression construct (FIG. 6A). Constructs encoding an additional c-terminal leucine residue on the wild-type LFA3 domain (LFA3-Fc d1) or M-variants (M1-d1 and M4-d1) where expressed and purified. LFA3-Fc d1, M1-d1 (also referred to as "M1d1"), and M4-d1 (also referred to as "M4d1") Fc fusion proteins comprise a LFA3 domain (SEQ ID NOs: 24, 26, and 28, respectively) fused to a human IgG1 Fc region (SEQ ID NO: 16) (Table 2). The corresponding nucleotide sequences are provided in Table 3. It was found that the d1-variant had decreased aggregate formation compared to protein expressed with the previously published domain boundary for an LFA3 Fc fusion protein, and increased thermal stability (FIGS. 6B and 6D). The addition of the domain boundary modification (d1) to the M1 or M4 background further increased the monomeric fraction of protein out of cell culture (FIG. 6C) and the thermal stability as measured by DSF (FIG. 6D).

Variants including an additional one (d1, +L) (FIG. 7A) or six (d3, +LESLPS) (FIG. 7B) endogenous amino acids were produced as Fc fusion proteins and characterized for stability and binding affinity. M1-d1 and M1-d3 (also referred to as "M1d3") Fc fusion proteins comprise a LFA3 domain (SEQ ID NOs: 26 and 27, respectively) fused to a human IgG1 Fc region (SEQ ID NO: 16) (Table 2). The corresponding nucleotide sequences are provided in Table 3. The two variants, M1-d1 and M1-d3, demonstrate similar CD2 binding affinity and in vitro thermal stability (FIGS. 7C and 7D).

An additional LFA3 variant M7 was designed to contain one additional wild type residue at position 86 relative to M1 (FIG. 8A). M7-d1 (also referred to as "M7d1") Fc fusion protein comprises a LFA3 domain (SEQ ID NO: 29) fused to a human IgG1 Fc region (SEQ ID NO: 16) (Table 2). The corresponding nucleotide sequence is disclosed in Table 3. M7-d1 was characterized to assess the monomeric fraction (FIG. 8B), thermal stability (FIG. 8C), and binding affinity to recombinant CD2 (FIG. 8D).

Variants LFA3-Fc and WT LFA3-Fc were characterized for stability and potential manufacturability attributes (Table 4 and Table 5). These assays found the M1-d1 (also known as "M1d1") variant to be significantly more stable than the wild-type Fc fusion in terms of monomeric protein expression, thermal stability, aggregation propensity, sensitivity to low pH hold, and freeze-thaw cycles (Table 4).

TABLE 4

Novel and useful molecular properties of LFA3-Fc variants

|  | WT LFA3-Fc | *M1-d1 engineered variant |
|---|---|---|
| Monomeric species off protein A (%) | 73.9% monomer 19% HMWS, 7.1% LMWS | >99% |
| Analytical SEC | 99.2% monomer | 99.6% monomer |
| Thermal stability by DSC/DSF | DSC: Tm1, 47° C. DSF: Tm1, 40° C. | DSC: Tm1, 65° C. DSF: Tm1, 60° C. |
| Forced aggregation propensity | 40° C. HMWS increases to ~23% 50° C. HMWS increases to ~29% | 40° C. no increase in HMWS 50° C. HMWS increases to ~3% |
| Low pH hold (5 hrs) | 11% HMWS, no increase in LMWS | 4% HMWS, no increase in LMWS |
| Freeze-thaw (5 cycles) | ~2% increase in HMWS | No increase in HMWS |
| Affinity by SPR to human recombinant CD2 ($K_D$) | 1.41-1.47 µM | 0.73-1.08 µM |
| Affinity by SPR to cyno recombinant CD2 ($K_D$) | 1.5 µM | 1.06 µM |

HMWS refers to high molecular weight species, and LMWS refers to low molecular weight species.
*exemplary embodiment encompassing all of the LFA3-Fc variants disclosed herein.

TABLE 5

Overview of the molecular properties of LFA3-Fc M1-d1 engineered variant

| Molecular properties | 3 predicted N-linked glycosylation sites, 1 putative deamidation site, 2 putative, isomerization sites, 1 methionine | Glycan cGE | Contains N-glycans common to antibody Fc Highly branched and sialylated (9.1 nmol sialic/nmol LFA3-Fc) |
|---|---|---|---|
| Expression | SSI pool cell line day 12 harvest yield ~150-300 mg/l | Process Impurities | rProA 39 ng/mg, HCP 293 ng/mg, DNA 27 ng/mg |
| Purification | Non-platform purification process; potential issues with low pH hold procedure and compatibility with TMAE purification step | F/T | No change after five cycles (5° C./-20° C.) |
| Viscosity | 11 cP at 150 mg/ml in MOD1 formulation | Shaking | 0.8-1.5% HMMS increase at 25 C. ~1% HMMS increase in Glu at 40 C. |
| Solubility | At least ~175 mg/ml in all tested buffers | Activity | No changes in ADCC EC50s with stability samples |
| SEC | All preps >99% SOI after Protein A. 0.8-1.5% HMMS increase at 25 C. ~1% HMMS increase in Glu at 40 C. | Immuno- genicity | Epivax immunogenicity index score -13.52; IRAMP recommendation moderate-high due to endogenous sequence |
| DSC | $T_m1$ 65° C. in Histidine buffer pH 5.8. | AC-SINS | Low AC-SINS score, Δλ max absorbance 1 |
| cGE | High purity under reducing and non-reducing conditions. No change at 5° C. and 25° C. 2-5% increase in LMMS by NRCGE at 40° C. | FcRn column elution | Low FcRn column elution time of -0.6 min |
| iCE | Complicated charge profile -15- 18 different species | Poly- specificity | DNA and insulin poly- specificity score of 1 |

Example 2: Further In Vitro and In Vivo Characterization of M1d1

Introduction

LFA3-Fc targets an important therapeutic pathway that has the potential—once optimized—to restore immunologic tolerance in Type 1 Diabetes (T1D), a disease that thus far has been largely refractory to disease-modifying interventions and therefore represents a large unmet medical need, particularly in children.

M1d1 (also referred to as "M1-d1," "LFA3-Fc M1d1," and "LFA3-Fc M1-d1") is a dimeric LFA3-Fc fusion protein, comprised of the first extracellular domain of LFA3 fused to an IgG1 Fc region. M1d1 has been engineered to contain four non-endogenous amino acids in the LFA3 extracellular domain to improve stability and manufacturability. Without wishing to be bound by theory, M1d1 may reduce the number of memory CD4 and CD8 T cells through ADCC/cytotoxicity while relatively sparing Treg and Tnaïve cells, and modulate CD2/LFA3 interaction, leading to improvement in Treg/$T_{EM}$ and Treg/$T_{CM}$ ratios in both CD4+ T cells and CD8+ T cells. M1d1 has demonstrated modulation of immune phenotype in cynomolgus monkeys consistent with proposed mechanism of action (MOA) and therapeutic hypothesis. Non-clinical studies with M1d1 suggest PK is linear and dose is proportional, and a non-GLP TK study did not reveal any safety findings beyond the anticipated reduction in lymphocytes. A summary of pharmacological properties is included below in Table 6, with data for the target CD4 memory cell population.

TABLE 6

Summary of novel and useful pharmacological properties of LFA3-Fc variants

|  | Cell binding LFA3-Fc binding correlates to CD2 expression CD4 $T_{mem}$ $K_d$ | MLR Inhibition of allo T cell response; Prolif/ cytokines CD4 $IC_{50}$ | Tet. Toxin Recall Inhibition of TT recall response; CD4 $T_{mem}$ IFNγ IFNγ $IC_{50}$ |
|---|---|---|---|
| *M1d1 | 94 pM (n = 3) | 0.302 nM (n = 8) | 1.34 nM (n = 3) |
| WT LFA3-Fc | 501 pM (n = 3) | 2.48 nM (n = 8) | 28.4 nM (n = 3) |

*exemplary embodiment encompassing all of the LFA3-Fc variants disclosed herein.

Methods

CD2 Expression Analysis

For lymphocyte subsets, human peripheral blood mononuclear cells (PBMCs) were isolated using Lymphoprep (Stemcell Technologies #07851). PBMCs from macaques were isolated using 90% Lymphoprep in PBS (Corning #21-040-CM) and resuspended in fluorescent-activated cell sorting (FACs) buffer (PBS plus 0.2% BSA (Jackson Immuno Research #001-000-173)). Human cells were blocked using Human TruStain FcX (BioLegend #422302). Two million PBMCs were stained per sample. For T-helper cell subsets, CD4 cells were isolated using Easy Sep kit (Stem Cell Technology #19052) using manufacturer's instruction and then 1 million cells were stained per sample. For surface staining, cells were fixed in intracellular (IC) Fixation buffer (Ebioscience #00-8222-49) prior to analysis. For FoxP3 staining, the human FoxP3 Buffer set (BD Pharmingen #560098) was used based on manufacturer's instructions. For human PBMCs, cells were stained with the following antibodies: CD4 BUV395, CD3 PerCp-e710, CD2 PE, CD45RO PeCγ7, CD8 FITC, CCR7 BV421, TIGIT APC, PD1 BV650, near IR viability (panel 1); or CD4 BUV 395, CD3 Percp-e710, CD2 PE, CD8 BUV 496, CD20 FITC, CD159a A647, CD25 BV421, CD127 BV605, and near IR viability. For cyno PBMCs, cells were stained as follows: CD95 BUV 395, CD4 PerCP-e710, CD2 PE, CD28 PeCγ7, CD8 BUV496, CD3 FITC, CD20 V450, CD159a APC, PD1 BV650, near-IR viability (panel 1); or CD4 Percpe710, CD3 FITC, CD25 BV421, CD2 PE, FoxP3 APC, and Near-IR viability. Cells were run on LSR Fortessa, and Quantibrite beads were run at the time of sample collection (as per manufacturer's instructions). Near infrared (JR) fluorescent reactive viability dye (Invitrogen #L34976) was used to discern viable cells. Data was expressed as the geometric mean florescence intensity (gMFI).

LFA3-Fc Competitive Binding Assay

PBMC and Subset Isolation

Trima residuals from healthy donors, from Trima apheresis collection and enriched for PBMCs, were obtained from Blood Centers of the Pacific (San Francisco, CA). PBMCs were isolated by density gradient centrifugation. Purified CD4/CD8 naïve, central memory, and effector memory populations were isolated from PBMCs by negative selection kits (StemCell Technologies).

T regulatory cells were isolated from whole blood using a CD4 Enrichment RosetteSep™ cocktail (STEMCELL Technologies) then by Florescence Activated Cell Sorting using markers CD4-Fluorescein isothiocyanate (FITC) CD127-PE, and CD25-APC. T regulatory cells are identified by $CD4^{hi}CD127^{lo}CD25^{hi}$. Isolated T regulatory cells were cultured expanded in X-VIVO medium (Lonza) in the presence of DynaBead Human Treg Expander beads (Invitrogen) for up to two weeks.

Cell Binding Assay

Following isolation, CD4 and CD8 subsets were plated at a density of $5 \times 10^4$ cells per well. Plates were spun down and resuspended in FACS buffer (PBS containing 2% BSA) containing human crystallized fragment Fc block (2 µl per well), serial dilutions of LFA3-Fc M1d1 or LFA3-Fc WT and competitor commercial anti-CD2-FITC (clone RPA2.10) to determine $K_d$. Competitor concentration was held constant ($3.23 \times 10^{-8}$ M) at a value lower than the $EC_{50}$ such that the competitor antibody could still be detected but was able to be competed off. Cells were incubated for 2 hours on ice. Cells were washed with FACS buffer three times and resuspended in 100 µl of FACS buffer containing viability dye. For CD4 effector and central memory distinction, CCR7-BV421 was included. After a 15-minute incubation, cells were washed with FACS buffer, resuspended in 50 µl FACS buffer and analyzed by flow cytometry.

Data Analysis $K_d$ for LFA3-Fc was calculated using Cheng Prusoff equation.

$$K_d = \frac{IC_{50}}{1 + \frac{[\text{competitor}]}{K_d \text{ competitor}}}$$

Cell binding curves were generated by plotting the geometric mean fluorescence intensity (gMFI) of competitor binding against the log of LFA3-Fc antibody concentration. Values were normalized with maximum binding being the average of samples with no competition and minimal values being samples with no competitor CD2-fluorescein isothiocyanate (FITC). Cell binding curves were generated for each of the PBMC cell subsets (FIG. 11). $IC_{50}$ values (effective concentration at 50% inhibition of maximal response) of the competitor was determined using GraphPad Prism® (Version 6.0, GraphPad Software, Inc, San Diego, CA) nonlinear-regression curve fits and a sigmoidal log of antagonist dose-response model.

MLR Assay

Donors were selected from a bank of frozen PBMCs based on complete mismatch of HLA genotypes. PBMCs from the "stimulator" donor were depleted of T cells and NK cells using a CD3 and CD56 positive selection kit. For all NK depletion assays, NK cells were also depleted from the "responder" donor using the CD56 positive selection kit. 112500 cells, or 75p, each of the stimulator and responder populations were added to wells of a 96-well U-bottom plate. Serial dilutions of LFA3-Fc protein were prepared at 3× and 75 µl of protein was added to each well. Plates were incubated at 37° C. for 5 days. Cells were spun down, washed in fluorescence-activated cell sorting (FACS) buffer (PBS containing 2% BSA), then stained with immunephenotyping antibodies for 15 minutes. The following antibodies were used: CD3 (BUV496), CD4 (BUV395), CD8 PerCp-e710, CD45RO PeCγ7, CD45RA FITC, CD25 PE-CF594, CD56 BV421, CD2-PE, and Near-IR viability. 10 µl of CountBright™ beads were added to each well immediately before flow cytometry analysis.

Absolute counts of CD4 memory, CD4 naïve, CD8 memory, CD8 naïve and CD56 NK cells were calculated. Percent response was reported for CD4 memory populations and calculated as:

$$\% \text{ response} = 100 \times \frac{(\text{response} - \text{unstimulated})}{(\text{stimulated} - \text{unstimulated})}$$

Percent inhibition of allogenic response was calculated as 100 minus the percent response. Values were plotted against the log of LFA3-Fc antibody concentration. Assay response was determined as a function of absolute counts of memory cells. $EC_{50}$ values were determined using GraphPad Prism® (Version 6.0, GraphPad Software Inc., San Diego, CA) nonlinear-regression curve fits and a sigmoidal log of agonist dose-response model.

TT Recall Assay

PBMCs isolated from Trima residuals were screened for reactivity to tetanus toxoid (Astarte Biologics). Strong positive responders were banked for use in TTR assays. In a 96-well U-bottom plate, 200 000 PBMCs per well were plated in 100 µl. LFA3-Fc polypeptides were prepared at 4× and 50 µl of each LFA3 protein was added to each well. 50 µl of tetanus toxoid protein (1 µg/mL) was added to each well and incubated at 37° C. for 5 days. Plates were centrifuged for 5 min at 16000 rpm. 125 µl of the supernatant was collected to analyze IFNγ production via ELISA. Cells were spun down, washed in FACS buffer (PBS containing 2% BSA), then stained with immunophenotyping antibodies for 15 minutes. The following antibodies were used: CD3 (BUV496), CD4 (BUV395), CD8 PerCp-e710, CD45RO PeCγ7, CD45RA FITC, CD25 PE-CF594, CD56 BV421, CD2-PE, and Near-IR viability. 10 µl of CountBright™ beads were added to each well immediately before flow cytometry analysis.

Concentration of IFNγ was used to determine percent response. Percent response was calculated as described above for the MLR assay. Percent inhibition of memory recall response was calculated as 100 minus the percent response. Values were plotted against the log of LFA3-Fc antibody concentration. $EC_{50}$ values were determined using GraphPad Prism® (Version 6.0, GraphPad Software Inc., San Diego, CA) nonlinear-regression curve fits and a sigmoidal log of agonist dose-response model.

PK Assay

Standards and quality controls (QCs) were prepared in cynomolgus monkey serum and then diluted 20-fold for the MRD in assay buffer (Scytek Superblock with 0.5M NaC). Samples were also diluted according to the MRD in assay buffer. Any additional dilution of the samples was performed in assay buffer containing 5% monkey serum and loaded onto a 96-well PCR plate. Biotinylated capture antibody (anti-LFA3, Invitrogen, MA1-19503) and AF647-labeled detection antibody (donkey anti-human IgG H+L, Jackson ImmunoResearch, 709-005-149) were prepared at 50 µg/mL and 1 µg/mL respectively and loaded onto a separate 96-well PCR plate. Plates, Gyros 1000 CDs, and wash buffers were set up on the Gyrolab instrument for processing and analysis.

Results

In Vitro Analyses

Figure 9:
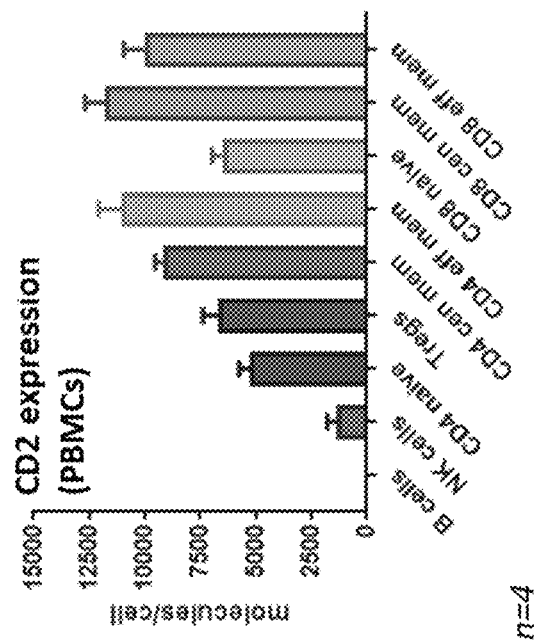
FIGS. 9 and 10: Exemplary graphs depicting CD2 levels on human PBMC resting (FIG. 9) and after TCR activation with anti-CD3/CD28 beads (FIG. 10). Mean±SEM from 4 donors is shown in FIG. 9, and a single donor is shown in FIG. 10. Data is expressed as the mean number (+/−SD) of molecules per cell. NK=natural killer; eff mem=effector memory; cen mem=central memory; Tregs=T regulatory.
Figure 10:
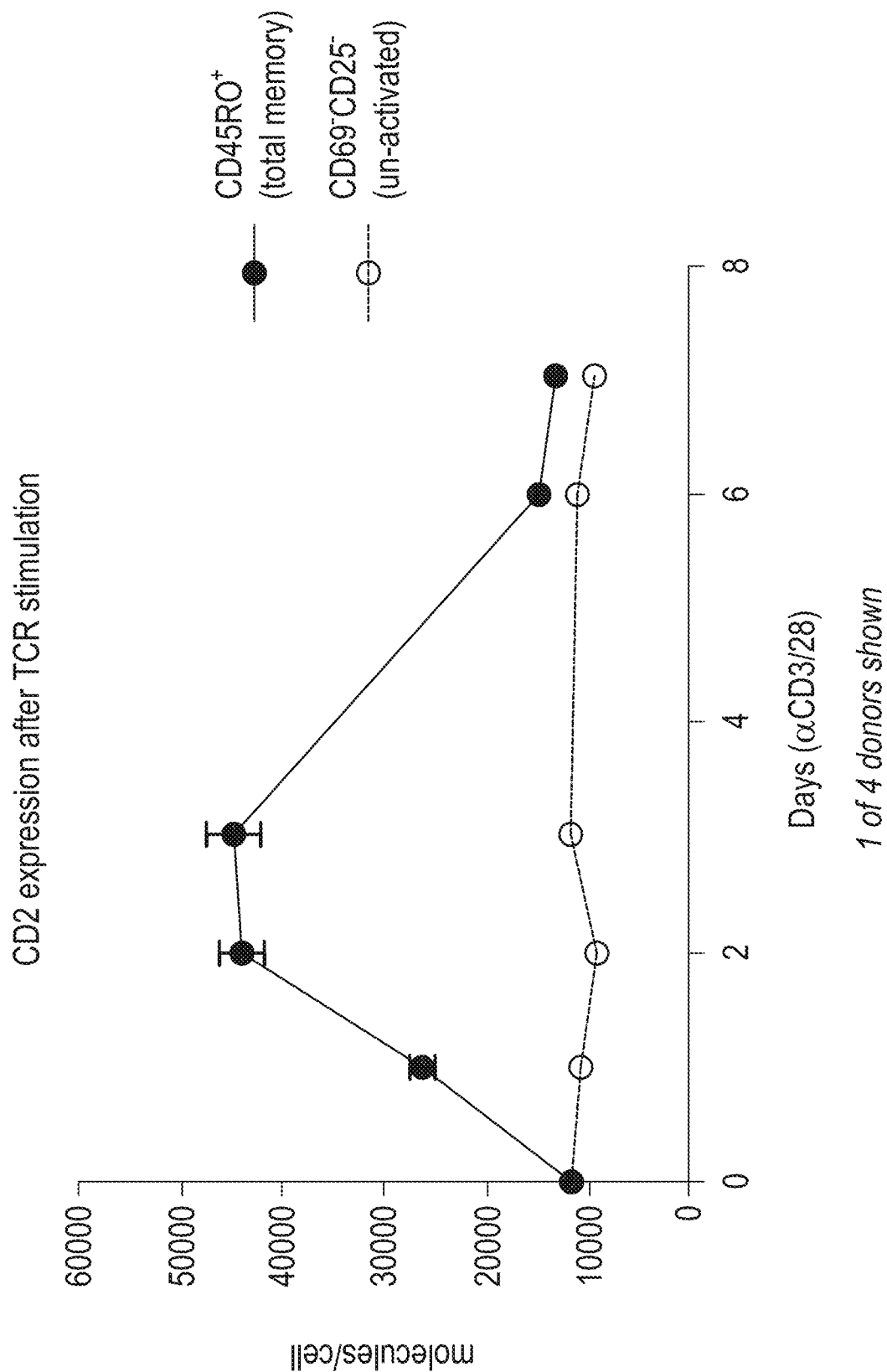
Figure 12A:
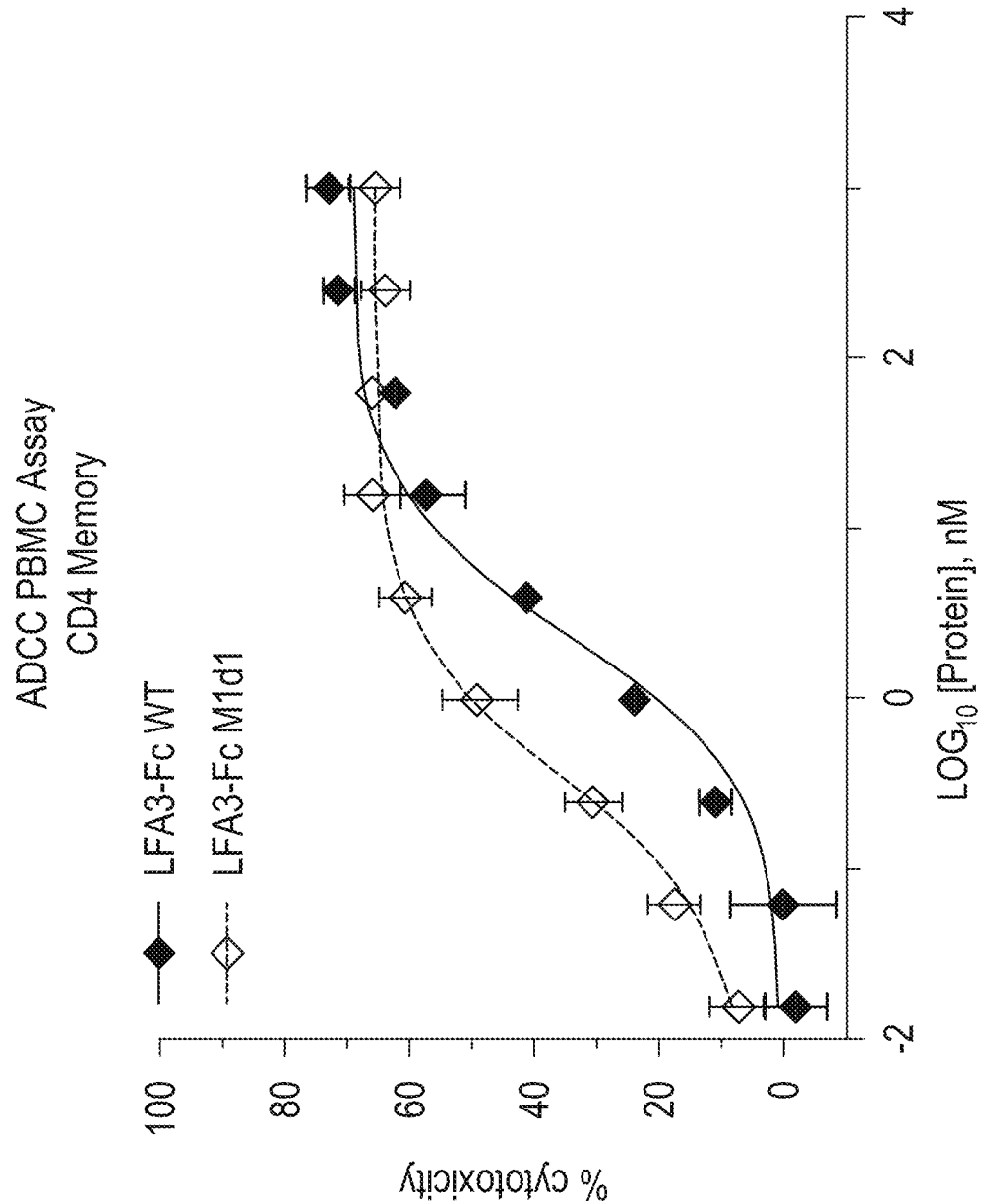
FIGS. 12A-12E: Exemplary human PBMC ADCC assay. PBMCs were co-cultured with increasing amounts of LFA3-Fc protein (LFA3-Fc M1d1 or LFA3-Fc WT), and cytotoxicity of memory CD4 (e.g., CD4 CD45RO+) cells is plotted in FIG. 12A. EC50 across donors is shown in FIG. 12B. Exemplary concentration dependent cytotoxicity of CD4 non-memory cells (e.g., CD4 CD45RO−), CD8 memory cells (e.g., CD8 CD45 RO+) and CD8 non-memory cells (e.g., CD8 CD45RO−) by LFA3-Fc proteins is depicted in FIG. 12C-12E. Data points represent the mean (n=5)+/− SEM.
Figure 12B:
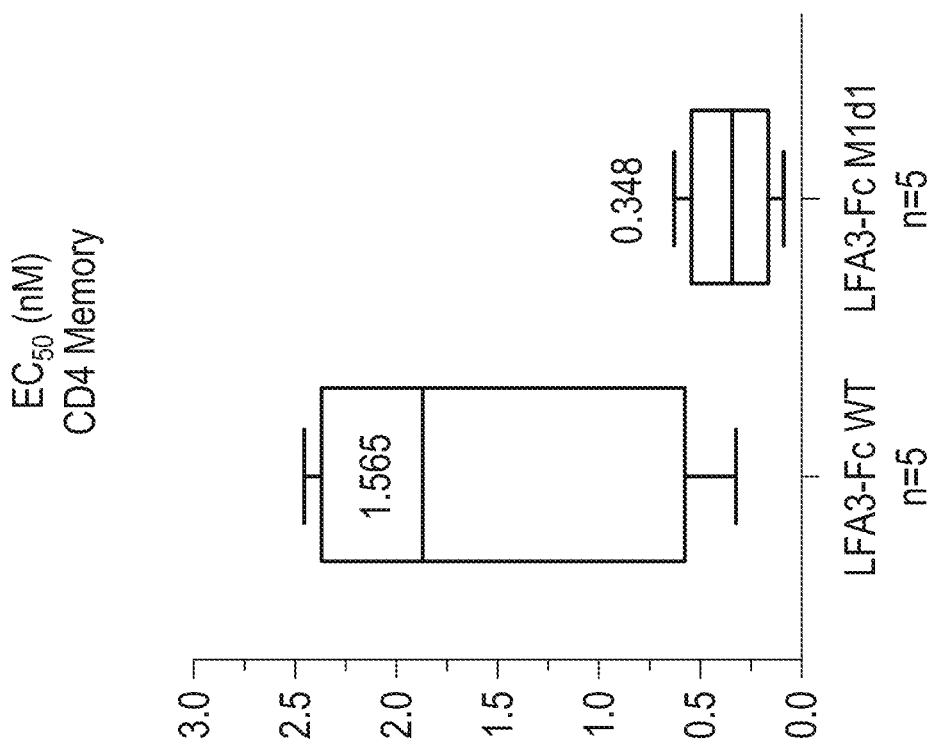
Figure 12C:
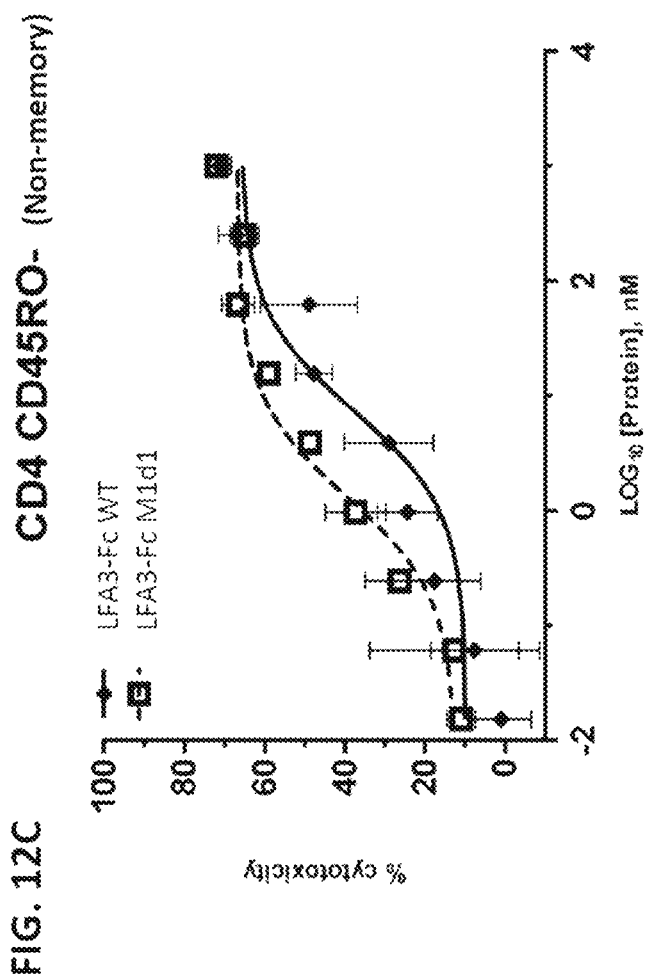
Figure 12E:
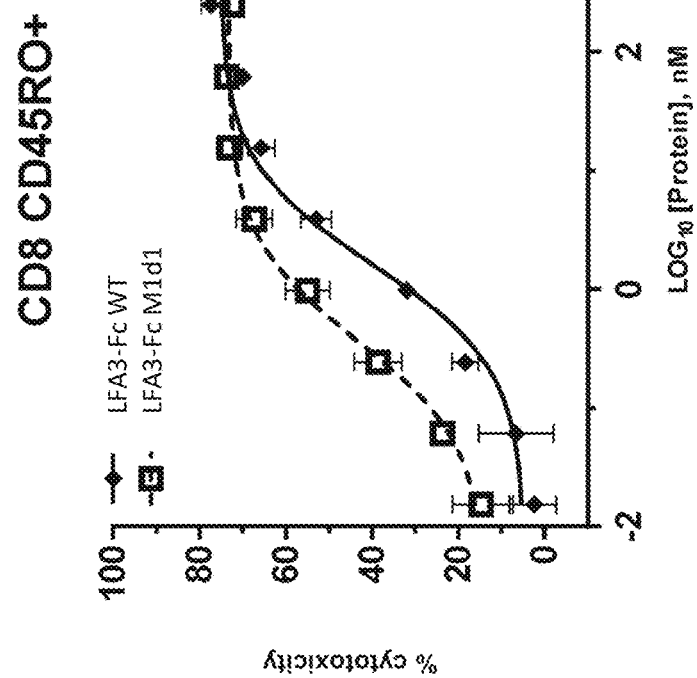
Figure 12D:
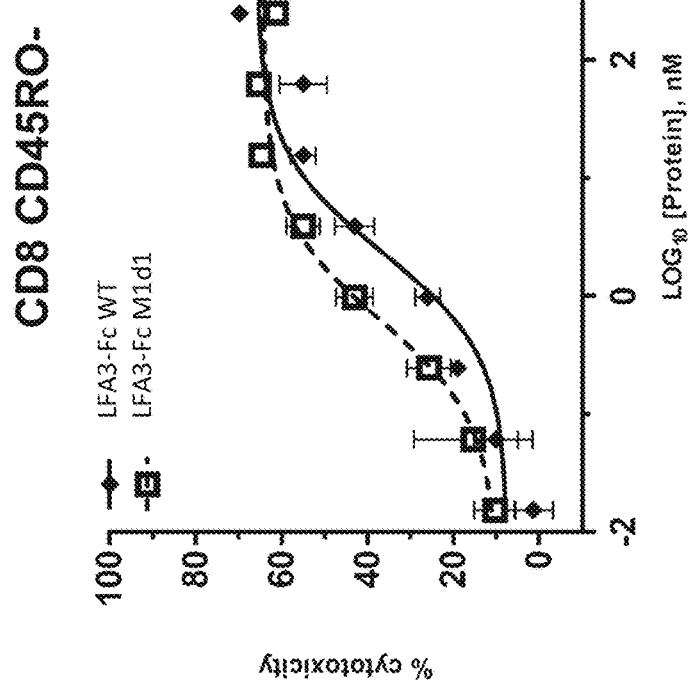

A key driver of tissue destruction and pathology in T1D are CD4+ $T_{EM}$ cells. While CD2 is expressed on all T cells, CD2 is expressed at highest levels on $T_{EM}$ cells. CD2 expression is increased a further 5-fold following TCR activation. CD2 levels (molecules per cell) on human cells are shown in FIGS. 9 and 10. M1d1 binding (max gMFI) correlates with level of CD2 expression on T cells. M1d1 has an IgG Fc with FcR binding effector function. In vitro pharmacology was characterized through: i) cell binding assays, ii) primary ADCC assay, iii) purified NK cell cytotoxicity assay, iv) inhibition of CD4 and CD8 proliferation from allogeneic stimulation in a mixed lymphocyte reaction (MLR) and, v) inhibition of CD4mem IFNγ production in an antigen recall assay using tetanus toxoid. Additionally, M1d1 may have non-ADCC dependent mechanisms of action. In vitro, this was demonstrated through depletion of NK cells from MLR assay, as well as use of Fc-effector function variant molecules. In all the in vitro assays, M1d1 was compared to WT LFA3-Fc molecule as a benchmark. Additional controls included an isotype control (mAb negative control, no Fc mutations), and an effector function variant of M1d1-Fc (eff null) that had no activity/inhibition in any of the below assays (data not shown). Without wishing to be bound by theory, these in vitro assays assessed the mechanisms of action of M1d1, which include the preferential targeting of $CD2^{hi}$ memory T cells, and subsequent inhibition of memory cell responses.

CD2 Expression Analysis

All T cells express CD2. However, the absolute expression differs on different cell subsets, with memory T cells expressing greater levels of CD2 than naïve T cells (FIG. 9). B cells do not express CD2, and NK cells express heterogeneous low levels of CD2. After activation, CD2 expression increased ~5-fold, and then returned to basal levels within one week (FIG. 10). This expression profile provides a window within which CD2hi $T_{EM}$ cells could be targeted while sparing Treg and Tnaïve cells.

In human PBMCs, quantification of CD2 molecules demonstrated the greatest number of molecules on CD4 and CD8 memory cells with specifically CD4 central memory ("cen mem") expressing an average of 9220 molecules; human CD4 effector memory ("eff mem") expressing an average of 11,000 molecules; human CD8 central memory expressing an average of 11,800 molecules; and human CD8 effector memory expressing an average of 10,000 molecules (Table 7, FIG. 9). Within the human CD8 memory cells, central memory had a larger number of molecules than effector memory (p=<0.05). Within the human CD4 cells, effector memory had more CD2 molecules than central memory (p=<0.05).

TABLE 7

CD2 quantification on lymphocyte subsets in human PBMCs

|  | B cells | NK cells | CD4 naïve | Tregs | CD4 cen memory | CD4 eff memory | CD8 naïve | CD8 cen memory | CD8 eff memory |
|---|---|---|---|---|---|---|---|---|---|
| average | 28.6 | 1370 | 5280 | 6720 | 9220 | 11000 | 6510 | 11800 | 10000 |
| SD | 2.34 | 441 | 496 | 668 | 335 | 1070 | 472 | 912 | 919 |

Cen memory = central memory;
eff memory = effector memory;
Tregs = T regulatory

Figure 17:
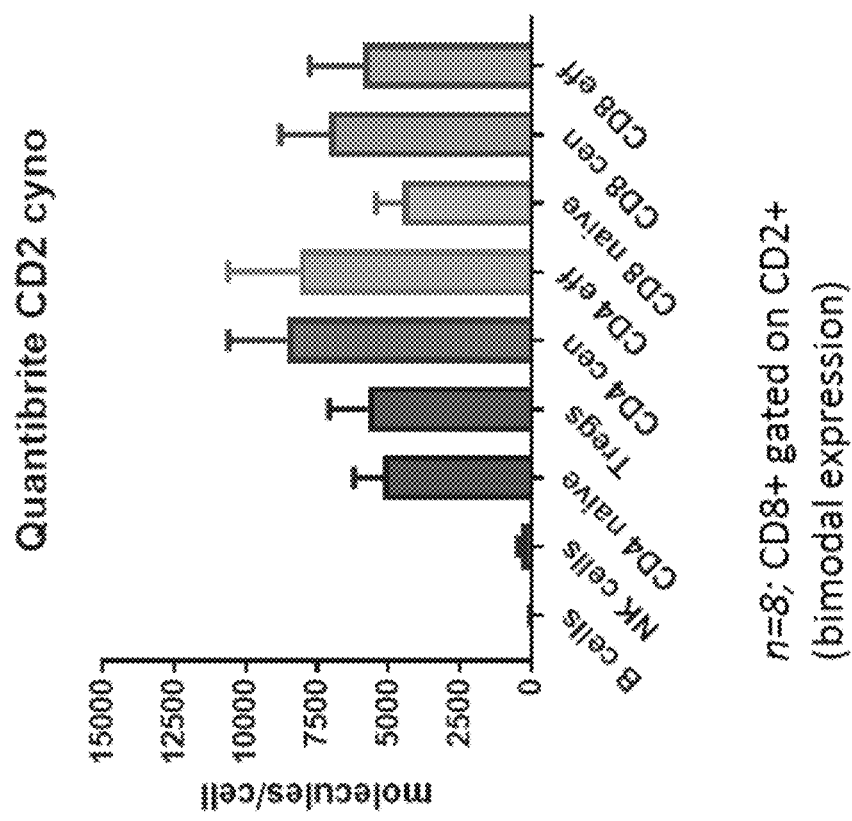
FIG. 17: Exemplary CD2 expression on cynomolgus monkey PBMCs. N=6; data is expressed as the mean number (+/−SD) of molecules per cell. NK=natural killer; eff mem=effector memory; cen mem=central memory; Tregs=T regulatory.

CD2 expression was quantified using Quantibrite analysis (FIG. 17). As with human, cynomolgus memory T cells express higher numbers of CD2 molecules per cell than do naïve cells. In cyno, but not human, CD8+ cells had bimodal CD2 expression, and ~10-20% were CD2 negative. Quantification of CD2 molecules demonstrated greatest number of molecules on CD4 and CD8 memory cells, with CD4 central memory cells expressing 8,570 molecules and CD4 effector memory expressing 8,140 molecules and CD8 central memory expressing 7,100 molecules and CD8 effector memory expressing 5,880 molecules (FIG. 17, Table 8).

TABLE 8

CD2 quantification on lymphocyte subsets in cynomolgus PBMCs.

|  | B cells | NK cells | CD4 naïve | Tregs | CD4 cen memory | CD4 eff memory | CD8 naïve | CD8 cen memory | CD8 eff memory |
|---|---|---|---|---|---|---|---|---|---|
| Average | 42.1 | 374 | 5200 | 5730 | 8570 | 8140 | 4510 | 7100 | 5880 |
| SD | 11 | 121 | 1020 | 1360 | 2040 | 2470 | 945 | 1690 | 1890 |

Negligible expression of CD2 was noted in both human and cyno B cells with 28.6 and 42.1 molecules, respectively. Human naïve CD8 and CD4 cells and Tregs have 6,510, 5,280 and 6,720 molecules, respectively, thus representing the lowest number of CD2 molecules within T lymphocyte subsets in human PBMCs. Cyno naïve CD8 and CD4 express 4,510 and 5,200 molecules, respectively, and thus have the lowest number within cyno T cell subsets.

Figure 25B:
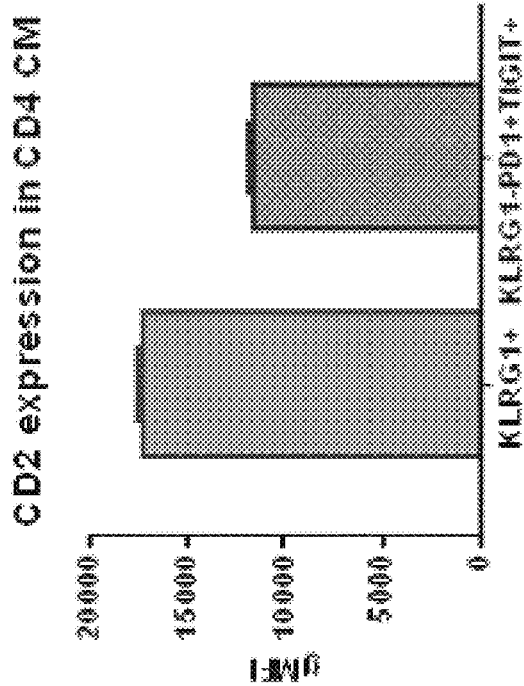
FIGS. 25A-25B: Exemplary quantification of CD2 expression on human KLRG1+ versus KLRG1-TIGIT+ PD1+ T helper cell subsets using quantibrite beads and flowcytometry.
Figure 25A:
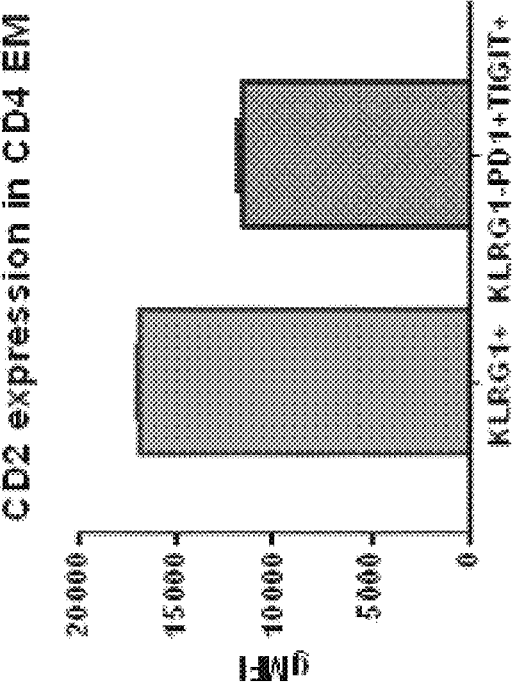

Within human CD4 memory cells, CD2 expression was 11,800 gMFI in the Klrg1-Tigit+PD1+ cells as compared to the Klrg1+ cells at 17,000 (FIG. 25A-25B). The expression of Klrg1-Tigit+PD1+ has been suggested to identify T cells that are anergic in phenotype.

Figures 26A, 26B:
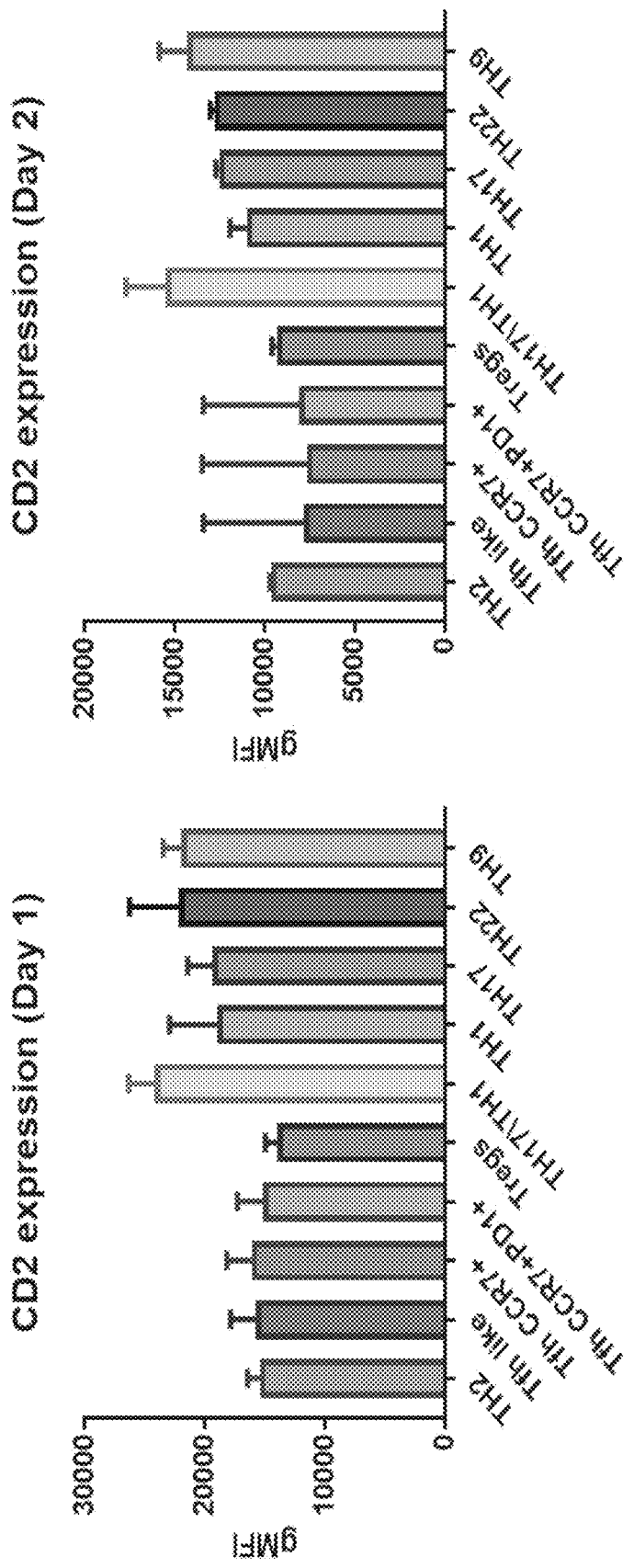
FIGS. 26A-26B: Exemplary quantification of CD2 expression on human T helper cell subsets using quantibrite beads and flow cytometry.

Within T helper cell subsets, CD2 expression was highest in the inflammatory Th17/Th1 and Th22 cells (FIG. 26A-26B) as compared to Tregs and Th2 cells.

TABLE 9

CD2 expression on human T helper subsets

|  | TH2 | Tfh like | Tfh CCR7+ | Tfh CCR7+ PD1+ | Tregs | TH17/Th1 | Th1 | TH17 | TH22 | TH9 |
|---|---|---|---|---|---|---|---|---|---|---|
| average | 12500 | 11800 | 11900 | 11600 | 11,600 | 19800 | 15000 | 16000 | 17500 | 18200 |
| SD | 3360 | 5740 | 6060 | 5260 | 2,720 | 5310 | 5170 | 4120 | 5920 | 4600 |

CCR7 = C-C chemokine receptor type 7;
PD1 = programmed cell death protein 1;
TH = T helper;
Tfh = T follicular helper;
Tregs = T regulatory In human and non-human primate PBMCs, all T cell subsets express CD2. Within the T cell compartment, non-regulatory memory T cells express the most CD2 molecules per cell, approximately 1.5-2-fold more CD2 molecules per cell than naïve T cells. These results indicate that important cell populations (e.g., T cells) express the target of the LFA3-Fc M1d1 therapeutic peptide. These data also indicate the immunophenotyping could be used to stratify patients for treatment with LFA3-Fc polypeptides.

LFA3-Fc Competitive Binding Analysis

The binding of LFA3-Fc to CD2 is a relatively low affinity interaction as measured by SPR (1 µM). It is difficult to achieve saturated primary T cell binding of LFA3-Fc, as wash stringency can significantly impact data. Therefore, a competitive binding assay was used with an anti-CD2 antibody to ascertain the apparent affinity of M1d1 for T cell subsets (Table 10 and FIG. 11). LFA3-Fc WT exhibited an average apparent affinity for CD4 memory cells and CD4 naïve cells of 0.501 and 0.391 nM, respectively (Table 10). LFA3-Fc Midi exhibited an average apparent affinity for CD4 memory cells and CD4 naïve cells of 0.094 and 0.054 nM respectively (Table 10). These studies demonstrate that LFA3-Fc WT and LFA3-Fc Midi bind to CD2+ cells (e.g., CD4 memory cells and CD4 naïve cells) and that LFA3-Fc M1d1 exhibits an approximately 5-fold greater affinity for cell surface CD2 than does LFA3-Fc WT. Thus, these studies demonstrate that the therapeutic polypeptide LFA3-Fc M1d1 exhibits increased affinity for the target surface marker CD2.

TABLE 10

LFA3-Fc binding to primary human T cells using competitive binding assay with an anti-CD2 antibody

| T cell Subset | Calculated Kd for RPA2.10 (nM) | Calculated IC$_{50}$ (nM) | | Calculated K$_d$ (nM) | |
|---|---|---|---|---|---|
| | | WT | M1d1 | WT | M1d1 |
| CD4 Memory | 23.7 | 2.32 | 0.55 | 0.623 | 0.148 |
| CD4 Memory | 23.7 | 1.29 | 0.25 | 0.345 | 0.068 |
| CD4 Memory | 42.0 | 0.95 | 0.12 | 0.535 | 0.067 |
| CD4 Memory average | | 1.52 | 0.307 | 0.501 | 0.094 |
| CD4 EM | 34 | 1.20 | 0.15 | 0.616 | 0.079 |
| CD4 CM | 44.7 | 0.88 | 0.11 | 0.514 | 0.064 |
| CD4 Naïve | 18.2 | 1.45 | 0.22 | 0.319 | 0.047 |
| CD4 Naïve | 23.8 | 1.09 | 0.14 | 0.463 | 0.061 |
| CD4 Naïve average | | 1.27 | 0.18 | 0.391 | 0.054 |
| CD8 Naïve | 14.8 | 0.71 | 0.09 | 0.222 | 0.030 |
| CD8 Naïve | 31.0 | 2.80 | 0.51 | 0.906 | 0.166 |
| CD8 Naïve average | | 1.76 | 0.3 | 0.564 | 0.098 |
| CD8 Memory | 11 | 0.59 | 0.12 | 0.151 | 0.031 |
| CD4 Treg (expnd'd) | 67.9 | 0.50 | 0.09 | 0.339 | 0.058 |

EM = effector memory; CM = central memory

MLR Assay

Figure 14A:
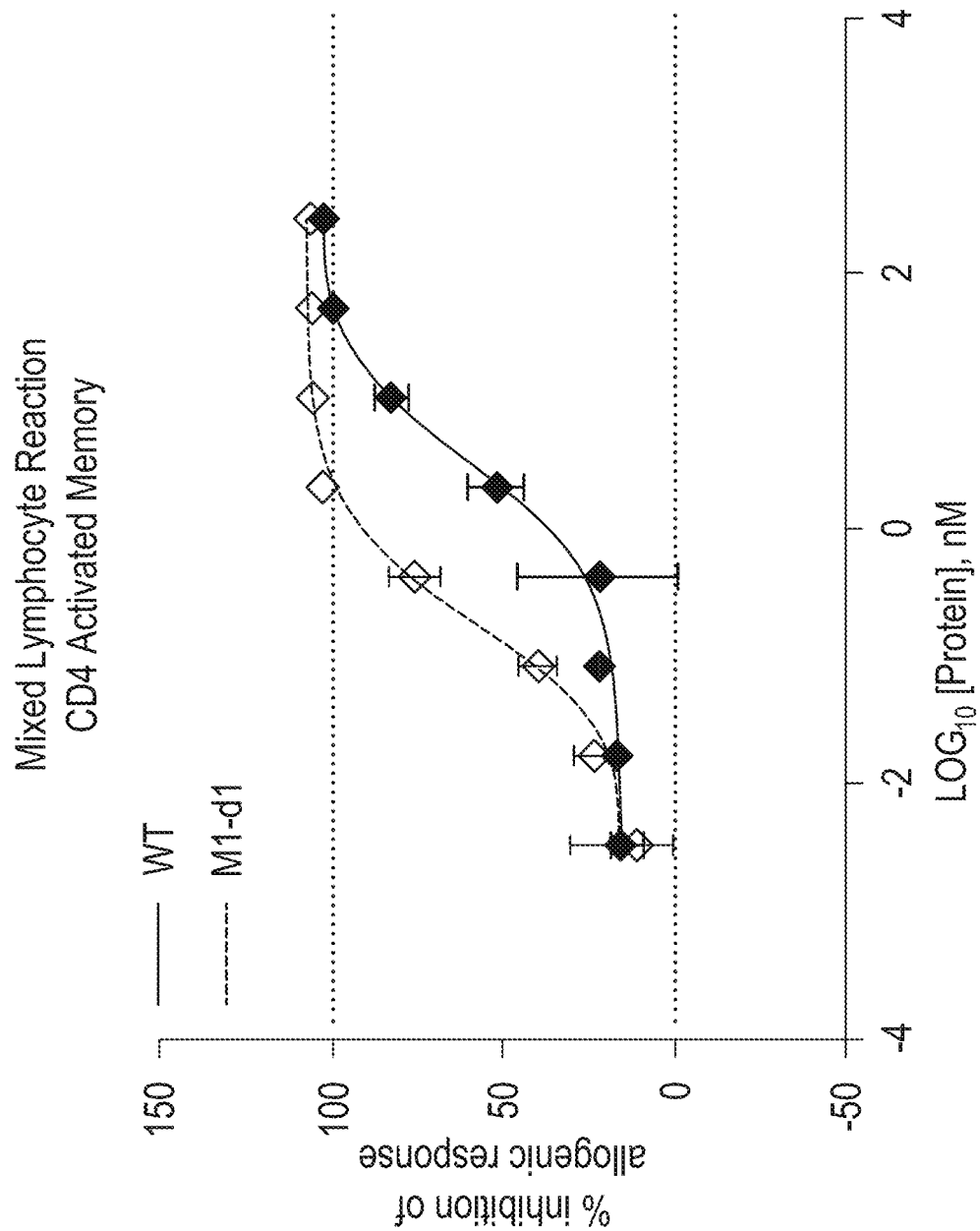
FIGS. 14A and 14B: Exemplary graphs depicting LFA3-Fc M1d1 ("M1d1") complete inhibition of CD4+ T cell expansion in response to allogeneic stimulation (MLR). Mean of triplicate wells+/−st. dev. for a single donor is shown in FIG. 14A. $IC_{50}$ across multiple donors is shown in FIG. 14B. "WT" refers to LFA3-Fc WT.
Figure 14B:
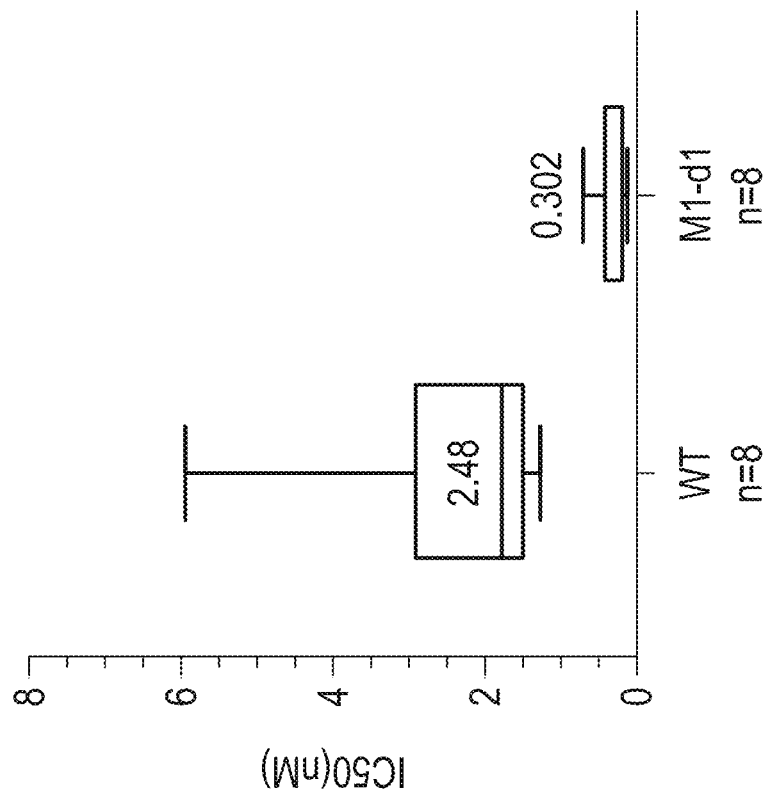

The Mixed Lymphocyte Reaction (MLR) response assesses CD4+ and CD8+ T cell response (e.g., expansion) to allogeneic stimulation, and includes responses by cells that were naïve at the time of stimulation. It is a more complex functional response and allows assessment of mechanisms beyond ADCC. M1d1 completely inhibited the expansion of CD4+ T cells (FIG. 14A) and CD8+ T cells (data not shown) in response to allogeneic stimulation and was more potent than WT LFA3-Fc (FIGS. 14A and 14B).

Figure 15A:
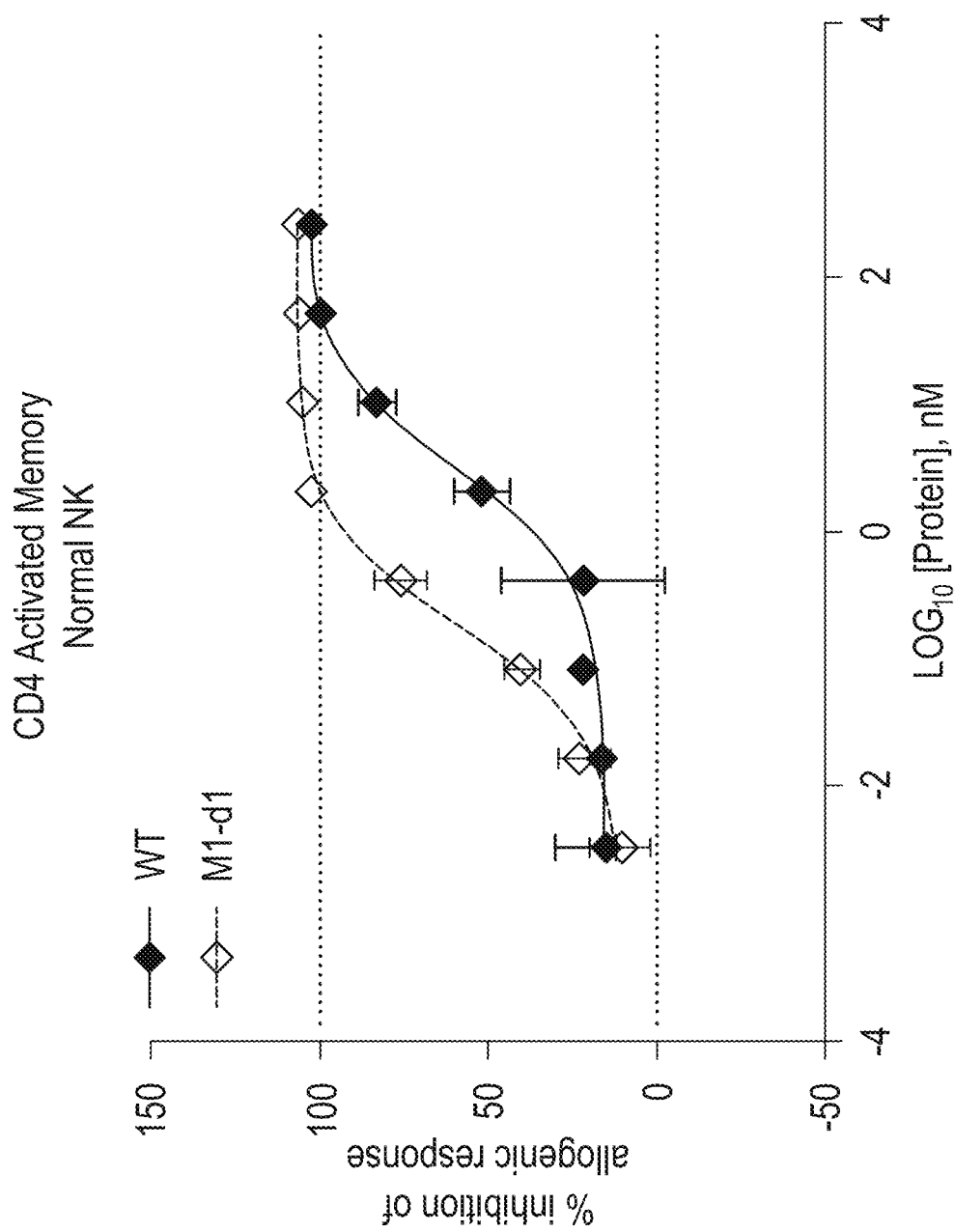
FIGS. 15A-15C: Exemplary graphs depicting LFA3-Fc M1d1 ("M1d1") inhibition of MLR in the absence of NK cells. NK cells were either untouched (FIG. 15A) or depleted (FIG. 15B) using magnetic isolation. Mean of triplicate wells+/−st. dev. for a single donor is shown in FIGS. 15A and 15B. $IC_{50}$ across repeat experiments is shown in FIG. 15C. "WT" refers to LFA3-Fc WT.
Figure 15B:
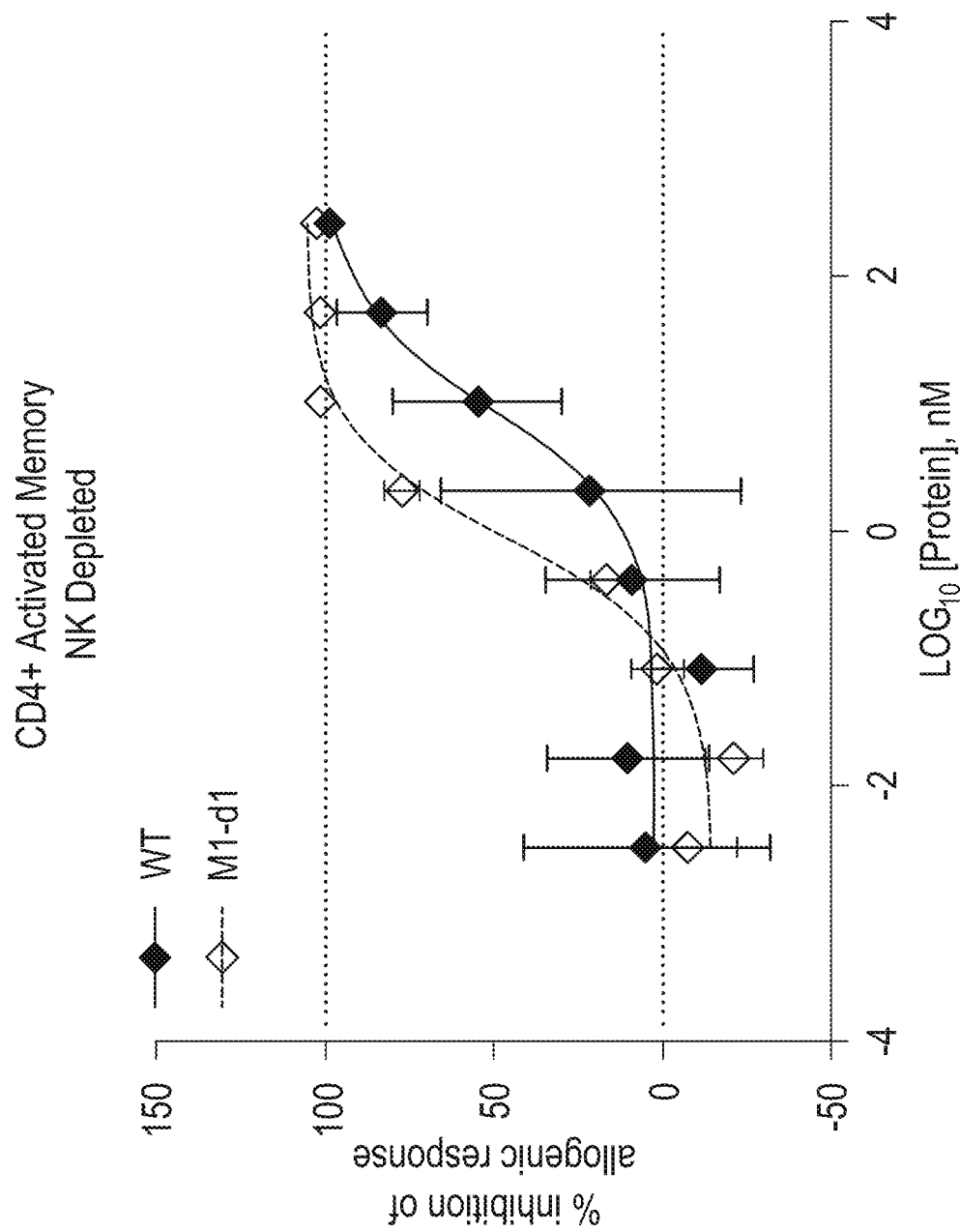
Figure 15C:
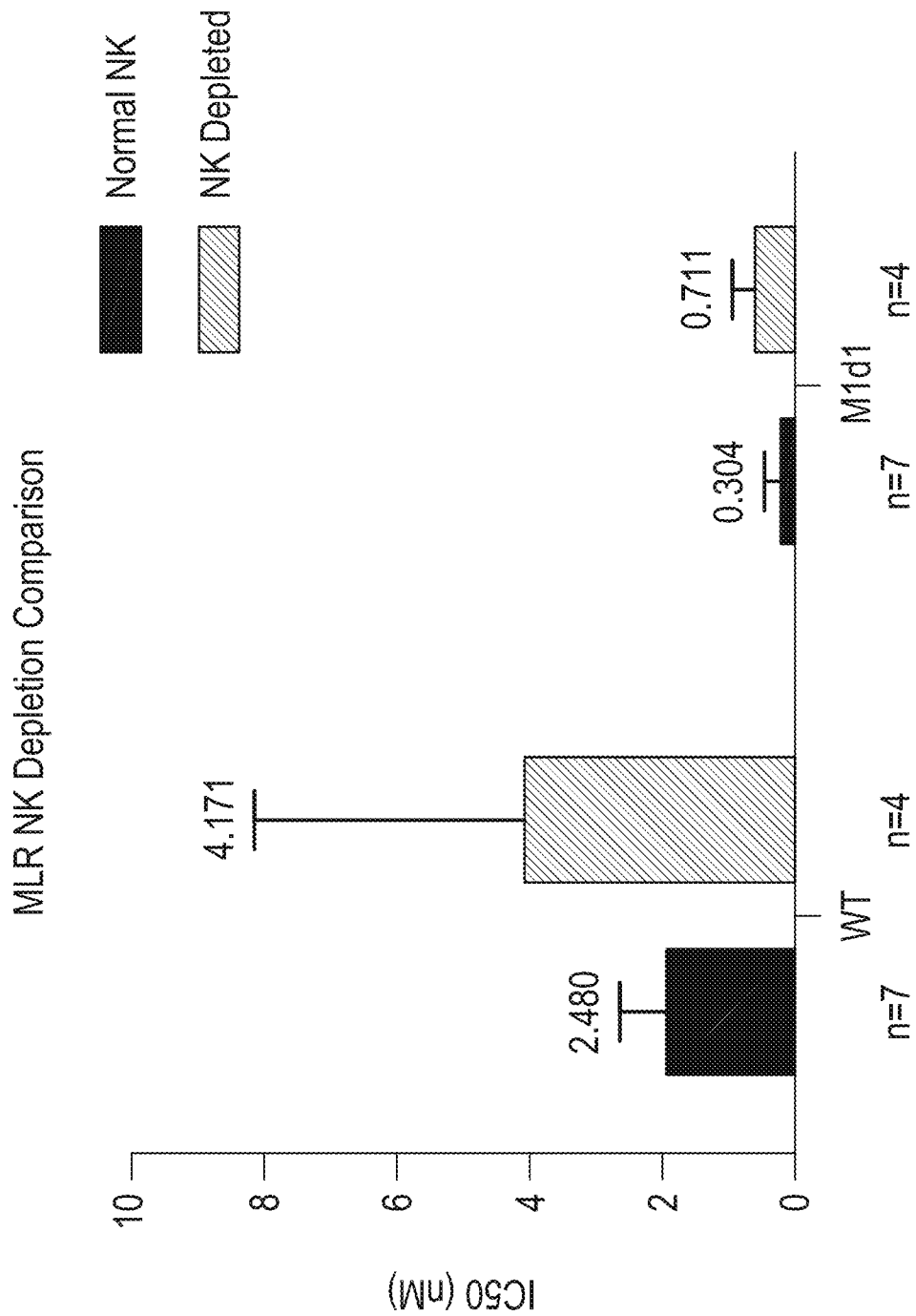

In order to assess in vitro whether M1d1 has mechanisms of action in addition to NK-mediated cell killing, NK cells were depleted from MLR assay. M1d1 inhibited CD4+ T cell expansion in MLR even in the absence of NK cells, although IC50 was increased (FIGS. 15A-15C). Additional supportive data were generated showing that LFA3-Fc effector function variants lacking CD16 binding (the FcR that is associated with ADCC) could also inhibit allogenic responses (data not shown). This is consistent with non-NK cell dependent mechanism of action associated with LFA3-Fc.

These studies demonstrate that the therapeutic polypeptide LFA3-Fc M1d1 inhibits T cell responses in allogenic MLR assays and that LFA3-Fc M1d1 has improved in vitro efficacy over that of LFA3-Fc WT.

TTR Assay

Figure 16A:
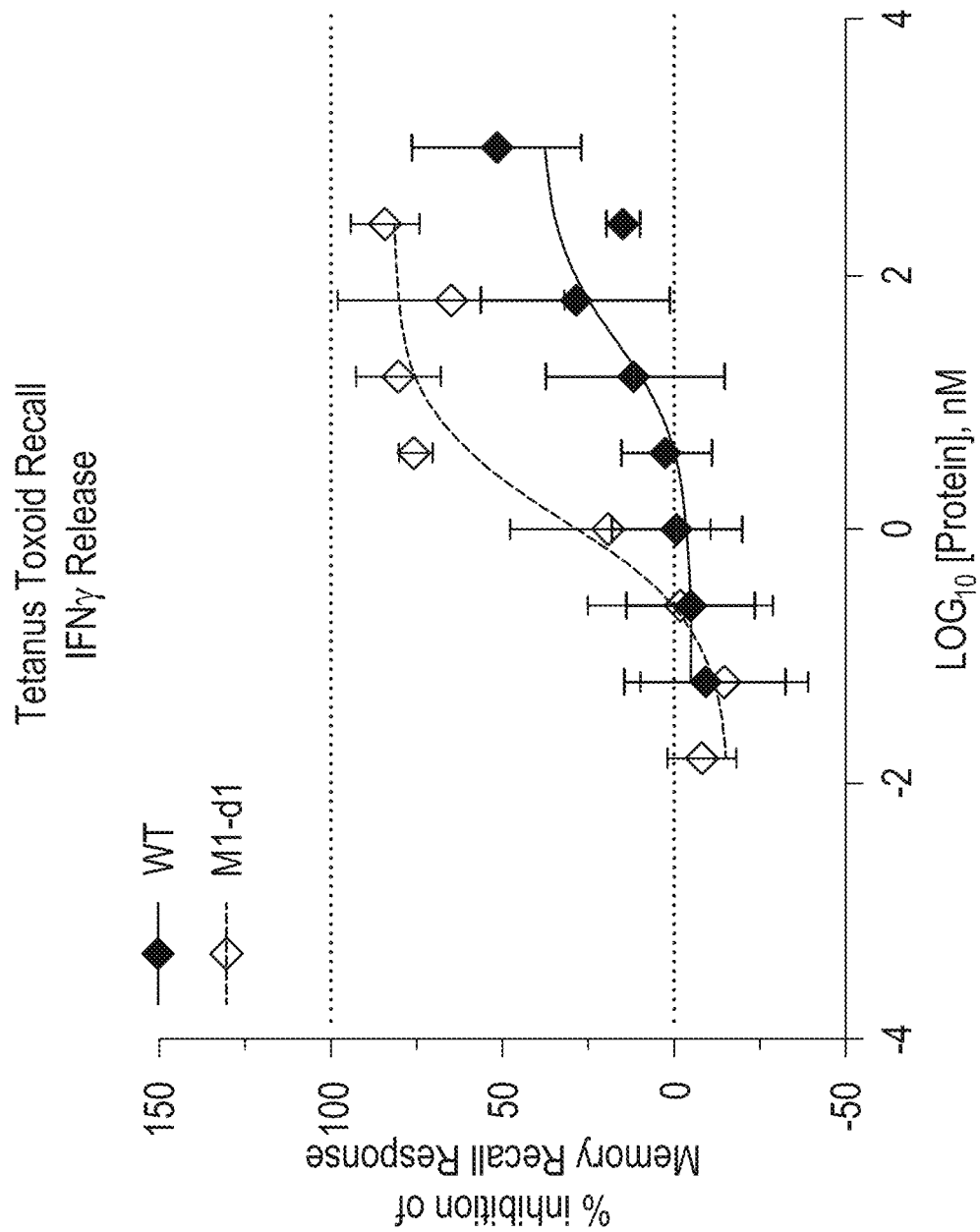
FIGS. 16A and 16B: Exemplary graphs depicting LFA3-Fc M1d1 ("M1-d1") inhibition of CD4 memory recall response to antigen tetanus toxoid (TT). Mean of triplicate wells+/−st. dev. for a single donor is shown in FIG. 16A. IC50 across multiple donors is shown in FIG. 16B. "WT" refers to LFA3-Fc WT.
Figure 16B:
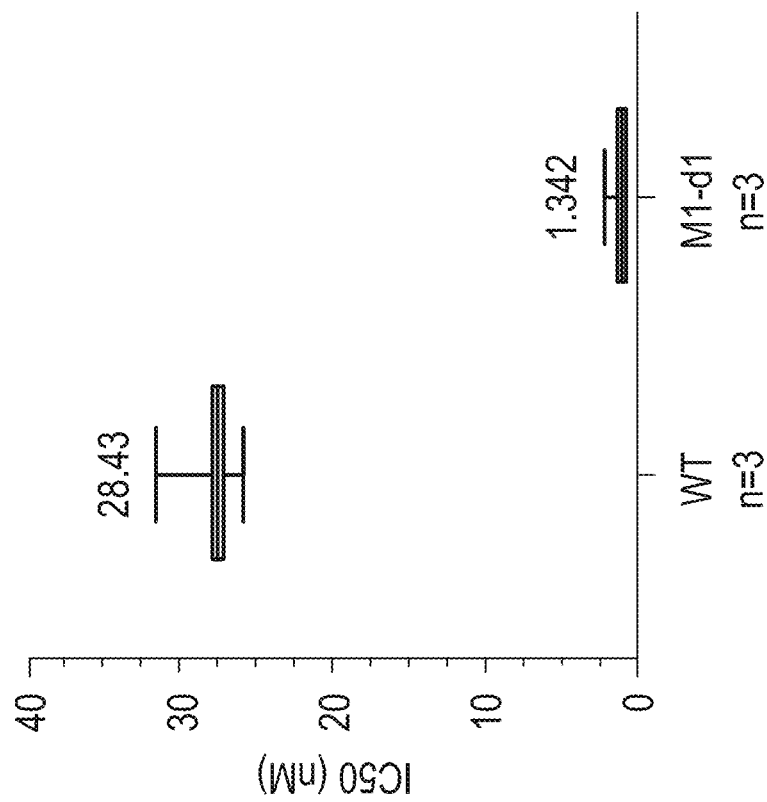

To assess inhibition of pre-existing memory cell responses, tetanus toxoid (TT) reactive donor PBMCs were stimulated with TT ex vivo. M1d1 completely inhibited ex vivo antigen specific memory cell expansion and cytokine secretion (IFNγ) in response to TT toxoid (FIGS. 16A and 16B). WT LFA3-Fc was less potent than M1d1 at inhibiting this response (FIGS. 16A and 16B). These studies demonstrate that the therapeutic polypeptide LFA3-Fc M1d1 inhibits T cell responses in TTR assays and that LFA3-Fc M1d1 has improved in vitro efficacy over that of LFA3-Fc WT.

Example 3: In Vivo Analyses

Human LFA3 does not bind to rodent CD2 but does bind non-human primate CD2. Non-human primate has been used to assess immune-modulation and memory T cell depletion from alefacept treatment (Weaver, et al (2009) Nat Med. 15(7):746-749).

Two studies have been conducted with M1d1 in cynomolgus monkey: the first was a single dose investigative study (17-MA005). The second study, 17MA057, is a repeat dose PK/PD study, designed with extensive immune-phenotype analysis to support understanding of dose response relationship, single and repeat dose effects, and recovery of the affected cells. A parallel dose response with WT LFA3-Fc was included. As no noticeable differences were observed with female monkeys, data from males and females are combined for analysis.

Single Dose IV Exploratory Toxicity Study with 8-Week Observational Phase (17MA005)

Cynomolgus monkeys were administered vehicle control or LFA3-Fc M1d1 at a dose of 0.3 mg/kg or 100 mg/kg via IV bolus injection once on Day 1. No test article-related mortality and no clinical signs were observed. There were no test article-related changes in any cell type evaluated in animals administered 0.3 mg/kg of LFA3-Fc M1d1. Test article-related changes in some lymphocyte subsets were seen in both male and female monkeys administered 100 mg/kg of LFA3-Fc M1d1 (Table 12) though all cell subsets returned to baseline values by Day 57 or before. Overall, $C_{max}$ and $AUC_{last}$ (from 1-1368 hours) values at 100 mg/kg were 3590 µg/mL and 238,00 µg*h/mL, respectively. The incidence of anti-drug antibody induction was 66% (⅔) for animals dosed with LFA3-Fc M1d1 at 0.3 mg/kg and 50% (½) for animals dosed with LFA3-Fc M1d1 at 100 mg/kg.

Peripheral blood samples were collected on Days −14, 1 (predose), 2, 4, 8, 15, 29, 43 and 57. The percentage of each lymphocyte subset was determined by flow cytometry. Administration of 100 mg/kg of LFA3-Fc M1d1 resulted in test article-related transient decreases from baseline in the number of total T cells, helper T cells, and cytotoxic T cells in the peripheral blood of at least 1 animal. There were also decreases in the numbers of naïve, central, and effector memory subsets of T helper cells and T cytotoxic cells.

Decreases were also observed in the number of CD25 Foxp3 T helper (T regulatory) cells and both the number and percentage of PD-1+ T cytotoxic cells. The range of these decreases for all subsets were 0.01-0.37×. Most of these decreases were observed on Day 15 and/or Day 29. All cell subsets returned to baseline values by Day 57 or before. There were no test article-related changes in the number of B cells and NK cells, or the percentage of PD-1+ T helper cells, or PD-1+ effector or central memory T helper and T cytotoxic cells. There were no test article-related changes in any cell type evaluated in animals administered 0.3 mg/kg of LFA3-Fc M1d1.

Figures 18A, 18B:
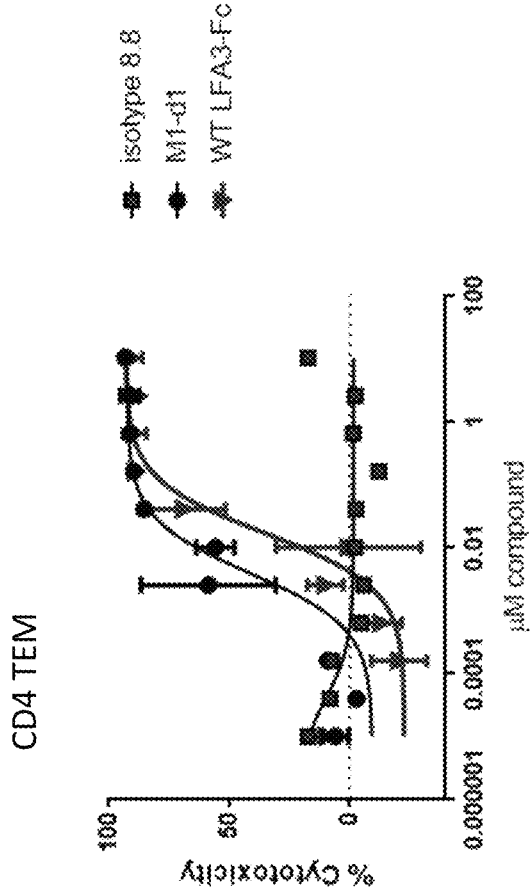
FIGS. 18A and 18B: Exemplary cyno PBMC ADCC assay. Cynomolgus monkey PBMCs were co-cultured with increasing amounts of LFA3-Fc polypeptides (M1d1 or WT), and cytotoxicity of CD4+ $T_{EM}$ cells is plotted. Mean of triplicate wells+/−st. dev. for a single donor is shown in FIG. 18A. EC50 for 3 donors is shown in FIG. 18B. "WT" refers to LFA3-Fc WT.

Cynomolgus monkey PBMCs were incubated with M1d1 or WT LFA3-Fc proteins ex vivo, and cytotoxicity was assessed using flow cytometry. M1d1 induced dose dependent CD4+ $T_{EM}$ cytotoxicity in vitro. M1d1 achieved comparable max cytotoxicity as WT LFA3-Fc and was more potent than WT LFA3-Fc molecule (FIGS. 18A and 18B). Overall, EC50s for cyno cells were higher than for human PBMCs.

4-Week IV Bolus PK/PD Study with 6-Week Observational Phase (17MA057)

The experimental design of 17MA057 is shown in FIG. 19. Cynomolgus monkeys were administered 0.03, 0.3 or 3 mg/kg/dose LFA3-Fc M1d1 or LFA3-Fc WT via IV bolus injection on Days 1, 8, 15 and 22 (i.e., once weekly for 4 weeks) followed by a 6-week observational phase. Blood samples were collected from all animals prior to the initiation of dosing, on dosing days and during the observational phase on Days 36, 43, 50, 57, 64 and 71. The percentage of each lymphocyte subset was determined by flow cytometry. Determination of changes in lymphocyte subsets following administration of LFA3-Fc M1d1 or LFA3-Fc WT was limited to total T cells, CD4+ T cells, CD8+ T cells, NK cells, B cells, CD4+ and CD8+ naïve, central and effector memory T cell and regulatory T cells. Changes were determined using absolute cell counts and the ratio to baseline values.

Changes in numbers of B cells and NK cells as compared to baseline were observed for animals administered LFA3-Fc M1d1. B cells increased for animals administered 0.3 (1.37×-1.94× baseline), 0.3 (1.41× baseline) or 3 (1.50×-2.92× baseline) mg/kg/done and NK cells decreased at ≥0.03 mg/kg/dose (0.27×-0.44× baseline) predominantly at 6 hours post-dose on 1 or more dosing days. Changes in B cells and NK cells trended back to baseline values by 24 hours post-dose for most animals.

Figure 20A:
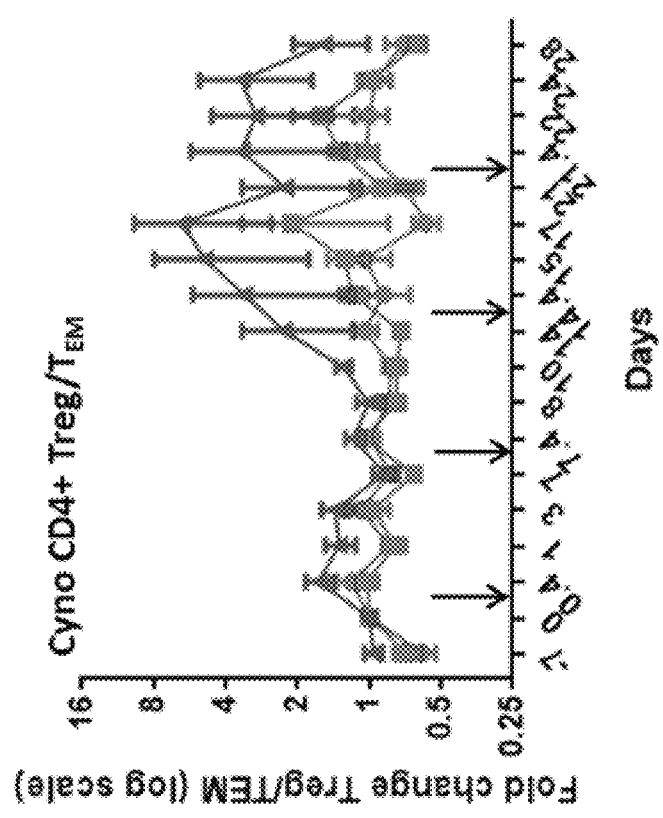
FIGS. 20A and 20B: LFA3-Fc M1d1 decreased CD4+ $T_{EM}$, and increased ratio of Tregs/CD4+ $T_{EM}$ following repeat dosing (black arrows). Exemplary data is plotted as fold change compared to pre-dose cell counts. Mean+/−SEM of 4 animals is shown.
Figure 20B:
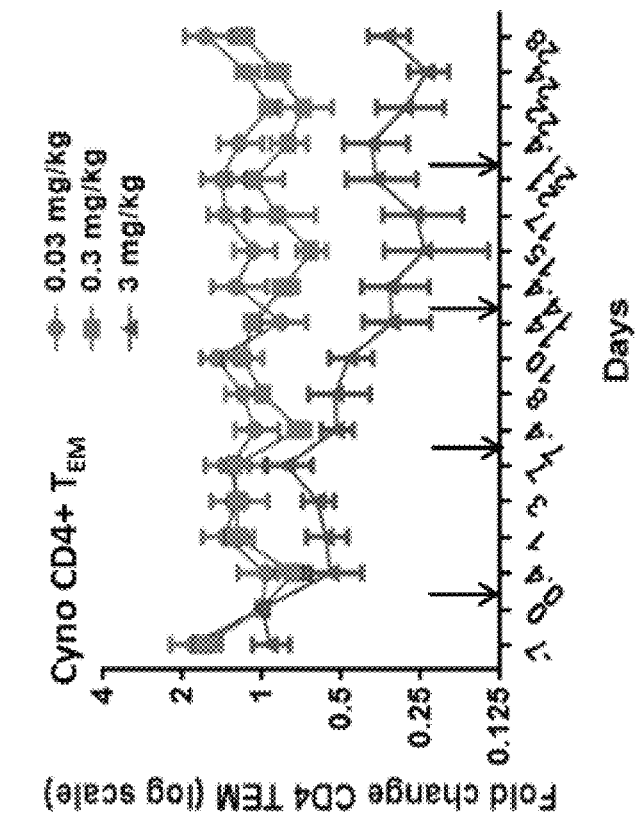
Figure 22A:
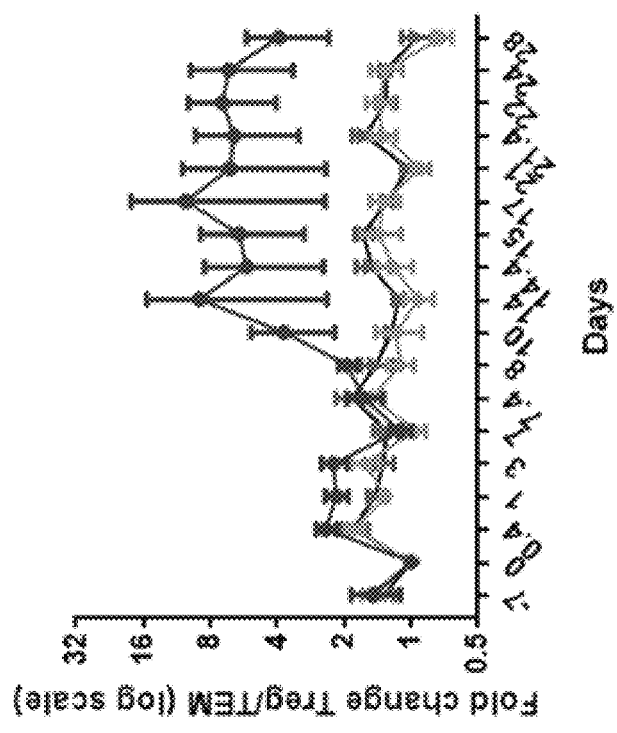
FIGS. 22A and 22B: LFA3-Fc WT decreased CD4+ $T_{EM}$ and increased the ratio of Tregs/CD4+ $T_{EM}$ following repeat dosing. Exemplary data is plotted as fold change compared to pre-dose cell counts. Mean+/−SEM of 4 animals is shown. "WT" refers to LFA3-Fc WT.
Figure 22B:
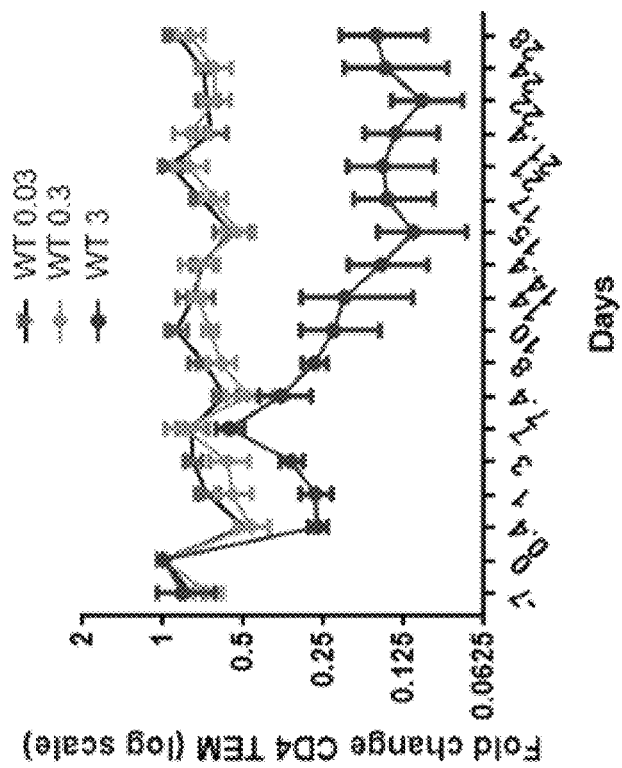
Figure 34B:
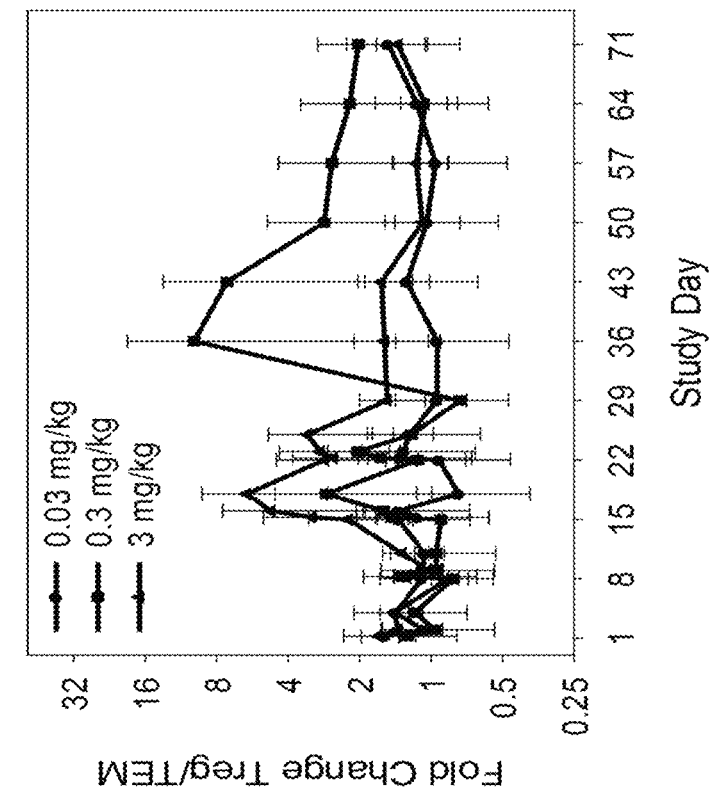
FIGS. 34A-34B: LFA3-Fc M1d1 decreased CD4+ $T_{EM}$, and increased ratio of Tregs/CD4+ $T_{EM}$ following repeat dosing. Exemplary data is plotted as fold change compared to pre-dose cell counts. Mean+/−SEM of 4 animals is shown.
Figure 34A:
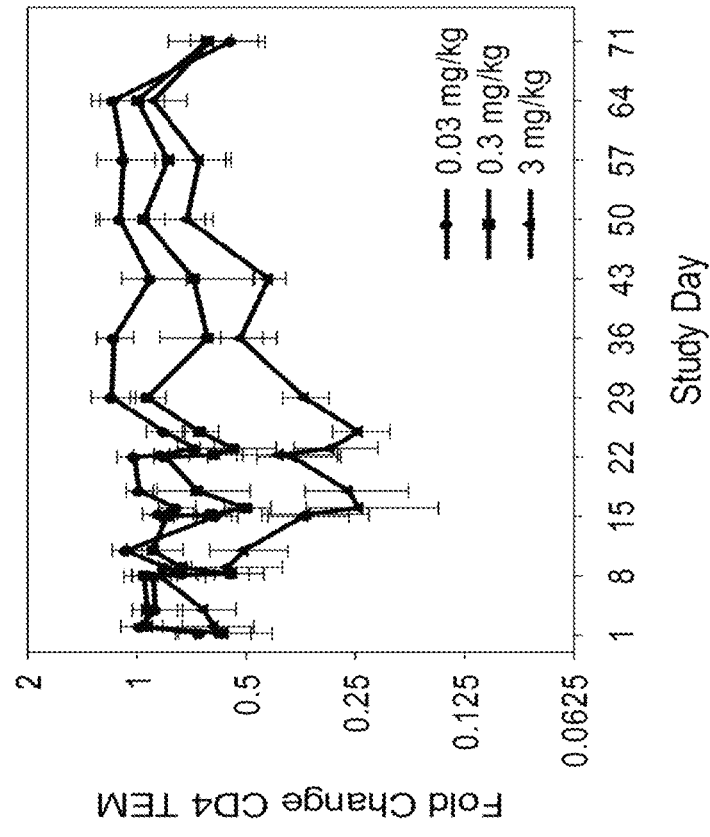
Figure 35B:
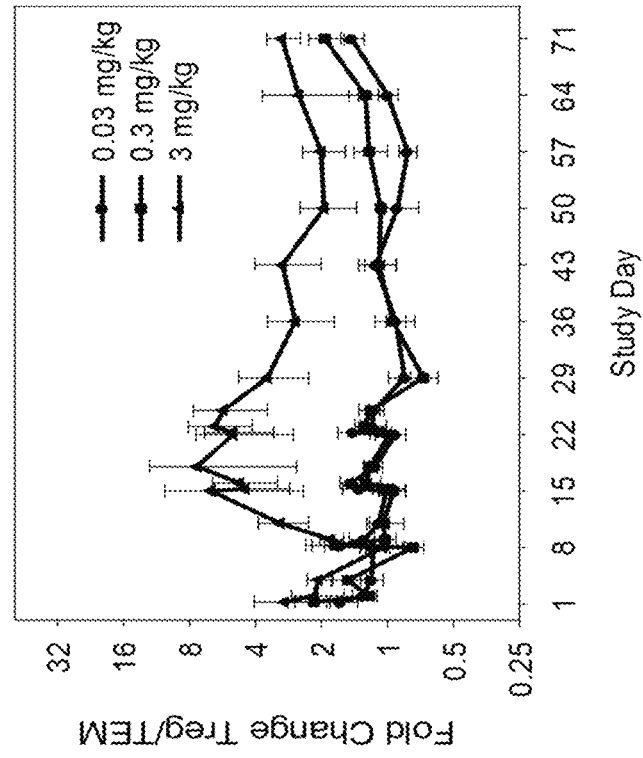
FIGS. 35A-35B: LFA3-Fc WT decreased CD4+ $T_E$ and increased the ratio of Tregs/CD4+ $T_E$ following repeat dosing. Exemplary data is plotted as fold change compared to pre-dose cell counts. Mean+/−SEM of 4 animals is shown.
Figure 35A:
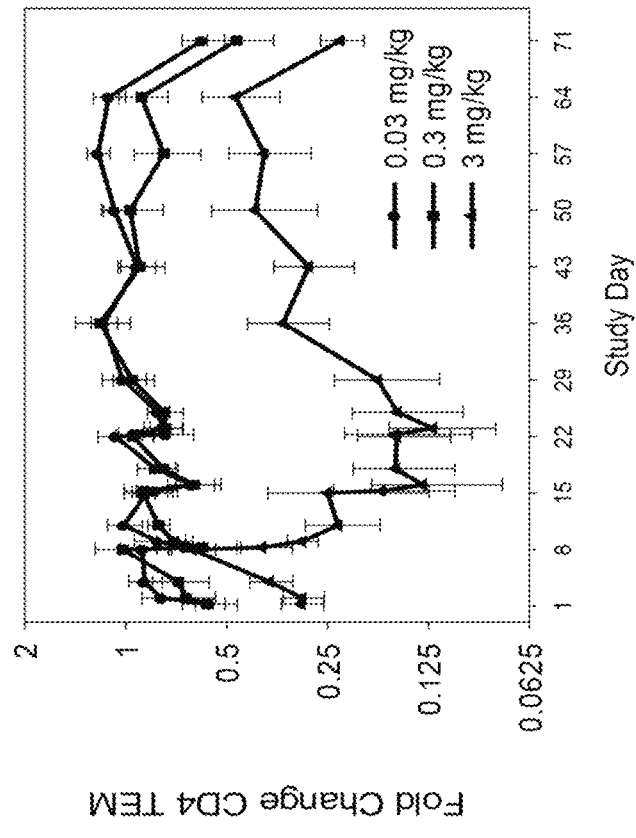

Repeat dosing of M1d1 decreased peripheral CD4+ $T_Em$ cells (FIGS. 20A and 34A). Tregs were relatively spared by M1d1, resulting in an increased ratio of Treg/$T_{EM}$ (FIGS. 20B and 34B). CD8+ $T_E$ cells decreased as well. There was minimal effect on $T_{naïve}$. Recovery phase was completed, and trends toward recovery or establishment of new baseline were evident by day 57.

Overall impact of M1d1 on total T cell counts is relatively modest (<50% decrease at 3 mg/kg) and does not meet threshold associated with immune-suppression (FIG. 21). B cells were not decreased by treatment (not shown). M1d1 preferentially targets CD2hi $T_{EM}$ cells in vivo (FIG. 21).

As mentioned above, a parallel dose response was included in study 17MA057 with WT LFA3-Fc for use as a benchmark. Repeat dosing of WT LFA3-Fc in cyno decreased CD4 EM cells and increased the ratio of Tregs/CD4+ $T_{EM}$ (FIGS. 22A and 22B and FIGS. 35A and 35B).

Figure 23A:
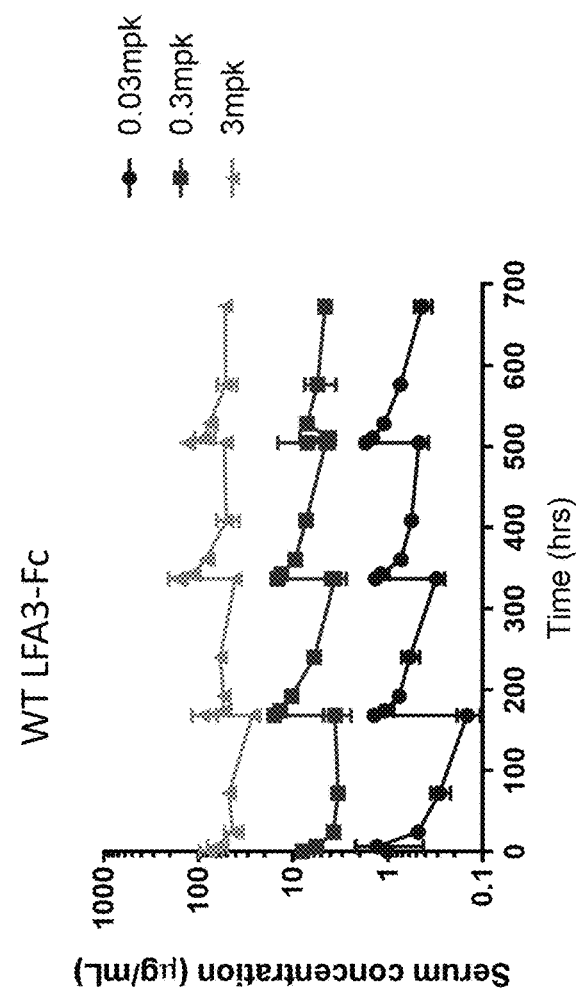
FIGS. 23A and 23B: Exemplary PK profile of M1d1 and LFA3-Fc WT in cynomolgus monkey from study 17MA057. Dose is proportional between 0.03-3 mg/kg.
Figure 23B:
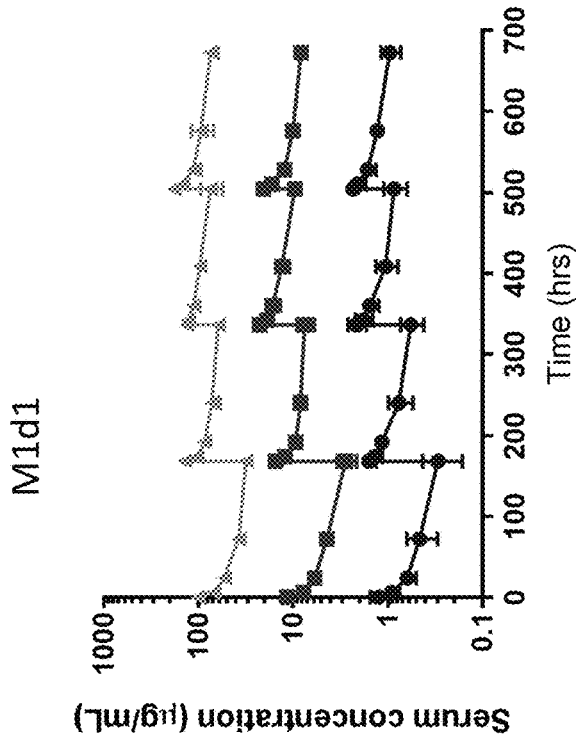

NHP PK parameters for M1d1 and WT LFA3-Fc were determined by fitting the NHP repeat-dose study data (weekly dosing of 0.03, 0.3 or 3 mg/kg for 4 weeks, followed by 6 weeks of recovery period) (FIGS. 23A and 23B) to a 2 compartmental PK model. Human PK parameters for alefacept were derived by digitizing clinical mean data (0.04, 0.15 and 0.2 mg/kg of single-dose (IV/IM/SC)) from the literature and fitting them to a 2 compartmental PK model. These PK parameters are shown below in Table 11. Clearance of M1d1 is 2-fold slower than that of WT LFA3-Fc.

LFA3-Fc M1d1 efficacious dose estimates were assessed. Assuming similar absorption of LFA3-Fc M1d1 via the subcutaneous route versus alefacept administered intramuscularly, and the estimated 2× lower clearance of LFA3-Fc M1d1 compared to alefacept, a weekly sc dose of 7.5 mg of LFA3-FC M1d1 would be efficacious in humans.

TABLE 11

| | PK parameters of M1d1 and WT LFA3-Fc | | | |
|---|---|---|---|---|
| PK Parameter | LFA3-Fc WT Monkey (% CV) | LFA3-Fc M1d1 Monkey (% CV) | Alefacept human % CV* | LFA3-Fc M1d1 human % CV** |
| Absorption rate (Ka) (1/hr) | | | 0.023 (7) | |
| Bioavailability (F) (%) | | | 59 (5) | |
| Central volume (V1) (mL/kg) | 37 (9) | 32 (5.0) | 49 (6) | 32 (5) |
| Peripheral volume (V2) (mL/kg) | 34 (15) | 27 (8) | 27 (10) | 27 (8) |
| Clearance from central (Cl) (mL/hr*kg) | 0.24 (4) | 0.11 (6) | 0.21 (6) | 0.11 (6) |
| Distribution clearance (Q) (mL//hr*kg) | 0.67 (32) | 0.70 (10) | 0.85 (45) | 0.70 (10) |

*based on published data; **predicted

M1d1-related adverse events were not observed in the single dose investigative toxicity study in monkeys. Decrease in T lymphocytes was the only test article-related changes in animals administered M1d1 at 100 mg/kg, with subsequent recovery by Day 57. Based on the published data with Alefacept, targets of toxicity are only those expected to be associated with moderate to marked depletion of CD2 positive lymphocytes, and related immunosuppression. An overview of M1d1 toxicology studies is provided in Table 12.

TABLE 12

Overview of M1d1 toxicology studies

| Studies | Results |
|---|---|
| Relevant tox species confirmed | Sequence homology (protein): monkey (>94%), dog (60%), rat (57%), mouse (52%). |
| | Biacore CD2 binding: No appreciable binding to mouse, rat or dog, binding to human and cyno CD2: Hu CD2 Kd (M): 1.10E−6; cyno CD2 Kd (M): 1.35E−6. |
| | Has an intended ADCC effector function as part of MOA. |
| | Minimal CDC effects (<10% percent of target cells killed). |
| Human CRA (0.1, 1, 10, 100 µg/mL) | TNF-α, IFN-γ and IL-6 measured. |
| | No meaningful cytokine release in the soluble phase CRA following incubation with blood samples from 8 healthy human donors. |
| Monkey TK study (0.3 and 100 mg/kg) 17MA005 | No test article-related clinical signs, body weight or food consumption effects observed at 100 mg/kg (>400X safety margin[a]). |
| | Test article-related changes in immunophenotyping compared with baseline values observed at 100 mg/kg. |
| | The male: transient ↓ in absolute numbers of all cell types except B cells and NK cells. |
| | The female: transient ↓ in T cytotoxic PD1+, T regulatory cells, T cytotoxic central and effector cells, T helper central and effector PD1+ cells as well as T cytotoxic central and effector PD1+ cells. |
| Monkey PK/PD study (0.03, 0.3 and 3 mg/kg) 17MA057 | No test article-related clinical signs, body weight or food consumption effects observed at all dose levels. Mean $C_{max}$ and $AUC_{168}$ of M1d1 at 3 mg/kg/dose were 181 µg/mL and 16,400 µg*h/mL on Day 22.[b] |

[a]Margin is an estimate based on predicted efficacious exposure from PK/PD study (17MA057): The predicted range for AUCss at efficacious dose for M1d1 is 16 to 550 µg*day/mL, dose range is 0.22-7.5 mg.
[b]$C_{max}$ = highest drug concentration observed in serum; $AUC_{168}$ = area under the time-drug concentration curve from 0-168 hours post dose.

Example 4: Biophysical Characterization and Stability Studies of LFA3-Fc M1d1 and LFA3-Fc WT The LFA3-Fc M1d1 (also known as "LFA3-Fc M1-d1" "M1d1" "M1-d1" or "M1d1-Pfe") and LFA3-Fc WT (also known as "WT LFA3-Fc") were characterized for biophysical properties and stability in order to predict comparative manufacturability properties.

Thermostability Assessment

Figure 27:
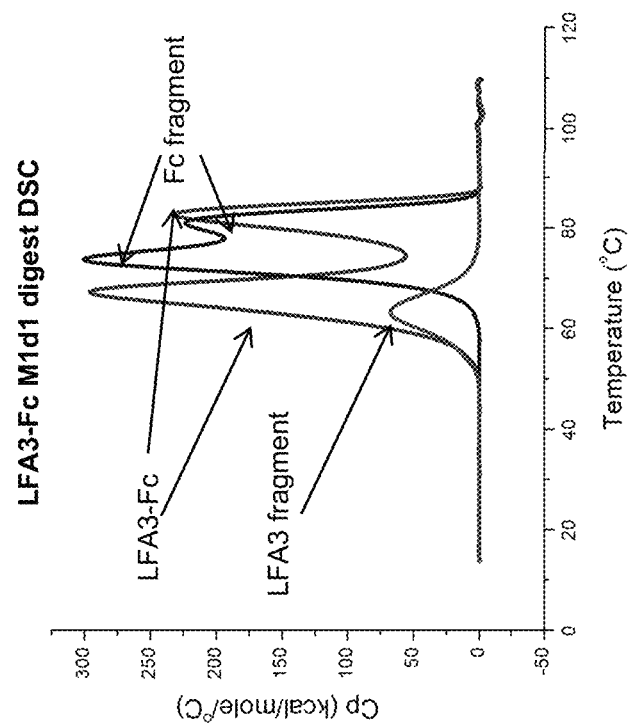
FIG. 27: Exemplary differential scanning calorimetry (DSC) profile of LFA3-Fc M1d1 formulated in Tris buffer pH 7.5, histidine buffer pH 5.8 or glutamate buffer pH 4.5.

The thermostability of LFA3-Fc M1d1 was assessed by DSC (differential scanning calorimetry) in Tris buffer, pH 7.5, histidine buffer, pH 5.8 and glutamate buffer, pH 4.5. The protein exhibited a transition temperature ($T_M1$) of greater than 65° C. in histidine and Tris buffers (Table 13 and FIG. 27).

TABLE 13

Thermal transition temperatures for LFA3-Fc M1d1

| Sample | $T_M1$ | $T_M2$ |
|---|---|---|
| LFA3-Fc M1d1 Tris pH 7.5 | 66.64 | 83.55 |
| LFA3-Fc M1d1 His pH 5.8 | 65.08 | 82.99 |
| LFA3-Fc M1d1 Glu pH 4.5 | 61.29 | 80.72 |

Figure 28:
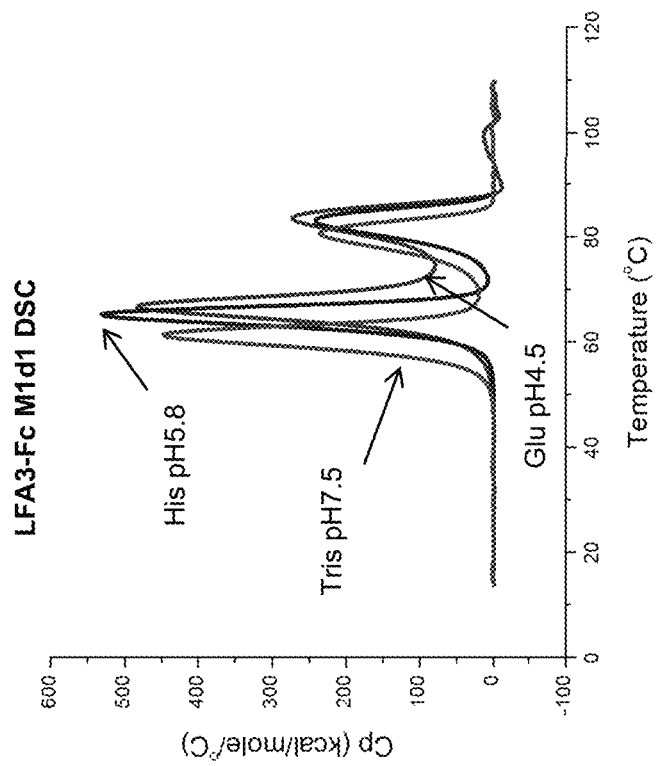
FIG. 28: Exemplary differential scanning calorimetry (DSC) profile of LFA3-Fc M1d1 following digestion with FabRICATOR® IdeS.

For separate analysis of the LFA3 domain and Fc domain (CH2 and CH3), samples were treated with FabRICATOR® IdeS (Genovis AB, Cambridge, Mass.) at 37° C. for 30 minutes. The LFA3 domain (also referred to as "LFA3 fragment") exhibited a thermal transition temperature close to the thermal transition temperature of the CH2 domain of the Fc fragment (FIG. 28).

The thermostability of LFA3-Fc M1d1 and LFA3-Fc WT was compared using DSC. LFA3-Fc WT had a lower thermal unfolding stability under all conditions relative to LFA3-Fc M1d1. The thermal unfolding stability of LFA3-Fc WT was significantly lower than the target temperature for an antibody (e.g., $T_M1 \geq 65°$ C.) (Table 14).

TABLE 14

Thermal transition temperatures for LFA3-Fc M1d1 and LFA3-Fc WT

| Condition | Sample | $T_M1$ |
|---|---|---|
| Tris pH 7.5 | LFA3-Fc Md1 | 66.3 |
| | LFA3-Fc WT | 59.7 |
| Histidine pH 5.8 | LFA3-Fc M1d1 | 64.01 |
| | LFA3-Fc WT | 60.9 |
| Glutamate pH 4.5 | LFA3-Fc M1d1 | 61.4 |
| | LFA3-Fc WT | 56.4 |

The thermostability of LFA3-Fc M1d1 and LFA3-Fc WT was compared using DSC followed by FabRICATOR® IdeS as described above. The digested LFA3 domain and the Fc domains (i.e., CH2 and CH3) were also analyzed separately. The M1d1 LFA3 domain/CH2 domain had significantly greater thermal unfolding stability than the WT LFA3 domain/CH2 domain (64.8° C. vs 52.2° C., respectively) (Table 15).

TABLE 15

Thermal transition temperatures for LFA3-Fc M1d1 and LFA3-Fc WT domains

| | LFA3/CH2 | LFA3 | CH2 | CH3 |
|---|---|---|---|---|
| LFA3-Fc M1d1 | 66.8 | — | — | 82.3 |
| M1d1 Fc | — | — | 73.4 | 80.7 |
| M1d1 LFA3 | — | 64.8 | — | — |
| LFA3-Fc WT | 53.2 | — | 67 | 83.2 |
| WT Fc | — | — | 73.4 | 81.7 |
| WT LFA3 | — | 52.2 | — | — |

Charge Heterogeneity

Figure 29A:
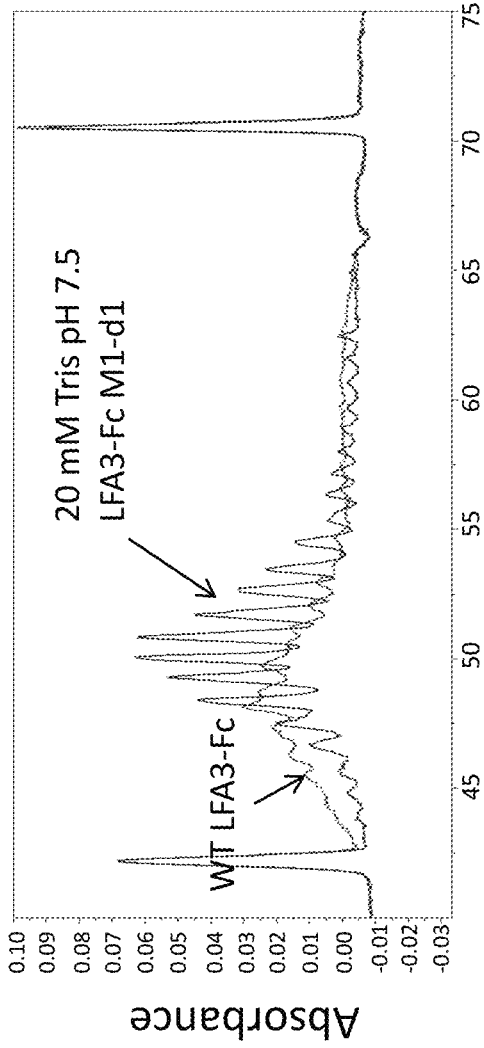
FIGS. 29A-29C: Exemplary charge heterogeneity analysis of LFA3-Fc M1-d1 (also referred to as LFA3-Fc M1d1) and WT LFA3-Fc (also referred to as LFA3-Fc WT) formulated in 20 mM Tris buffer pH 7.5 (FIG. 29A) 20 mM histidine buffer pH 5.8 (FIG. 29B) or 20 mM glutamate buffer pH 4.5 (FIG. 29C).
Figure 29B:
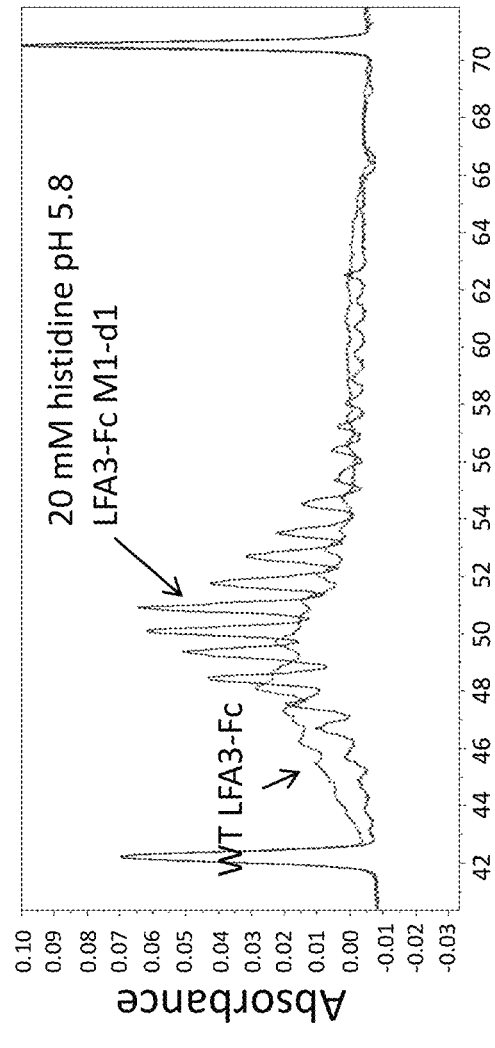
Figure 29C:
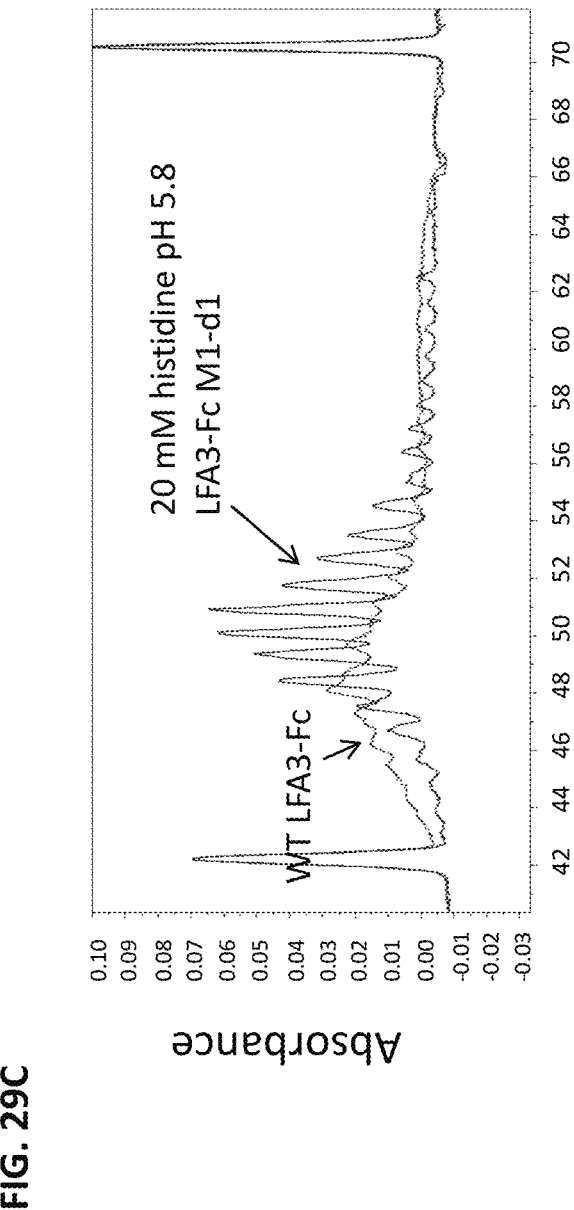

The change heterogeneity of LFA3-Fc M1d1 and LFA3-Fc WT was assessed by isoelectric capillary electrophoresis under three conditions: 20 mM Tris pH 7.5, 20 mM histidine pH 5.8 and 20 mM glutamate pH 4.5. Both molecules exhibited a complicated charge profile comprising 15-18 different species (FIG. 29A-29C). The heterogeneity of both LFA3-Fc WT and M1d1 (>20 pI species) reflects acidic sialic acid modifications on the six LFA3-Fc N-linked glycan sites. Lower resolution of the LFA3-Fc WT compound was observed as compared to LFA3-Fc M1d1.

Stability

The stability of LFA3-Fc M1d1 and LFA3-Fc WT were assessed in time course studies over 2, 4 or 6 weeks. Samples were subject to centrifugal ultrafiltration/diafiltration using a 30K molecular weight cut-off regenerated cellulose filter (Amicon). 25 µl or 100 µl of each polypeptide formulation (Table 16) were filled in a 500 µl cryovial. Study conditions are provided in Table 16.

TABLE 16

Stability study conditions

| Polypeptide concentration (mg/mL) | Formulation | Temperature | Time (weeks) |
|---|---|---|---|
| 150 | 20 mM Tris pH 7.5 8.5% sucrose 0.05 mg/mL EDTA | 5° C. or 25° C. | 2, 4, 6 |
| 150 | 20 mM histidine pH 5.8 8.5% sucrose 0.05 mg/mL EDTA | 5° C. or 25° C. | 2, 4, 6 |
| 150 | 20 mM glutamate pH 4.5 8.5% trehalose 0.05 mg/mL EDTA | 5° C. or 25° C. | 2, 4, 6 |
| 5 | 20 mM Tris pH 7.5 | 40° C. | 2, 4 |
| 5 | 20 mM histidine pH 5.8 | 40° C. | 2, 4 |
| 5 | 20 mM glutamate pH 4.8 | 40° C. | 2, 4 |

Capillary Gel Electrophoresis.

Polypeptides were analyzed at 2, 4 and 6 weeks by capillary gel electrophoresis (CGE), under non-reducing conditions (NR), for fragmentation as shown by an increase in the percentage of low molecular mass species (LMMS). There was a significant increase in fragmentation of LFA3-Fc WT at 40° C. as compared to the LFA3-Fc M1d1 (FIG. 30A-30C). At 25° C., the trend toward an increased percentage of LMMS was seen in the LFA3-Fc WT samples, however there was no increase in the percentage of LMMS in the LFA3-Fc M1d1 samples (data not shown). There was no significant change in the percentage of LMMS at 5° C. for either LFA3-Fc WT or M1d1 (data not shown). The stability of LFA3-Fc M1d1 in each of the buffer formulations was similar. However, LFA3-Fc WT was significantly more stable when formulated in Tris as compared to histidine or glutamate.

LFA3-Fc WT preparations were ~97% pure under reducing and non-reducing conditions. LFA3-Fc M1d1 preparations were ~99% pure under reducing and non-reducing conditions.

Size Exclusion Chromatography

Figure 31A:
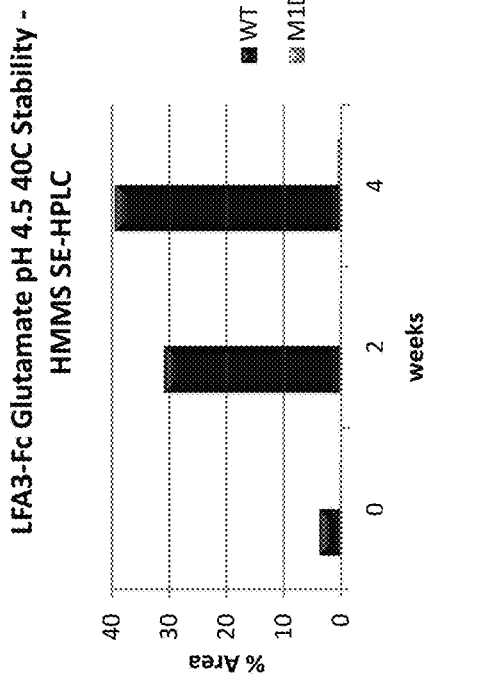
FIGS. 31A-31D: Exemplary size exclusion high performance liquid chromatography (SE-HPLC) analysis of LFA3-Fc M1d1 and LFA3-Fc WT formulated in Tris buffer pH 7.5 (FIG. 31A), histidine buffer pH 5.8 (FIG. 31B) or glutamate buffer pH 4.5 (FIG. 31C) at time 0 and following storage at 40° C. for 2 or 4 weeks. The percentage of low molecular mass species (LMMS) (FIG. 31D) and high molecular mass species (HMMS) (FIG. 31A-31C) was quantified.
Figure 31B:
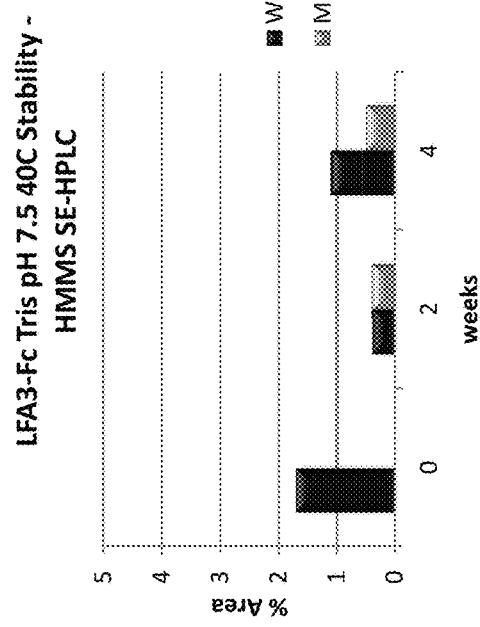
Figure 31C:
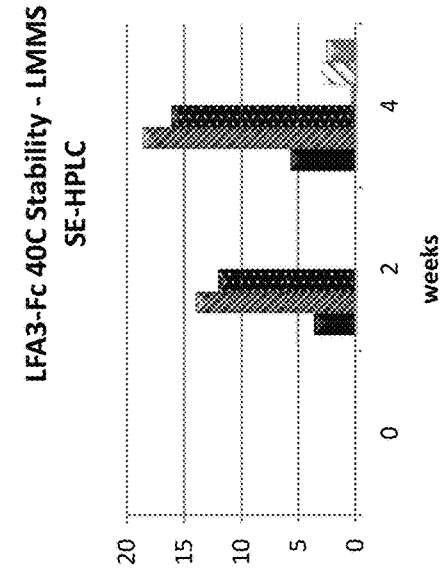
Figure 31D:
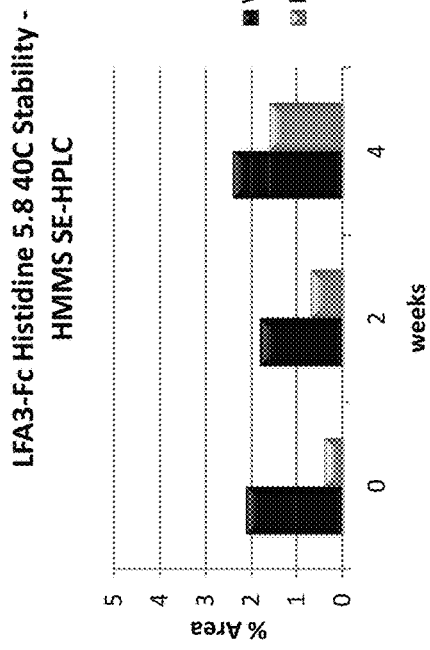

Polypeptides were analyzed by size exclusion high performance liquid chromatography (SE-HPLC) following storage for 2 or 4 weeks at 40° C. (FIG. 31A-31D). There was a significant increase in aggregation, as shown by an increase in the percentage of high molecular mass species (HMMS), in the LFA3-Fc WT glutamate formulation at week 2 and week 4 as compared to week 0, and as compared to LFA3-Fc M1d1 formulated in glutamate buffer (FIG. 31C). There was also a pronounced increase in LMMS formation in the LFA3-Fc WT formulated in glutamate or histidine buffer (FIG. 31D). A 2-3% increase in LMMS was observed at 4 weeks in the LFA3-Fc M1d1 histidine and glutamate formulations (FIG. 31D).

Polypeptides were analyzed by SE-HPLC following storage for 2, 4 or 6 weeks at 25° C. (FIG. 32A-32D). A higher starting percentage of HMMS was detected in the LFA3-Fc WT formulations as compared to the LFA3-Fc M1d1 formulations. A 1-2% increase in HMMS was detected in the LFA3-Fc M1d1 formulations, whereas the HMMS increased by 2-10% in the LFA3-Fc WT formulations. The most significant increase in the percentage of HMMS (~10%) was detected in LFA3-Fc WT formulated in glutamate/trehalose buffer (FIG. 32C). No significant increase in LMMS was observed in any formulation of LFA3-Fc M1d1, whereas an increase of ~7% in LMMS was detected at 6 weeks in the LFA3-Fc WT formulated in the histidine/sucrose buffer and the glutamate/trehalose buffer (FIG. 32D).

Figure 33A:
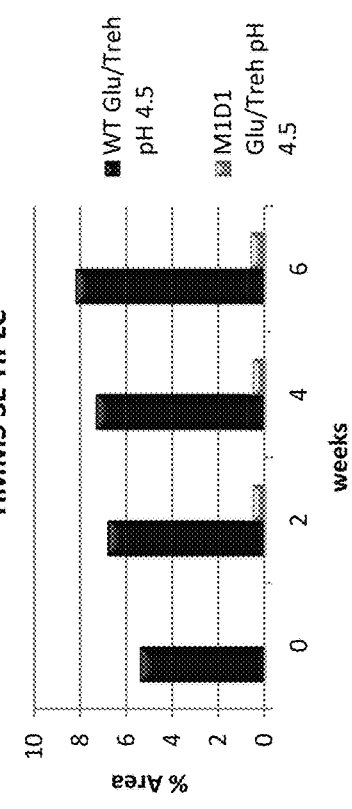
FIGS. 33A-33D: Exemplary size exclusion high performance liquid chromatography (SE-HPLC) analysis of LFA3-Fc M1d1 and LFA3-Fc WT formulated in Tris/sucrose buffer pH 7.5 (FIG. 33A), histidine/sucrose buffer pH 5.8 (FIG. 33B) or glutamate/trehalose buffer pH 4.5 (FIG. 33C) at time 0 and following storage at 5° C. for 2, 4 or 6 weeks. The percentage of low molecular mass species (LMMS) (FIG. 33D) and high molecular mass species (HMMS) (FIGS. 33A-33C) was quantified.
Figure 33C:
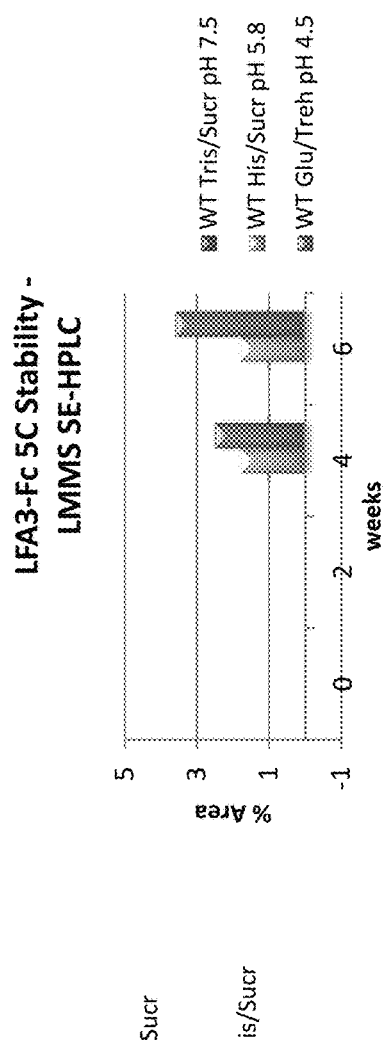
Figure 33B:
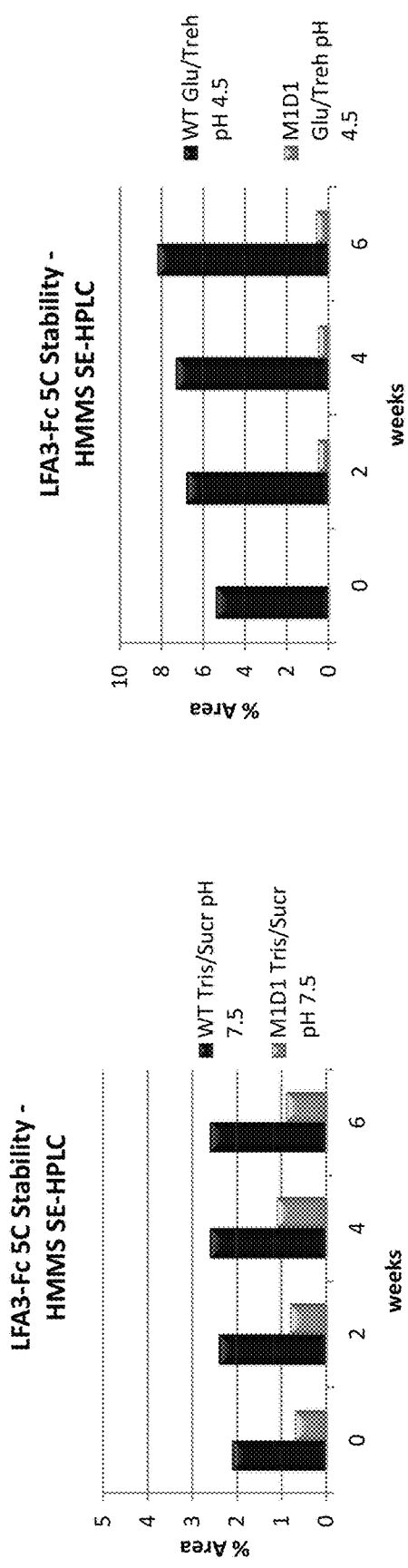
Figure 33D:
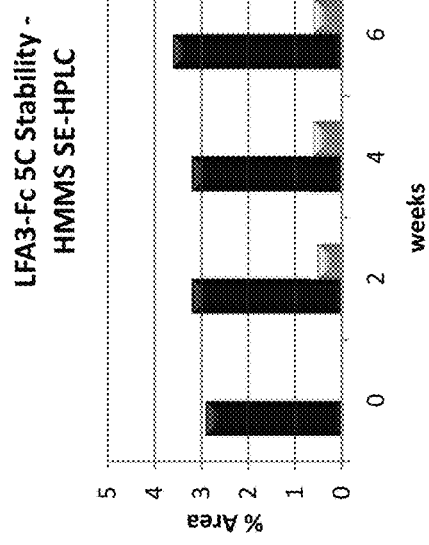

Polypeptides were analyzed by SE-HPLC following storage for 2, 4 or 6 weeks at 5° C. (FIG. 33A-33D). A higher starting percentage of HMMS was detected in the LFA3-Fc WT formulations as compared to the LFA3-Fc M1d1 formulations (FIG. 33A-33C). The most significant increase in the percentage of HMMS was detected in LFA3-Fc WT formulated in glutamate/trehalose buffer after storage for 6 weeks (~2.8% increase) (FIG. 33C).

Overall, LFA3-Fc M1d1 showed superior stability against fragmentation as compared to LFA3-Fc WT under all conditions tested. In particular, LFA3-Fc WT exhibited significant instability at low pH in the formulations tested. LFA3-Fc WT aggregation rate was higher at 25° C. as compared to 40° C. in Tris and histidine buffers which may indicate a concentration dependence or excipient incompatibility.

Solubility

The solubility of LFA3-Fc WT was tested up to 165 mg/mL in a buffer comprising glutamate, trehalose and EDTA at pH 4.5. The solubility of LFA3-Fc M1d1 was tested up to 148 mg/mL in a buffer comprising glutamate, trehalose and EDTA at pH 4.5.

Glycan Analysis

Both the LFA3-Fc WT and LFA3-Fc M1d1 polypeptides comprised N-glycans characteristic of antibody Fc domains. The LFA3 domain of the WT polypeptide comprised highly branched glycans and approximately 22 nmol sialic acid/nmol of LFA3-Fc WT polypeptide. The LFA3 domain of the M1d1 polypeptide also comprised highly branched glycans and approximately 14 nmol sialic acid/nmole of LFA3-Fc M1d1 polypeptide.

Example 5: Antibody-Dependent Cellular Cytotoxicity (ADCC) of LFA3-Fc M1d1

The in vitro ADCC of LFA3-Fc M1d1 and LFA3-Fc WT against human T cells was characterized in this study. CD2 is expressed on all T cells with expression greatest on memory T cells as compared to naïve or regulatory T cells. LFA3-Fc binds to CD2 and a major mechanism of action is ADCC.

This study demonstrated that LFA3-Fc M1d1 is 3-4 fold more potent at inducing ADCC of memory CD4 cells than LFA3-Fc WT. Also, LFA3-Fc M1d1 preferentially targeted memory CD4+ T cells as compared to naïve T cells.

Methods

PBMC ADCC Assay and Flow Cytometry

PBMCs from healthy human donors were isolated by density gradient centrifugation using SepMate™ tubes and Lymphoprep™ according to the manufacturer's instructions (STEMCELL Technologies, Tukwila, Wash.). Following isolation, PBMCs were plated in complete RPMI medium at a density of $2.0 \times 10^5$ cells per well in round-bottom, 96-well plates. In this assay, the PMBCs are the source of the natural killer (NK) effector cells and the target T-cells (CD4 memory and non-memory, CD8 memory and non-memory). Memory and non-memory cells were distinguished based on CD45RO expression (memory cells are CD45RO+; non-memory cells are CD45RO−). Serial dilutions of LFA3-Fc fusion proteins were added to the wells and the cells were incubated at 37° C., 5% $CO_2$ for approximately 20 hours.

The plates were centrifuged at 300×g (gravities) for 5 minutes at room temperature (RT). PBMCs were washed with ice-cold Fluorescence-activated cell sorting (FACS) buffer and resuspended in 50 μL of ice-cold FACS buffer containing fluorescence-conjugated antibodies for staining lymphocyte subsets. The staining panel included: CD3 (BUV496), CD4 (BUV395), CD8 (PerCP-e710), CD45RO (PeCγ7), CD45RA (FITC), CD25 (PE-CF594), CD56 (BV421), CD2 (PE), and Near-infrared (IR) viability.

After incubation for 15-30 minutes at 4° C., PBMCs were washed with ice-cold FACS buffer twice and resuspended in 100 μL of 0.5% paraformaldehyde (PFA) in PBS. CountBright™ Absolute Counting Beads (Thermo Fisher Scientific) were added to each well (10 μL). Plates were analyzed by flow cytometry (BD LSRFortessas™ Cell Analyzer).

NK Titration Cytotoxicity Assay

Freshly isolated PBMCs were allowed to rest overnight in complete RPMI+10% FBS at $5 \times 10^6$ cells/ml. The following day target cells (CD4 Memory, CD4 Naïve, or B cells) were isolated using isolation kits from STEMCELL Technologies. Corresponding natural killer (NK) cells from the same donor were also isolated. A volume of 50 μL of target cells were plated at 30,000 cells/well in a 96-well V-bottom plate. NK cells were prepared in 2-fold serial dilutions and 50 μL were added to target cells. LFA3-Fc polypeptides were prepared at 10× for a final working concentration of 100 nM. A volume of 11 μL of polypeptide was added to appropriate wells and plates were incubated for 4 hours at 37° C. Plates were washed and stained with staining buffer containing Annexin V Alexa Fluor 488, 7-AAD, CD56 BV421, and CD4 APH-H7 for 30 minutes. Cells were washed with Annexin V binding buffer, fixed for 10 minutes with 2% PFA in PBS, washed, then analyzed by flow cytometry. CountBright™ beads were included in each well to determine absolute counts.

Data Analysis

The cytotoxicity titration curves were generated by plotting the percentage of cytotoxicity of the antigen binding population against the log of LFA3-Fc polypeptide concentration. Percentage of cytotoxicity was calculated as the difference in absolute counts of live cells between the untreated controls, minus experimental sample, divided by untreated controls, multiplied by 100. Percent specific cytotoxicity was calculated as the difference in absolute counts of live cells between the untreated controls, minus experimental sample, divided by the difference between untreated controls, minus isotype control, multiplied by 100. Effective concentration at 50% of maximal response ($EC_{50}$) values were determined using GraphPad Prism® (version 6.0, GraphPad Software, Inc, San Diego, CA) nonlinear-regression curve fits and a sigmoidal log of agonist dose-response model.

Results

LFA3-Fc WT and LFA3-Fc M1d1 induced ADCC in all cell types tested. LFA3-Fc M1d1 demonstrated increased ADCC potency in memory and non-memory cells as compared to LFA3-Fc WT (Table 17, FIG. 12A-12E).

TABLE 17

Induction of ADCC by LFA3-Fc polypeptide

| Cell type | LFA3-Fc M1d1 $EC_{50}$ (nM) | | LFA3-Fc WT $EC_{50}$ (nM) | |
| --- | --- | --- | --- | --- |
| | Mean | SEM | Mean | SEM |
| CD4 CD45RO + memory cells | 0.348 | 0.098 | 1.559 | 0.425 |
| CD4 CD45RO − non-memory cells | 1.256 | 0.446 | 4.466 | 2.447 |
| CD8 CD45RO + memory cells | 0.716 | 0.116 | 57.2 | 55.2 |
| CD8 CD45RO − non-memory cells | 0.787 | 0.279 | 49.7 | 47.3 | n = 5 for each cell type

LFA3-Fc WT and LFA3-Fc M1d1 induced preferential killing of isolated memory cells, which express high levels of CD2, as compared to naïve cells or B cells.

TABLE 18

NK cytotoxicity

| | Maximum cytotoxicity (%) | |
| --- | --- | --- |
| Cell type | LFA3-Fc M1d1 | LFA3-Fc WT |
| CD4 memory | 51.39 | 51.49 |
| CD4 naïve | 19.36 | 28.74 |
| B cell | 4.08 | ND |

ND = not determined

Figure 13B:
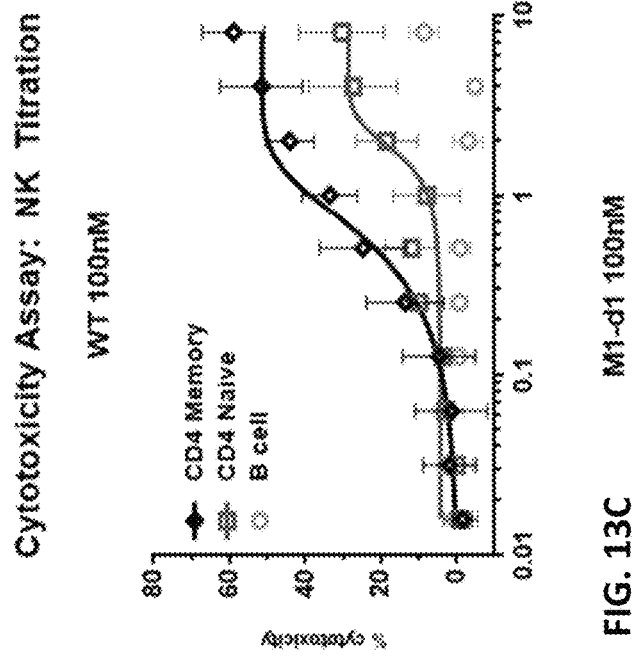
FIGS. 13A-13C: Exemplary graphs depicting cytotoxicity assays with purified NK cells co-cultured with target cells in a fixed amount of LFA3-Fc M1d1 or LFA3-Fc WT.
Figure 13C:
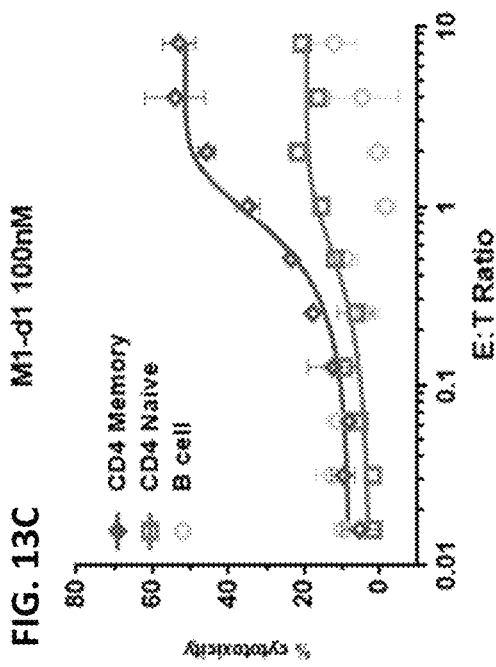
Figure 13A:
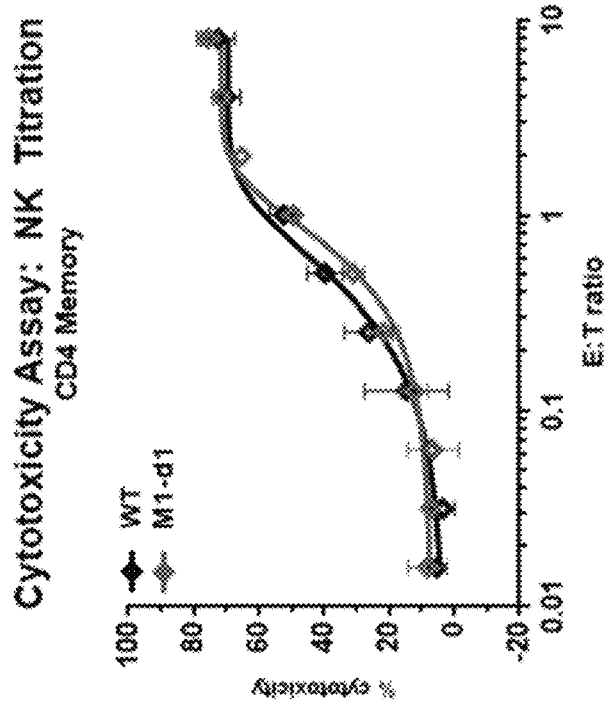

An alternative assay to assess NK mediated cytotoxicity uses purified NK cells cultured at increasing ratios with target cells. An NK titration cytotoxicity assay using more concentrated polypeptide over multiple donors corroborated preferential killing of isolated memory cells. Purified target cell populations (CD4 memory, CD4 naïve and B cells) were cultured with NK cells at various effector to target ratios and 100 nM of LFA3-Fc WT or LFA3-Fc M1d1 (FIG. 13B-13C). At an effector to target ration (E:T) of 10:1, and protein concentration of 100 nM, LFA3-Fc WT and LFA3-Fc M1d1 induced cytotoxicity in CD4 memory cells and naïve cells (Table 19).

TABLE 19

NK cytotoxicity

| | LFA3-Fc M1d1 maximum cytotoxicity (%) | | LFA3-Fc WT maximum cytotoxicity (%) | |
| --- | --- | --- | --- | --- |
| Cell type | Mean | SEM | Mean | SEM |
| CD4 memory cells | 22.31 | 4.23 | 9.07 | 2.31 |
| CD4 naïve cells | 3.98 | 2.86 | 0.14 | 1.99 | n = 3 for each cell type

This study exemplified LFA3-Fc protein induction of ADCC of CD2+ T cells in in vitro assays using human PBMCs. LFA3-Fc M1d1 was 3-4 fold more potent at inducing ADCC of memory CD4 cells than LFA3-Fc WT. LFA3-Fc M1d1 preferentially targets memory CD4+ T cells, known to express higher levels of CD2 protein as compared to naïve CD4 T cells. Thus, these studies demonstrate that the therapeutic polypeptide LFA3-Fc M1d1 induces ADCC of target CD2+ T cells.

TABLE 20

Novel and useful characteristics of LFA3-Fc variants

| Characteristic | LFA3-Fc WT | LFA-Fc M1d1* |
|---|---|---|
| amino acid sequence | | |
| LFA3 domain | SEQ ID NO: 3 | SEQ ID NO: 26 |
| changes relative to SEQ ID NO: 3 | | A36V, L38F, F43V, M86F, 92insL |
| Fc domain | SEQ ID NO: 128 | SEQ ID NO: 16 |
| changes relative to SEQ ID NO: 128 | | D136E, L138M, 226delK |
| LFA3-Fc | SEQ ID NO: 4 | SEQ ID NO: 69 |
| changes relative to SEQ ID NO: 4 | | A36V, L38F, F43V, M86F, V92_D93insL, D228E, L230M, 319delK |
| Nucleotide sequence | | |
| LFA3 domain | SEQ ID NO: 126 | SEQ ID NO: 53 |
| Fc domain | SEQ ID NO: 127 | SEQ ID NO: 43 |
| LFA3-Fc | SEQ ID NO: 125 | SEQ ID NO: 123 |
| ADCC | | |
| CD4 $T_{mem}$ $EC_{50}$ | 1.559 +/− 0.425 nM | 0.348 +/− 0.098 nM |
| CD4 $T_{non-mem}$ $EC_{50}$ | 4.466 +/− 2.447 nM | 1.256 +/− 0.446 nM |
| CD8 $T_{mem}$ $EC_{50}$ | 57.2 +/− 55.2 nM | 0.716 +/− 0.116 nM |
| CD8 $T_{non-mem}$ $EC_{50}$ | 49.7 +/− 47.3 nM | 0.787 +/− 0.279 nM |
| Thermal stability of LFA3-Fc | | |
| Tris pH 7.5 | 59.7° | 66.3° |
| Histidine pH 5.8 | 60.9° | 64.01° |
| Glutamate pH 4.5 | 56.4° | 61.4° |
| Thermal stability | | |
| DSC | Tm1, 47° C. | Tm1, 65° C. |
| DSF | Tm1, 40° C. | Tm1 60° C. |
| Thermal stability of LFA3 domain | 52.2° | 64.8° |
| Time-course stability | Significant instability at low pH; higher aggregation rate at 25° C. and 40° C. | Superior stability for fragmentation |
| Purity | 97% | 99% |
| Solubility in glutamate, trehalose and EDTA buffer, pH4.5 | 165 mg/mL | 148 mg/mL |
| Glycan composition | 22 nmol sialic acid/nmol polypeptide | 9-14 nmol sialic acid/nmol polypeptide |
| Yield | 4.95 mg/20 mL culture | 7 mg/20 mL culture |
| Monomeric species off protein A (%) | 73.9% monomer; 18% HMWS; 7.1% LMWS | >99% monomer |
| Analytical SEC | 99.2% monomer | 99.6% monomer |
| DSC | Tm1, 47° C. | Tm1, 65° C. |
| DSF | Tm1, 40° C. | Tm1 60° C. |
| Forced aggregation propensity | 40° C. HMWS increased to ~23% | 40° C. no increase in HMWS |
| | 50° C. HMWS increased to ~29% | 50° C. HMWS increased to 3% |
| Low pH hold (5 hrs) | 11% HMWS, no increase in LMWS | 4% HMWS, no increase in LMWS |
| Freeze-thaw (5 cycles) | ~2% increase in HMWS | No increase in HWS |
| Affinity by SPR to human recombinant CD2 ($K_D$) | 1.41-1.47 μM | 0.73-1.08 μM |
| Affinity by SPR to cyno recombinant CD2 ($K_D$) | 1.5 μM | 1.06 μM |
| Cell binding (CD4 $T_{mem}$) $K_d$ | 501 pM | 94 pM |
| MLR ($IC_{50}$) | 2.48 nM | 0.302 nM |
| TTR ($IC_{50}$) | 28.4 nM | 1.34 nM |

*exemplary embodiment encompassing all of the LFA3-Fc variants disclosed herein.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety for all purposes. In the event that one or more of the incorporated literature and similar materials differs from or contradicts this application, including but not limited to defined terms, term usage, described techniques, or the like, this application controls.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An isolated polypeptide molecule that specifically binds to CD2,
wherein the polypeptide molecule comprises an amino acid sequence having at least about 95% identity to the amino acid sequence of SEQ ID NO: 69, and wherein the polypeptide molecule consists of one or more substitutions at residues 36, 38, 43, 45, 77, and 86 relative to SEQ ID NO: 3, numbered according to SEQ ID NO: 3.

2. The isolated polypeptide molecule of claim 1, wherein the polypeptide molecule comprises an amino acid sequence of SEQ ID NO: 69.

3. An isolated polypeptide that specifically binds to CD2, comprising an LFA3 domain comprising an amino acid sequence having at least about 95% identity to an amino acid sequence selected from the group consisting of SEQ ID NOs: 17-41, wherein the LFA3 domain comprises one or more substitutions at residues 36, 38, 43, 45, 77, and 86 relative to SEQ ID NO: 3, numbered according to SEQ ID NO: 3.

4. The isolated polypeptide of claim 3, wherein: (a) the amino acid sequence is SEQ ID NO: 17, 18, 19, 20, 21, 22 or 23 and wherein the C-terminal boundary of the LFA3 domain is extended to further comprise the amino acid residue of Leu or the amino acid sequence of LESLPS (SEQ ID NO: 118); or
(b) the LFA3 domain comprises an amino acid sequence having the amino acid sequence of SEQ ID NO: 26.

5. The isolated polypeptide of claim 3, further comprising a second domain,
wherein the second domain comprises an immunoglobulin protein;
wherein the second domain comprises an Fc region of a heavy chain; or
wherein the second domain comprises a hinge region, a CH2 region, and a CH3 region; or wherein the second domain comprises an Fc domain comprising an amino acid sequence having at least about 75% identity to SEQ ID NO: 16.

6. The isolated polypeptide of claim 5, wherein:
(a) the isolated polypeptide further comprises a linker, wherein the linker links the N-terminus of the second domain to the C-terminus of the LFA3 domain; and/or
(b) the second domain is capable of forming a dimer with another second domain; and/or
(c) the second domain is capable of mediating antibody-dependent cell-mediated cytotoxicity (ADCC).

7. The isolated polypeptide of claim 5, wherein:
(a) the LFA3 domain comprises a polypeptide comprising an amino acid sequence of SEQ ID NO: 26; and
the Fc domain comprises a polypeptide comprising an amino acid sequence having at least 90% identity to SEQ ID NO: 16; or
(b) the polypeptide has at least 95% identity to the amino acid sequence of SEQ ID NO: 4, and the amino acid sequence consists of one or more mutations at residues 36, 38, 43, 86, 92, 228 and 230 numbered according to SEQ ID NO: 4.

8. The isolated polypeptide of claim 7, wherein the one or more mutations at residues 36, 38, 43, 86, 92, 228 and 230 numbered according to SEQ ID NO: 4 are A36V, L38F, F43V, M86F, V92_D93insL, D228E and L230M.

9. An isolated polypeptide comprising an LFA3 domain, wherein the LFA3 domain comprises an amino acid sequence having at least 95% identity to the amino acid sequence of SEQ ID NO: 3 with one or more mutations at residues 36, 38, 43 and 86, numbered according to SEQ ID NO: 3.

10. The isolated polypeptide of claim 9, wherein the C-terminal boundary of the LFA3 domain is extended to further comprise the amino acid residue of Leu or the amino acid sequence of LESLPS (SEQ ID NO: 118).

11. The isolated polypeptide of claim 9, wherein the one or more mutations at residues 36, 38, 43 and 86 numbered according to SEQ ID NO: 3 are A36V, L38F, F43V and M86F.

12. A pharmaceutical composition comprising the polypeptide molecule of claim 1 and a pharmaceutically acceptable carrier or excipient.

13. A method for treating an immune disease, disorder or condition mediated by CD2 in a human subject in need thereof, said method comprising administering to the subject an effective amount of the pharmaceutical composition of claim 12, wherein said disease, disorder or condition is selected from the group consisting of: type 1 diabetes, psoriasis, plaque psoriasis, palmoplantaris pustulosis, pustular psoriasis of palms and soles, pustulosis palmaris et plantaris, pustulosis of palms and soles, atopic dermatitis, lichen planus, graft-versus-host disease (GVHD), vitiligo, *Pityriasis rubra pilaris*, transplantation, psoriatic arthritis, a disease, disorder, or condition requiring allogeneic hematopoietic stem cell transplantation, thalassemia, sickle cell disease, glanzmann thrombasthenia, Wiskott-Aldrich syndrome, chronic-granulomatous disease, severe congenital neutropenia, leukocyte adhesion deficiency, Schwachman-Diamond syndrome, Diamond-Blackfan anemia, Fanconi anemia, Dyskeratosis-congenita, Chediak-Higashi syndrome, aplastic anemia, alopecia areata, and T cell lymphoma.

14. The method of claim 13, wherein the transplantation is an organ transplantation.

15. The method of claim 14, wherein the organ transplantation is a kidney transplantation.

16. The method of claim 13, wherein the T cell lymphoma is cutaneous T cell lymphoma or peripheral T cell non-Hodgkin's lymphoma.

\* \* \* \* \*